United States Patent
Cogan et al.

(10) Patent No.: US 7,214,802 B2
(45) Date of Patent: May 8, 2007

(54) ANTI-CYTOKINE HETEROCYCLIC COMPOUNDS

(75) Inventors: Derek Cogan, Sandy Hook, CT (US); Ming-Hong Hao, Ridgefield, CT (US); Victor Marc Kamhi, Framingham, MA (US); Craig Andrew Miller, Danbury, CT (US); Matthew Russell Netherton, Danbury, CT (US); Alan David Swinamer, Bethel, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 176 days.

(21) Appl. No.: 11/074,354

(22) Filed: Mar. 7, 2005

(65) Prior Publication Data

US 2006/0079519 A1    Apr. 13, 2006

Related U.S. Application Data

(60) Provisional application No. 60/551,445, filed on Mar. 9, 2004.

(51) Int. Cl.
C07D 249/06 (2006.01)
C07D 231/12 (2006.01)
C07D 401/04 (2006.01)
A61K 31/4192 (2006.01)
A61K 31/429 (2006.01)
A61K 31/4025 (2006.01)
A61K 31/402 (2006.01)

(52) U.S. Cl. .................. 548/255; 548/312.4; 548/126; 548/302.7; 548/204; 546/275.4; 546/208; 544/370; 544/333; 514/359; 514/397; 514/368; 514/387; 514/365; 514/341; 514/326; 514/252.14

(58) Field of Classification Search ................ 548/255, 548/312.4, 126, 302.7, 204; 546/275.4, 208; 544/370, 333; 514/359, 397, 368, 387, 365, 514/341, 326, 256, 252.14

See application file for complete search history.

(56) References Cited

U.S. PATENT DOCUMENTS

| 5,859,041 | A | 1/1999 | Liverton et al. |
| 6,348,480 | B1 | 2/2002 | Kubota et al. |
| 6,451,820 | B1 | 9/2002 | Sharma |
| 6,506,747 | B1 | 1/2003 | Betageri et al. |
| 2005/0004176 | A1 | 1/2005 | Dyckman et al. |

FOREIGN PATENT DOCUMENTS

| DE | 4302051 A1 | 7/1994 |
| EP | 1 024 138 A1 | 8/2000 |
| WO | WO 96/32382 A1 | 10/1996 |
| WO | WO 97 47618 A1 | 12/1997 |
| WO | WO 99/51580 A1 | 10/1999 |
| WO | WO 99/62885 A1 | 12/1999 |
| WO | WO 00/24735 A1 | 5/2000 |
| WO | WO 01 72740 A1 | 10/2001 |
| WO | WO 03/02910 A1 | 1/2003 |
| WO | WO 03/22820 A1 | 3/2003 |
| WO | WO 03/030902 A1 | 4/2003 |
| WO | WO 2003030902 A1 * | 4/2003 |
| WO | WO 03/063781 A2 | 8/2003 |

OTHER PUBLICATIONS

English Translation for DE 43 02 051 A1.

* cited by examiner

Primary Examiner—Kamal A. Saeed
Assistant Examiner—Michael P. Barker
(74) Attorney, Agent, or Firm—Michael Morris; Mary-Ellen M. Devlin; Anthony P. Bottino

(57) ABSTRACT

Disclosed compounds of formula (I)

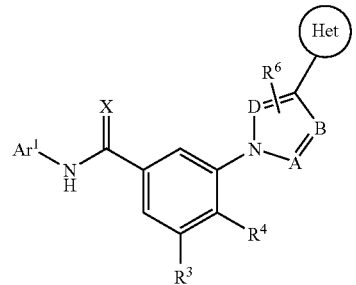

which inhibit production of cytokines involved in inflammatory processes and are thus useful for treating diseases and pathological conditions involving inflammation such as chronic inflammatory disease. Also disclosed are processes for preparing these compounds and pharmaceutical compositions comprising these compounds.

18 Claims, No Drawings

ANTI-CYTOKINE HETEROCYCLIC COMPOUNDS

APPLICATION DATA

This application claims benefit to U.S. provisional application No. 60/551,445 filed Mar. 9, 2004.

1. TECHNICAL FIELD

This invention relates to compounds of formula (I)

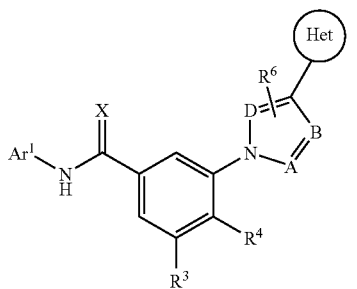

The compounds of the invention inhibit production of cytokines involved in inflammatory processes and are thus useful for treating diseases and pathological conditions involving inflammation such as chronic inflammatory disease. This invention also relates to processes for preparing these compounds and to pharmaceutical compositions comprising these compounds.

2. BACKGROUND INFORMATION

Tumor necrosis factor (TNF) and interleukin-1 (IL-1) are important biological entities collectively referred to as proinflammatory cytokines which play a role in cytokine mediated diseases. These, along with several other related molecules, mediate the inflammatory response associated with the immunological recognition of infectious agents. The inflammatory response plays an important role in limiting and controlling pathogenic infections.

Elevated levels of proinflammatory cytokines are also associated with a number of diseases of autoimmunity such as toxic shock syndrome, rheumatoid arthritis, osteoarthritis, diabetes and inflammatory bowel disease (Dinarello, C. A., et al., 1984, *Rev. Infect. Disease* 6:51). In these diseases, chronic elevation of inflammation exacerbates or causes much of the pathophysiology observed. For example, rheumatoid synovial tissue becomes invaded with inflammatory cells that result in destruction to cartilage and bone (Koch, A. E., et al., 1995, *J. Invest. Med.* 43: 28–38). Studies suggest that inflammatory changes mediated by cytokines may be involved in endothelial cell pathogenesis including restenosis after percutaneous transluminal coronary angioplasty (PTCA) (Tashiro, H., et al., 2001 March, *Coron Artery Dis* 12(2):107–13). An important and accepted therapeutic approach for potential drug intervention in these diseases is the reduction of proinflammatory cytokines such as TNF (also referred to in its secreted cell-free form as TNFα) and IL-1β. A number of anti-cytokine therapies are currently in clinical trials. Efficacy has been demonstrated with a monoclonal antibody directed against TNFα in a number of autoimmune diseases (Heath, P., "CDP571: An Engineered Human IgG4 Anti-TNFα Antibody" IBC Meeting on Cytokine Antagonists, Philadelphia, Pa., Apr. 24-5, 1997). These include the treatment of rheumatoid arthritis, Crohn's disease and ulcerative colitis (Rankin, E. C. C., et al., 1997, *British J. Rheum.* 35: 334–342 and Stack, W. A., et al., 1997, *Lancet* 349: 521–524). The monoclonal antibody is thought to function by binding to both soluble TNFα and to membrane bound TNF.

A soluble TNFα receptor has been engineered that interacts with TNFα. The approach is similar to that described above for the monoclonal antibodies directed against TNFα; both agents bind to soluble TNFα, thus reducing its concentration. One version of this construct, called Enbrel (Immunex, Seattle, Wash.) recently demonstrated efficacy in a Phase III clinical trial for the treatment of rheumatoid arthritis (Brower et al., 1997, *Nature Biotechnology* 15: 1240). Another version of the TNFα receptor, Ro 45-2081 (Hoffman-LaRoche Inc., Nutley, N.J.) has demonstrated efficacy in various animal models of allergic lung inflammation and acute lung injury. Ro 45-2081 is a recombinant chimeric molecule constructed from the soluble 55 kDa human TNF receptor fused to the hinge region of the heavy chain IgG1 gene and expressed in eukaryotic cells (Renzetti, et al., 1997, *Inflamm. Res.* 46: S143).

IL-1 has been implicated as an immunological effector molecule in a large number of disease processes. IL-1 receptor antagonist (IL-1ra) had been examined in human clinical trials. Efficacy has been demonstrated for the treatment of rheumatoid arthritis (Antril, Amgen). In a phase III human clinical trial IL-1ra reduced the mortality rate in patients with septic shock syndrome (Dinarello, 1995, *Nutrution* 11, 492). Osteoarthritis is a slow progressive disease characterized by destruction of the articular cartilage. IL-1 is detected in synovial fluid and in the cartilage matrix of osteoarthritic joints. Antagonists of IL-1 have been shown to diminish the degradation of cartilage matrix components in a variety of experimental models of arthritis (Chevalier, 1997, *Biomed Pharmacother.* 51, 58). Nitric oxide (NO) is a mediator of cardiovascular homeostasis, neurotransmission and immune function; recently it has been shown to have important effects in the modulation of bone remodeling. Cytokines such as IL-1 and TNF are potent stimulators of NO production. NO is an important regulatory molecule in bone with effects on cells of the osteoblast and osteoclast lineage (Evans, et al., 1996, *J Bone Miner Res.* 11, 300). The promotion of beta-cell destruction leading to insulin dependent diabetes mellitus shows dependence on IL-1. Some of this damage may be mediated through other effectors such as prostaglandins and thromboxanes. IL-1 can effect this process by controlling the level of both cyclooxygenase II and inducible nitric oxide synthetase expression (McDaniel et al., 1996, *Proc Soc Exp Biol Med.* 211, 24).

Inhibitors of cytokine production are expected to block inducible cyclooxygenase (COX-2) expression. COX-2 expression has been shown to be increased by cytokines and it is believed to be the isoform of cyclooxygenase responsible for inflammation (M. K. O'Banion et al., *Proc. Natl. Acad. Sci. U.S.A.,* 1992, 89, 4888.) Accordingly, inhibitors of cytokines such as IL-1 would be expected to exhibit efficacy against those disorders currently treated with COX inhibitors such as the familiar NSAIDs. These disorders include acute and chronic pain as well as symptoms of inflammation and cardiovascular disease.

Elevation of several cytokines has been demonstrated during active inflammatory bowel disease (IBD). A mucosal imbalance of intestinal IL-1 and IL-1ra is present in patients with IBD. Insufficient production of endogenous IL-1ra may contribute to the pathogenesis of IBD (Cominelli, et al., 1996, *Aliment Pharmacol Ther.* 10, 49). Alzheimer disease is characterized by the presence of beta-amyloid protein deposits, neurofibrillary tangles and cholinergic dysfunction throughout the hippocampal region.

The structural and metabolic damage found in Alzheimer disease is possibly due to a sustained elevation of IL-1 (Holden, et al., 1995, *Med Hypotheses,* 45, 559). A role for IL-1 in the pathogenesis of human immunodeficiency virus (HIV) has been identified. IL-1ra showed a clear relationship to acute inflammatory events as well as to the different disease stages in the pathophysiology of HIV infection (Kreuzer, et al., 1997, *Clin Exp Immunol.* 109, 54). IL-1 and TNF are both involved in periodontal disease. The destructive process associated with periodontal disease may be due to a disregulation of both IL-1 and TNF (Howells, 1995, *Oral Dis.* 1, 266).

Proinflammatory cytokines such as TNFα and IL-1β are also important mediators of septic shock and associated cardiopulmonary dysfunction, acute respiratory distress syndrome (ARDS) and multiple organ failure. In a study of patients presenting at a hospital with sepsis, a correlation was found between TNFα and IL-6 levels and septic complications (Terregino et al., 2000, *Ann. Emerg. Med.,* 35, 26). TNFα has also been implicated in cachexia and muscle degradation, associated with HIV infection (Lahdiverta et al., 1988, *Amer. J. Med.,* 85, 289). Obesity is associated with an increase incidence of infection, diabetes and cardiovascular disease. Abnormalities in TNFα expression have been noted for each of the above conditions (Loffreda, et al., 1998, *FASEB J.* 12, 57). It has been proposed that elevated levels of TNFα are involved in other eating related disorders such as anorexia and bulimia nervosa. Pathophysiological parallels are drawn between anorexia nervosa and cancer cachexia (Holden, et al., 1996, *Med Hypotheses* 47, 423). An inhibitor of TNFα production, HU-211, was shown to improve the outcome of closed brain injury in an experimental model (Shohami, et al., 1997, *J Neuroimmunol.* 72, 169). Atherosclerosis is known to have an inflammatory component and cytokines such as IL-1 and TNF have been suggested to promote the disease. In an animal model an IL-1 receptor antagonist was shown to inhibit fatty streak formation (Elhage et al., 1998, *Circulation,* 97, 242).

TNFα levels are elevated in airways of patients with chronic obstructive pulmonary disease and it may contribute to the pathogenesis of this disease (M. A. Higham et al., 2000, *Eur. Respiratory J.,* 15, 281). Circulating TNFα may also contribute to weight loss associated with this disease (N. Takabatake et al., 2000, *Amer. J. Resp. & Crit. Care Med.,* 161 (4 Pt 1), 1179). Elevated TNFα levels have also been found to be associated with congestive heart failure and the level has been correlated with severity of the disease (A. M. Feldman et al., 2000, *J. Amer. College of Cardiology,* 35, 537). In addition, TNFα has been implicated in reperfusion injury in lung (Borjesson et al., 2000, *Amer. J. Physiol.,* 278, L3-12), kidney (Lemay et al., 2000, *Transplantation,* 69, 959), and the nervous system (Mitsui et al., 1999, *Brain Res.,* 844, 192).

TNFα is also a potent osteoclastogenic agent and is involved in bone resorption and diseases involving bone resorption (Abu-Amer et al., 2000, *J. Biol. Chem.,* 275, 27307). It has also been found highly expressed in chondrocytes of patients with traumatic arthritis (Melchiorri et al., 2000, *Arthritis and Rheumatism,* 41, 2165). TNFα has also been shown to play a key role in the development of glomerulonephritis (Le Hir et al., 1998, *Laboratory Investigation,* 78, 1625).

The abnormal expression of inducible nitric oxide synthetase (iNOS) has been associated with hypertension in the spontaneously hypertensive rat (Chou et al., 1998, *Hypertension,* 31, 643). IL-1 has a role in the expression of iNOS and therefore may also have a role in the pathogenesis of hypertension (Singh et al., 1996, *Amer. J. Hypertension,* 9, 867).

IL-1 has also been shown to induce uveitis in rats which could be inhibited with IL-1 blockers. (Xuan et al., 1998, *J. Ocular Pharmacol. and Ther.,* 14, 31). Cytokines including IL-1, TNF and GM-CSF have been shown to stimulate proliferation of acute myelogenous leukemia blasts (Bruserud, 1996, *Leukemia Res.* 20, 65). IL-1 was shown to be essential for the development of both irritant and allergic contact dermatitis. Epicutaneous sensitization can be prevented by the administration of an anti-IL-1 monoclonal antibody before epicutaneous application of an allergen (Muller, et al., 1996, *Am J Contact Dermat.* 7, 177). Data obtained from IL-1 knock out mice indicates the critical involvement in fever for this cytokine (Kluger et al., 1998, *Clin Exp Pharmacol Physiol.* 25, 141). A variety of cytokines including TNF, IL-1, IL-6 and IL-8 initiate the acute-phase $$ reaction which is stereotyped in fever, malaise, myalgia, headaches, cellular hypermetabolism and multiple endocrine and enzyme responses (Beisel, 1995, *Am J Clin Nutr.* 62, 813). The production of these inflammatory cytokines rapidly follows trauma or pathogenic organism invasion.

Other proinflammatory cytokines have been correlated with a variety of disease states. IL-8 correlates with influx of neutrophils into sites of inflammation or injury. Blocking antibodies against IL-8 have demonstrated a role for IL-8 in the neutrophil associated tissue injury in acute inflammation (Harada et al., 1996, *Molecular Medicine Today* 2, 482). Therefore, an inhibitor of IL-8 production may be useful in the treatment of diseases mediated predominantly by neutrophils such as stroke and myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, hemodialysis, leukopherisis, granulocyte transfusion associated syndromes, and necrotizing enterocolitis.

Rhinovirus triggers the production of various proinflammatory cytokines, predominantly IL-8, which results in symptomatic illnesses such as acute rhinitis (Winther et al., 1998, *Am J Rhinol.* 12, 17).

Other diseases that are effected by IL-8 include myocardial ischemia and reperfusion, inflammatory bowel disease and many others.

The proinflammatory cytokine IL-6 has been implicated with the acute phase response. IL-6 is a growth factor in a number in oncological diseases including multiple myeloma and related plasma cell dyscrasias (Treon, et al., 1998, *Current Opinion in Hematology* 5: 42). It has also been shown to be an important mediator of inflammation within the central nervous system. Elevated levels of IL-6 are found in several neurological disorders including AIDS dementia complex, Alzheimer's disease, multiple sclerosis, systemic lupus erythematosus, CNS trauma and viral and bacterial meningitis (Gruol, et al., 1997, *Molecular Neurobiology* 15: 307). IL-6 also plays a significant role in osteoporosis. In murine models it has been shown to effect bone resorption and to induce osteoclast activity (Ershler et al., 1997, *Development and Comparative Immunol.* 21: 487). Marked cytokine differences, such as IL-6 levels, exist in vivo between osteoclasts of normal bone and bone from patients with Paget's disease (Mills, et al., 1997, *Calcif Tissue Int.* 61, 16). A number of cytokines have been shown to be involved in cancer cachexia. The severity of key parameters of cachexia can be reduced by treatment with anti IL-6 antibodies or with IL-6 receptor antagonists (Strassmann, et al., 1995, *Cytokins Mol Ther.* 1, 107). Several infectious diseases, such as influenza, indicate IL-6 and IFN alpha as key factors in both symptom formation and in host defense (Hayden, et al., 1998, *J Clin Invest.* 101, 643). Overexpression of IL-6 has been implicated in the pathology of a number of diseases including multiple myeloma, rheumatoid arthritis, Castleman's disease, psoriasis and post-menopausal osteoporosis (Simpson, et al., 1997, *Protein Sci.* 6, 929). Compounds that interfered with the production of cytokines including IL-6, and TNF were effective in blocking a passive cutaneous anaphylaxis in mice (Scholz et al., 1998, *J. Med. Chem.*, 41, 1050).

GM-CSF is another proinflammatory cytokine with relevance to a number of therapeutic diseases. It influences not only proliferation and differentiation of stem cells but also regulates several other cells involved in acute and chronic inflammation. Treatment with GM-CSF has been attempted in a number of disease states including burn-wound healing, skin-graft resolution as well as cytostatic and radiotherapy induced mucositis (Masucci, 1996, *Medical Oncology* 13: 149). GM-CSF also appears to play a role in the replication of human immunodeficiency virus (HIV) in cells of macrophage lineage with relevance to AIDS therapy (Crowe et al., 1997, *Journal of Leukocyte Biology* 62, 41). Bronchial asthma is characterised by an inflammatory process in lungs. Involved cytokines include GM-CSF amongst others (Lee, 1998, *J R Coll Physicians Lond* 32, 56).

Interferon γ (IFN γ) has been implicated in a number of diseases. It has been associated with increased collagen deposition that is a central histopathological feature of graft-versus-host disease (Parkman, 1998, *Curr Opin Hematol.* 5, 22). Following kidney transplantation, a patient was diagnosed with acute myelogenous leukemia. Retrospective analysis of peripheral blood cytokines revealed elevated levels of GM-CSF and IFN γ. These elevated levels coincided with a rise in peripheral blood white cell count (Burke, et al., 1995, *Leuk Lymphoma.* 19, 173). The development of insulin-dependent diabetes (Type 1) can be correlated with the accumulation in pancreatic islet cells of T-cells producing IFN γ (Ablumunits, et al., 1998, *J Autoimmun.* 11, 73). IFN γ along with TNF, IL-2 and IL-6 lead to the activation of most peripheral T-cells prior to the development of lesions in the central nervous system for diseases such as multiple sclerosis (MS) and AIDS dementia complex (Martino et al., 1998, *Ann Neurol.* 43, 340). Atherosclerotic lesions result in arterial disease that can lead to cardiac and cerebral infarction. Many activated immune cells are present in these lesions, mainly T-cells and macrophages. These cells produce large amounts of proinflammatory cytokines such as TNF, IL-1 and IFN γ. These cytokines are thought to be involved in promoting apoptosis or programmed cell death of the surrounding vascular smooth muscle cells resulting in the atherosclerotic lesions (Geng, 1997, *Heart Vessels Suppl* 12, 76). Allergic subjects produce mRNA specific for IFN γ following challenge with Vespula venom (Bonay, et al., 1997, *Clin Exp Immunol.* 109, 342). The expression of a number of cytokines, including IFN γ has been shown to increase following a delayed type hypersensitivity reaction thus indicating a role for IFN γ in atopic dermatitis (Szepietowski, et al, 1997, *Br J Dermatol.* 137, 195). Histopathologic and immunohistologic studies were performed in cases of fatal cerebral malaria. Evidence for elevated IFN γ amongst other cytokines was observed indicating a role in this disease (Udomsangpetch et al., 1997, *Am J Trop Med Hyg.* 57, 501). The importance of free radical species in the pathogenesis of various infectious diseases has been established. The nitric oxide synthesis pathway is activated in response to infection with certain viruses via the induction of proinflammatory cytokines such as IFN γ (Akaike, et al., 1998, *Proc Soc Exp Biol Med.* 217, 64). Patients, chronically infected with hepatitis B virus (HBV) can develop cirrhosis and hepatocellular carcinoma. Viral gene expression and replication in HBV transgenic mice can be suppressed by a post-transcriptional mechanism mediated by IFN γ, TNF and IL-2 (Chisari, et al., 1995, *Springer Semin Immunopathol.* 17, 26 1). IFN γ can selectively inhibit cytokine induced bone resorption. It appears to do this via the intermediacy of nitric oxide (NO) which is an important regulatory molecule in bone remodeling. NO may be involved as a mediator of bone disease for such diseases as: rheumatoid arthritis, tumor associated osteolysis and postmenopausal osteoporosis (Evans, et al., 1996, *J Bone Miner Res.* 11, 300). Studies with gene deficient mice have demonstrated that the IL-12 dependent production of IFN γ is critical in the control of early parasitic growth. Although this process is independent of nitric oxide the control of chronic infection does appear to be NO dependent (Alexander et al., 1997, *Philos Trans R Soc Lond B Biol Sci* 352, 1355). NO is an important vasodilator and convincing evidence exists for its role in cardiovascular shock (Kilbourn, et al., 1997, *Dis Mon.* 43, 277). IFN γ is required for progression of chronic intestinal inflammation in such diseases as Crohn's disease and inflammatory bowel disease (IBD) presumably through the intermediacy of CD4+ lymphocytes probably of the TH1 phenotype (Sartor 1996, *Aliment Pharmacol Ther.* 10 Suppl 2, 43). An elevated level of serum IgE is associated with various atopic diseases such as bronchial asthma and atopic dermatitis. The level of IFN γ was negatively correlated with serum IgE suggesting a role for IFN γ in atopic patients (Teramoto et al., 1998, *Clin Exp Allergy* 28, 74).

WO 01/01986 discloses particular compounds alleged to having the ability to inhibit TNF-alpha. Certain compounds disclosed in WO 01/01986 are indicated to be effective in treating the following diseases: dementia associated with HIV infection, glaucoma, optic-neuropathy, optic neuritis, retinal ischemia, laser induced optic damage, surgery or trauma-induced proliferative vitreoretinopathy, cerebral ischemia, hypoxia-ischemia, hypoglycemia, domoic acid poisoning, anoxia, carbon monoxide or manganese or cyanide poisoning, Huntington's disease, Alzheimer's disease, Parkinson's disease, meningitis, multiple sclerosis and other demyelinating diseases, amyotrophic lateral sclerosis, head and spinal cord trauma, seizures, convulsions, olivopontocerebellar atrophy, neuropathic pain syndromes, diabetic neuropathy, HIV-related neuropathy, MERRF and MELAS syndromes, Leber's disease, Wernicke's encephalophathy, Rett syndrome, homocysteinuria, hyperprolinemia, hyperhomocysteinemia, nonketotic hyperglycinemia, hydroxybutyric aminoaciduria, sulfite oxidase deficiency, combined systems disease, lead encephalopathy, Tourett's syndrome, hepatic encephalopathy, drug addiction, drug tolerance, drug dependency, depression, anxiety and schizophrenia. WO 02/32862 discloses that inhibitors of pro-inflammatory cytokines including TNFα are allegedly useful for treating acute and chronic inflammation in the lung caused by inhalation of smoke such as cigarette smoke. TNFα anatagonists are apparently also useful for the treatment of endometriosis, see EP 1022027 A1. Infliximab, in clinical trials for RA, has also been indicated to be useful for treating various inflammatory diseases including Behcet's disease, uveitis and ankylosing spondylitis. Pancreatitis may also be regulated by inflammatory mediator production, see J Surg Res 2000 May 15 90(2)95–101; Shock 1998 Sep. 10(3): 160–75. p38MAP kinase pathway plays an role in B.burgdorferi-elicited inflammation and may be useful in treating inflammation induced by the Lyme disease agent. Anguita, J. et. al., *The Journal of Immunology,* 2002,168:6352–6357.

Compounds which modulate release of one or more of the aforementioned inflammatory cytokines can be useful in treating diseases associated with release of these cytokines. For example, WO 98/52558 discloses heteroaryl urea compounds which are indicated to be useful in treating cytokine mediated diseases. WO 99/23091 discloses another class of urea compounds which are useful as anti-inflammatory agents. WO 99/32463 relates to aryl ureas and their use in treating cytokine diseases and proteolytic enzyme mediated disease. WO 00/41698 discloses aryl ureas said to be useful in treating p38 MAP kinase diseases.

Compounds active against p38 MAP kinase can also be useful for treating various types of cancers as described in WO 03/068223.

U.S. Pat. No. 5,162,360 discloses N-substituted aryl-N'-heterocyclic substituted urea compounds which are described as being useful for treating hypercholesterolemia and atheroclerosis. Di-substituted aryl and heteroaryl compounds are also disclosed in U.S. Pat. Nos. 6,080,763; 6,319,921; 6,297,381 and 6,358,945. The compounds in the patents are alleged to possess anti-cytokine activity and are therefore useful in treating diseases associated with inflammation.

The work cited above supports the principle that inhibition of cytokine production will be beneficial in the treatment of cytokine mediated diseases. Therefore a need exists for small molecule inhibitors for treating these diseases with optimized efficacy, pharmacokinetic and safety profiles.

BRIEF SUMMARY OF THE INVENTION

The work cited above supports the principle that inhibition of cytokine production with small molecule compounds will be beneficial in the treatment of various disease states.

It is therefore an object of the invention to provide compounds of formula (I)

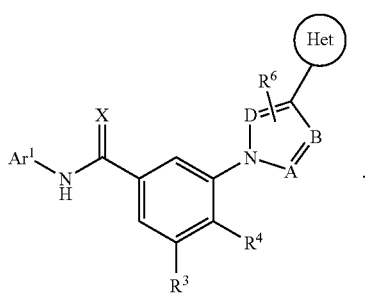

It is a further object of the invention to provide methods for treating cytokine mediated diseases and pathological conditions involving inflammation such as chronic inflammatory disease, using the novel compounds of the invention.

It is yet a further object of the invention to provide pharmaceutical compositions and processes of preparation of the above-mentioned novel compounds.

DETAILED DESCRIPTION OF THE INVENTION

In the broadest generic embodiment, there is provided compounds of the formula (I)

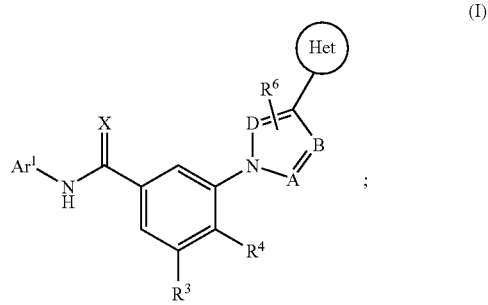

wherein:
$Ar^1$ is chosen from (i), (ii) and (iii) below:
i) a carbocycle substituted by $R^1$, $R^2$ and $R^x$,

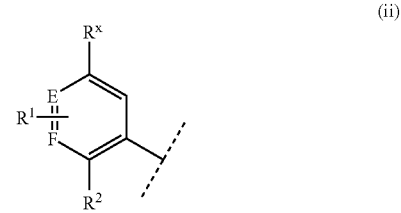

wherein one E or F is nitrogen and other is carbon, $R^1$ is covalently attached to either E or F, and when nitrogen is $N-R^1$ the double between E and F is not present;

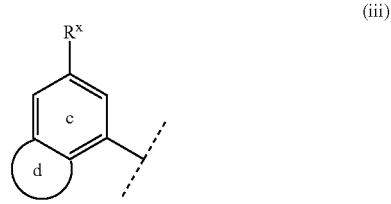

wherein c is a benzo ring fused to ring d which is a 5–7 membered heterocyclic ring optionally substituted by an oxo (=O) group and one to two R groups each independently being H or C1–3 alkyl;
$R^1$ is chosen from hydrogen, $NO_2$, $-N(R^c)_2$, $J-C(O)-N(R^c)-$, $J-S(O)_m-N(R^c)-$, $C1-6$ alkyl$S(O)_m-$
or $R^1$ is chosen from C1–6 alkyl, C3–7 cylcoalkyl, C1–5 alkoxyl or C3–7 cycloalkoxyl, C1–5 alkylthiol or C3–7 cycloalkylthiol, C1–5 acyl, C1–5 alkoxycarbonyl, C1–5 acyloxy, C1–5 acylamino, C2–5 alkenyl, C2–5 alkynyl, heterocycle, heterocycleC1–6 alkyl, heteroaryl, heteroarylC1–6 alkyl and nitrile; each of the aforementioned where possible are optionally partially or fully halogenated or are optionally further substituted with alkylsulfonylamino, aminocarboxyl, alkoxyl, amino, alkylamino, dialkylamino, hydroxyl, oxo, nitro or nitrile;

R² is chosen from:
hydrogen, halogen, nitrile, C1–5 alkylS(O)$_m$—, arylS(O)$_m$, J-O—C(O)—O—, N(R$^c$)$_2$—C(O)—(CH$_2$)$_n$—, C1–6 acetyl, aroyl, C1–6alkoxycarbonyl, C1–6 alkyl, C3–7cycloalkyl, C1–6 alkoxy, C3–5cycloalkoxy, C1–5 alkylC1–5 alkoxy, hydroxy, hydroxy C1–5 alkyl, and amino optionally mono- or di-substituted by C1–5 alkyl, aryl or aryl C1–5 alkyl; each of the aforementioned where possible are optionally partially or fully halogenated or are optionally further substituted with C1–3 alkyl, alkylsulfonylamino, alkoxyl, amino, alkylamino, dialkylamino, hydroxyl, oxo, nitro or nitrile;

each R$^x$ is chosen from C1–6 alkyl or C3–7 cycloalkyl each being optionally substituted by C1–3 alkyl and optionally partially or fully halogenated, C1–4 acyl, aroyl, C1–4 alkoxy, C1–5alkylS(O)$_m$—, each may optionally be partially or fully halogenated, halogen, C1–6 alkoxycarbonyl, carbocyclesulfonyl;

each R$^c$ is independently hydrogen or C1–5 alkyl;
D, A and B in

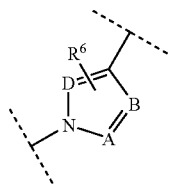

of the formula (I) are each independently chosen from N or CH wherein the hydrogen atom is optionally replaced by R$^6$;
Het is a heterocyclic or heteroaryl ring wherein Het is optionally substituted by one to three R$^5$;
m is 0,1 or 2
J is chosen from C1–10 alkyl and C3–7cycloalkyl each optionally substituted by R$^b$;
R$^3$, R$^4$, R$^6$, R$^7$ and R$^8$ are each independently chosen from hydrogen, halogen, C1–5alkyl, C1–5 alkoxy, C1–5 alkylC1–5 alkoxy, hydroxy, hydroxy C1–5 alkyl or amino optionally mono- or di-substituted by C1–5 alkyl, aryl or aryl C1–5 alkyl;
R$^5$ is:
R$^a$, —O—R$^a$, —S(O)$_m$—R$^a$, —N(R$^a$)$_2$, —C(O)—R$^a$, —NH(CR$^7$R$^8$)$_n$—R$^a$, N(R$^a$)$_2$—(CH$_2$)$_{1-2}$— —(CR$^7$R$^8$)$_n$—R$^a$, —O(CR$^7$R$^8$)$_n$—R$^a$, —C(O)—O(CR$^7$R$^8$)$_n$R$^a$, —C(O)(CR$^7$R$^8$)$_n$—R$^a$ —C(O)C(O)R$^a$, —C(O)C(O)OR$^a$, —C(O)NHR$^a$, or —C(O)NH(CR$^7$R$^8$)$_n$—, each optionally substituted by C1–3 alkyl, halogen or hydroxy, wherein n is 1–5;
or R$^5$ is aryl, heteroaryl or heterocyclyl each optionally substituted by R$^a$;
R$^a$ and R$^b$ are each independently chosen from hydrogen, C1–6 alkyl, hydroxyC1–5 alkyl, C2–5 alkenyl, C2–5 alkynyl, carbocycle, carbocycleC0–2 alkyl, aryl, heterocycle, heteroaryl, C1–5 alkoxy, C1–5 alkylthio, amino, C1–5 alkylamino, C1–5 dialkylamino, arylamino, aryl C1–5 alkylamino, diarylamino, C1–5 acyl, C1–5 alkoxycarbonyl, C1–5 acyloxy, C1–5 acylamino, each of the aforementioned are optionally partially or fully halogenated, or R$^a$ and R$^b$ are chosen from C1–5 alkylsulphonylamino, hydroxy, oxo, halogen, —CF$_3$, —CH$_2$—CF$_3$, nitro and nitrile, wherein each carbocycle, heterocycle or heteroaryl for R$^a$ and R$^b$ is optionally substituted by amino, C1–3 alkyl, halogen or hydroxy; and
X is O or S or the pharmaceutically acceptable salts, acids, esters or isomers thereof.

In another embodiment, there are provided compounds of the formula (I) as described above and wherein

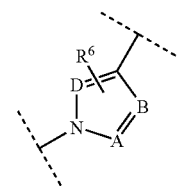

of the formula (I) is chosen from:

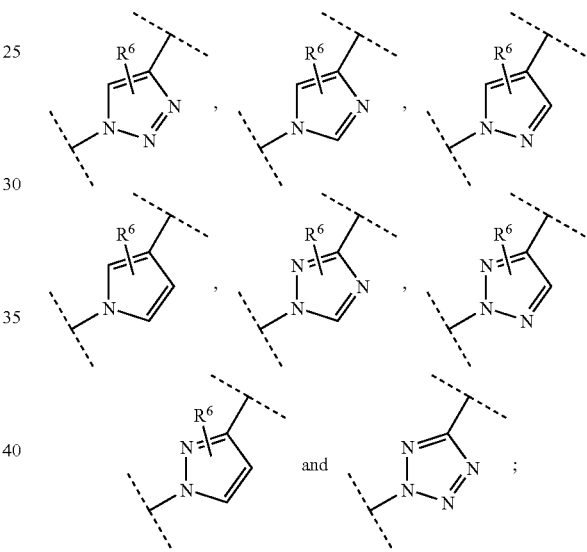

Het is

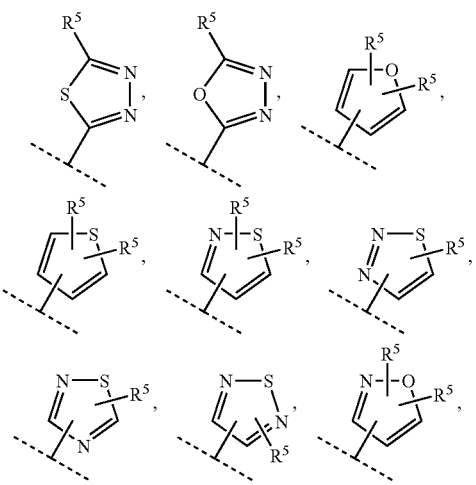

-continued

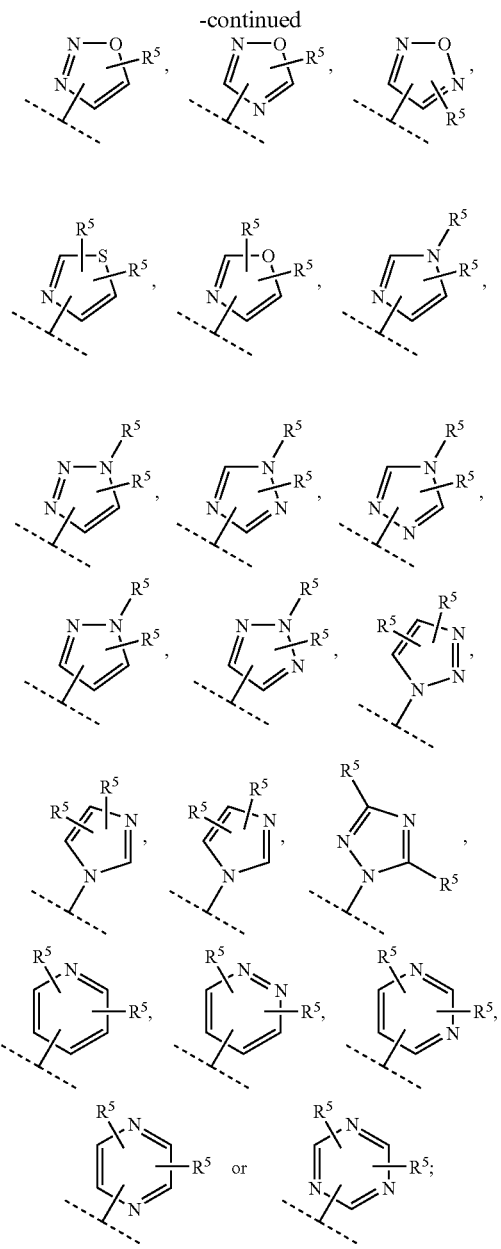

J is chosen from C1–10 alkyl, aryl and C3–7 cycloalkyl each optionally substituted by $R^b$;

$R^2$ is independently chosen from hydrogen, J-O—C(O)—O—, C1–6 alkoxy, C1–6 alkyl, C1–6 acetyl, aroyl, halogen, methoxycarbonyl, phenylsulfonyl, C1–5 alkylS(O)$_m$— and C3–7 cycloalkyl optionally substituted by C1–3 alkyl, each $R^2$ where possible may be optionally partially or fully halogenated;

$R^1$ is chosen from H, C1–6 alkyl, C1–5 alkylS(O)$_m$—, J-S(O)$_m$—N($R^c$)—, C1–5 alkoxyl, C1–5 alkylthiol, NH$_2$—C(O)—(CH$_2$)$_n$—, ($R^c$)$_2$N C1–6 alkyl, C1–5acylNH—, —NH$_2$, —NO$_2$, heteroaryl chosen from pyrazole, triazole, imidazole and tetrazole, and nitrile;

ring d is a 5–6 membered heterocyclic ring such that rings c and d fuse to form the following:

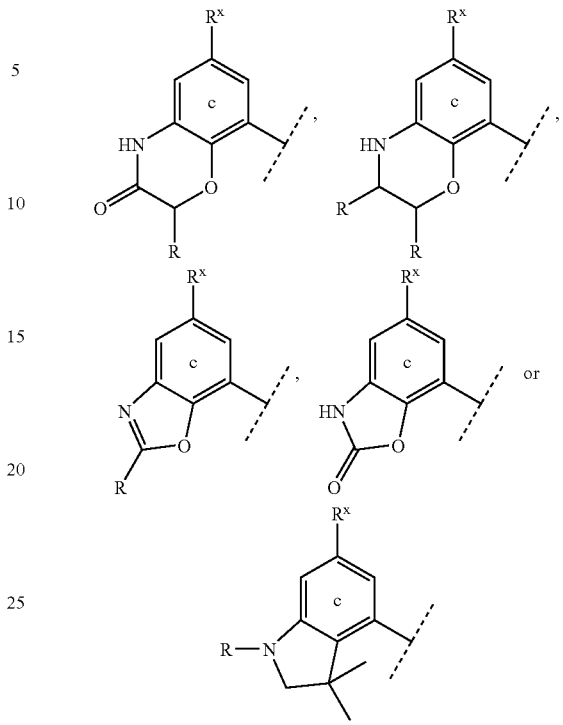

where each R is independently H or C1–3 alkyl;

$R^3$ and $R^4$ are each independently chosen from hydrogen, C1–3 alkoxy, C1–3 alkyl and halogen;

n is 1–4;

$R^a$ and $R^b$ are each independently chosen from hydrogen, C1–6 alkyl, C2–5 alkenyl, C2–5 alkynyl, C3–8 cycloalkylC0–2 alkyl, aryl, C1–5 alkoxy, C1–5 alkylthio, amino, C1–5 alkylamino, C1–5 dialkylamino, arylamino, C1–5 acyl, C1–5 alkoxycarbonyl, C1–5 acyloxy, C1–5 acylamino, aryl C1–5alkylamino, C1–5 alkylsulphonylamino, hydroxy, halogen, —CF$_3$, —CH$_2$—CF$_3$ nitro, nitrile, or $R^a$ and $R^b$ are chosen from; heterocycle chosen from pyrrolidinyl, pyrrolinyl, morpholinyl, thiomorpholinyl, thiomorpholinyl sulfoxide, thiomorpholinyl sulfone, dioxalanyl, piperidinyl, piperazinyl, homopiperazinyl, tetrahydrofuranyl, tetrahydropyranyl, tetrahydrofuranyl, 1,3-dioxolanone, 1,3-dioxanone, 1,4-dioxanyl, piperidinonyl, tetrahydropyrimidonyl, aziridinyl, pentamethylene sulfide, pentamethylene sulfoxide, pentamethylene sulfone, tetramethylene sulfide, tetramethylene sulfoxide and tetramethylene sulfone and heteroaryl chosen from thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl, naphthyridinyl, indazolyl, triazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl and imidazo[4,5-b]pyridinyl; wherein each aryl, heterocycle or heteroaryl for $R^a$ and $R^b$ is optionally substituted by amino, C1–3 alkyl, halogen or hydroxy;

and X is O.

In yet another embodiment, there are provided compounds of the formula (I) as described immediately above and wherein Ar$^1$ is chosen from (i) and (ii);

R$^5$ is:
a) R$^a$, —O—R$^a$, —S(O)$_m$—R$^a$, —N(R$^a$)$_2$, N(R$^a$)$_2$—(CH$_2$)$_{1-2}$—, —NH(CR$^7$R$^8$)$_n$—R$^a$, —(CR$^7$R$^8$)$_n$—R$^a$ or —O(CR$^7$R8)$_n$—R$^a$;

or R$^5$ is:
b) —C(O)—R$^a$, —C(O)—O(CR$^7$R$^8$)$_n$—R$^a$, —C(O)(CR$^7$R$^8$)$_n$—R$^a$, —C(O)NHR$^a$, —C(O)NH(CR$^7$R$^8$)$_n$—, —C(O)C(O)R$^a$ or —C(O)C(O)OR$^a$; each of the above R$^5$ is optionally substituted by C1–3 alkyl, halogen or hydroxyl, and wherein n is 1–3

In yet another embodiment, there are provided compounds of the formula (I) as described immediately above and wherein Ar$^1$ is:

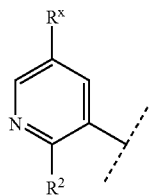

or Ar$^1$ is cyclobutyl, phenyl, naphthyl, tetrahydronaphthyl, indanyl and indenyl each substituted with one R$^1$, one R$^x$, and one R$^2$ group;

R$^1$ is nitrile, NO$_2$, NH$_2$, C1–3acylNH—,

J-S(O)$_{m-N(R^c)}$— where J is C1–10 alkyl, or R$^1$ is

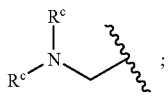

R$^2$ is independently chosen from C1–6 alkyl, C1–6 alkylS(O)$_m$—, C1–3 alkoxy and C3–6 cycloalkyl optionally substituted by C1–3 alkyl, each may optionally be partially or fully halogenated;

R$^3$ and R$^4$ are each independently chosen from hydrogen, C1–3 alkyl, fluoro and chloro;

R$^6$ is chosen from hydrogen and amino;

n is 1–2;

R$^a$ and R$^b$ are each independently chosen from hydrogen, C1–6 alkyl, C3–7 cycloalkylC0–2 alkyl, aryl, C1–5 alkoxy, amino, C1–5 alkylamino, C1–5 dialkylamino, arylamino, aryl C1–5alkylamino, C1–3 acyl, C1–5 alkoxycarbonyl, C1–5 acyloxy, C1–5 acylamino, C1–5 sulphonylamino, hydroxy, halogen, —CF$_3$, —CH$_2$—CF$_3$ nitro, nitrile; or R$^a$ is chosen from pyrrolidinyl, pyrrolinyl, morpholinyl, thiomorpholinyl, thiomorpholinyl sulfoxide, thiomorpholinyl sulfone, piperidinyl, piperazinyl, homopiperazinyl, piperidinonyl, tetrahydropyrimidonyl, aziridinyl, isoxazolyl, oxazolyl, thiazolyl, thiadiazolyl, tetrazolyl, pyrazolyl, pyrrolyl, imidazolyl, pyridinyl, pyrimidinyl, pyrazinyl and pyridazinyl; wherein each aryl, heterocycle or heteroaryl for R$^a$ and R$^b$ is optionally substituted by amino, C1–3 alkyl, halogen or hydroxy.

In yet still another embodiment, there are provided compounds of the formula (I) as described immediately above and wherein Ar$^1$ is

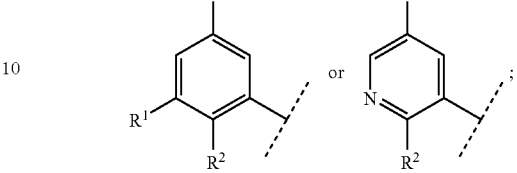

R$^1$ is:

J-S(O)$_2$—NH—, where J is C1–5 alkyl, or R$^1$ is nitrile, NO$_2$, NH$_2$ or C1–3acylNH—, wherein R$^x$=R$^2$ each are independently chosen from C1–5 alkyl, C1–5 alkylS(O)$_m$—, C1–4 alkoxy and and C3–5 cycloalkyl optionally substituted by C1–2 alkyl, each may optionally be partially or fully halogenated;

R$^8$ is hydrogen, methyl, ethyl, CH$_2$OH and CH$_2$OCH$_3$.

In yet another embodiment, there are provided compounds of the formula (I) as described immediately above and wherein R$^a$ is chosen from hydrogen, C1–6 alkyl, C3–6 cycloalkylC0–2 alkyl, phenyl, C1–5 alkoxy, amino, C1–5 alkylamino, C1–5 dialkylamino, arylamino, aryl C1–5alkylamino, C1–3 acyl, C1–5 alkoxycarbonyl, C1–5 acyloxy, C1–5 acylamino, hydroxy, halogen, —CF$_3$, —CH$_2$—CF$_3$;

or R$^a$ is chosen from morpholinyl, thiomorpholinyl, thiomorpholinyl sulfoxide, thiomorpholinyl sulfone, piperazinyl, homopiperazinyl, pyrrolidinyl, piperidinyl, piperidinonyl, pyridinyl, pyrimidinyl, pyrazinyl and pyridazinyl wherein each phenyl, heterocycle or heteroaryl for R$^a$ is optionally substituted by amino, C1–3 alkyl, halogen or hydroxy.

In yet another embodiment, there are provided compounds of the formula (I) as described immediately above and wherein R$^a$ is chosen from hydrogen, C1–6 alkyl, C3–6 cycloalkyl, phenyl, C1–5 alkoxy, C1–5 alkoxycarbonyl, amino, C1–5 alkylamino, C1–5 dialkylamino, arylamino, aryl C1–5alkylamino, C1–5 acyloxy, C1–5 acylamino, hydroxy, halogen, —CF$_3$, —CH$_2$—CF$_3$; or R$^a$ is chosen morpholinyl, piperidinyl piperazinyl, homopiperazinyl, pyrrolidinyl and pyridinyl wherein each phenyl, heterocycle or heteroaryl for R$^a$ is optionally substituted by amino, C1–3 alkyl, halogen or hydroxy.

In yet another embodiment, there are provided compounds of the formula (I) as described immediately above and wherein

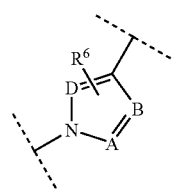

of the formula (I) is chosen from:

15

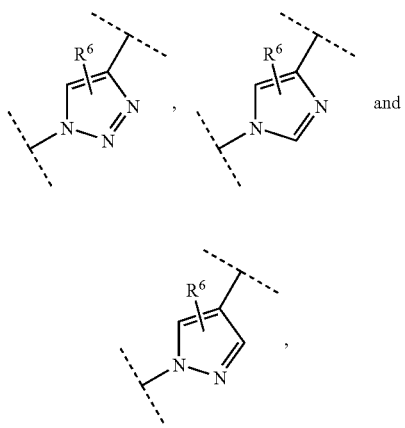

Het is;

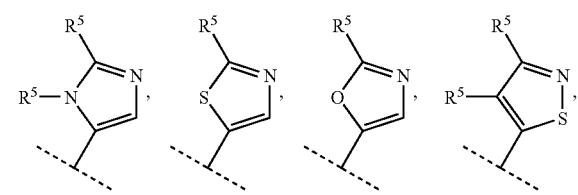

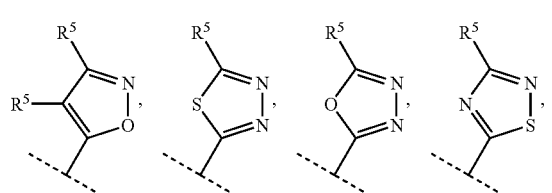

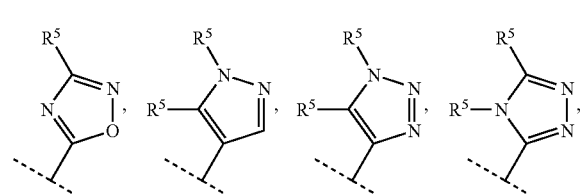

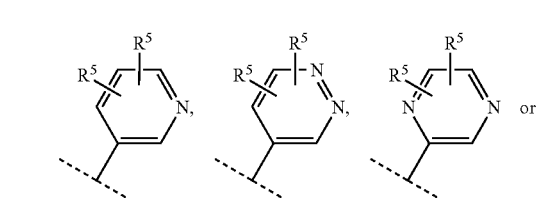

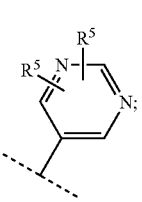

16

Ar¹ is

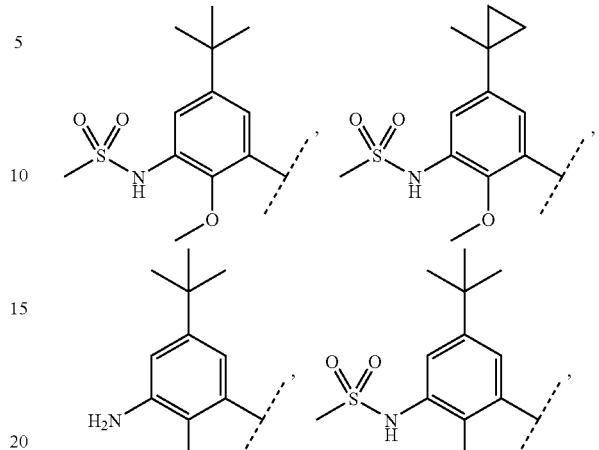

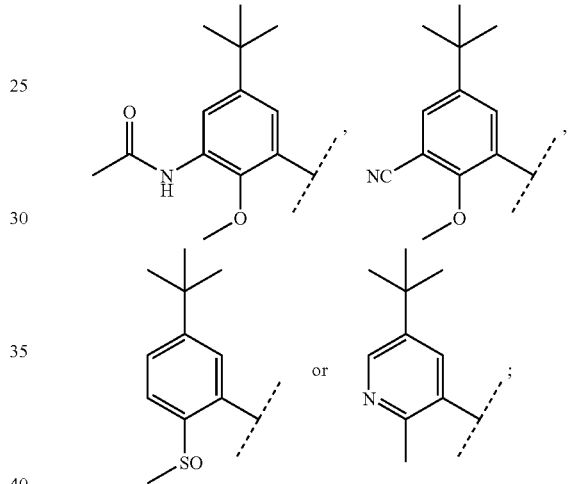

R⁵ is:
C1–5 alkyl, C3–6 cycloalkyl, N(Rᵃ)₂(CH₂)₁₋₂—, halogen, C1–3 alkoxy, hydroxy, —N(Rᵃ)₂, —CF₃, —CH₂—CF₃, aryl, —S(O)ₘ—Rᵃ, —NH(CR⁷R⁸)ₙ—Rᵃ or —(CR⁷R⁸)ₙ—N(Rᵃ)₂ each optionally substituted by C1–3 alkyl, halogen or hydroxy,
or R⁵ is —C(O)Rᵃ, —C(O)C(O)Rᵃ, —C(O)NHRᵃ.
Rᵃ is chosen from hydrogen, morpholinyl, piperidinyl, piperazinyl, pyrrolidinyl, pyridinyl, C₁₋₅ mono or dialkylamino, arylamino, C3–6cylcoalkyl, C1–5 alkyl and C1–3 alkoxy wherein each phenyl or heterocycle for Rᵃ is optionally substituted by amino, C1–3 alkyl, halogen or hydroxyl.

The following are preferred embodiments of Het combined with

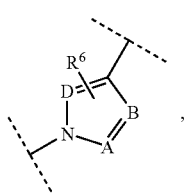

and wherein Ar¹, X, R³, R⁴ of the formula (I) are as defined in any one of the first seven embodiments provided hereinabove and wherein:

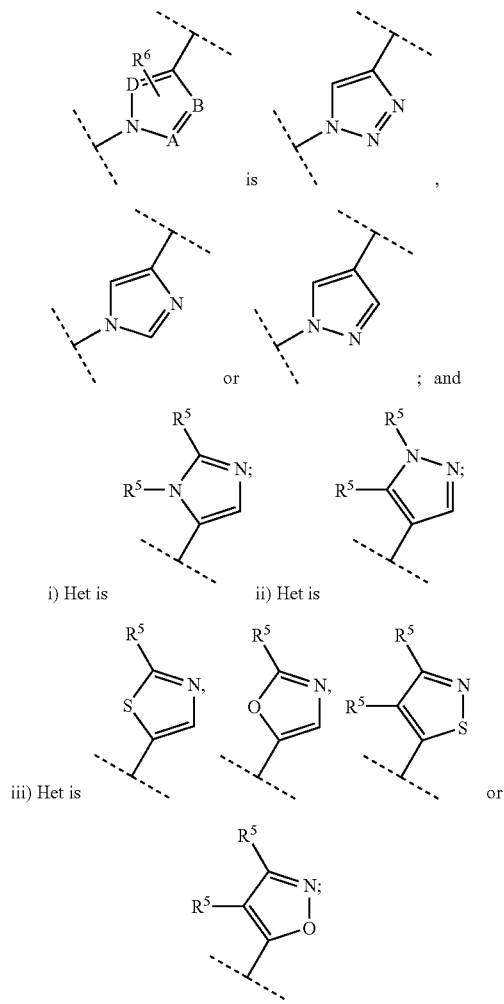

i) Het is ii) Het is iii) Het is or

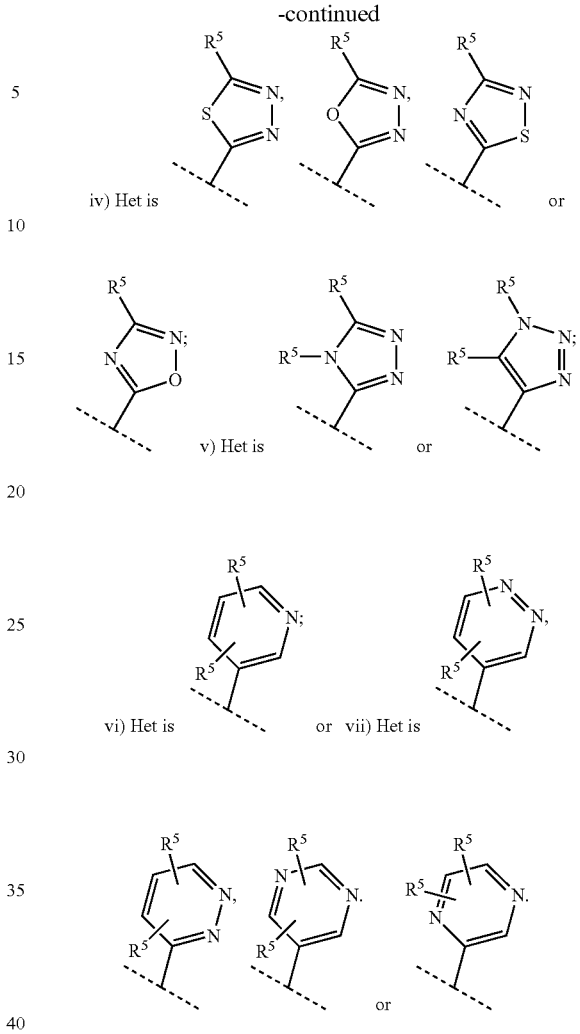

iv) Het is or v) Het is or vi) Het is or vii) Het is or

The following are representative compounds of the invention which can be made according to the general schemes and working examples below:

TABLE I

| Structure | Name |
| --- | --- |
| 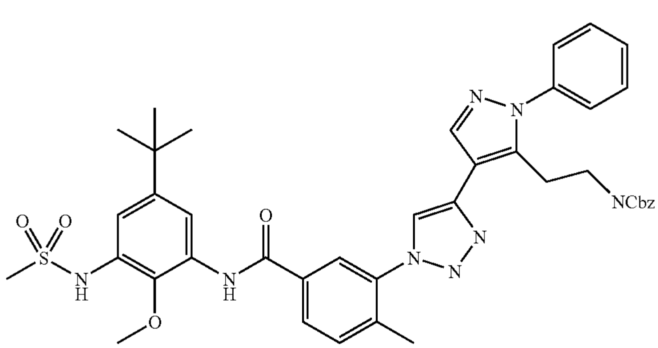 | [2-(4-{1-[5-(5-tert-Butyl-3-methanesulfonylamino-2-methoxy-phenylcarbamoyl)-2-methyl-phenyl]-1H-1,2,3-triazol-4-yl}-2-phenyl-2H-pyrazol-3-yl)-ethyl]-carbamic acid benzyl ester |

TABLE I-continued

| Structure | Name |
|---|---|
| 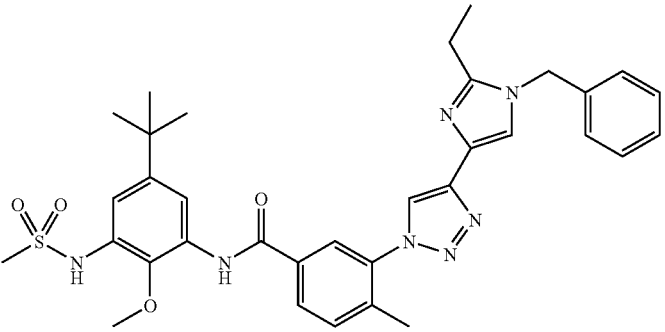 | 3-[4-(1-Benzyl-2-ethyl-1H-imidazol-4-yl)-1,2,3-triazol-1-yl]-N-(5-tert-butyl-3-methanesulfonylamino-2-methoxy-phenyl)-4-methyl-benzamide |
| 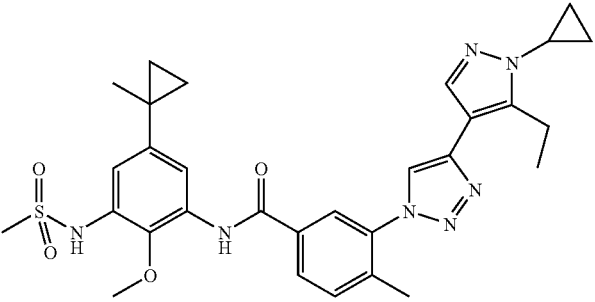 | 3-[4-(1-Cyclopropyl-5-ethyl-1H-pyrazol-4-yl)-1,2,3-triazol-1-yl]-N-[3-methanesulfonylamino-2-methoxy-5-(1-methyl-cyclopropyl)-phenyl]-4-methyl-benzamide |
| 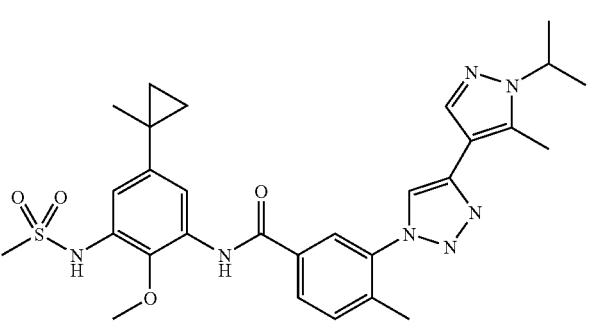 | 3-[4-(1-Isopropyl-5-methyl-1H-pyrazol-4-yl)-1,2,3-triazol-1-yl]-N-[3-methanesulfonylamino-2-methoxy-5-(1-methyl-cyclopropyl)-phenyl]-4-methyl-benzamide |
| 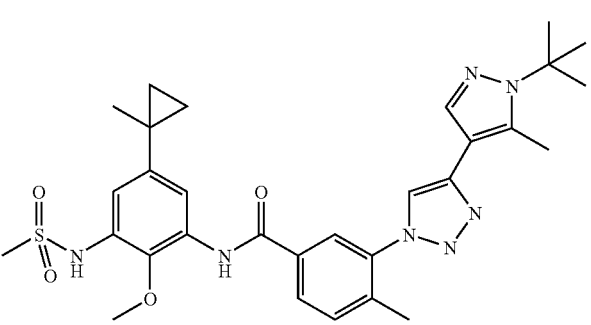 | 3-[4-(1-tert-Butyl-5-methyl-1H-pyrazol-4-yl)-1,2,3-triazol-1-yl]-N-[3-methanesulfonylamino-2-methoxy-5-(1-methyl-cyclopropyl)-phenyl]-4-methyl-benzamide |

TABLE I-continued

| Structure | Name |
|---|---|
| 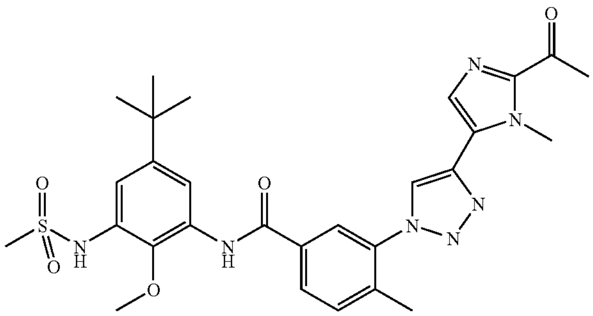 | 3-[4-(2-Acetyl-3-methyl-3H-imidazol-4-yl)-1,2,3-triazol-1-yl]-N-(5-tert-butyl-3-methanesulfonylamino-2-methoxy-phenyl)-4-methyl-benzamide |
| 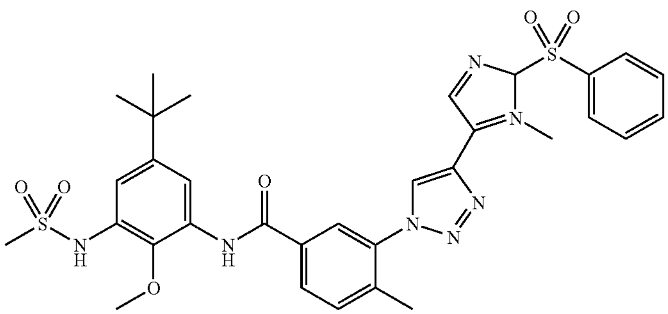 | 3-[4-(2-Benzenesulfonyl-3-methyl-3H-imidazol-4-yl)-1,2,3-triazol-1-yl]-N-(5-tert-butyl-3-methanesulfonylamino-2-methoxy-phenyl)-4-methyl-benzamide |
| 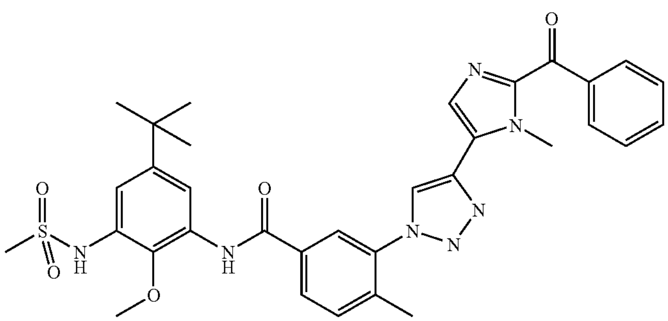 | 3-[4-(2-Benzoyl-3-methyl-3H-imidazol-4-yl)-1,2,3-triazol-1-yl]-N-(5-tert-butyl-3-methanesulfonylamino-2-methoxy-phenyl)-4-methyl-benzamide |
| 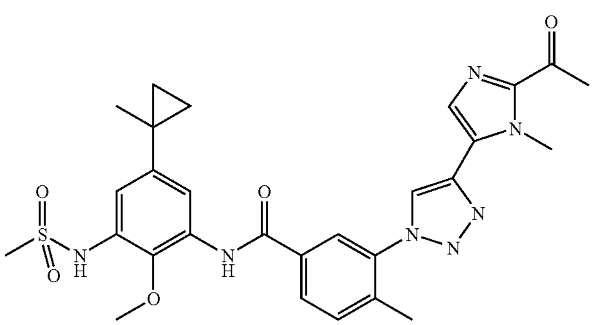 | 3-[4-(2-Benzoyl-3-methyl-3H-imidazol-4-yl)-1,2,3-triazol-1-yl]-N-[3-methanesulfonylamino-2-methoxy-5-(1-methyl-cyclopropyl)-phenyl]-4-methyl-benzamide |
| 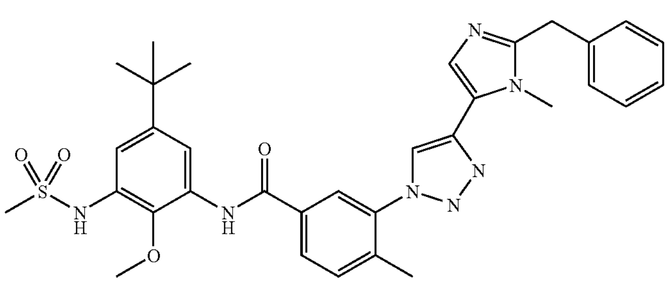 | 3-[4-(2-Benzyl-3-methyl-3H-imidazol-4-yl)-1,2,3-triazol-1-yl]-N-(5-tert-butyl-3-methanesulfonylamino-2-methoxy-phenyl)-4-methyl-benzamide |

TABLE I-continued

| Structure | Name |
|---|---|
| 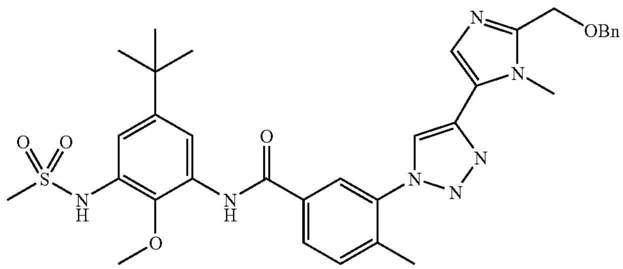 | 3-[4-(2-Benzyloxymethyl-3-methyl-3H-imidazol-4-yl)-[1,2,3]triazol-1-yl]-N-(5-tert-butyl-3-methanesulfonylamino-2-methoxy-phenyl)-4-methyl-benzamide |
| 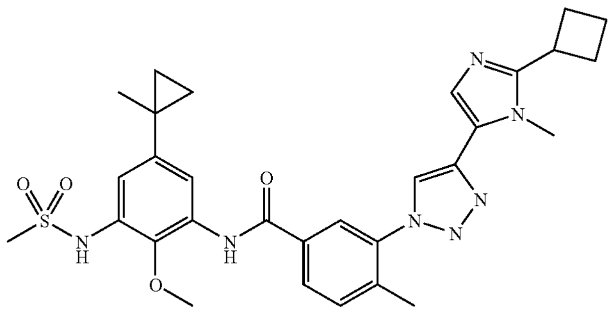 | 3-[4-(2-Cyclobutyl-3-methyl-3H-imidazol-4-yl)-1,2,3-triazol-1-yl]-N-[3-methanesulfonylamino-2-methoxy-5-(1-methyl-cyclopropyl)-phenyl]-4-methyl-benzamide |
| 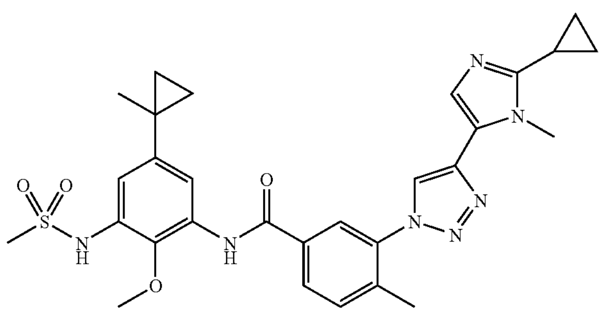 | 3-[4-(2-Cyclopropyl-3-methyl-3H-imidazol-4-yl)-1,2,3-triazol-1-yl]-N-[3-methanesulfonylamino-2-methoxy-5-(1-methyl-cyclopropyl)-phenyl]-4-methyl-benzamide |
| 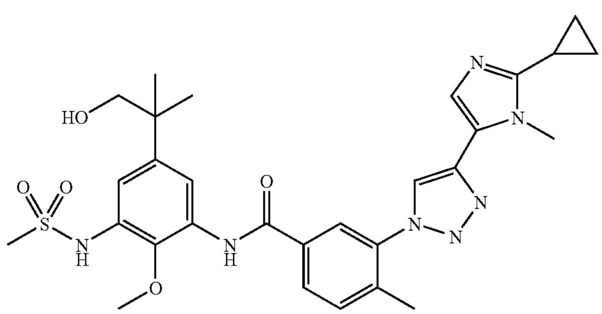 | 3-[4-(2-Cyclopropyl-3-methyl-3H-imidazol-4-yl)-1,2,3-triazol-1-yl]-N-[5-(2-hydroxy-1,1-dimethyl-ethyl)-3-methanesulfonylamino-2-methoxy-phenyl]-4-methyl-benzamide |
| 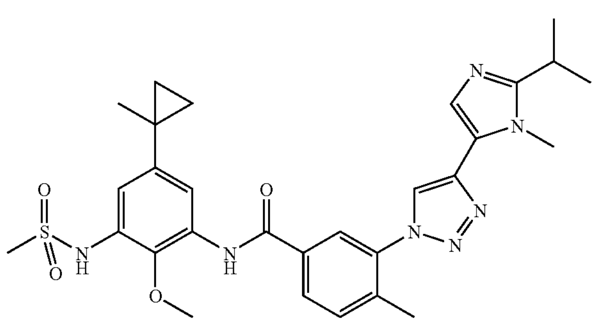 | 3-[4-(2-Isopropyl-3-methyl-3H-imidazol-4-yl)-1,2,3-triazol-1-yl]-N-[3-methanesulfonylamino-2-methoxy-5-(1-methyl-cyclopropyl)-phenyl]-4-methyl-benzamide |

TABLE I-continued

| Structure | Name |
|---|---|
| 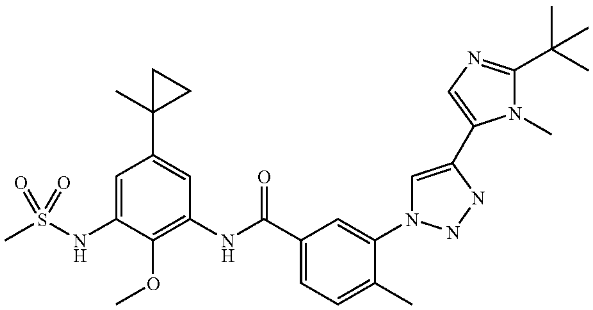 | 3-[4-(2-tert-Butyl-3-methyl-3H-imidazol-4-yl)-1,2,3-triazol-1-yl]-N-[3-methanesulfonylamino-2-methoxy-5-(1-methyl-cyclopropyl)-phenyl]-4-methyl-benzamide |
| 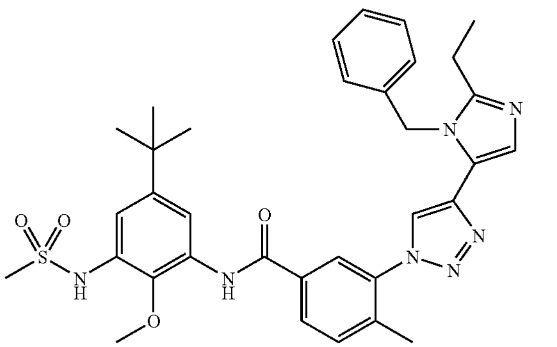 | 3-[4-(3-Benzyl-2-ethyl-3H-imidazol-4-yl)-1,2,3-triazol-1-yl]-N-(5-tert-butyl-3-methanesulfonylamino-2-methoxy-phenyl)-4-methyl-benzamide |
| 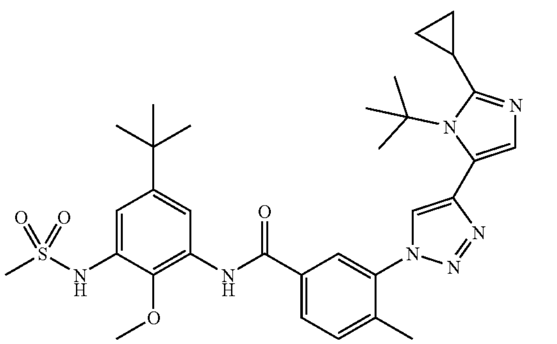 | 3-[4-(3-tert-Butyl-2-cyclopropyl-3H-imidazol-4-yl)-1,2,3-triazol-1-yl]-N-(5-tert-butyl-3-methanesulfonylamino-2-methoxy-phenyl)-4-methyl-benzamide |
| 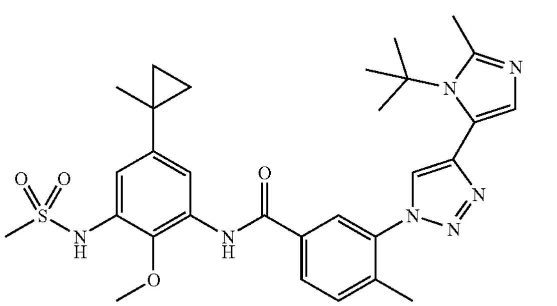 | 3-[4-(3-tert-Butyl-2-methyl-3H-imidazol-4-yl)-1,2,3-triazol-1-yl]-N-[3-methanesulfonylamino-2-methoxy-5-(1-methyl-cyclopropyl)-phenyl]-4-methyl-benzamide |
| 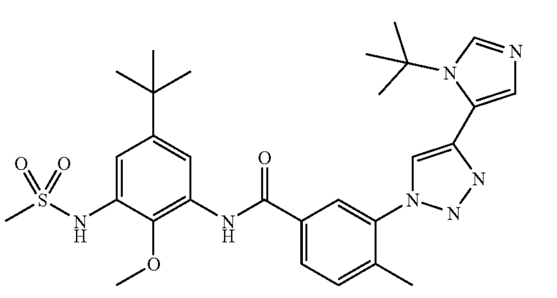 | 3-[4-(3-tert-Butyl-3H-imidazol-4-yl)-1,2,3-triazol-1-yl]-N-(5-tert-butyl-3-methanesulfonylamino-2-methoxy-phenyl)-4-methyl-benzamide |

TABLE I-continued

| Structure | Name |
|---|---|
| 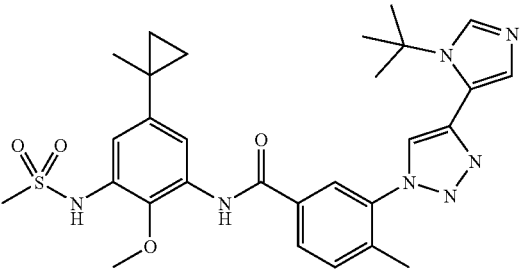 | 3-[4-(3-tert-Butyl-3H-imidazol-4-yl)-1,2,3-triazol-1-yl]-N-[3-methanesulfonylamino-2-methoxy-5-(1-methyl-cyclopropyl)-phenyl]-4-methyl-benzamide |
| 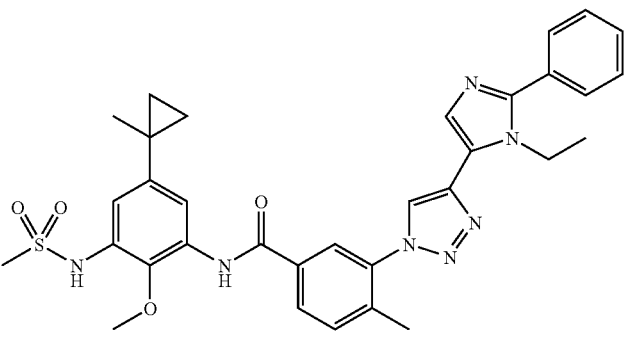 | 3-[4-(5-Ethyl-1-phenyl-1H-pyrazol-4-yl)-1,2,3-triazol-1-yl]-N-[3-methanesulfonylamino-2-methoxy-5-(1-methyl-cyclopropyl)-phenyl]-4-methyl-benzamide |
| 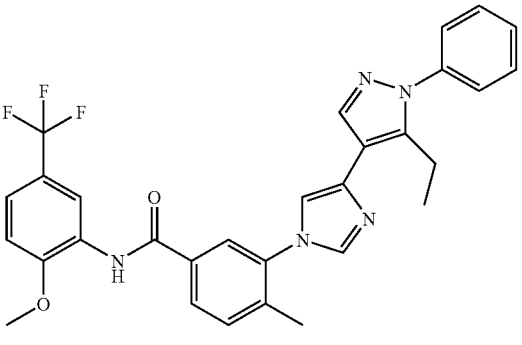 | 3-[4-(5-Ethyl-1-phenyl-1H-pyrazol-4-yl)-imidazol-1-yl]-N-(2-methoxy-5-trifluoromethyl-phenyl)-4-methyl-benzamide |
| 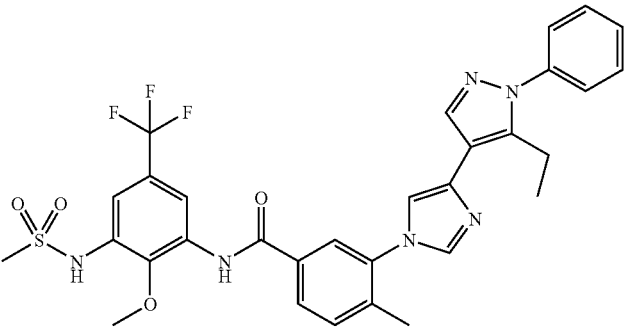 | 3-[4-(5-Ethyl-1-phenyl-1H-pyrazol-4-yl)-imidazol-1-yl]-N-(3-methanesulfonylamino-2-methoxy-5-trifluoromethyl-phenyl)-4-methyl-benzamide |

TABLE I-continued

| Structure | Name |
|---|---|
| | 3-[4-(5-Ethyl-1-phenyl-1H-pyrazol-4-yl)-imidazol-1-yl]-N-[3-methanesulfonylamino-2-methoxy-5-(1-methyl-cyclopropyl)-phenyl]-4-methyl-benzamide |
| | 3-[4-(5-Ethyl-1-phenyl-1H-pyrazol-4-yl)-imidazol-1-yl]-N-[3-methanesulfonylamino-2-methoxy-5-(1-methyl-cyclopropyl)-phenyl]-4-methyl-benzamide |
| 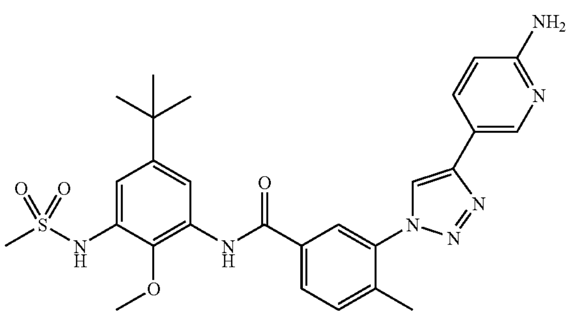 | 3-[4-(6-Amino-pyridin-3-yl)-1,2,3-triazol-1-yl]-N-(5-tert-butyl-3-methanesulfonylamino-2-methoxy-phenyl)-4-methyl-benzamide |
| 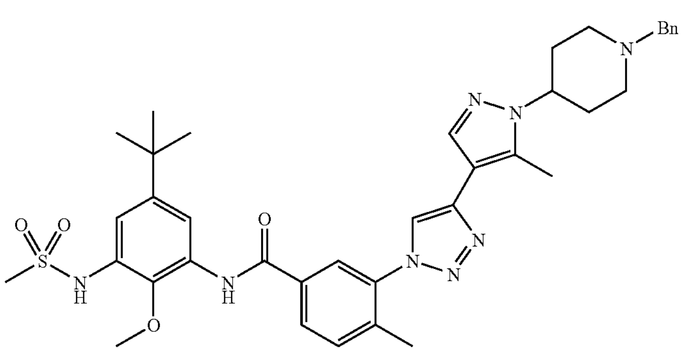 | 3-{4-[1-(1-Benzyl-piperidin-4-yl)-5-methyl-1H-pyrazol-4-yl]-1,2,3-triazol-1-yl}-N-(5-ert-butyl-3-methanesulfonylamino-2-methoxy-phenyl)-4-methyl-benzamide |

TABLE I-continued

| Structure | Name |
|---|---|
| 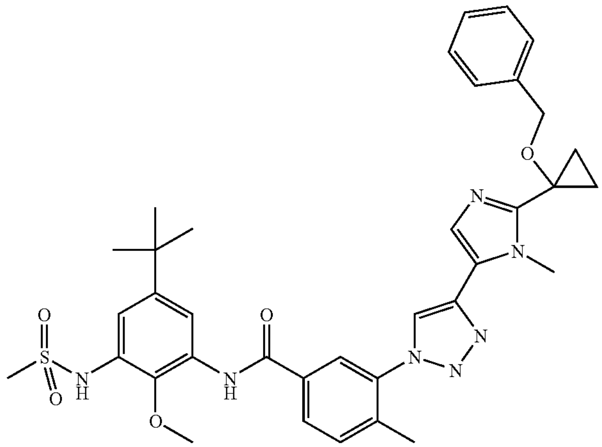 | 3-{4-[2-(1-Benzyloxy-cyclopropyl)-3-methyl-3H-imidazol-4-yl]-1,2,3-triazol-1-yl}-N-(5-tert-butyl-3-methanesulfonylamino-2-methoxy-phenyl)-4-methyl-benzamide |
| 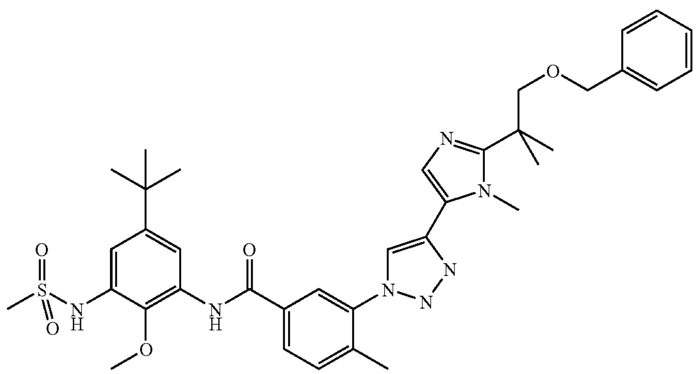 | 3-{4-[2-(2-Benzyloxy-1,1-dimethyl-ethyl)-3-methyl-3H-imidazol-4-yl]-1,2,3-triazol-1-yl}-N-(5-tert-butyl-3-methanesulfonylamino-2-methoxy-phenyl)-4-methyl-benzamide |
| 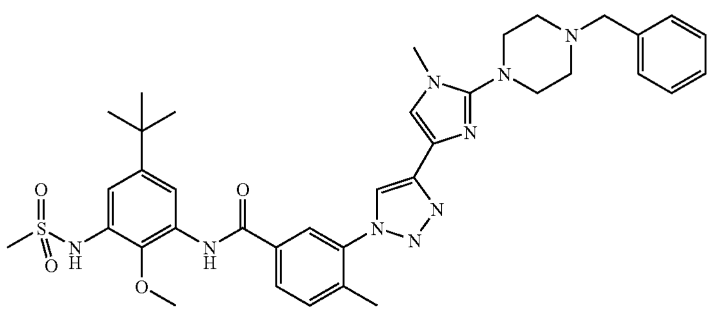 | 3-{4-[2-(4-Benzyl-piperazin-1-yl)-1-methyl-1H-imidazol-4-yl]-1,2,3-triazol-1-yl}-N-(5-tert-butyl-3-methanesulfonylamino-2-methoxy-phenyl)-4-methyl-benzamide |
| 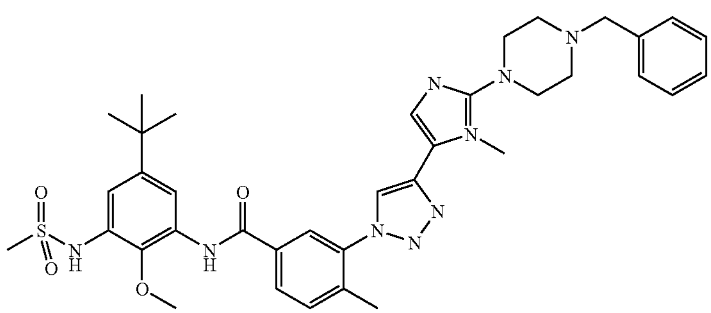 | 3-{4-[2-(4-Benzyl-piperazin-1-yl)-3-methyl-3H-imidazol-4-yl]-1,2,3-triazol-1-yl}-N-(5-tert-butyl-3-methanesulfonylamino-2-methoxy-phenyl)-4-methyl-benzamide |

TABLE I-continued

| Structure | Name |
|---|---|
| 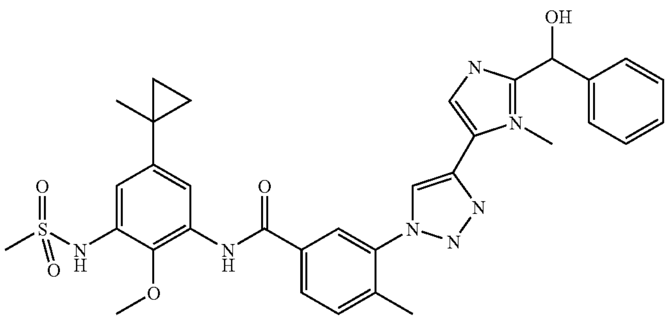 | 3-{4-[2-(Hydroxy-phenyl-methyl)-3-methyl-3H-imidazol-4-yl]-1,2,3-triazol-1-yl}-N-[3-methanesulfonylamino-2-methoxy-5-(1-methyl-cyclopropyl)-phenyl]-4-methyl-benzamide |
| 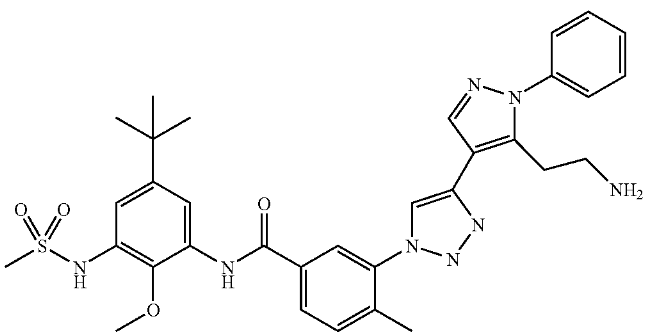 | 3-{4-[5-(2-Amino-ethyl)-1-phenyl-1H-pyrazol-4-yl]-1,2,3-triazol-1-yl}-N-(5-tert-butyl-3-methanesulfonylamino-2-methoxy-phenyl)-4-methyl-benzamide |
| 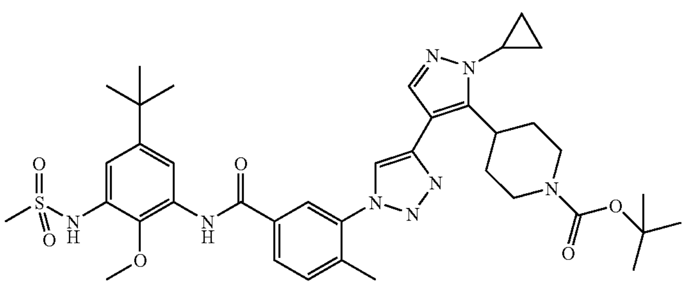 | 4-(4-{1-[5-(5-tert-Butyl-3-methanesulfonylamino-2-methoxy-phenylcarbamoyl)-2-methyl-phenyl]-1H-1,2,3-triazol-4-yl}-2-cyclopropyl-2H-pyrazol-3-yl)-piperidine-1-carboxylic acid tert-butyl ester |
| 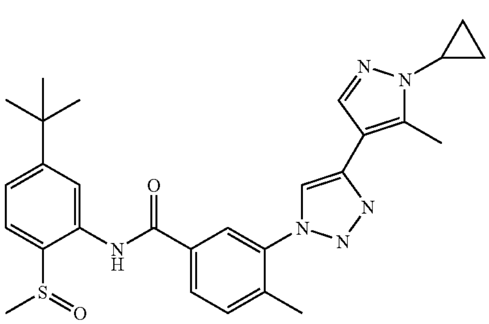 | N-(5-tert-Butyl-2-methanesulfinyl-phenyl)-3-[4-(2-cyclopropyl-3-methyl-3H-imidazol-4-yl)-1,2,3-triazol-1-yl]-4-methyl-benzamide |

TABLE I-continued

| Structure | Name |
|---|---|
| 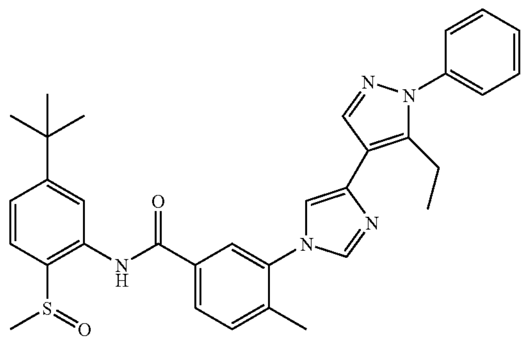 | N-(5-tert-Butyl-2-methanesulfinyl-phenyl)-3-[4-(5-ethyl-1-phenyl-1H-pyrazol-4-yl)-imidazol-1-yl]-4-methyl-benzamide |
| 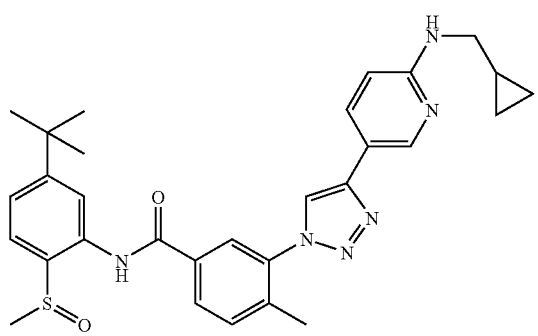 | N-(5-tert-Butyl-2-methanesulfinyl-phenyl)-3-{4-[6-(cyclopropylmethyl-amino)-pyridin-3-yl]-1,2,3-triazol-1-yl}-4-methyl-benzamide |
| 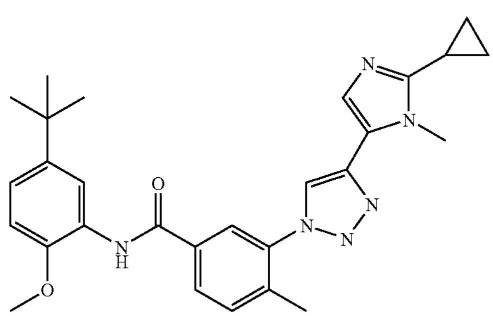 | N-(5-tert-Butyl-2-methoxy-phenyl)-3-[4-(2-cyclopropyl-3-methyl-3H-imidazol-4-yl)-1,2,3-triazol-1-yl]-4-methyl-benzamide |
| 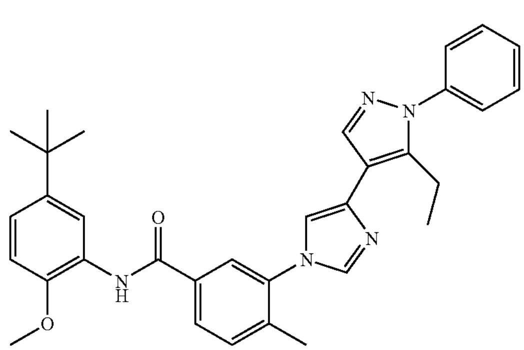 | N-(5-tert-Butyl-2-methoxy-phenyl)-3-[4-(5-ethyl-1-phenyl-1H-pyrazol-4-yl)-imidazol-1-yl]-4-methyl-benzamide |

TABLE I-continued

| Structure | Name |
|---|---|
| 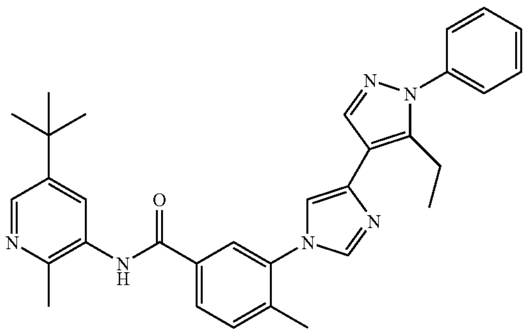 | N-(5-tert-Butyl-2-methyl-pyridin-3-yl)-3-[4-(5-ethyl-1-phenyl-1H-pyrazol-4-yl)-imidazol-1-yl]-4-methyl-benzamide |
| 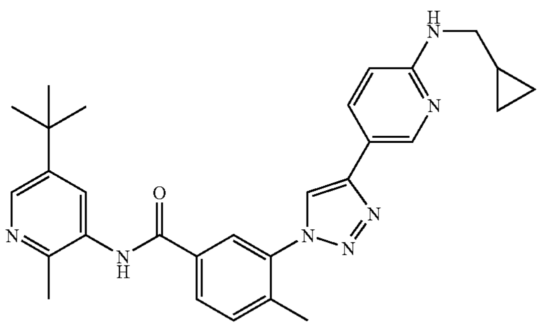 | N-(5-tert-Butyl-2-methyl-pyridin-3-yl)-3-{4-[6-(cyclopropylmethyl-amino)-pyridin-3-yl]-1,2,3-triazol-1-yl}-4-methyl-benzamide |
| 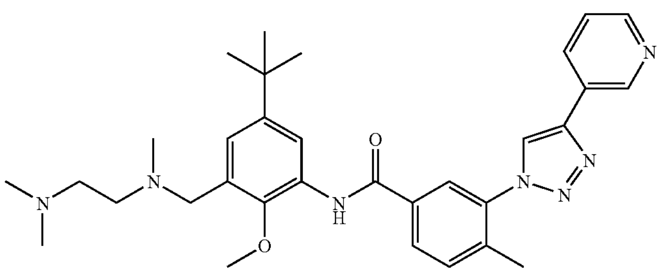 | N-(5-tert-Butyl-3-{[(2-dimethylamino-ethyl)-methyl-amino]-methyl}-2-methoxy-phenyl)-4-methyl-3-(4-pyridin-3-yl-1,2,3-triazol-1-yl)-benzamide |
| 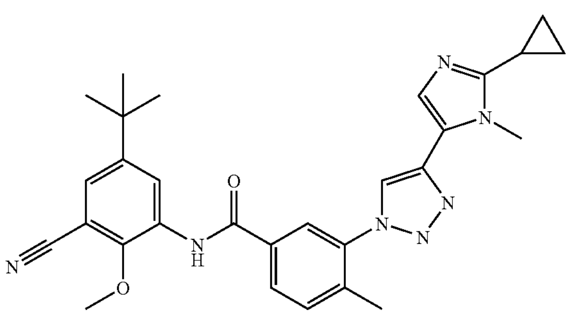 | N-(5-tert-Butyl-3-cyano-2-methoxy-phenyl)-3-[4-(2-cyclopropyl-3-methyl-3H-imidazol-4-yl)-1,2,3-triazol-1-yl]-4-methyl-benzamide |
| 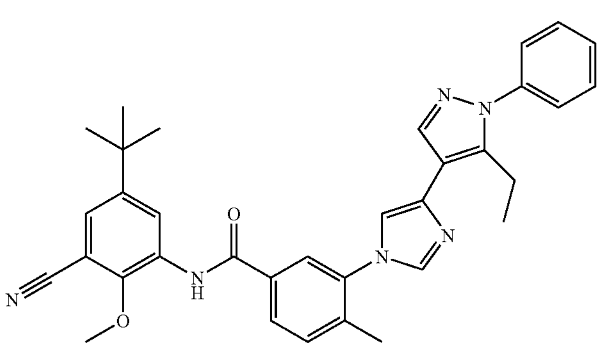 | N-(5-tert-Butyl-3-cyano-2-methoxy-phenyl)-3-[4-(5-ethyl-1-phenyl-1H-pyrazol-4-yl)-imidazol-1-yl]-4-methyl-benzamide |

TABLE I-continued

| Structure | Name |
|---|---|
| 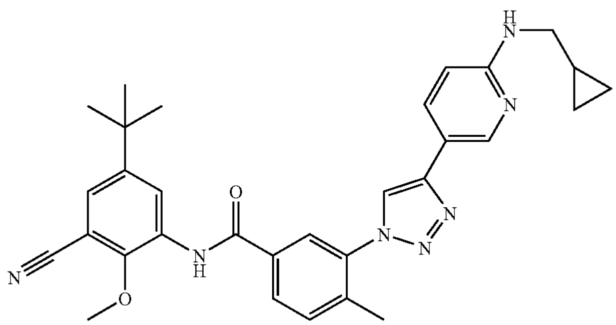 | N-(5-tert-Butyl-3-cyano-2-methoxy-phenyl)-3-{4-[6-(cyclopropylmethyl-amino)-pyridin-3-yl]-1,2,3-triazol-1-yl}-4-methyl-benzamide |
| 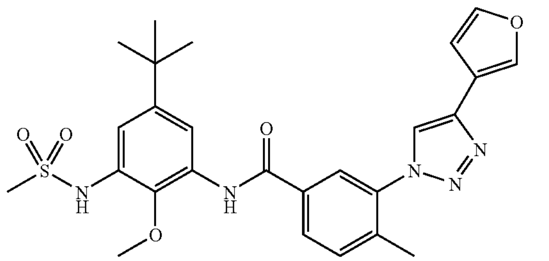 | N-(5-tert-Butyl-3-methanesulfonylamino-2-methoxy-phenyl)-3-(4-furan-3-yl-1,2,3-triazol-1-yl)-4-methyl-benzamide |
| 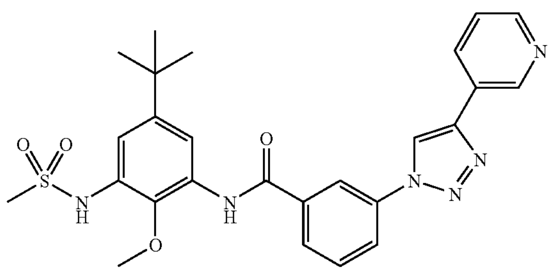 | N-(5-tert-Butyl-3-methanesulfonylamino-2-methoxy-phenyl)-3-(4-pyridin-3-yl-1,2,3-triazol-1-yl)-benzamide |
| 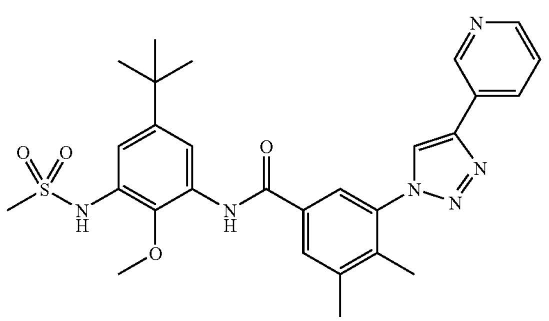 | N-(5-tert-Butyl-3-methanesulfonylamino-2-methoxy-phenyl)-3,4-dimethyl-5-(4-pyridin-3-yl-1,2,3-triazol-1-yl)-benzamide |
| 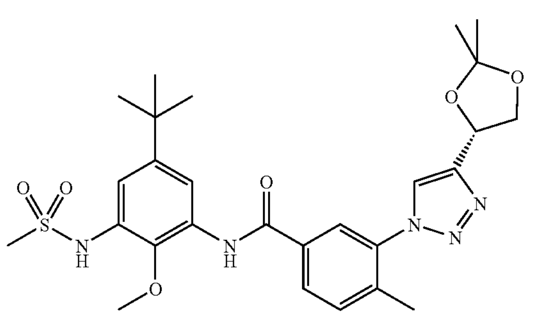 | N-(5-tert-Butyl-3-methanesulfonylamino-2-methoxy-phenyl)-3-[4-((S)-2,2-dimethyl-1,3-dioxolan-4-yl)-1,2,3-triazol-1-yl]-4-methyl-benzamide |

TABLE I-continued

| Structure | Name |
|---|---|
| 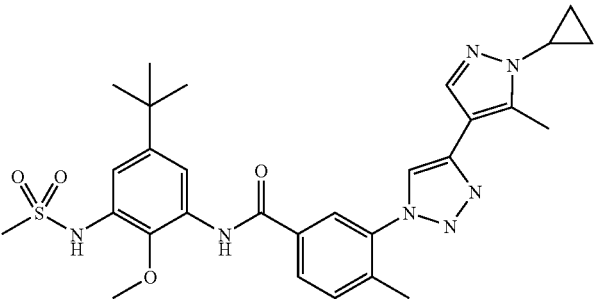 | N-(5-tert-Butyl-3-methanesulfonylamino-2-methoxyphenyl)-3-[4-(1-cyclopropyl-5-methyl-1H-pyrazol-4-yl)-1,2,3-triazol-1-yl]-4-methyl-benzamide |
| 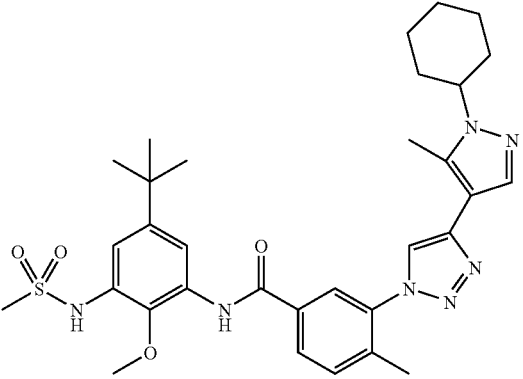 | N-(5-tert-Butyl-3-methanesulfonylamino-2-methoxyphenyl)-3-[4-(1-cyclohexyl-5-methyl-1H-pyrazol-4-yl)-1,2,3-triazol-1-yl]-4-methyl-benzamide |
| 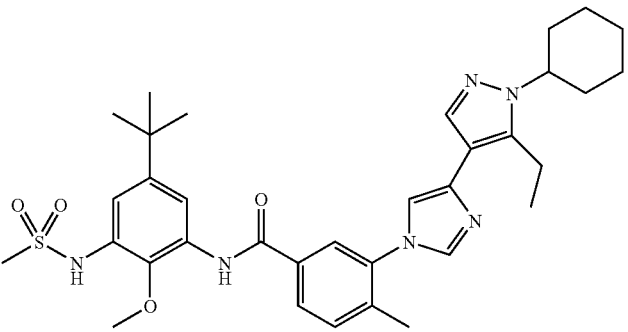 | N-(5-tert-Butyl-3-methanesulfonylamino-2-methoxyphenyl)-3-[4-(1-cyclohexyl-5-ethyl-1H-pyrazol-4-yl)-1,2,3-triazol-1-yl]-4-methyl-benzamide |
| 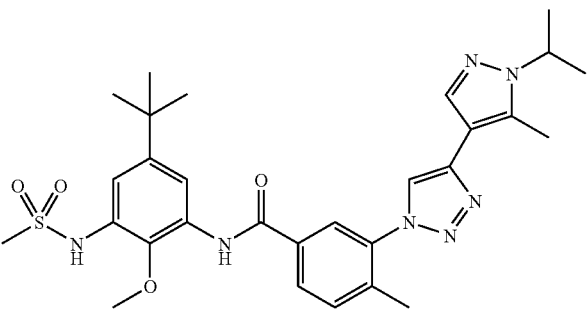 | N-(5-tert-Butyl-3-methanesulfonylamino-2-methoxyphenyl)-3-[4-(1-isopropyl-5-methyl-1H-pyrazol-4-yl)-1,2,3-triazol-1-yl]-4-methyl-benzamide |

TABLE I-continued

| Structure | Name |
|---|---|
| 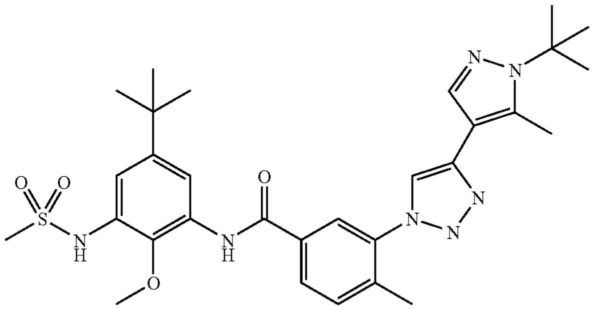 | N-(5-tert-Butyl-3-methanesulfonylamino-2-methoxy-phenyl)-3-[4-(1-tert-butyl-5-methy[-1H-pyrazol-4-yl)-1,2,3-triazol-1-yl]-4-methyl-benzamide |
| 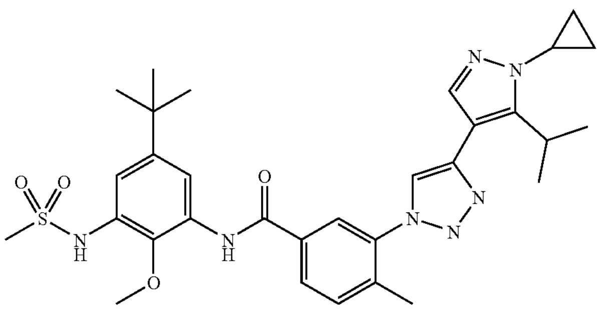 | N-(5-tert-Butyl-3-methanesulfonylamino-2-methoxy-phenyl)-3-[4-(1-cyclopropyl-5-isopropyl-1H-pyrazol-4-yl)-1,2,3-triazol-1-yl]-4-methyl-benzamide |
| 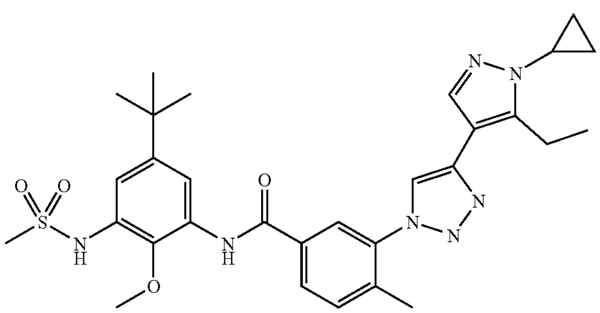 | N-(5-tert-Butyl-3-methanesulfonylamino-2-methoxy-phenyl)-3-[4-(1-cyclopropyl-5-ethyl-1H-pyrazol-4-yl)-1,2,3-triazol-1-yl]-4-methyl-benzamide |
| 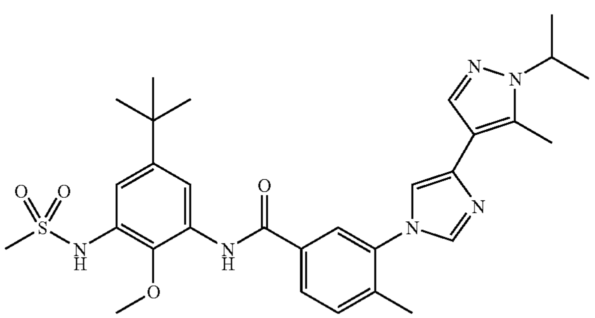 | N-(5-tert-Butyl-3-methanesulfonylamino-2-methoxy-phenyl)-3-[4-(1-isopropyl-5-methyl-1H-pyrazol-4-yl)-imidazol-1-yl]-4-methyl-benzamide |
| 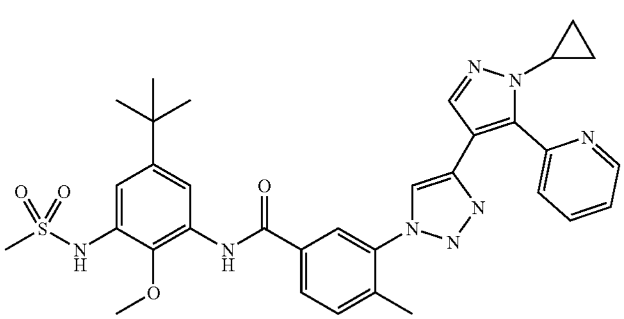 | N-(5-tert-Butyl-3-methanesulfonylamino-2-methoxy-phenyl)-3-[4-(1-cyclopropyl-5-pyridin-2-yl-1H-pyrazol-4-yl)-1,2,3-triazol-1-yl]-4-methyl-benzamide |

TABLE I-continued

| Structure | Name |
|---|---|
| 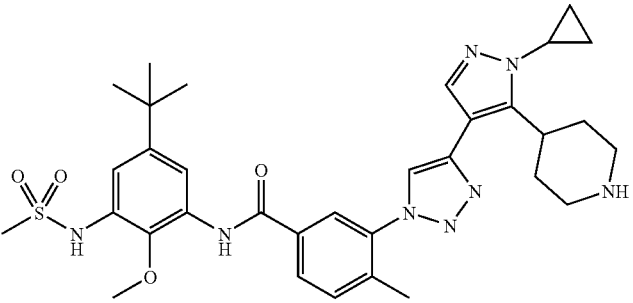 | N-(5-tert-Butyl-3-methanesulfonylamino-2-methoxy-phenyl)-3-[4-(1-cyclopropyl-5-piperidin-4-yl-1H-pyrazol-4-yl)-1,2,3-triazol-1-yl]-4-methyl-benzamide |
| 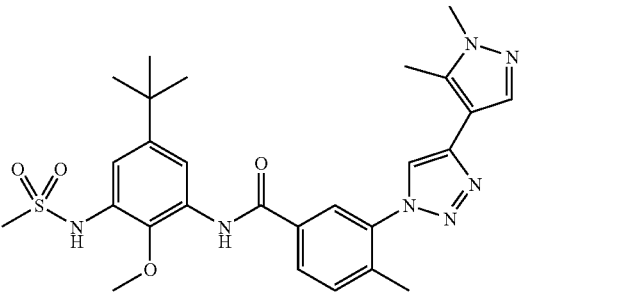 | N-(5-tert-Butyl-3-methanesulfonylamino-2-methoxy-phenyl)-3-[4-(1,5-dimethyl-1H-pyrazol-4-yl)-1,2,3-triazol-1-yl]-4-methyl-benzamide |
| 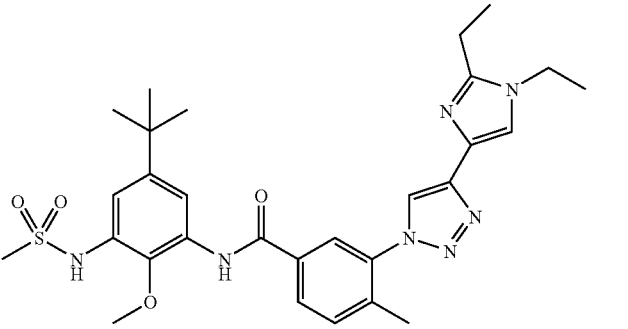 | N-(5-tert-Butyl-3-methanesulfonylamino-2-methoxy-phenyl)-3-[4-(1,2-diethyl-1H-imidazol-4-yl)-1,2,3-triazol-1-yl]-4-methyl-benzamide |
| 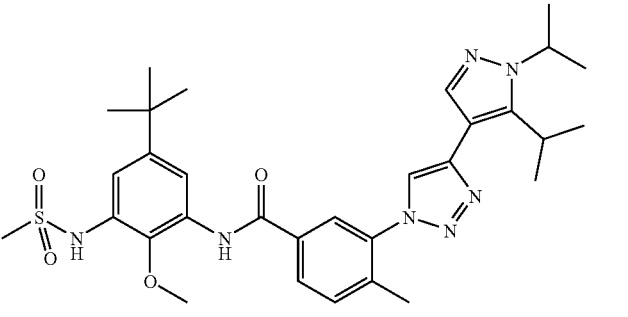 | N-(5-tert-Butyl-3-methanesulfonylamino-2-methoxy-phenyl)-3-[4-(1,5-diisopropyl-1H-pyrazol-4-yl)-1,2,3-triazol-1-yl]-4-methyl-benzamide |
| 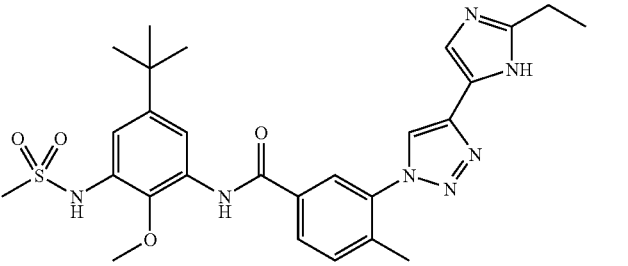 | N-(5-tert-Butyl-3-methanesulfonylamino-2-methoxy-phenyl)-3-[4-(2-ethyl-3H-imidazol-4-yl)-1,2,3-triazol-1-yl]-4-methyl-benzamide |

TABLE I-continued

| Structure | Name |
|---|---|
|  | N-(5-tert-Butyl-3-methanesulfonylamino-2-methoxyphenyl)-3-[4-(2-isopropyl-3-methyl-3H-imidazol-4-yl)-1,2,3-triazol-1-yl]-4-methyl-benzamide |
|  | N-(5-tert-Butyl-3-methanesulfonylamino-2-methoxyphenyl)-3-[4-(2-tert-butyl-3-methyl-3H-imidazol-4-yl)-1,2,3-triazol-1-yl]-4-methyl-benzamide |
|  | N-(5-tert-Butyl-3-methanesulfonylamino-2-methoxyphenyl)-3-[4-(2-cyclopropyl-3-methyl-3H-imidazol-4-yl)-1,2,3-triazol-1-yl]-4-methyl-benzamide |
|  | N-(5-tert-Butyl-3-methanesulfonylamino-2-methoxyphenyl)-3-[4-(2-cyclopropyl-1-methyl-1H-imidazol-4-yl)-1,2,3-triazol-1-yl]-4-methyl-benzamide |
|  | N-(5-tert-Butyl-3-methanesulfonylamino-2-methoxyphenyl)-3-[4-(2-cyclopropyl-3-isopropyl-3H-imidazol-4-yl)-1,2,3-triazol-1-yl]-4-methyl-benzamide |

TABLE I-continued

| Structure | Name |
|---|---|
| 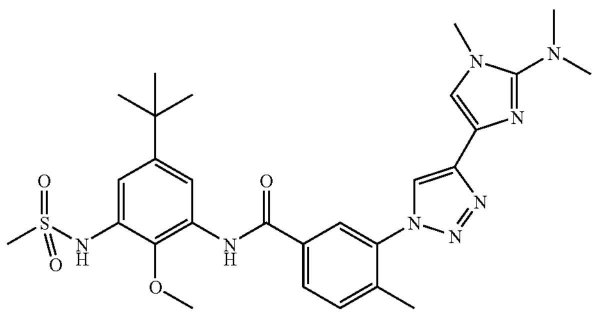 | N-(5-tert-Butyl-3-methanesulfonylamino-2-methoxy-phenyl)-3-[4-(2-dimethylamino-1-methyl-1H-imidazol-4-yl)-1,2,3-triazol-1-yl]-4-methyl-benzamide |
| 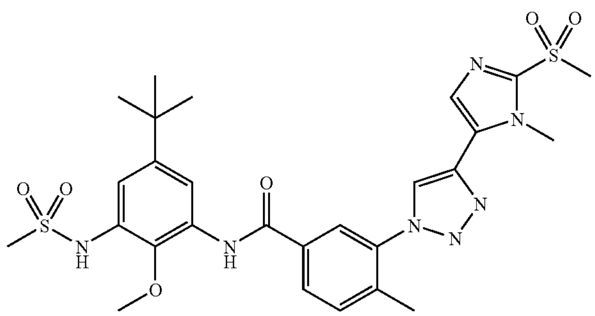 | N-(5-tert-Butyl-3-methanesulfonylamino-2-methoxy-phenyl)-3-[4-(2-methanesulfonyl-3-methyl-3H-imidazol-4-yl)-1,2,3-triazol-1-yl]-4-methyl-benzamide |
| 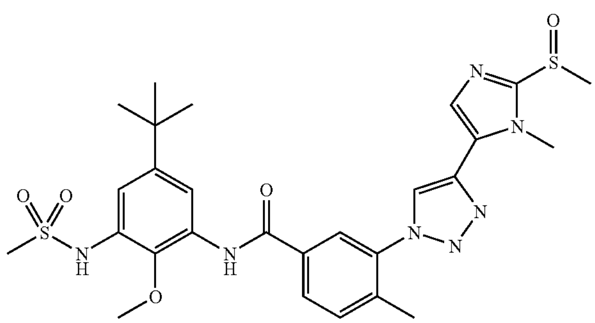 | N-(5-tert-Butyl-3-methanesulfonylamino-2-methoxy-phenyl)-3-[4-(2-methanesulfinyl-3-methyl-3H-imidazol-4-yl)-1,2,3-triazol-1-yl]-4-methyl-benzamide |
| 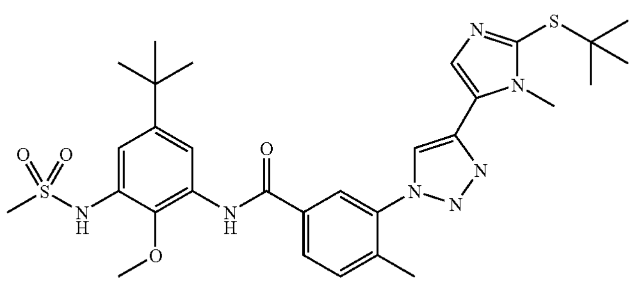 | N-(5-tert-Butyl-3-methanesulfonylamino-2-methoxy-phenyl)-3-[4-(2-tert-butylsulfanyl-3-methyl-3H-imidazol-4-yl)-1,2,3-triazol-1-yl]-4-methyl-benzamide |
| 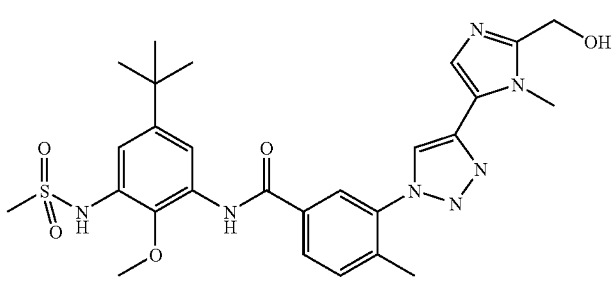 | N-(5-tert-Butyl-3-methanesulfonylamino-2-methoxy-phenyl)-3-[4-(2-hydroxymethyl-3-methyl-3H-imidazol-4-yl)-1,2,3-triazol-1-yl]-4-methyl-benzamide |

TABLE I-continued

| Structure | Name |
|---|---|
| 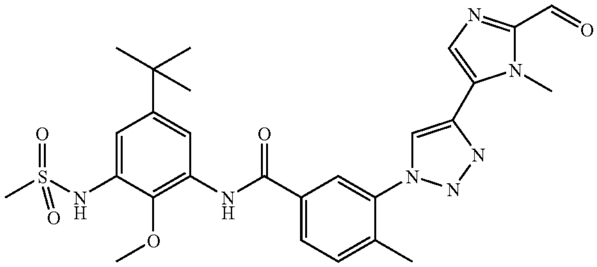 | N-(5-tert-Butyl-3-methanesulfonylamino-2-methoxy-phenyl)-3-[4-(2-formyl-3-methyl-3H-imidazol-4-yl)-1,2,3-triazol-1-yl]-4-methyl-benzamide |
| 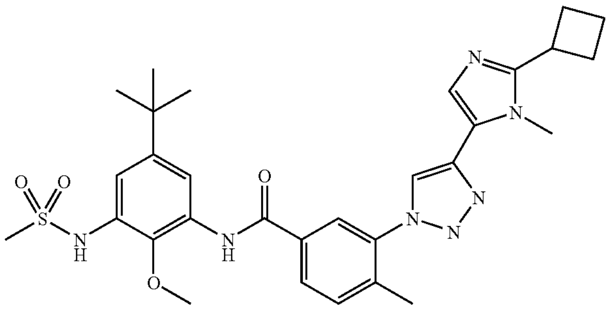 | N-(5-tert-Butyl-3-methanesulfonylamino-2-methoxy-phenyl)-3-[4-(2-cyclobutyl-3-methyl-3H-imidazol-4-yl)-1,2,3-triazol-1-yl]-4-methyl-benzamide |
| 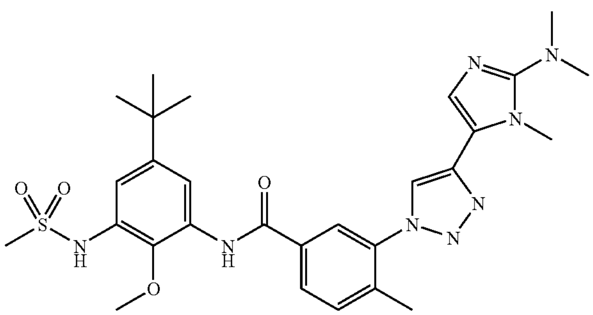 | N-(5-tert-Butyl-3-methanesulfonylamino-2-methoxy-phenyl)-3-[4-(2-dimethylamino-3-methyl-3H-imidazol-4-yl)-[1,2,3]triazol-1-yl]-4-methyl-benzamide |
| 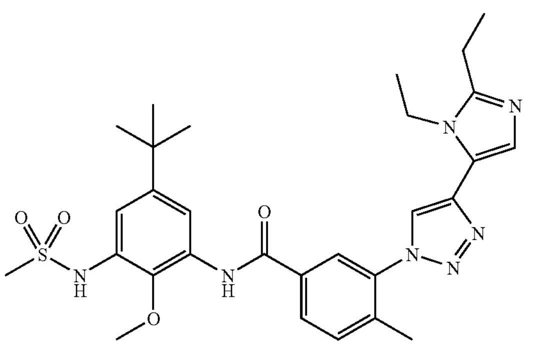 | N-(5-tert-Butyl-3-methanesulfonylamino-2-methoxy-phenyl)-3-[4-(2,3-diethyl-3H-imidazol-4-yl)-1,2,3-triazol-1-yl]-4-methyl-benzamide |
| 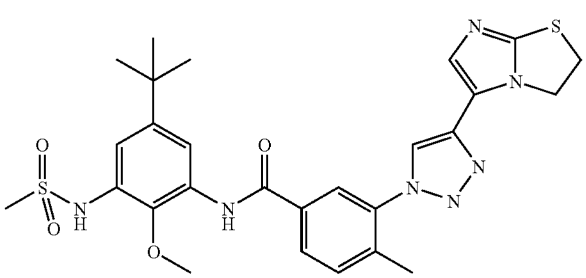 | N-(5-tert-Butyl-3-methanesulfonylamino-2-methoxy-phenyl)-3-[4-(2,3-dihydro-imidazo[2,1-b]thiazol-5-yl)-1,2,3-triazol-1-yl]-4-methyl-benzamide |

TABLE I-continued

| Structure | Name |
|---|---|
| 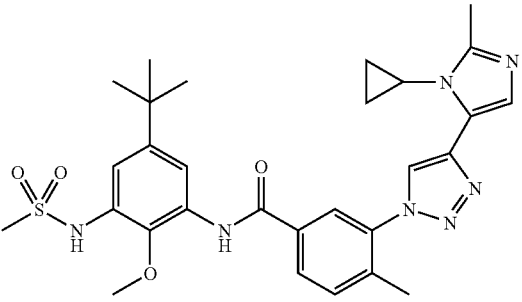 | N-(5-tert-Butyl-3-methanesulfonylamino-2-methoxy-phenyl)-3-[4-(3-cyclopropyl-2-methyl-3H-imidazol-4-yl)-1,2,3-triazol-1-yl]-4-methyl-benzamide |
| 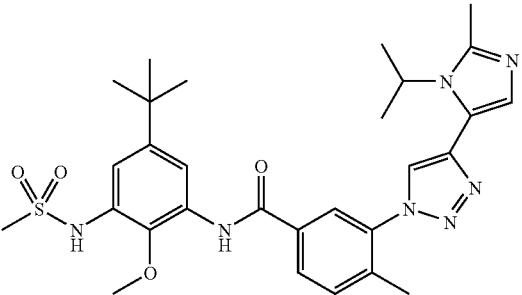 | N-(5-tert-Butyl-3-methanesulfonylamino-2-methoxy-phenyl)-3-[4-(3-isopropyl-2-methyl-3H-imidazol-4-yl)-1,2,3-triazol-1-yl]-4-methyl-benzamide |
| 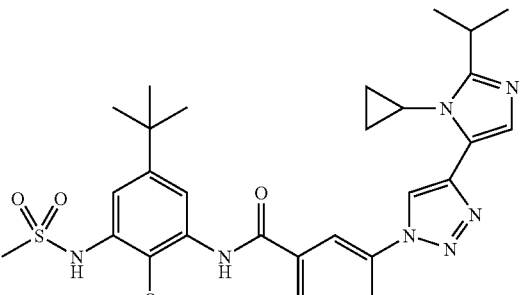 | N-(5-tert-Butyl-3-methanesulfonylamino-2-methoxy-phenyl)-3-[4-(3-cyclopropyl-2-isopropyl-3H-imidazol-4-yl)-1,2,3-triazol-1-yl]-4-methyl-benzamide |
| 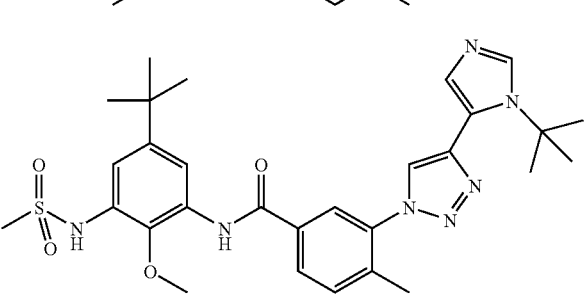 | N-(5-tert-Butyl-3-methanesulfonylamino-2-methoxy-phenyl)-3-[4-(3-tert-butyl-2-methyl-3H-imidazol-4-yl)-1,2,3-triazol-1-yl]-4-methyl-benzamide |
| 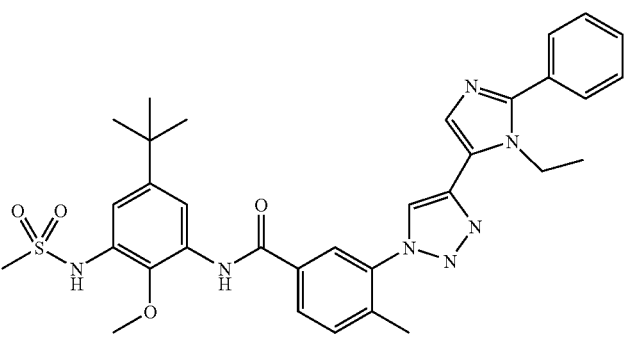 | N-(5-tert-Butyl-3-methanesulfonylamino-2-methoxy-phenyl)-3-[4-(3-ethyl-2-phenyl-3H-imidazol-4-yl)-1,2,3-triazol-1-yl]-4-methyl-benzamide |

TABLE I-continued

| Structure | Name |
|---|---|
| 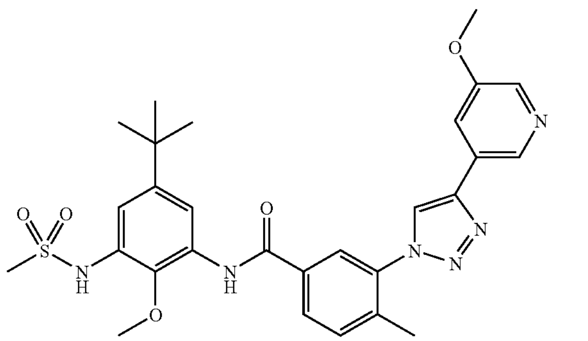 | N-(5-tert-Butyl-3-methanesulfonylamino-2-methoxy-phenyl)-3-[4-(5-methoxy-pyridin-3-yl)-1,2,3-triazol-1-yl]-4-methyl-benzamide |
| 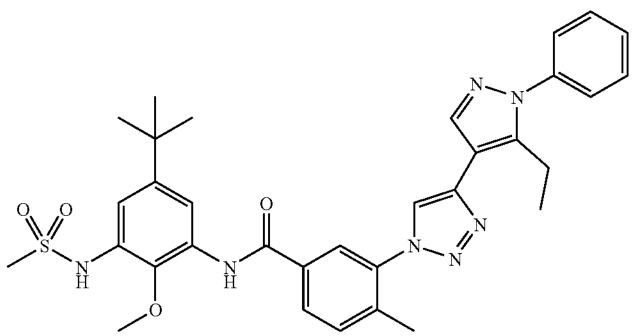 | N-(5-tert-Butyl-3-methanesulfonylamino-2-methoxy-phenyl)-3-[4-(5-ethyl-1-phenyl-1H-pyrazol-4-yl)-1,2,3-triazol-1-yl]-4-methyl-benzamide |
| 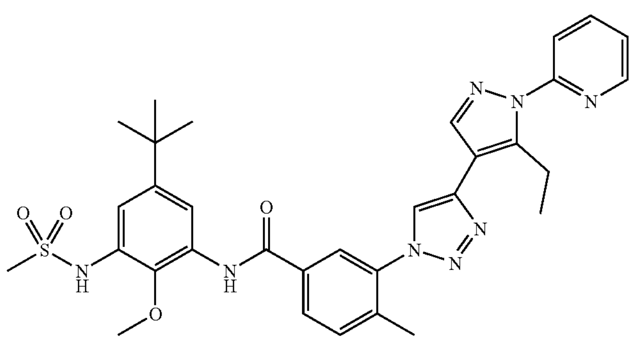 | N-(5-tert-Butyl-3-methanesulfonylamino-2-methoxy-phenyl)-3-[4-(5-ethyl-1-pyridin-2-yl-1H-pyrazol-4-yl)-1,2,3-triazol-1-yl]-4-methyl-benzamide |
| 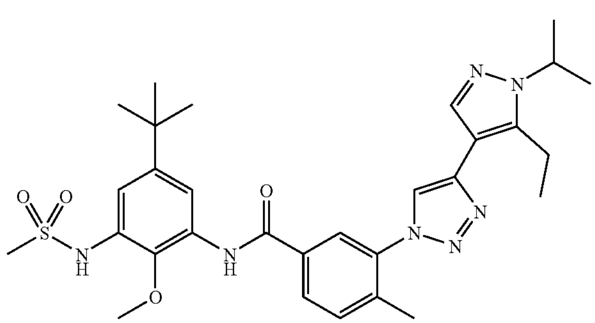 | N-(5-tert-Butyl-3-methanesulfonylamino-2-methoxy-phenyl)-3-[4-(5-ethyl-1-isopropyl-1H-pyrazol-4-yl)-1,2,3-triazol-1-yl]-4-methyl-benzamide |

TABLE I-continued

| Structure | Name |
|---|---|
| 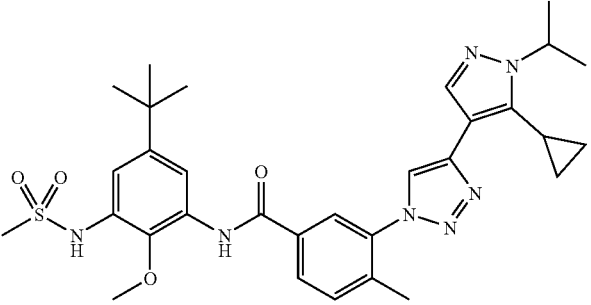 | N-(5-tert-Butyl-3-methanesulfonylamino-2-methoxy-phenyl)-3-[4-(5-cyclopropyl-1-isopropyl-1H-pyrazol-4-yl)-1,2,3-triazol-1-yl]-4-methyl-benzamide |
| 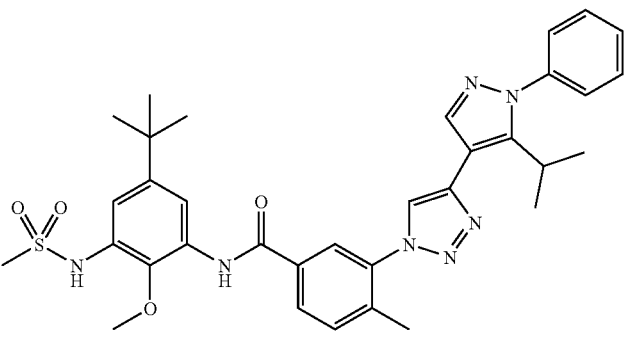 | N-(5-tert-Butyl-3-methanesulfonylamino-2-methoxy-phenyl)-3-[4-(5-isopropyl-1-phenyl-1H-pyrazol-4-yl)-1,2,3-triazol-1-yl]-4-methyl-benzamide |
| 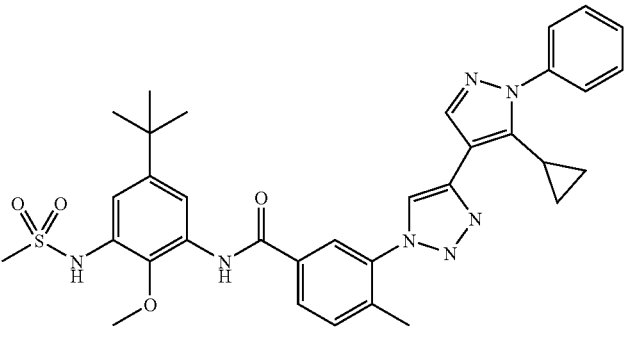 | N-(5-tert-Butyl-3-methanesulfonylamino-2-methoxy-phenyl)-3-[4-(5-cyclopropyl-1-phenyl-1H-pyrazol-4-yl)-1,2,3-triazol-1-yl]-4-methyl-benzamide |
| 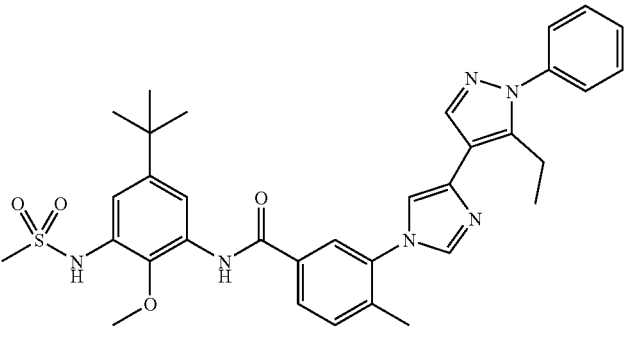 | N-(5-tert-Butyl-3-methanesulfonylamino-2-methoxy-phenyl)-3-[4-(5-ethyl-1-phenyl-1H-pyrazol-4-yl)-imidazol-1-yl]-4-methyl-benzamide |

TABLE I-continued

| Structure | Name |
|---|---|
| 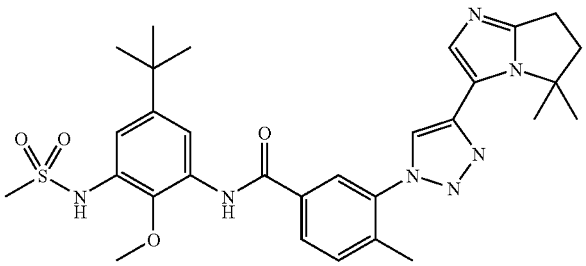 | N-(5-tert-Butyl-3-methanesulfonylamino-2-methoxy-phenyl)-3-[4-(5,5-dimethyl-6,7-dihydro-5H-pyrrolo[1,2-a]imidazol-3-yl)-[1,2,3]triazol-1-yl]-4-methyl-benzamide |
| 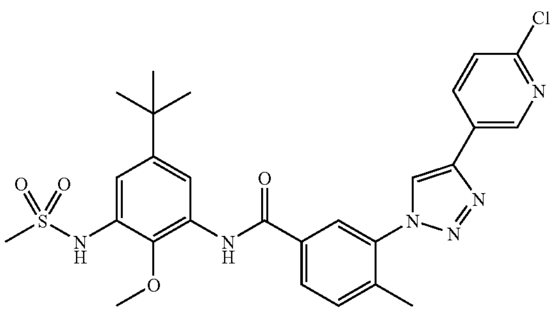 | N-(5-tert-Butyl-3-methanesulfonylamino-2-methoxy-phenyl)-3-[4-(6-chloro-pyridin-3-yl)-1,2,3-triazol-1-yl]-4-methyl-benzamide |
| 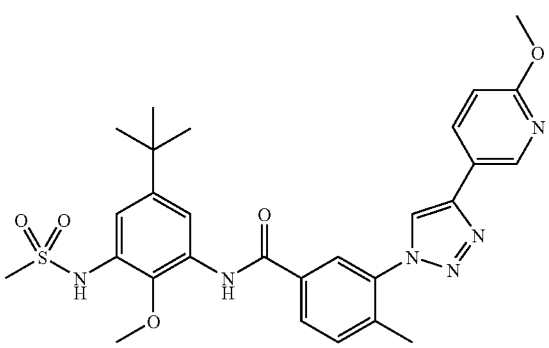 | N-(5-tert-Butyl-3-methanesulfonylamino-2-methoxy-phenyl)-3-[4-(6-methoxy-pyridin-3-yl)-1,2,3-triazol-1-yl]-4-methyl-benzamide |
| 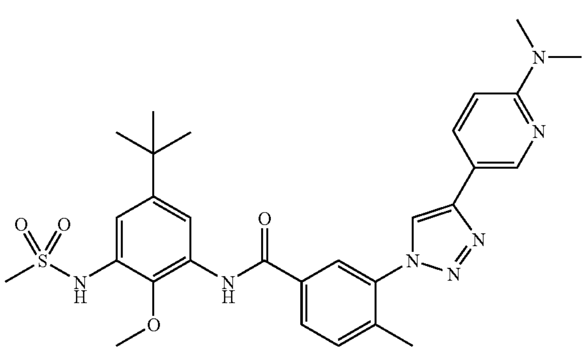 | N-(5-tert-Butyl-3-methanesulfonylamino-2-methoxy-phenyl)-3-[4-(6-dimethylamino-pyridin-3-yl)-1,2,3-triazol-1-yl]-4-methyl-benzamide |

TABLE I-continued

| Structure | Name |
|---|---|
| 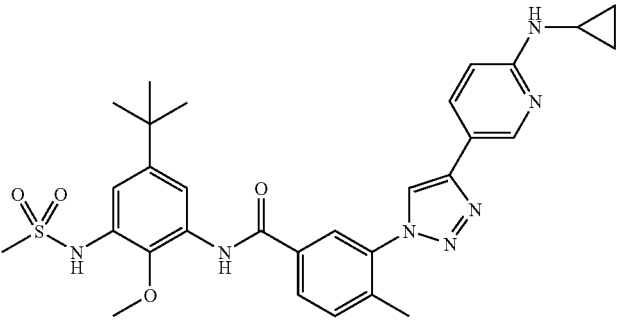 | N-(5-tert-Butyl-3-methanesulfonylamino-2-methoxy-phenyl)-3-[4-(6-cyclopropylamino-pyridin-3-yl)-1,2,3-triazol-1-yl]-4-methyl-benzamide |
| 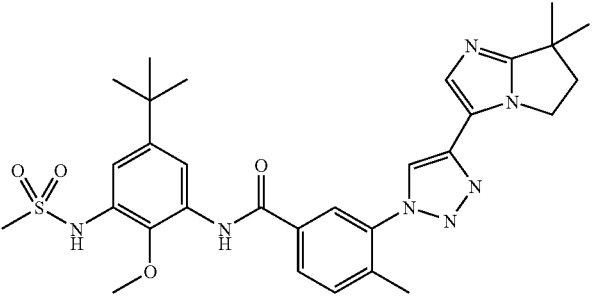 | N-(5-tert-Butyl-3-methanesulfonylamino-2-methoxy-phenyl)-3-[4-(7,7-dimethyl-6,7-dihydro-5H-pyrrolo[1,2-a]imidazol-3-yl)-1,2,3-triazol-1-yl]-4-methyl-benzamide |
| 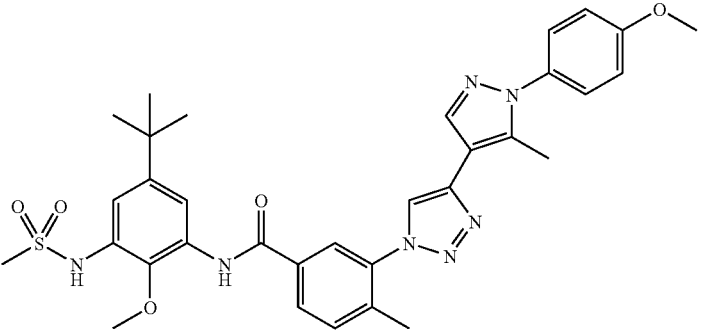 | N-(5-tert-Butyl-3-methanesulfonylamino-2-methoxy-phenyl)-3-{4-[1-(4-methoxy-phenyl)-5-methyl-1H-pyrazol-4-yl]-1,2,3-triazol-1-yl}-4-methyl-benzamide |
| 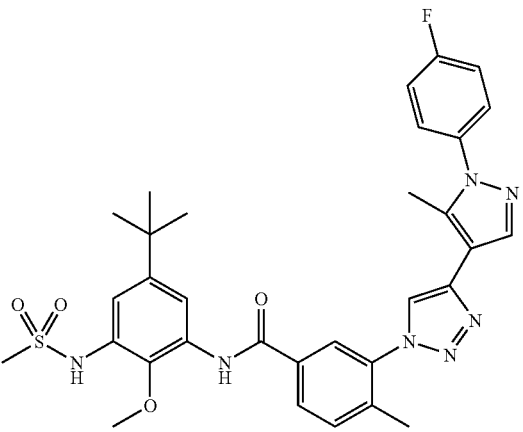 | N-(5-tert-Butyl-3-methanesulfonylamino-2-methoxy-phenyl)-3-{4-[1-(4-fluoro-phenyl)-5-methyl-1H-pyrazol-4-yl]-1,2,3-triazol-1-yl}-4-methyl-benzamide |

TABLE I-continued

| Structure | Name |
|---|---|
| 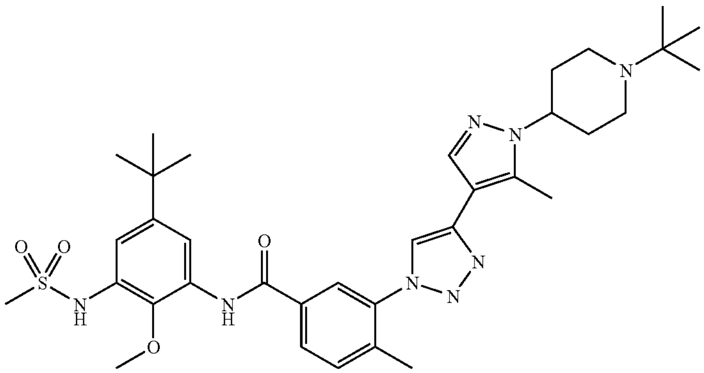 | N-(5-tert-Butyl-3-methanesulfonylamino-2-methoxy-phenyl)-3-{4-[1-(1-tert-butyl-piperidin-4-yl)-5-methyl-1H-pyrazol-4-yl]-1,2,3-triazol-1-yl}-4-methyl-benzamide |
| 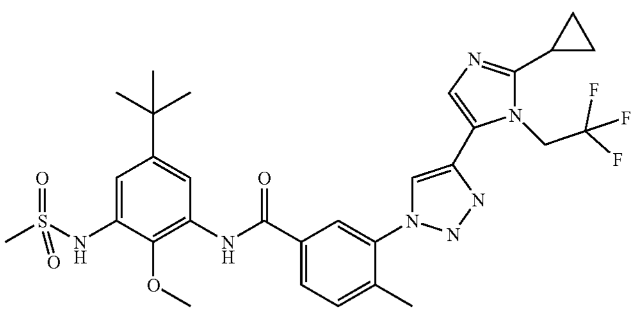 | N-(5-tert-Butyl-3-methanesulfonylamino-2-methoxy-phenyl)-3-{4-[2-cyclopropyl-3-(2,2,2-trifluoro-ethyl)-3H-imidazol-4-yl]-1,2,3-triazol-1-yl}-4-methyl-benzamide |
| 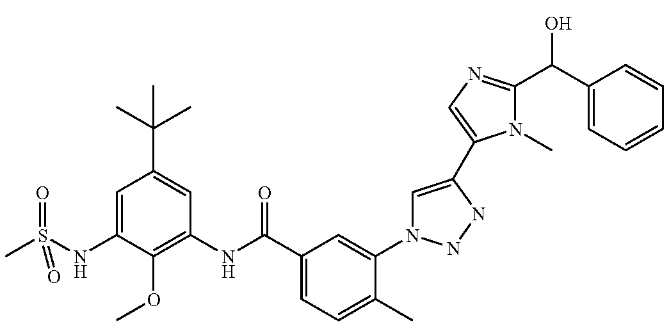 | N-(5-tert-Butyl-3-methanesulfonylamino-2-methoxy-phenyl)-3-{4-[2-(hydroxy-phenyl-methyl)-3-methyl-3H-imidazol-4-yl]-1,2,3-triazol-1-yl}-4-methyl-benzamide |
| 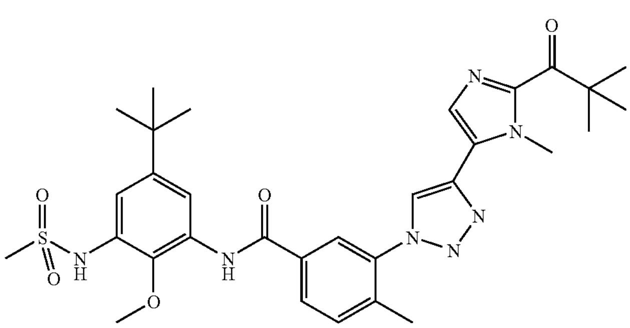 | N-(5-tert-Butyl-3-methanesulfonylamino-2-methoxy-phenyl)-3-{4-[2-(2,2-dimethyl-propionyl)-3-methyl-3H-imidazol-4-yl]-1,2,3-triazol-1-yl}-4-methyl-benzamide |

TABLE I-continued

| Structure | Name |
|---|---|
| 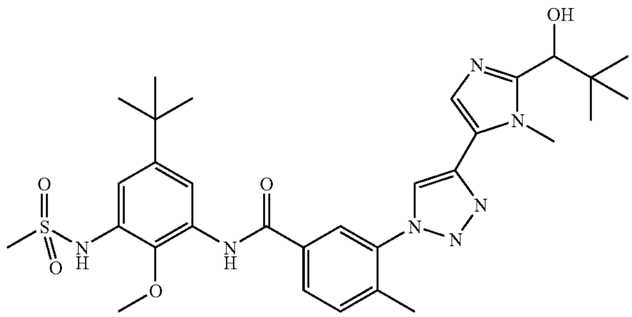 | N-(5-tert-Butyl-3-methanesulfonylamino-2-methoxy-phenyl)-3-{4-[2-(1-hydroxy-2,2-dimethyl-propyl)-3-methyl-3H-imidazol-4-yl]-1,2,3-triazol-1-yl}-4-methyl-benzamide |
| 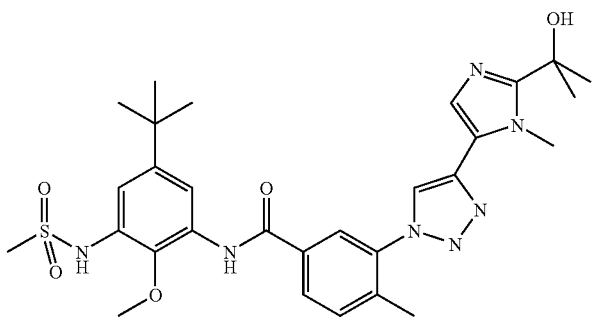 | N-(5-tert-Butyl-3-methanesulfonylamino-2-methoxy-phenyl)-3-{4-[2-(1-hydroxy-1-methyl-ethyl)-3-methyl-3H-imidazol-4-yl]-1,2,3-triazol-1-yl}-4-methyl-benzamide |
| 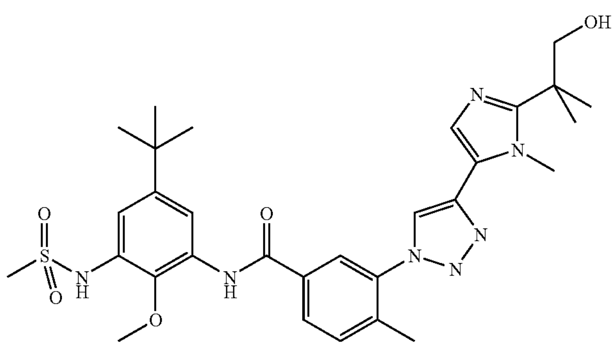 | N-(5-tert-Butyl-3-methanesulfonylamino-2-methoxy-phenyl)-3-{4-[2-(2-hydroxy-1,1-dimethyl-ethyl)-3-methyl-3H-imidazol-4-yl]-1,2,3-triazol-1-yl}-4-methyl-benzamide |
| 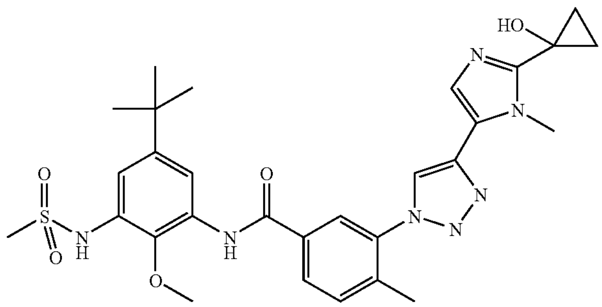 | N-(5-tert-Butyl-3-methanesulfonylamino-2-methoxy-phenyl)-3-{4-[2-(1-hydroxy-cyclopropyl)-3-methyl-3H-imidazol-4-yl]-1,2,3-triazol-1-yl}-4-methyl-benzamide |

TABLE I-continued

| Structure | Name |
|---|---|
| 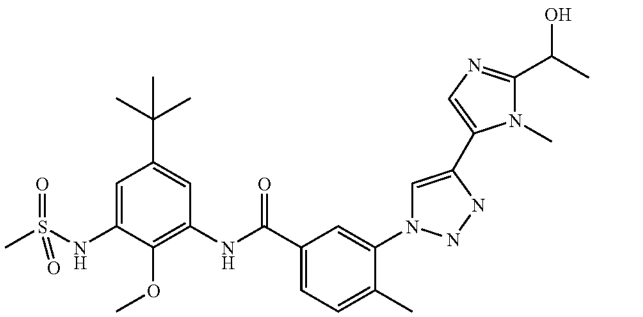 | N-(5-tert-Butyl-3-methanesulfonylamino-2-methoxy-phenyl)-3-{4-[2-(1-hydroxy-ethyl)-3-methyl-3H-imidazol-4-yl]-1,2,3-triazol-1-yl}-4-methyl-benzamide |
| 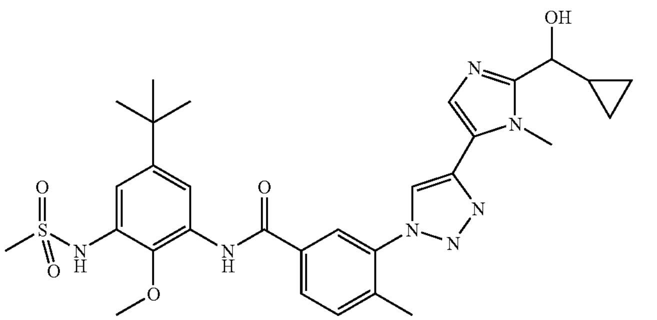 | N-(5-tert-Butyl-3-methanesulfonylamino-2-methoxy-phenyl)-3-{4-[2-(cyclopropyl-hydroxy-methyl)-3-methyl-3H-imidazol-4-yl]-1,2,3-triazol-1-yl}-4-methyl-benzamide |
| 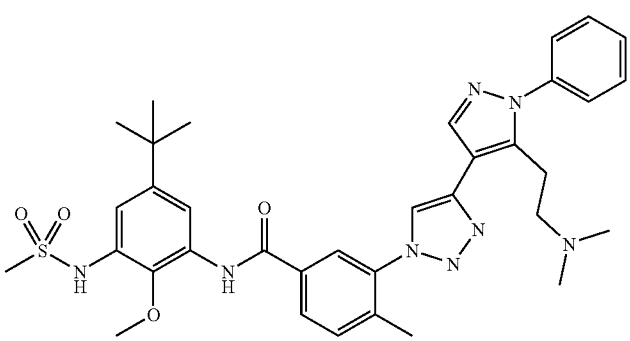 | N-(5-tert-Butyl-3-methanesulfonylamino-2-methoxy-phenyl)-3-{4-[5-(2-dimethylamino-ethyl)-1-phenyl-1H-pyrazol-4-yl]-1,2,3-triazol-1-yl}-4-methyl-benzamide |
| 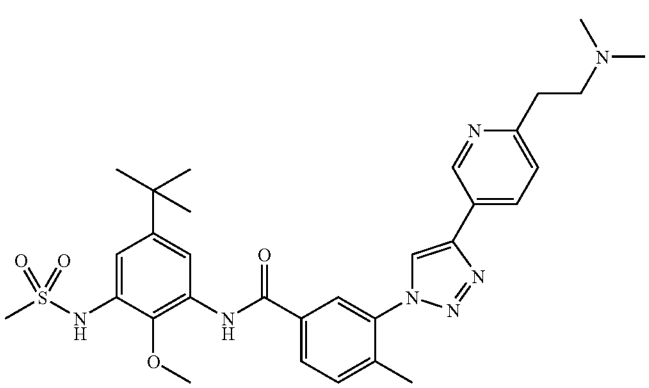 | N-(5-tert-Butyl-3-methanesulfonylamino-2-methoxy-phenyl)-3-{4-[6-(2-dimethylamino-ethyl)-pyridin-3-yl]-1,2,3-triazol-1-yl}-4-methyl-benzamide |

TABLE I-continued

| Structure | Name |
|---|---|
| 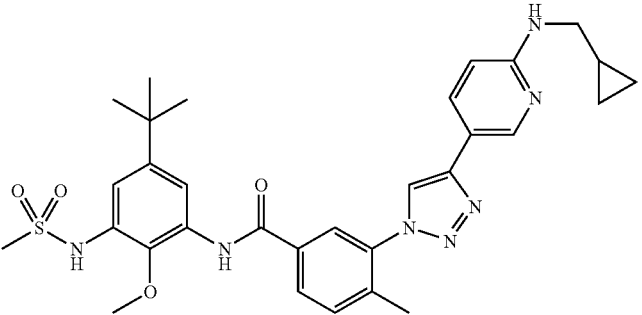 | N-(5-tert-Butyl-3-methanesulfonylamino-2-methoxy-phenyl)-3-{4-[6-(cyclopropylmethyl-amino)-pyridin-3-yl]-12,3-triazol-1-yl}-4-methyl-benzamide |
| 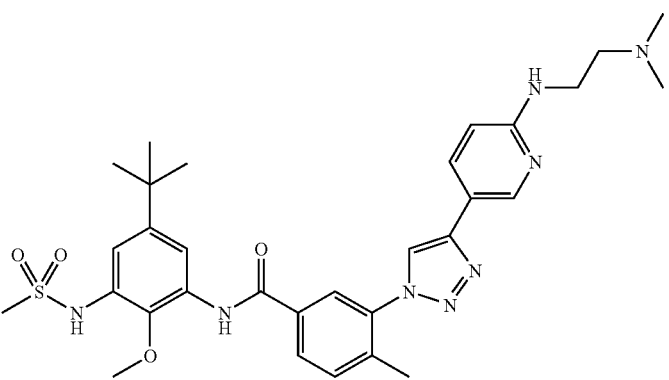 | N-(5-tert-Butyl-3-methanesulfonylamino-2-methoxy-phenyl)-3-{4-[6-(2-dimethylamino-ethylamino)-pyridin-3-yl]-1,2,3-triazol-1-yl}-4-methyl-benzamide |
| 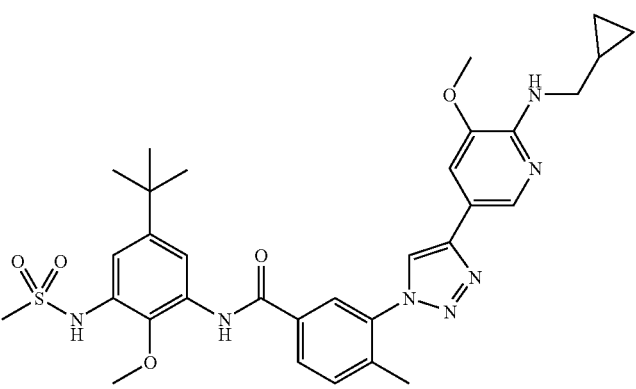 | N-(5-tert-Butyl-3-methanesulfonylamino-2-methoxy-phenyl)-3-{4-[6-(cyclopropylmethyl-amino)-5-methoxy-pyridin-3-yl]-1,2,3-triazol-1-yl}-4-methyl-benzamide |
| 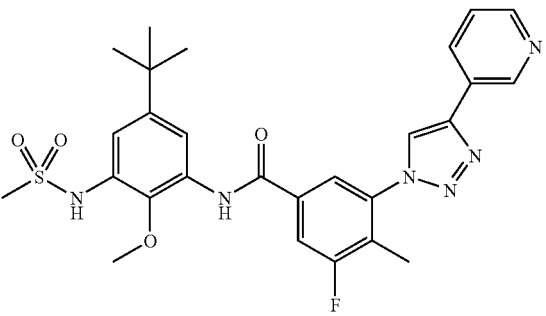 | N-(5-tert-Butyl-3-methanesulfonylamino-2-methoxy-phenyl)-3-fluoro-4-methyl-5-(4-pyridin-3-yl-1,2,3-triazol-1-yl)-benzamide |

TABLE I-continued

| Structure | Name |
|---|---|
| 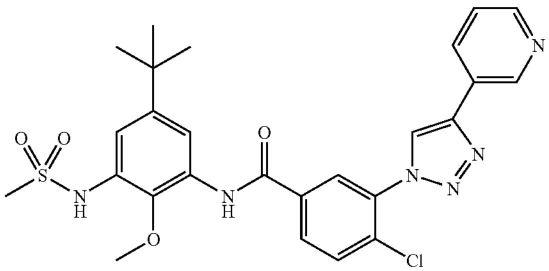 | N-(5-tert-Butyl-3-methanesulfonylamino-2-methoxy-phenyl)-4-chloro-3-(4-pyridin-3-yl-1,2,3-triazol-1-yl)-benzamide |
| 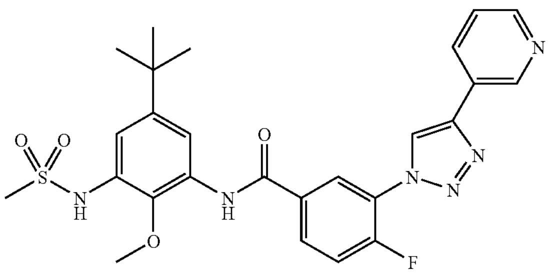 | N-(5-tert-Butyl-3-methanesulfonylamino-2-methoxy-phenyl)-4-fluoro-3-(4-pyridin-3-yl-1,2,3-triazol-1-yl)-benzamide |
| 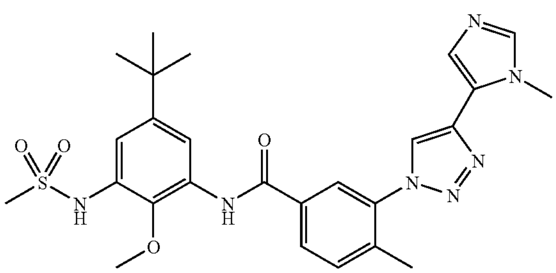 | N-(5-tert-Butyl-3-methanesulfonylamino-2-methoxy-phenyl)-4-methyl-3-[4-(3-methyl-3H-imidazol-4-yl)-1,2,3-triazol-1-yl]-benzamide |
| 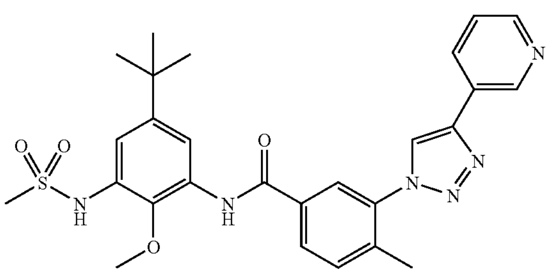 | N-(5-tert-Butyl-3-methanesulfonylamino-2-methoxy-phenyl)-4-methyl-3-(4-pyridin-3-yl-1,2,3-triazol-1-yl)-benzamide |
| 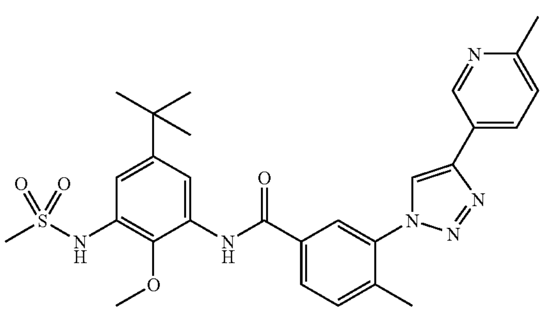 | N-(5-tert-Butyl-3-methanesulfonylamino-2-methoxy-phenyl)-4-methyl-3-[4-(6-methyl-pyridin-3-yl)-1,2,3-triazol-1-yl]-benzamide |

TABLE I-continued

| Structure | Name |
| --- | --- |
| 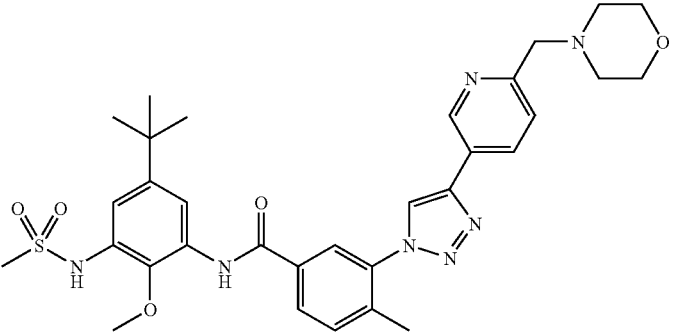 | N-(5-tert-Butyl-3-methanesulfonylamino-2-methoxy-phenyl)-4-methyl-3-[4-(6-morpholin-4-ylmethyl-pyridin-3-yl)-1,2,3-triazol-1-yl]-benzamide |
| 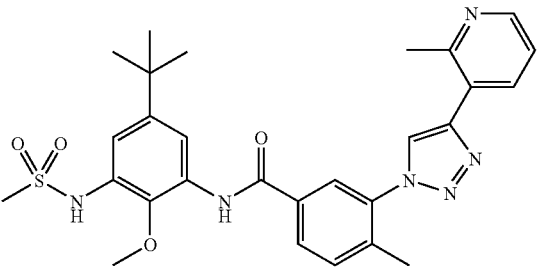 | N-(5-tert-Butyl-3-methanesulfonylamino-2-methoxy-phenyl)-4-methyl-3-[4-(2-methyl-pyridin-3-yl)-1,2,3-triazol-1-yl]-benzamide |
| 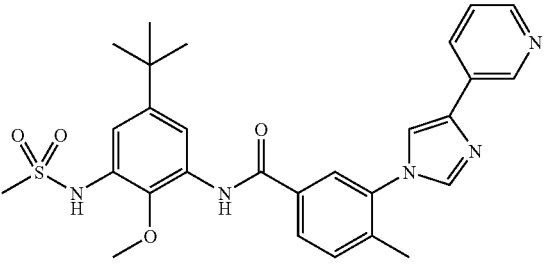 | N-(5-tert-Butyl-3-methanesulfonylamino-2-methoxy-phenyl)-4-methyl-3-(4-pyridin-3-yl-imidazol-1-yl)-benzamide |
| 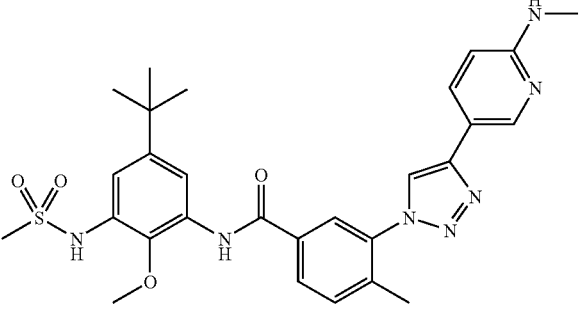 | N-(5-tert-Butyl-3-methanesulfonylamino-2-methoxy-phenyl)-4-methyl-3-[4-(6-methylamino-pyridin-3-yl)-1,2,3-triazol-1-yl]-benzamide |
| 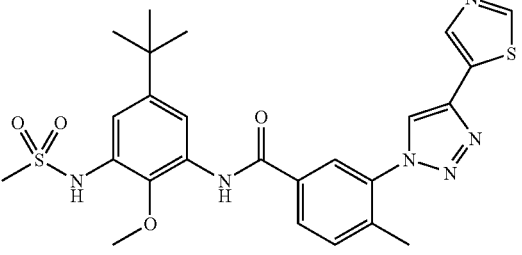 | N-(5-tert-Butyl-3-methanesulfonylamino-2-methoxy-phenyl)-4-methyl-3-(4-thiazol-5-yl-1,2,3-triazol-1-yl)-benzamide |

TABLE I-continued

| Structure | Name |
|---|---|
|  | N-(5-tert-Butyl-3-methanesulfonylamino-2-methoxyphenyl)-4-methyl-3-(4-pyrimidin-5-yl-1,2,3-triazol-1-yl)-benzamide |
|  | N-(5-tert-Butyl-3-methanesulfonylamino-2-methoxyphenyl)-4-methyl-3-[4-(6-trifluoromethyl-pyridin-3-yl)-1,2,3-triazol-1-yl]-benzamide |
|  | N-(5-tert-Butyl-3-methanesulfonylamino-2-methoxyphenyl)-4-methyl-3-[4-(tetrahydrofuran-3-yl)-1,2,3-triazol-1-yl]-benzamide |
|  | N-(5-tert-Butyl-3-methanesulfonylamino-2-methoxyphenyl)-4-methyl-3-[4-(5-methyl-1-phenyl-1H-pyrazol-4-yl)-1,2,3-triazol-1-yl]-benzamide |
|  | N-(5-tert-Butyl-3-methanesulfonylamino-2-methoxyphenyl)-4-methyl-3-[4-(4-methyl-pyridin-3-yl)-1,2,3-triazol-1-yl]-benzamide |

TABLE I-continued

| Structure | Name |
|---|---|
| 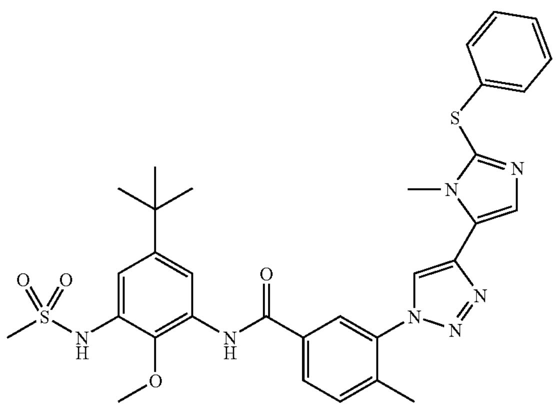 | N-(5-tert-Butyl-3-methanesulfonylamino-2-methoxy-phenyl)-4-methyl-3-[4-(3-methyl-2-phenylsulfanyl-3H-imidazol-4-yl)-1,2,3-triazol-1-yl]-benzamide |
| 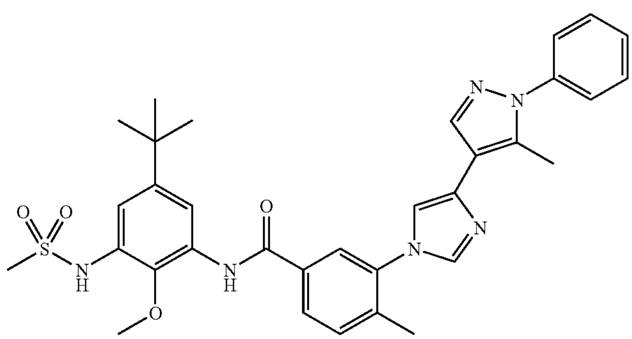 | N-(5-tert-Butyl-3-methanesulfonylamino-2-methoxy-phenyl)-4-methyl-3-[4-(5-methyl-1-phenyl-1H-pyrazol-4-yl)-imidazol-1-yl]-benzamide |
| 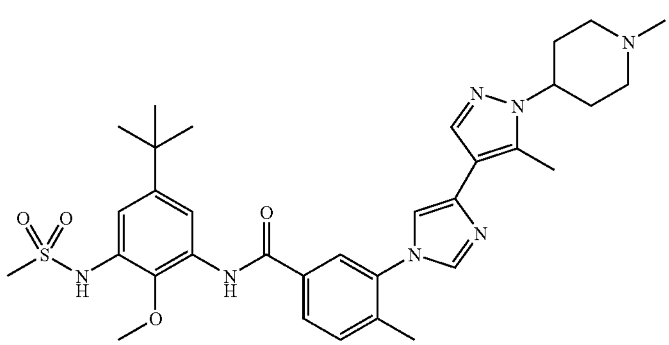 | N-(5-tert-Butyl-3-methanesulfonylamino-2-methoxy-phenyl)-4-methyl-3-{4-[5-methyl-1-(1-methyl-piperidin-4-yl)-1H-pyrazol-4-yl]-1,2,3-triazol-1-yl}-benzamide |
| 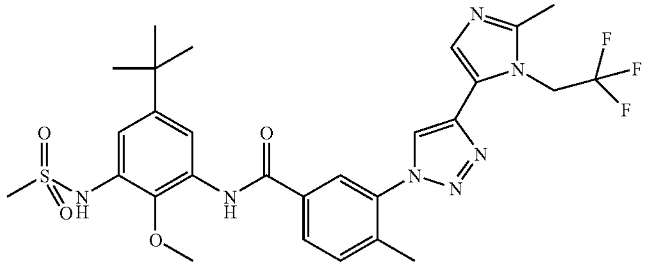 | N-(5-tert-Butyl-3-methanesulfonylamino-2-methoxy-phenyl)-4-methyl-3-{4-[2-methyl-3-(2,2,2-trifluoro-ethyl)-3H-imidazol-4-yl]-1,2,3-triazol-1-yl}-benzamide |

TABLE I-continued

| Structure | Name |
|---|---|
| 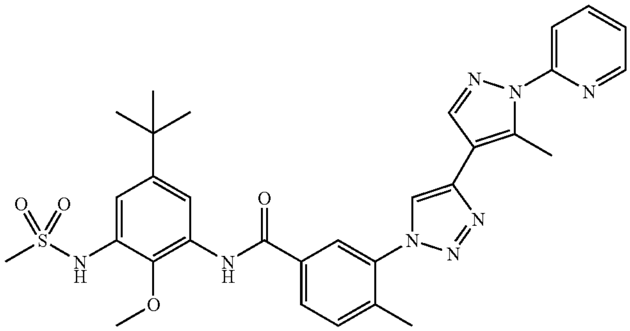 | N-(5-tert-Butyl-3-methanesulfonylamino-2-methoxy-phenyl)-4-methyl-3-[4-(5-methyl-1-pyridin-2-yl-1H-pyrazol-4-yl)-1,2,3-triazol-1-yl]-benzamide |
| 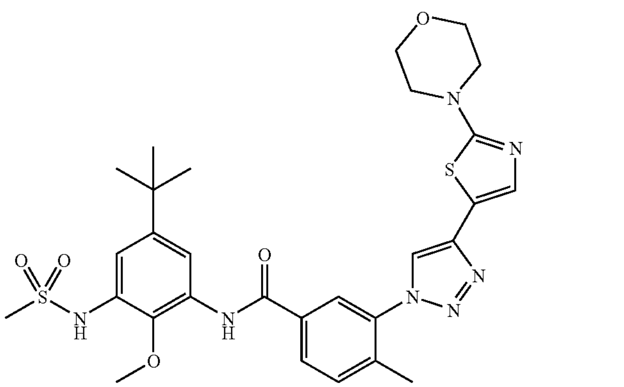 | N-(5-tert-Butyl-3-methanesulfonylamino-2-methoxy-phenyl)-4-methyl-3-[4-(2-morpholin-4-yl-thiazol-5-yl)-1,2,3-triazol-1-yl]-benzamide |
| 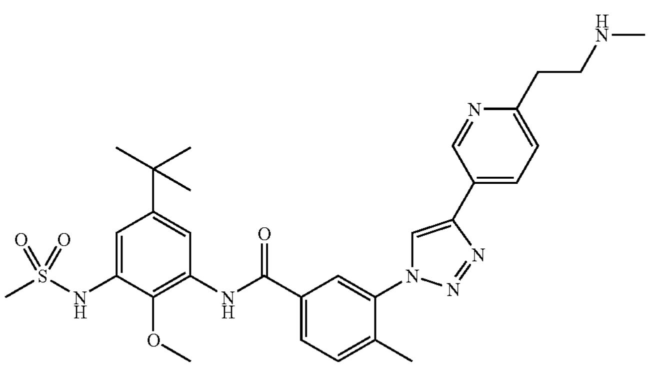 | N-(5-tert-Butyl-3-methanesulfonylamino-2-methoxy-phenyl)-4-methyl-3-{4-[6-(2-methylamino-ethyl)-pyridin-3-yl]-1,2,3-triazol-1-yl}-benzamide |
| 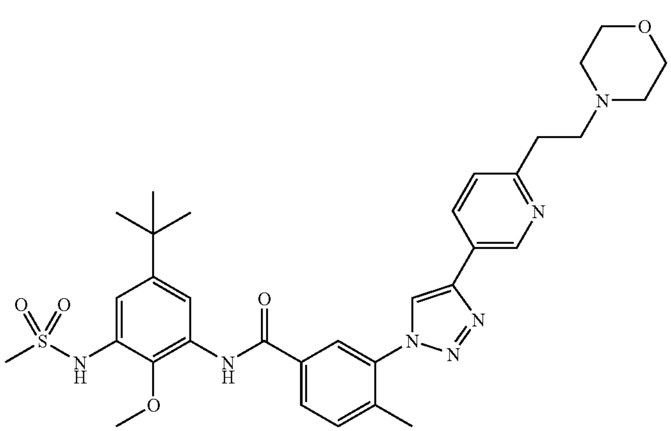 | N-(5-tert-Butyl-3-methanesulfonylamino-2-methoxy-phenyl)-4-methyl-3-{4-[6-(2-morpholin-4-yl-ethyl)-pyridin-3-yl]-1,2,3-triazol-1-yl}-benzamide |

TABLE I-continued

| Structure | Name |
|---|---|
| 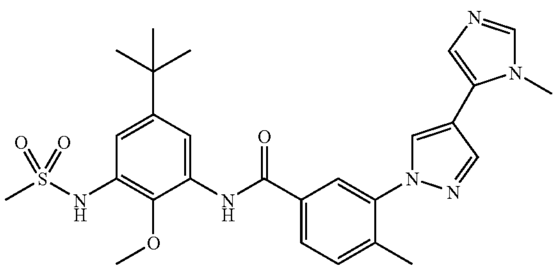 | N-(5-tert-Butyl-3-methanesulfonylamino-2-methoxy-phenyl)-4-methyl-3-[4-(3-methyl-3H-imidazol-4-yl)-pyrazol-1-yl]-benzamide |
| 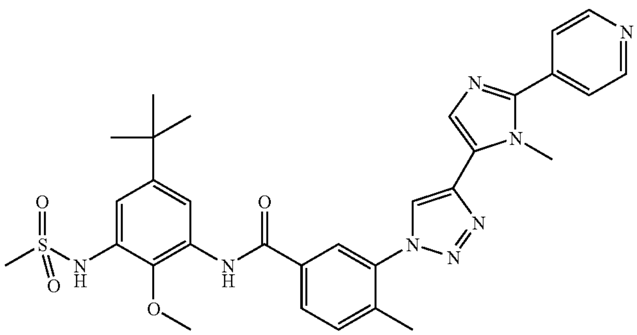 | N-(5-tert-Butyl-3-methanesulfonylamino-2-methoxy-phenyl)-4-methyl-3-[4-(3-methyl-2-pyridin-4-yl-3H-imidazol-4-yl)-1,2,3-triazol-1-yl]-benzamide |
| 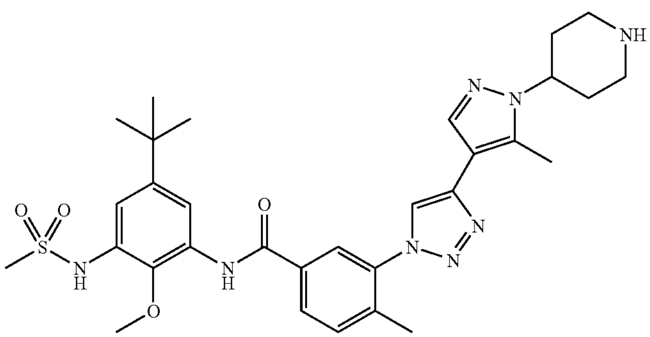 | N-(5-tert-Butyl-3-methanesulfonylamino-2-methoxy-phenyl)-4-methyl-3-[4-(5-methyl-1-piperidin-4-yl-1H-pyrazol-4-yl)-1,2,3-triazol-1-yl]-benzamide |
| 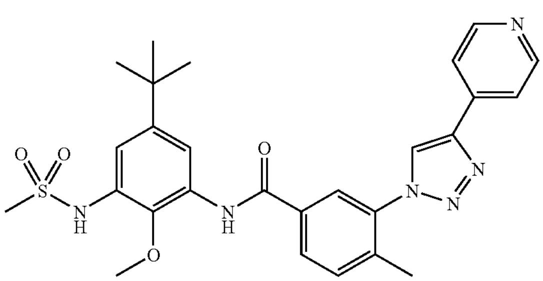 | N-(5-tert-Butyl-3-methanesulfonylamino-2-methoxy-phenyl)-4-methyl-3-(4-pyridin-4-yl-[1,2,3]triazol-1-yl)-benzamide |
| 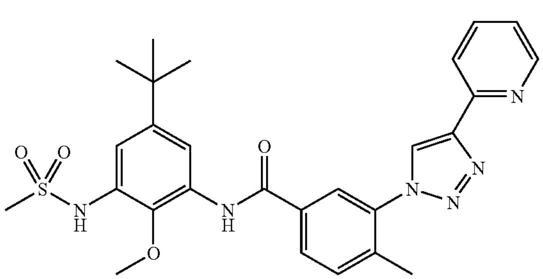 | N-(5-tert-Butyl-3-methanesulfonylamino-2-methoxy-phenyl)-4-methyl-3-(4-pyridin-2-yl-[1,2,3]triazol-1-yl)-benzamide |

TABLE I-continued

| Structure | Name |
|---|---|
| 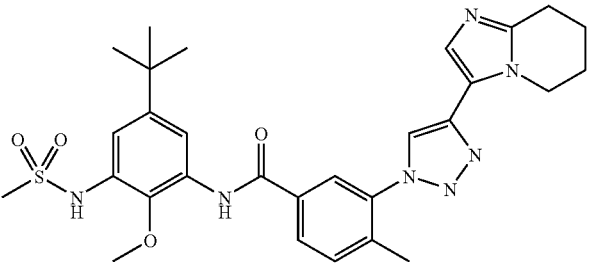 | N-(5-tert-Butyl-3-methanesulfonylamino-2-methoxy-phenyl)-4-methyl-3-[4-(5,6,7,8-tetrahydro-imidazo[1,2-a]pyridin-3-yl)-1,2,3-triazol-1-yl]-benzamide |
| 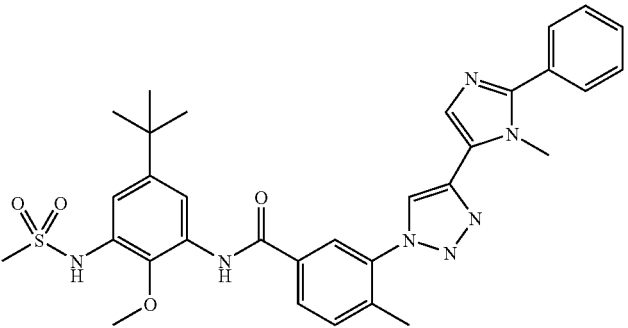 | N-(5-tert-Butyl-3-methanesulfonylamino-2-methoxy-phenyl)-4-methyl-3-[4-(3-methyl-2-phenyl-3H-imidazol-4-yl)-1,2,3-triazol-1-yl]-benzamide |
| 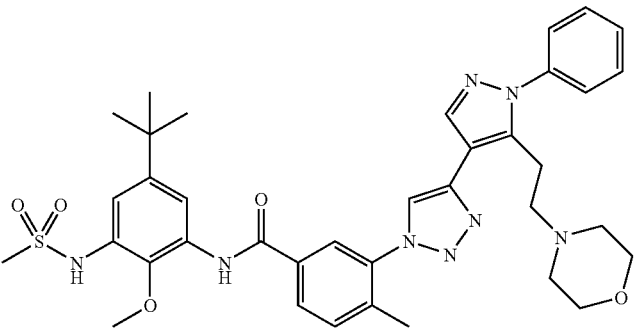 | N-(5-tert-Butyl-3-methanesulfonylamino-2-methoxy-phenyl)-4-methyl-3-{4-[5-(2-morpholin-4-yl-ethyl)-1-phenyl-1H-pyrazol-4-yl]-1,2,3-triazol-benzamide |
| 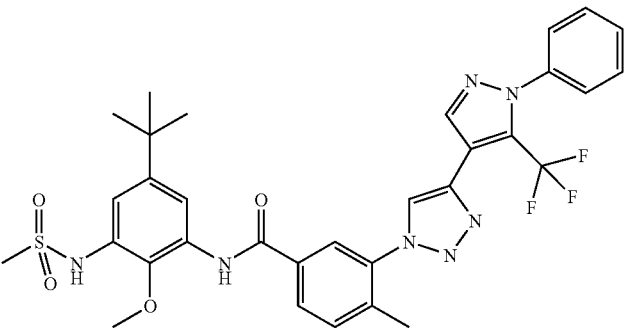 | N-(5-tert-Butyl-3-methanesulfonylamino-2-methoxy-phenyl)-4-methyl-3-[4-(1-phenyl-5-trifluoromethyl-1H-pyrazol-4-yl)-1,2,3-triazol-1-yl]-benzamide |

TABLE I-continued

| Structure | Name |
|---|---|
|  | N-(5-tert-Butyl-3-methanesulfonylamino-2-methoxyphenyl)-4-methyl-3-[4-(1-methyl-2-piperazin-1-yl-1H-imidazol-4-yl)-1,2,3-triazol-1-yl]-beflzamide |
|  | N-(5-tert-Butyl-3-methanesulfonylamino-2-methoxyphenyl)-4-methyl-3-[4-(3-methyl-2-piperazin-1-yl-3H-imidazol-4-yl)-1,2,3-triazol-1-yl]-benzamide |
|  | N-(5-tert-Butyl-3-methanesulfonylamino-2-methoxyphenyl)-4-methyl-3-[4-[spiro(6,7-dihydro-5H-pyrrolo[1,2-a]imidazol-3-yl-5-cyclohexane)]-[1,2,3]triazol-1-yl]-benzamide |
|  | N-(5-tert-Butyl-3-methanesulfonylamino-2-methoxyphenyl)-4-methyl-3-{4-[3-methyl-2-(1-methyl-cyclopropyl)-3H-imidazol-4-yl]-1,2,3-triazol-1-yl}-benzamide |

TABLE I-continued

| Structure | Name |
|---|---|
| 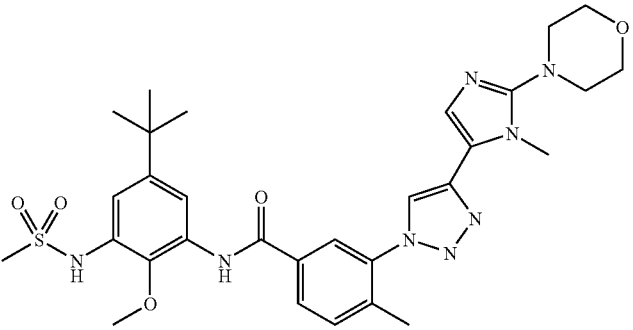 | N-(5-tert-Butyl-3-methanesulfonylamino-2-methoxy-phenyl)-4-methyl-3-[4-(3-methyl-2-morpholin-4-yl-3H-imidazol-4-yl)-1,2,3-triazol-1-yl]-benzamide |
| 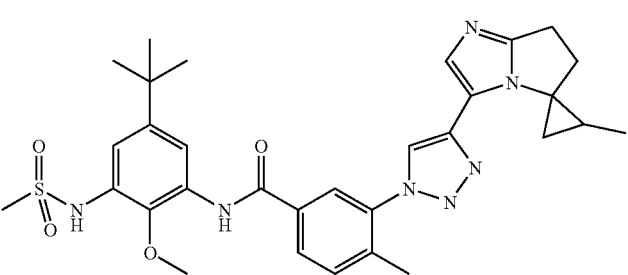 | N-(5-tert-Butyl-3-methanesulfonylamino-2-methoxy-phenyl)-4-methyl-3-[4-[spiro(6,7-dihydro-5H-pyrrolo[1,2-a]imidazol-3-yl-5-(2'-methyl-cycloproane))]-[1,2,3]triazol-1-yl]-benzamide |
| 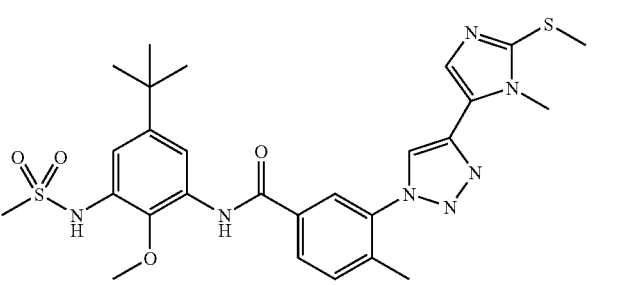 | N-(5-tert-Butyl-3-methanesulfonylamino-2-methoxy-phenyl)-4-methyl-3-[4-(3-methyl-2-methylsulfanyl-3H-imidazol-4-yl)-1,2,3-triazol-1-yl]-benzamide |
| 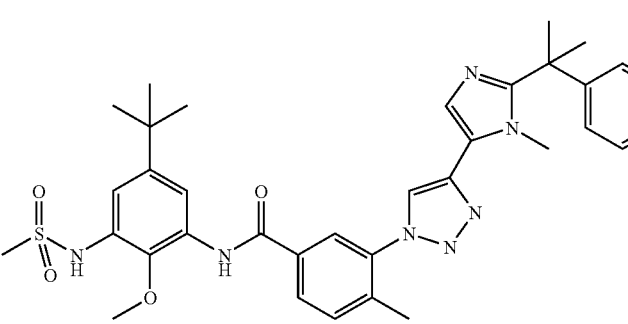 | N-(5-tert-Butyl-3-methanesulfonylamino-2-methoxy-phenyl)-4-methyl-3-{4-{3-methyl-2-(1-methyl-1-phenyl-ethyl)-3H-imidazol-4-yl]-1,2,3-triazol-1-yl}-benzamide |
| 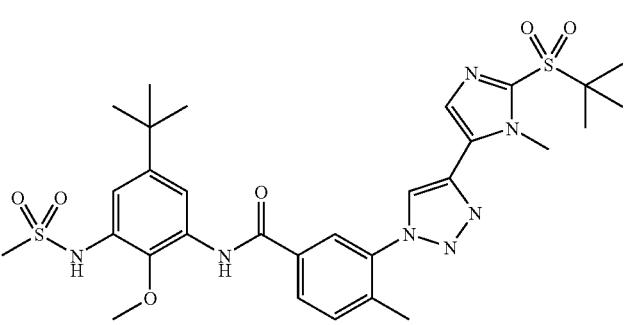 | N-(5-tert-Butyl-3-methanesulfonylamino-2-methoxy-phenyl)-4-methyl-3-{4-[3-methyl-2-(2-methyl-propane-2-sulfonyl)-3H-imidazol-4-yl]-1,2,3-triazol-1-yl}-benzamide |

TABLE I-continued

| Structure | Name |
|---|---|
| 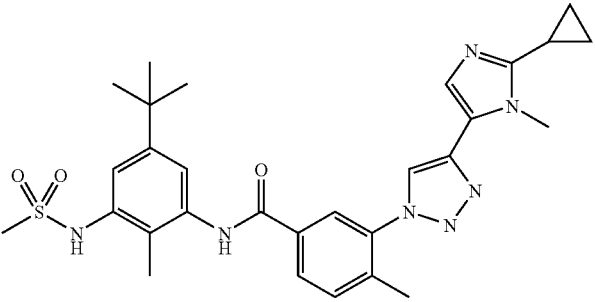 | N-(5-tert-Butyl-3-methanesulfonylamino-2-methyl-phenyl)-3-[4-(2-cyclopropyl-3-methyl-3H-imidazol-4-yl)-1,2,3-triazol-1-yl]-4-methyl-benzamide |
| 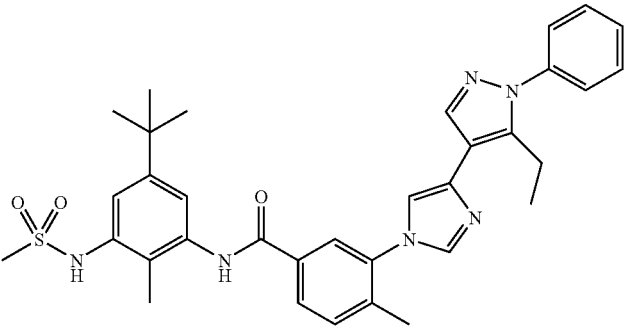 | N-(5-tert-Butyl-3-methanesulfonylamino-2-methyl-phenyl)-3-[4-(5-ethyl-1-phenyl-1H-pyrazol-4-yl)-imidazol-1-yl]-4-methyl-benzamide |
| 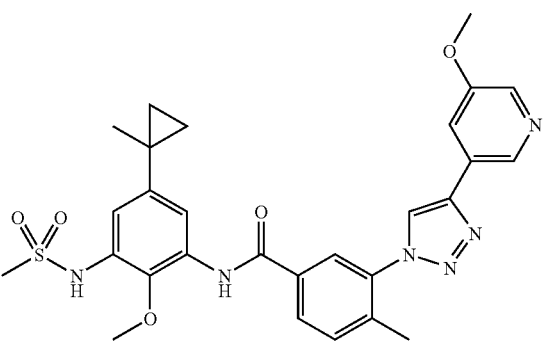 | N-[3-Methanesulfonylamino-2-methoxy-5-(1-methyl-cyclopropyl)-phenyl]-3-[4-(5-methoxy-pyridin-3-yl)-1,2,3-triazol-1-yl]-4-methyl-benzamide |
| 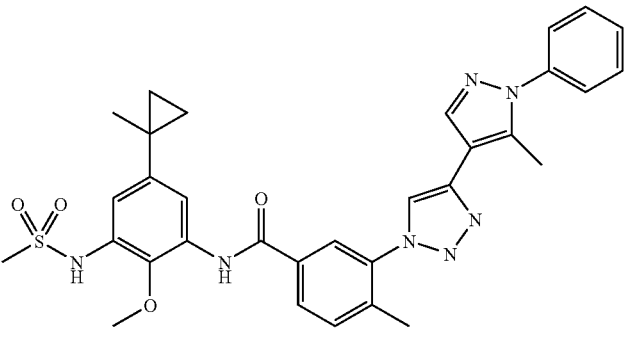 | N-[3-Methanesulfonylamino-2-methoxy-5-(1-methyl-cyclopropyl)-phenyl]-4-methyl-3-[4-(5-methyl-1-phenyl-1H-pyrazol-4-yl)-1,2,3-triazol-1-yl]-benzamide |

TABLE I-continued

| Structure | Name |
|---|---|
| 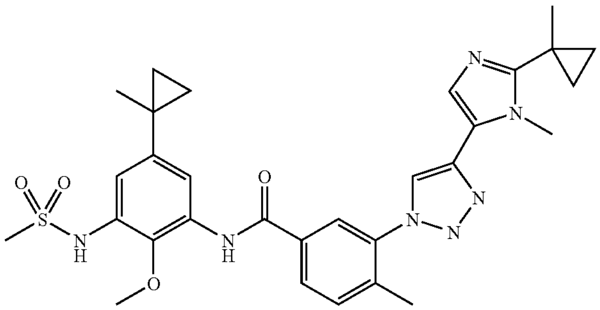 | N-[3-Methanesulfonylamino-2-methoxy-5-(1-methyl-cyclopropyl)-phenyl]-4-methyl-3-{4-[3-methyl-2-(1-methyl-cyclopropyl)-3H-imidazol-4-yl]-1,2,3-triazol-1-yl}-benzamide |
| 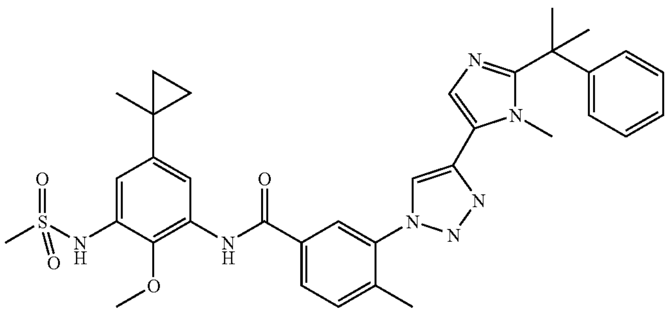 | N-[3-Methanesulfonylamino-2-methoxy-5-(1-methyl-cyclopropyl)-phenyl]-4-methyl-3-{4-[3-methyl-2-(1-methyl-1-phenyl-ethyl)-3H-imidazol-4-yl]-1,2,3-triazol-1-yl}-benzamide |
|  | N-[5-(2-Hydroxy-1,1-dimethyl-ethyl)-3-methanesulfonylamino-2-methoxy-phenyl]-4-methyl-3-{4-[3-methyl-2-(1-methyl-cyclopropyl)-3H-imidazol-4-yl]-1,2,3-triazol-1-yl}-benzamide | or the pharmaceutically acceptable salts, acids, esters or isomers thereof

In all the compounds disclosed hereinabove in this application, in the event the nomenclature is in conflict with the structure, it shall be understood that the compound is defined by the structure.

Of particular importance according to the invention are compounds of formula (I) for use as pharmaceutical compositions with an anti-cytokine activity.

The invention also relates to the use of a compound of formula (I) for preparing a pharmaceutical composition for the treatment and/or prevention of a cytokine mediated disease or condition or oncological disease.

The invention also relates to pharmaceutical preparations, containing as active substance one or more compounds of formula (I) or the pharmaceutically acceptable derivatives thereof, optionally combined with conventional excipients and/or carriers.

The invention includes the use of any compounds of described above containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations.

'Isomer' shall be understood to include any of the compounds as described above as racemates and racemic mixtures, single enantiomers, diastereomeric mixtures and individual diastereomers. All such isomeric forms of these compounds are expressly included in the present invention.

Some of the compounds of formula (I) can exist in more than one tautomeric form. The invention includes methods using all such tautomers.

The invention includes the use of any compounds of described above containing one or more isotopically-labelled form. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^{2}H$, $^{3}H$, $^{13}C$, $^{14}C$, 15N, $^{18}O$, $^{17}O$, $^{31}P$, $^{32}P$, $^{35}$S, $^{18}$F, and $^{36}$Cl, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

All terms as used herein in this specification, unless otherwise stated, shall be understood in their ordinary meaning as known in the art. For example, "C1–4alkoxy" is a C1–4alkyl with a terminal oxygen, such as methoxy, ethoxy, propoxy, butoxy. All alkyl, alkenyl and alkynyl groups shall be understood as being branched or unbranched where structurally possible and unless otherwise specified. Other more specific definitions are as follows:

Carbocycles include hydrocarbon rings containing from three to twelve carbon atoms. These carbocycles may be either aromatic either aromatic or non-aromatic ring systems. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl. Certain terms for cycloalkyl such as cyclobutanyl and cyclobutyl shall be used interchangeably.

The term "heterocycle" refers to a stable nonaromatic 4–8 membered (but preferably, 5 or 6 membered) monocyclic or nonaromatic 8–11 membered bicyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure. Unless otherwise stated, heterocycles include but are not limited to, for example pyrrolidinyl, pyrrolinyl, morpholinyl, thiomorpholinyl, thiomorpholinyl sulfoxide, thiomorpholinyl sulfone, dioxalanyl, piperidinyl, piperazinyl, tetrahydrofuranyl, tetrahydropyranyl, tetrahydrofuranyl, 1,3-dioxolanone, 1,3-dioxanone, 1,4-dioxanyl, piperidinonyl, tetrahydropyrimidonyl, pentamethylene sulfide, pentamethylene sulfoxide, pentamethylene sulfone, tetramethylene sulfide, tetramethylene sulfoxide and tetramethylene sulfone.

The term "heteroaryl" shall be understood to mean an aromatic 5–8 membered monocyclic or 8–11 membered bicyclic ring containing 1–4 heteroatoms such as N,O and S. Unless otherwise stated, such heteroaryls include aziridinyl, thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl, naphthyridinyl, indazolyl, triazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl and imidazo[4,5-b]pyridinyl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in defintions such as but not limited to: alkoxycarbonyl, acyl, amido and thioxo.

The term "aryl" as used herein shall be understood to mean aromatic carbocycle or heteroaryl as defined herein. Each aryl or heteroaryl unless otherwise specified includes it's partially or fully hydrogenated derivative. For example, quinolinyl may include decahydroquinolinyl and tetrahydroquinolinyl, naphthyl may include it's hydrogenated derivatives such as tetrahydranaphthyl. Other partially or fully hydrogenated derivatives of the aryl and heteroaryl compounds described herein will be apparent to one of ordinary skill in the art.

As used herein, "nitrogen" and "sulfur" include any oxidized form of nitrogen and sulfur and the quaternized form of any basic nitrogen. . For example, for an —S—C1–6 alkyl radical, unless otherwise specified, this shall be understood to include —S(O)—C1–6 alkyl and —S(O)$_2$—C1–6 alkyl, likewise, —S—R$^a$ may be represented as phenyl-S(O)$_m$— when R$^a$ is phenyl and where m is 0, 1 or 2.

The term "halogen" as used in the present specification shall be understood to mean bromine, chlorine, fluorine or iodine, preferably fluorine. The definitions "partially or fully halogenated"; partially or fully fluorinated; "substituted by one or more halogen atoms", includes for example, mono, di or tri halo derivatives on one or more carbon atoms. For alkyl, a nonlimiting example would be —CH$_2$CHF$_2$, —CF$_3$ etc.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—(C$_1$–C$_4$ alkyl)$_4$$^+$ salts.

In addition, within the scope of the invention is use of prodrugs of compounds of the formula (I). Prodrugs include those compounds that, upon simple chemical transforma tion, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

General Synthetic Methods

The invention additionally provides for methods of making the compounds of formula (I). The compounds of the invention may be prepared by the general methods and examples presented below, and methods known to those of ordinary skill in the art. In the schemes below, unless otherwise specified, $Ar^1$, $R^1$—$R^6$ and X in the formulas shown below shall have the meanings defined for these groups in the definition of the formula (I) of the invention, described hereinabove. Intermediates used in the syntheses below are either commercially available or easily prepared by methods known to those skilled in the art. Further reference in this regard may be made to U.S. Pat. No. 6,358,945, U.S. application Ser. Nos. 09/714,539, 09/834,797, 10/120,028, 10/143,322 and 10/147,675, U.S. provisional application Nos. 60/567,693, 60/526,569, 60/570,284. Each of the aforementioned are incorporated in their entirety.

Reaction progress may be monitored by conventional methods such as thin layer chromatography (TLC). Intermediates and products may be purified by methods known in the art, including column chromatography, HPLC or recrystallization.

In the discussion below, Q represents the ring between the phenyl ring and het of formula I as shown below:

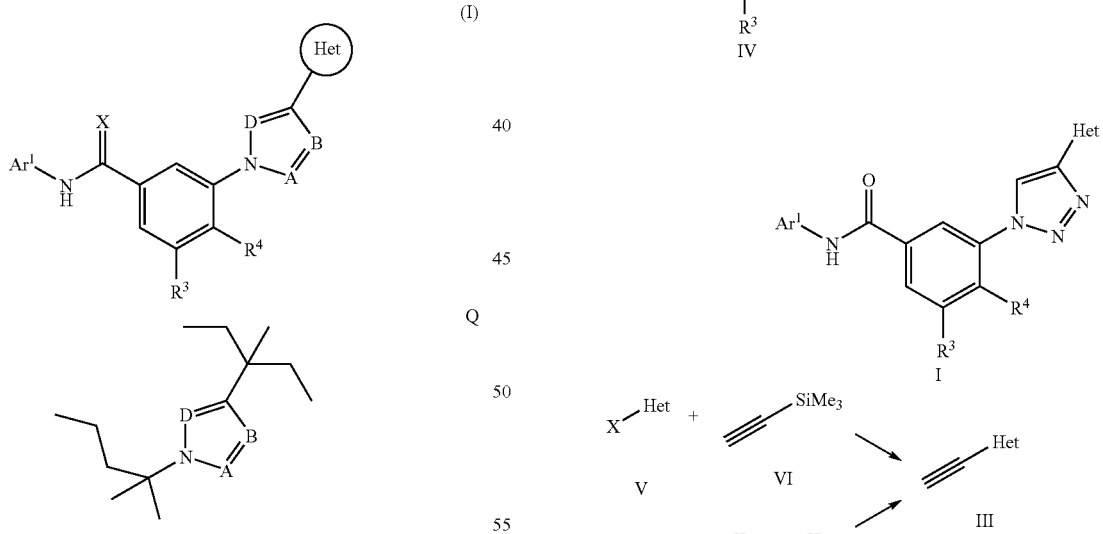

Compounds of formula (I) having Q=a triazole (A=B=N, D=CH) may be prepared as illustrated in Scheme I. An azide intermediate II is reacted with a heteroaryl acetylene intermediate III in a suitable solvent such as EtOH, optionally in the presence of a copper salt such as $CuSO_4$ with an appropriate reductant such as sodium ascorbate (Rostovtsev, V. V. et al. *Angew. Chem., Int. Ed. Engl.* 2002, 41, 2596), and optionally while heating to provide the triazole intermediate IV. Coupling of the carboxylic acid of IV with the desired aniline $Ar^1NH_2$ using standard coupling conditions known in the art provides the desired compound of formula (I) or a precursor which may be further modified by methods known in the art to provide the desired compound of formula (I). The heteroaryl acetylene intermediate III may be prepared by reaction of intermediate V, where X is I, Br, Cl or —$OSO_2CF_3$, with trimethylsilylacetylene VI, in the presence of a suitable catalyst such as $(Ph_3P)PdCl_2$, a copper salt such as CuI and a suitable base such as $Et_3N$, followed by reaction with tetrabutylammonium bromide to remove the trimethylsilyl group. Alternatively, one may react a heteroaryl aldehyde VII with dimethyl 2-oxo-1-diazopropylphosphinate in the presence of a suitable base such as $K_2CO_3$ to provide the desired intermediate III.

Scheme I

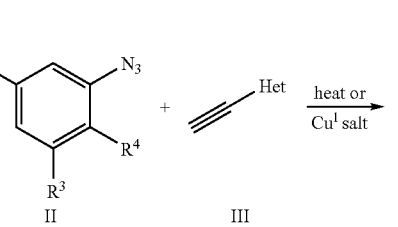

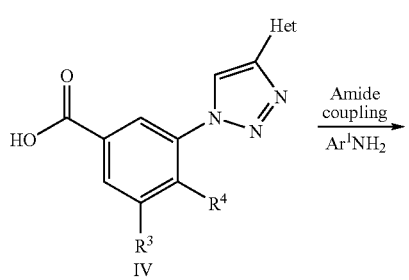

The sequence of reactions may be reversed as illustrated in Scheme II. Using this procedure, the amide coupling step is carried out first with intermediate II to provide intermediate VIII. This is then followed by reaction with the heteroaryl acetylene intermediate III to provide the desired compound of formula (I).

Scheme II

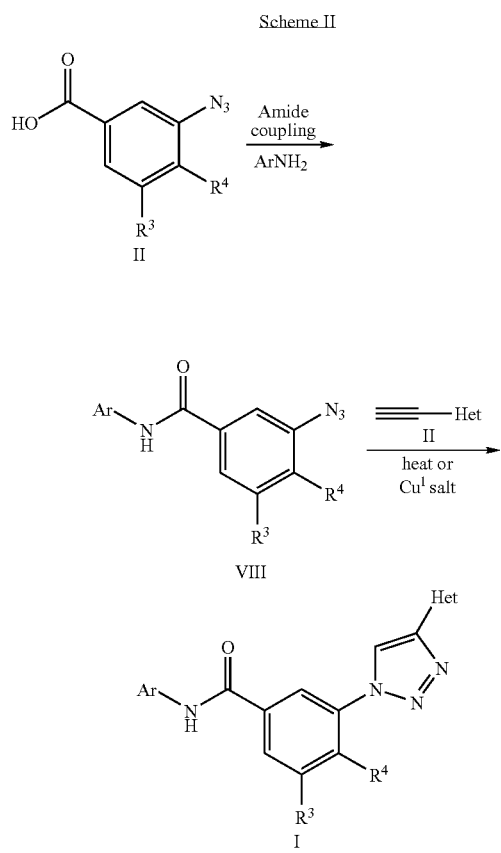

Heteroaryl aldehydes VII shown in Scheme I may be commercially available or readily prepared from commercially available intermediates by methods known in the art. For example, as illustrated in Scheme III, heteroaryl aldehydes may be prepared by direct reduction of the corresponding ester IX, for example by reaction with diisobutylaluminum hydride. Alternatively, one may reduce the ester IX to an alcohol X by treatment with a suitable reducing agent such as lithium aluminum hydride. The alcohol can then be oxidized to aldehyde VII by treatment with a suitable oxidizing agent such as $MnO_2$. Starting esters XI may be commercially available, prepared from commercially available carboxylic acids or prepared by methods known in the art. In addition, many heteroaryl aldehydes may be prepared by direct formylation of a heteroaryl moiety. For example, treatment of an optionally substituted heteroaryl moiety XI with a suitable base such as n-BuLi, in a suitable solvent such as THF, preferably while cooling at about −78° C., followed by treatment with a formylating agent such as dimethylformamide (XII) provides a heteroaryl aldehyde VII.

Scheme III

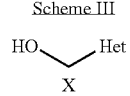

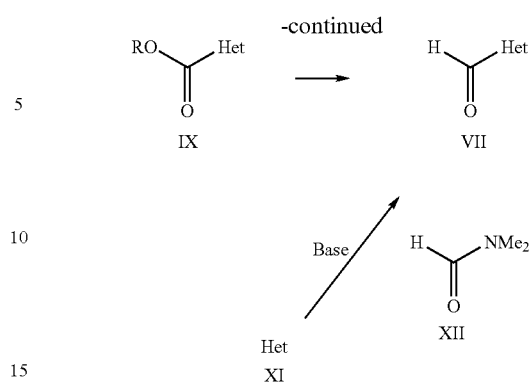

Compounds of formula (I) having Q=imidazole (B=N; A=D=CH) may be prepared as described in Scheme IV. Aniline intermediate XIII is reacted with a heteroaryl ketone XIV where Y is a leaving group such as Cl, Br or I, to provide the substituted aniline XV. Reaction of XV with a thiocyanate salt such as potassium thiocyanate provides the 2-mercaptoimidazole intermediate XVI. Treatment of XVI with $NaNO_2$ in $HNO_3$ provides imidazole intermediate XVII. Intermediate XVII may then be hydrolyzed and coupled with the desired aniline intermediate as described above to provide the desired compound of formula (I).

Scheme IV

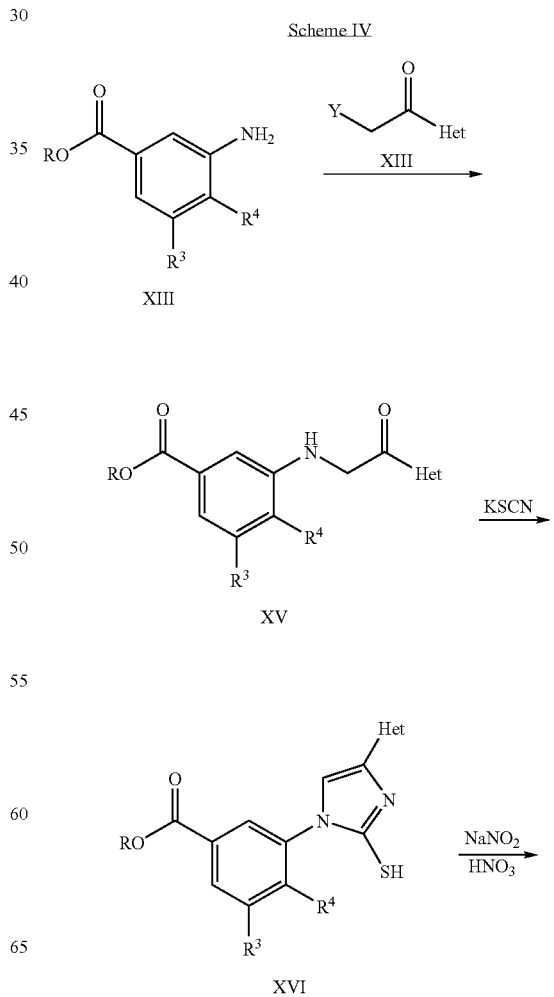

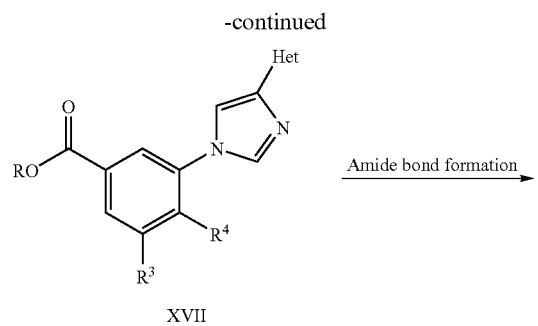

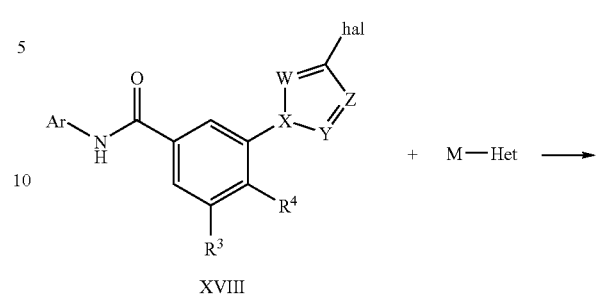

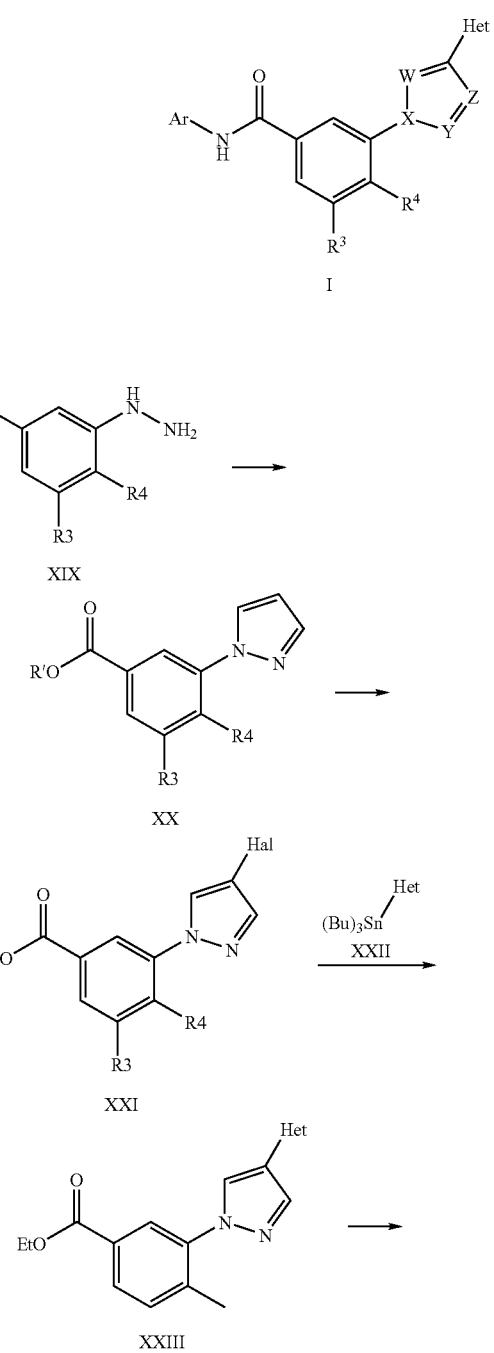

Another method that may be used to obtain compounds of formula (I) is illustrated in Scheme V. Halogenated intermediate XVIII, where hal=Br, I or Cl, may be coupled with a derivatized heteroaryl moiety (M-Het) using reactions well known in the art. For example, if M is a trialkyltin moiety one may perform a Stille coupling (see for example J. K. Stille, *Angew. Chem. Int. Ed. Engl.*, 1986, 25, 508; for a review, see V. Farina et al., *Org. Reac.*, 1997, 50, 1). Alternatively, if M is a boronic acid group, one may perform a Suzuki cross coupling reaction (see for example J. Hassan et al., *Chem Rev.*, 2002, 102, 1359 and N. Miyaura and A. Suzuki, *Chem. Rev.*, 1995, 95, 2457) to obtain the desired compound.

A more specific example is illustrated in Scheme V for the synthesis of a compound of formula (I) having Q=pyrazole (X=Y=N; W=Z=C). Using this method the phenyl hydrazine intermediate XIX is treated with malondialdehyde(bismethylacetal) in the presence of an acid such as HCl to provide pyrazole XX. Halogenation, for example by treatment of XX with bromine, provides XXI (Hal=Br). Treatment of XXI with trialkylstannanylheteroaryl intermediate, for example a tributylstannanylheteroaryl XXII, in the presence of a palladium catalyst such as Pd(PPh$_3$)$_4$, in a suitable solvent such as dioxane, while heating at about 100° C., provides coupled intermediate XXIII. Hydrolysis of the ester on intermediate XXIII, and coupling of the resulting carboxylic acid with an aniline intermediate as described above in Schemes I and IV provides the desired compound of formula (I).

-continued

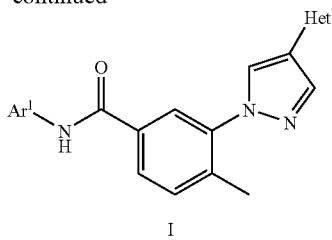

I

SYNTHETIC EXAMPLES

Abbreviations
Boc tert-butyloxycarbonyl
m-CPBA m-Chloro-peroxybenzoic acid
CDI Carbonyl diimidazole
DIBAL-H Diisobutyl aluminum hydride
DIPEA N,N-Diisopropyl ethylamine
DMAP 4-Dimethylaminopyridine
DMF Dimethylformamide
HATU O-(7-azabenzotriazol-1-yl)-N,N,N',N'-tetramethyluronium hexafluorophosphate
HOBt 1-Hydroxybenzotriazole
LHMDS Lithium hexamethyldisilazide
MTBE Methyl tert-butyl ether
NMP N-methyl-2-pyrrolidinone
PS Polystyrene
TBAF Tetrabutylammonium fluoride
TBD 1,5,7-Triazabicyclo[4.4.0]dec-5-ene
THF Tetrahydrofuran
TMEDA Tetramethylethylenediamine
TMS Trimethylsilyl Example 1

N-(5-tert-butyl-3-methanesulfonylamino-2-methoxyphenyl)-3-[4-(6-chloro-pyridin-3-yl)-[1,2,3]triazol-1-yl]-4-methyl-benzamide

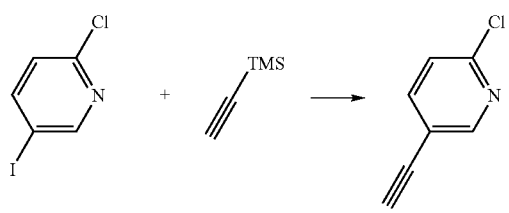

To 2-chloro-5-iodopyridine (Aldrich; 2.44 g, 10.2 mmol), (PPh$_3$)$_2$PdCl$_2$ (360 mg, 0.51 mmol) and CuI (97 mg, 0.51 mmol) under N$_2$ were added 35 mL of Et$_3$N and 1.00 g (10.2 mmol) of Me$_3$SiCCH. The pale green/brown suspension was stirred for six days under N$_2$. The mixture was concentrated and the resulting suspension was stirred with 50 mL of hot hexanes, and the orange solution was separated from the the insoluble material. The remaining residue was washed three more times with hot hexanes, and the combined washes were concentrated and chromatographed. After careful concentration, 1.4 g of 2-chloro-5-trimethylsilanylethynyl-pyridine was obtained as a beige solid.

A 1 M solution of TBAF in THF (12 mL) was added to 500 mg (2.38 mmol) of 2-chloro-5-trimethylsilanylethynylpyridine and the black solution was stirred overnight. The mixture was concentrated, the resulting residue was stirred in 50 mL of Et$_2$O for 1 h, and the liquid was decanted from the solids. This washing procedure was repeated twice, and the combined washes were concentrated and chromatographed to provide 240 mg of 2-chloro-5-ethynylpyridine as a colorless solid.

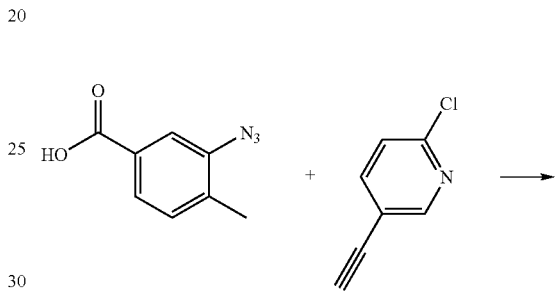

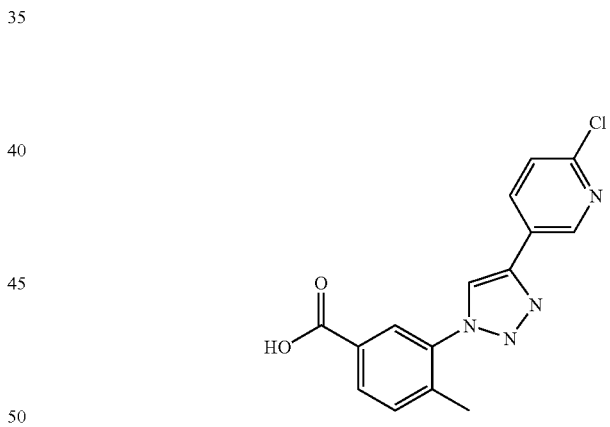

To a suspension of 308 mg (1.75 mmol) of 3-azido-4-methyl benzoic acid (U.S. Ser. No. 04/102,492) and 240 mg (1.75 mmol) of 2-chloro-5-ethynylpyridine in 1 mL of water and 2 mL of EtOH was added 243 µL (1.75 mmol) of Et$_3$N. To this solution was added 1.75 mL of 1M aqueous sodium ascorbate followed by 1.75 mL of 0.1 M aqueous of CuSO$_4$ and the resulting yellow suspension was stirred for two days. A 1 M solution of acetic acid in water (1.75 mL) was added along with an additional 2 mL of water. The suspension was stirred for 1 h, then was filtered, washed with water (2×2 mL) and hexanes (2×10 mL), and dried under suction to provide 470 mg of 3-[4-(6-chloro-pyridin-3-yl)-1,2,3-triazol-1-yl]-4-methyl-benzoic acid.

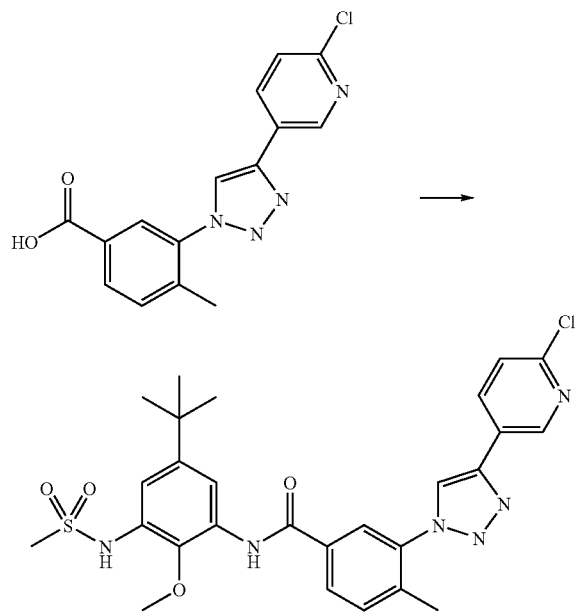

3-[4-(6-Chloro-pyridin-3-yl)-1,2,3-triazol-1-yl]-4-methyl-benzoic acid (470 mg; 1.49 mmol), N-(3-amino-5-tert-butyl-2-methoxy-phenyl)-methane-sulfonamide (WO 02/083628) (488 mg; 1.79 mmol), and 0.87 mL (5.0 mmol) of DIPEA were combined in 15 mL DMF. Then 1.14 g (2.99 mmol) of HATU and 403 mg (2.99 mmol) of HOBt were added and the dark brown solution was stirred overnight at room temperature. The mixture was then partitioned between EtOAc and water. The layers were separated and the organic portion was washed with water (2×50 mL), brine (50 mL), dried (MgSO$_4$), filtered, and concentrated. Chromatography provided 375 mg (0.66 mmol; 44%) of the title compound with 95% purity. ESI MS m/z 569 [C$_{27}$H$_{29}$ClN$_6$O$_4$S+H]$^+$.

Example 2

N-(5-tert-Butyl-2-methyl-pyridin-3-yl)-3-{4-[6-(cyclopropylmethyl-amino)-pyridin-3-yl]-[1,2,3]triazol-1-yl}-4-methyl-benzamide

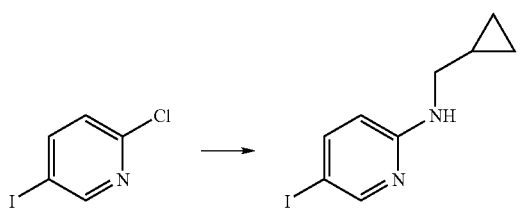

A solution of 500 mg (2.09 mmol) of 2-chloro-5-iodo pyridine in 1.64 g (23.1 mmol) of aminomethylcyclopropane was heated to 100° C. in a sealed tube for 48 h. The mixture was then concentrated, dissolved in EtOAc, washes with water and brine, dried with MgSO$_4$, filtered, and concentrated. Recrystallization from hexanes provided 440 mg (1.61 mmol; 77%) of cyclopropylmethyl-(5-iodo-pyridin-2-yl)-amine. ESI MS m/z 275 [C$_9$H$_{11}$ IN$_2$+H]$^+$.

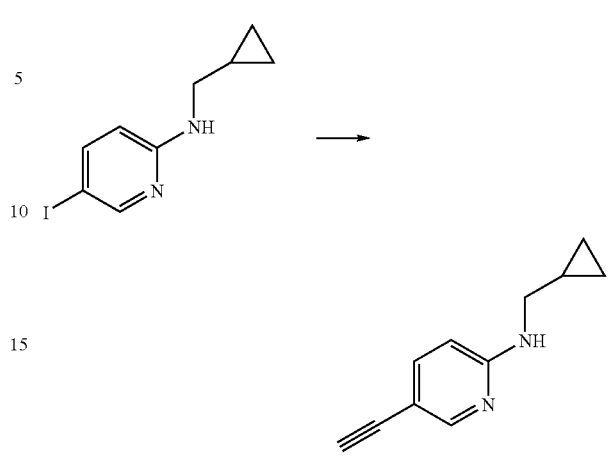

To 1.14 g (4.16 mmol) of cyclopropylmethyl-(5-iodo-pyridin-2-yl)-amine, 150 mg (0.21 mmol) of (PPh$_3$)$_2$PdCl$_2$, and 40 mg (0.21 mmol) of CuI under N$_2$ were added 11 mL of Et$_3$N and 0.59 mL (8.3 mmol) of Me$_3$SiCCH. The pale green/yellow suspension was stirred overnight, concentrated, and then partitioned between EtOAc and water. The organic portion was washed with water, brine, dried (Na$_2$SO$_4$), filtered, concentrated, and chromatographed (0–30% EtOAc in hexanes) provided a red-brown solid. The residue was stirred with 10 mL of refluxing hexanes. The mixture was filtered, and the solids were washed twice with 5 mL of hot hexanes. The filtrate and washes were combined and concentrated to provide 855 mg of cyclopropylmethyl-(5-trimethylsilanylethynyl-pyridin-2-yl)-amine as a yellow fluffy solid.

To a 0° C. solution of 855 mg (3.50 mmol) of cyclopropylmethyl-(5-trimethylsilanylethynyl-pyridin-2-yl)-amine in 7 mL of THF, was slowly added 7.0 mL (7.0 mmol) of 1M TBAF in THF. The mixture was stirred for 2 h, then poured into water and extracted with Et$_2$O. The Et$_2$O was washed with brine. The washes were extracted once with Et$_2$O, and the combined extracts were diluted with 10 mL of CH$_2$Cl$_2$ and left to sit for 10 min. The solution was then decanted from the water that had separated, and was dried with Na$_2$SO$_4$, filtered, concentrated, and chromatographed (1–20% EtOAc in hexanes) to provide 467 mg of 2-(cyclopropylmethyl)amino-5-ethynyl pyridine.

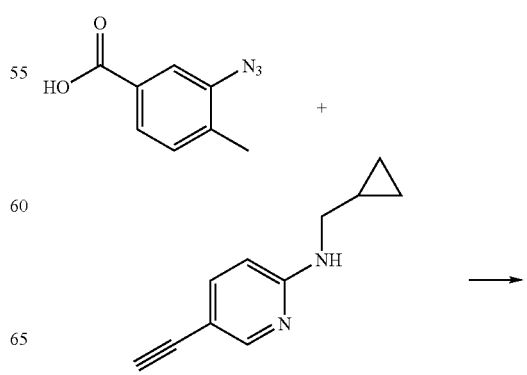

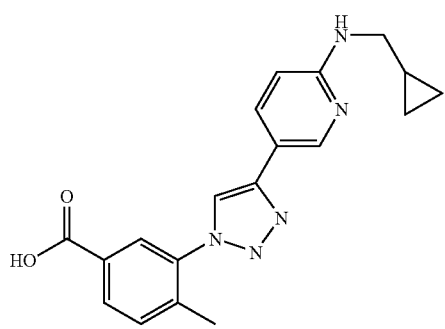

3-Azido-4-methyl benzoic acid (497 mg; 2.81 mmol) was suspended in 6.5 mL of EtOH. To this mixture was added 4N NaOH until the mixture became homogeneous, followed then by 2-(cyclopropylmethyl)amino-5-ethynyl pyridine (460 mg; 2.61 mmol) and 529 mg (2.67 mmol) of sodium ascorbate in 0.7 mL of water. The mixture was stirred rapidly as 2.67 mL of a 0.1 M CuSO$_4$ solution was added. A yellow precipitate formed and the mixture was stirred rapidly for 14 h. The mixture was poured into water and acidified carefullly with HOAc. The resulting precipitate was filtered and washed with water. A fine yellow powder was isolated. This material was crushed in 1 mL of MeOH and 5 mL of NH$_4$OH was added. The resulting green mixture was stirred for 10 min, then HOAc was carefully added until a white precipitate formed (pH 8–9). The precipitate was filtered and washed with 1% HOAc in water, then with water and hexanes to provide 607 mg (1.74 mmol; 65%) of 3-{4-[6-(cyclopropylmethyl-amino)-pyridin-3-yl]-1,2,3-triazol-1-yl}-4-methyl-benzoic acid.

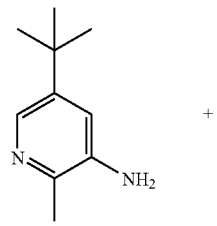 +

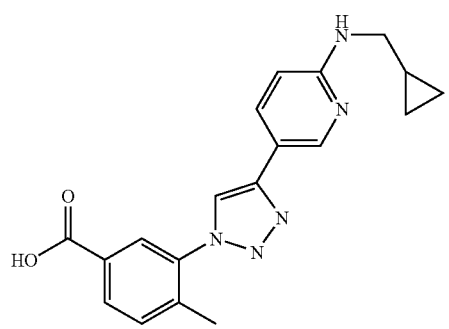 →

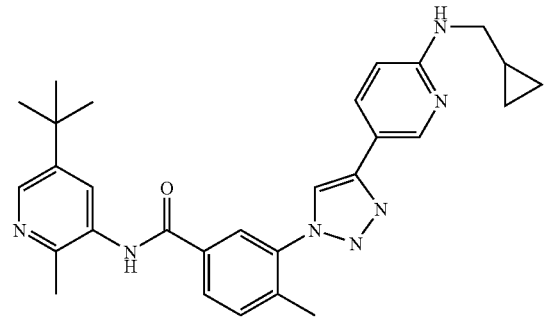

Example 2 was prepared by coupling 3-{4-[6-(cyclopropylmethyl-amino)-pyridin-3-yl]-1,2,3-triazol-1-yl}-4-methyl-benzoic acid with 5-tert-butyl-2-methyl-pyridin-3-ylamine (See U.S. provisional application 60/567,693) in the same manner as Example 1. ESI MS m/z 496 [C$_{29}$H$_{33}$N$_7$O+H]$^+$.

Example 3

N-(5-tert-Butyl-3-methanesulfonylamino-2-methoxy-phenyl)-4-methyl-3-(4-pyridin-2-yl-[1,2,3]triazol-1-yl)-benzamide

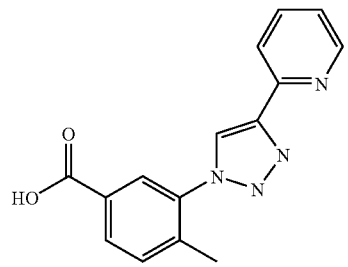

4-Methyl-3-(4-pyridin-2-yl-[1,2,3]triazol-1-yl)-benzoic acid was prepared from 3-azido-4-methyl benzoic acid and 2-ethynyl pyridine (Aldrich) in the same manner as 3-[4-(6-chloro-pyridin-3-yl)-1,2,3-triazol-1-yl]-4-methyl-benzoic acid (Example 1).

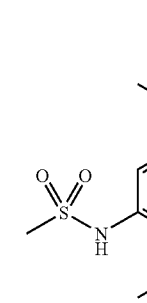

Example 3 was prepared by coupling 4-methyl-3-(4-pyridin-2-yl-[1,2,3]triazol-1-yl)-benzoic acid with N-(3-amino-5-tert-butyl-2-methoxy-phenyl)-methane-sulfonamide in the same manner as Example 1. ESI MS m/z 533 [C$_{27}$H$_{30}$N$_6$O$_4$S+H]$^+$.

Example 4

N-(5-tert-Butyl-3-cyano-2-methoxy-phenyl)-3-{4-[6-(cyclopropylmethyl-amino)-pyridin-3-yl]-[1,2,3]triazol-1-yl}-4-methyl-benzamide

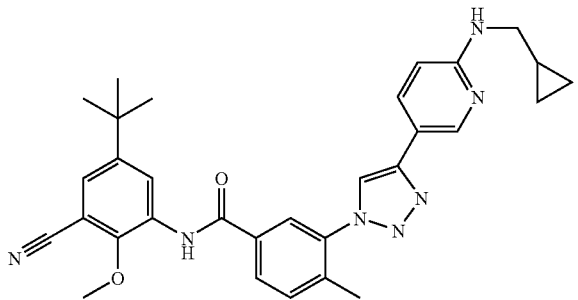

Example 4 was prepared by coupling 3-{4-[6-(cyclopropylmethyl-amino)-pyridin-3-yl]-1,2,3-triazol-1-yl}-4-methoxy-benzoic acid with 3-amino-5-tert-butyl-2-methyl-benzonitrile (See U.S. provisional application 60/567,693) in the same manner as Example 1. ESI MS m/z 536 $[C_{31}H_{33}N_7O+H]^+$.

Example 5

N-(5-tert-Butyl-3-methanesulfonylamino-2-methoxy-phenyl)-4-fluoro-3-(4-pyridin-3-yl-[1,2,3]triazol-1-yl)-benzamide

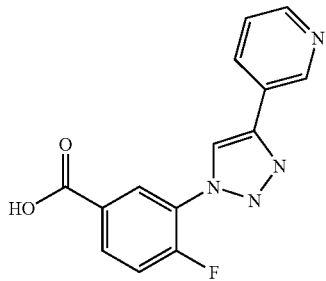

4-Fluoro-3-(4-pyridin-3-yl-[1,2,3]triazol-1-yl)-benzoic acid was prepared from 3-azido-4-fluoro benzoic acid (U.S. Ser. No. 04/102,492) and 3-ethynyl pyridine (Aldrich) in the same manner as 3-[4-(6-chloro-pyridin-3-yl)-1,2,3-triazol-1-yl]-4-methyl-benzoic acid (Example 1).

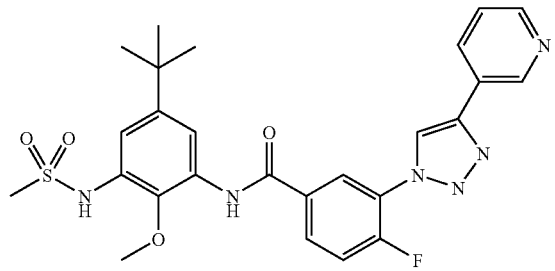

Example 5 was prepared by coupling 4-fluoro-3-(4-pyridin-3-yl-[1,2,3]triazol-1-yl)-benzoic acid with N-(3-amino-5-tert-butyl-2-methoxy-phenyl)-methane-sulfonamide in the same manner as Example 1. ESI MS m/z 539 $[C_{26}H_{27}FN_6O_4S+H]^+$.

Example 6

N-(5-tert-Butyl-2-methanesulfinyl-phenyl)-3-{4-[6-(cyclopropylmethyl-amino)-pyridin-3-yl]-[1,2,3]triazol-1-yl}-4-methyl-benzamide

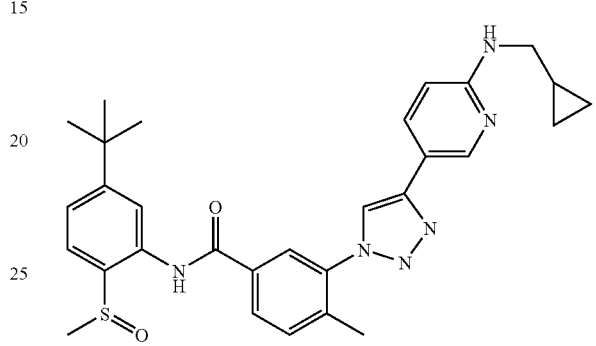

Example 6 was prepared by coupling 3-{4-[6-(cyclopropylmethyl-amino)-pyridin-3-yl]-1,2,3-triazol-1-yl}-4-methyl-benzoic acid with 5-tert-butyl-2-methanesulfinyl-phenylamine (see U.S. provisional application 60/526,569) in the same manner as Example 1. ESI MS m/z 543 $[C_{30}H_{34}N_6O_2S+H]^+$.

Example 7

N-(5-tert-Butyl-3-methanesulfonylamino-2-methoxy-phenyl)-4-methyl-3-[4-(6-methyl-pyridin-3-yl)-[1,2,3]triazol-1-yl]-benzamide

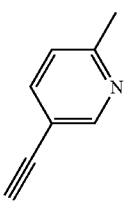

In a flask under $N_2$ were added 87 mg (0.23 mmoL) of $(CH_3CN)_2PdCl_2$ and 36 mg (0.19 mmol) of CuI, followed by 5 mL of dioxane, 131 mg (0.454 mmol) of t-BuP.HBF$_4$, 649 mg (3.77 mmol) of 2-methyl-5-bromo pyridine (Fluka), 1.3 mL (9.4 mmol) of Me$_3$SiCCH, and finally 0.64 mL (4.5 mmol) of i-Pr$_2$NH. The mixture was stirred for one hour, filtered through celite, and the celite was washed with EtOAc. The filtrate was washed with water and brine, and the washes were extracted once with EtOAc. The combined extracts were dried with Na$_2$SO$_4$, filtered, concentrated, and chromatographed (0–2% MeOH in CH$_2$Cl$_2$) to provide 646 mg of 2-methyl-5-trimethylsilanylethynyl-pyridine.

A mixture of 654 mg (3.45 mmol) of 2-methyl-5-trimethylsilanylethynyl-pyridine and 8 mL of 1 M TBAF in THF was stirred for 2 h. The mixture was concentrated and chromatographed (10–50% EtOAc in hexanes) to provide 301 mg of 2-methyl-5-ethynyl pyridine.

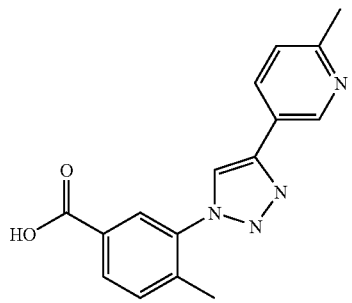

4-Methyl-3-[4-(6-methyl-pyridin-3-yl)-[1,2,3]triazol-1-yl]-benzoic acid was prepared from 3-azido-4-methyl benzoic acid and 2-methyl-5-ethynyl pyridine in the same manner as 3-[4-(6-chloro-pyridin-3-yl)-1,2,3-triazol-1-yl]-4-methyl-benzoic acid (Example 1).

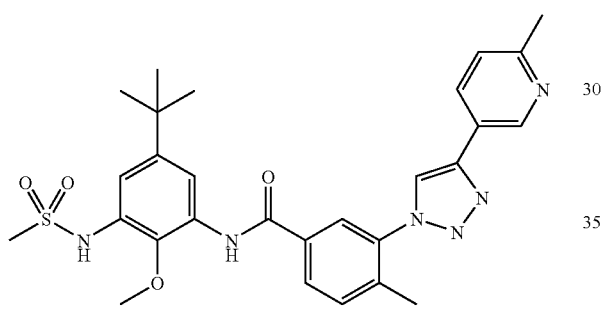

Example 7 was prepared by coupling 4-methyl-3-[4-(6-methyl-pyridin-3-yl)-[1,2,3]triazol-1-yl]-benzoic acid with N-(3-amino-5-tert-butyl-2-methoxy-phenyl)-methane-sulfonamide in the same manner as Example 1. ESI MS m/z 547 $[C_{28}H_{32}N_6O_4S+H]^+$.

Example 8

N-(5-tert-Butyl-3-methanesulfonylamino-2-methoxy-phenyl)-3,4-dimethyl-5-(4-pyridin-3-yl-[1,2,3]triazol-1-yl)-benzamide

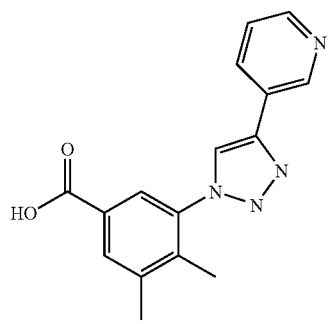

A suspension of 100 mg (0.52 mmol) of 3-azido-4,5-dimethyl benzoic acid (U.S. Ser. No. 04/102,492), 54 mg (0.52 mmol) of 3-ethynyl pyridine, and 200 μL of EtOH was heated to 120° C. in a sealed tube for 12 h. The mixture was cooled and diluted with 500 μL of EtOH. The mixture was filtered and the solids were washed with EtOH (3×0.5 mL). The solids were dried to provide 50 mg of 3,4-dimethyl-5-(4-pyridin-3-yl-[1,2,3]triazol-1-yl)-benzoic acid.

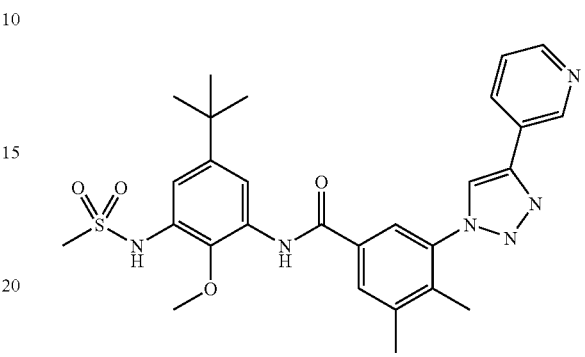

Example 8 was prepared by coupling 3,4-dimethyl-5-(4-pyridin-3-yl-[1,2,3]triazol-1-yl)-benzoic acid with N-(3-amino-5-tert-butyl-2-methoxy-phenyl)-methane-sulfonamide in the same manner as Example 1. ESI MS m/z 549 $[C_{28}H_{32}N_6O_4S+H]^+$.

Example 9

N-(5-tert-Butyl-3-methanesulfonylamino-2-methoxy-phenyl)-4-methyl-3-[4-(2-methyl-pyridin-3-yl)-[1,2,3]triazol-1-yl]-benzamide

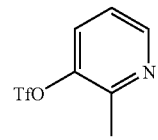

To an ice-cold suspension of 3-hydroxy-2-methylpyridine (2.00 g; 18.3 mmol) and N-phenyltriflimide (6.55 g; 18.3 mmol) in 50 mL of CH$_2$Cl$_2$ was added dropwise 2.70 mL (19.4 mmol) of Et$_3$N. The resulting suspension was stirred for 1 h at 0° C. and for an additional 2 h at room temperature. The mixture was then washed twice with 20 mL of 1M NaOH, once with half-saturated K$_2$CO$_3$, and once with brine. The extract was dried with Na$_2$SO$_4$, filtered, and concentrated to provide trifluoro-methanesulfonic acid 2-methyl-pyridin-3-yl ester as a pale brown oil. ESI MS m/z 242 $[C_7H_6F_3NO_3S+H]^+$.

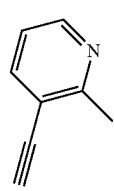

2-Methyl-3-ethynyl pyridine was prepared from trifluoromethanesulfonic acid 2-methyl-pyridin-3-yl ester in the same manner as 2-chloro-5-ethynyl-pyridine (Example 1).

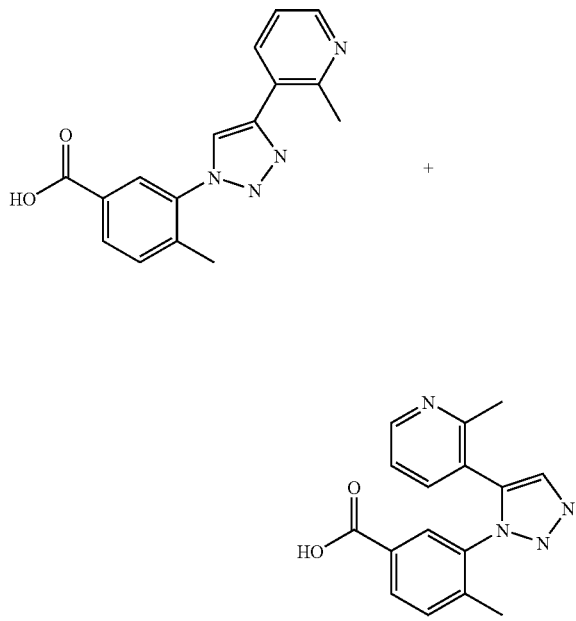

4-Methyl-3-[4-(2-methyl-pyridin-3-yl)-[1,2,3]triazol-1-yl]-benzoic acid (5:3 mixture with 4-methyl-3-[5-(2-methyl-pyridin-3-yl)-[1,2,3]triazol-1-yl]-benzoic acid) was prepared from 3-azido-4-methyl benzoic acid and 2-methyl-3-ethynyl pyridine in the same manner as 3,4-dimethyl-5-(4-pyridin-3-yl-[1,2,3]triazol-1-yl)-benzoic acid (Example 8).

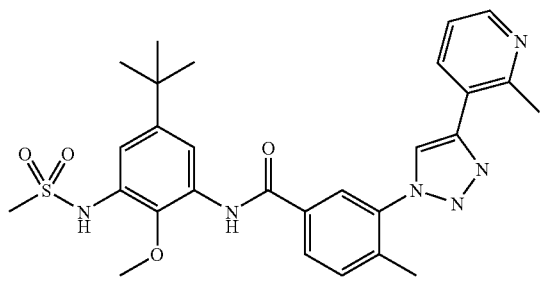

Example 9 was prepared by coupling 4-methyl-3-[4-(2-methyl-pyridin-3-yl)-[1,2,3]triazol-1-yl]-benzoic acid (5:3 mixture with 4-methyl-3-[5-(2-methyl-pyridin-3-yl)-[1,2,3]triazol-1-yl]-benzoic acid) with N-(3-amino-5-tert-butyl-2-methoxy-phenyl)-methane-sulfonamide in the same manner as Example 1. Preparative HPLC was used to separate N-(5-tert-butyl-3-methanesulfonylamino-2-methoxy-phenyl)-4-methyl-3-[4-(2-methyl-pyridin-3-yl)-[1,2,3]triazol-1-yl]-benzamide from N-(5-tert-Butyl-3-methanesulfonylamino-2-methoxy-phenyl)-4-methyl-3-[5-(2-methyl-pyridin-3-yl)-[1,2,3]triazol-1-yl]-benzamide. ESI MS m/z 549 [$C_{28}H_{32}N_6O_4S$+H]$^+$.

Example 10

N-(5-tert-Butyl-3-{[(2-dimethylamino-ethyl)-methyl-amino]-methyl}-2-methoxy-phenyl)-4-methyl-3-(4-pyridin-3-yl-[1,2,3]triazol-1-yl)-benzamide

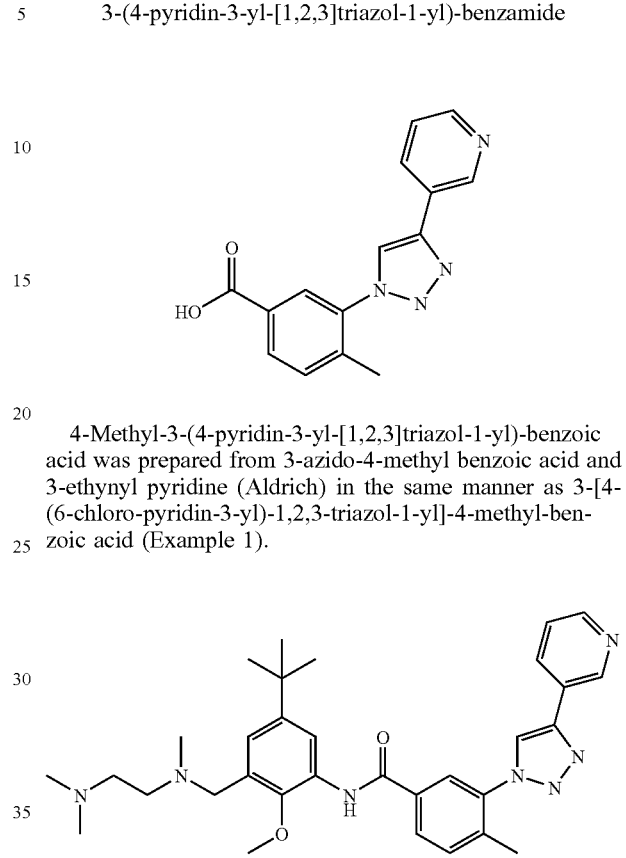

4-Methyl-3-(4-pyridin-3-yl-[1,2,3]triazol-1-yl)-benzoic acid was prepared from 3-azido-4-methyl benzoic acid and 3-ethynyl pyridine (Aldrich) in the same manner as 3-[4-(6-chloro-pyridin-3-yl)-1,2,3-triazol-1-yl]-4-methyl-benzoic acid (Example 1).

Example 10 was prepared by coupling 4-methyl-3-(4-pyridin-3-yl-[1,2,3]triazol-1-yl)-benzoic acid with N-(3-amino-5-tert-butyl-2-methoxy-benzyl)-N,N',N'-trimethyl-ethane-1,2-diamine (see U.S. provisional application 60/526,569) in the same manner as Example 1. ESI MS m/z 554 [$C_{32}H_{41}N_7O_2$–H]$^-$.

Example 11

N-(5-tert-Butyl-3-methanesulfonylamino-2-methoxy-phenyl)-4-chloro-3-(4-pyridin-3-yl-[1,2,3]triazol-1-yl)-benzamide

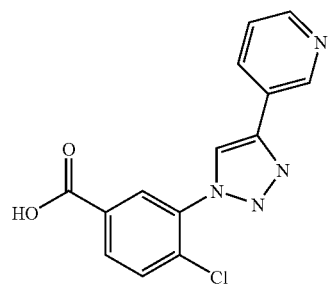

4-Chloro-3-(4-pyridin-3-yl-[1,2,3]triazol-1-yl)-benzoic acid was prepared from 3-azido-4-chloro benzoic acid (U.S.

Ser. No. 04/102,492) and 3-ethynyl pyridine (Aldrich) in the same manner as 3-[4-(6-chloro-pyridin-3-yl)-1,2,3-triazol-1-yl]-4-methyl-benzoic acid (Example 1).

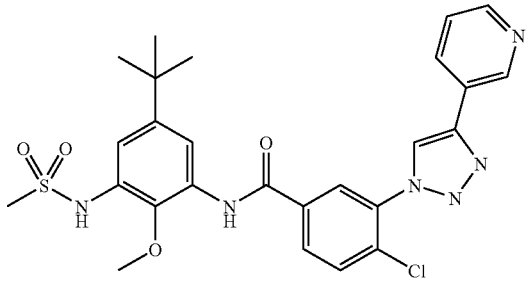

Example 11 was prepared by coupling 4-chloro-3-(4-pyridin-3-yl-[1,2,3]triazol-1-yl)-benzoic acid with N-(3-amino-5-tert-butyl-2-methoxy-phenyl)-methane-sulfonamide in the same manner as Example 1. ESI MS m/z 555 $[C_{26}H_{27}ClN_6O_4S+H]^+$.

Example 12

N-[3-Methanesulfonylamino-2-methoxy-5-(1-methyl-cyclopropyl)-phenyl]-3-[4-(5-methoxy-pyridin-3-yl)-[1,2,3]triazol-1-yl]-4-methyl-benzamide

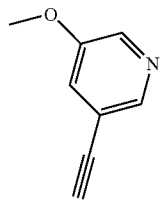

5-Ethynyl-3-methoxy pyridine was prepared from 5-bromo-3-methoxy pyridine (Frontier) in the same manner as 2-chloro-5-ethynyl-pyridine (Example 1).

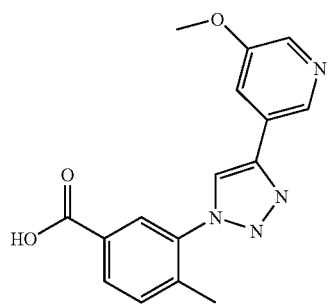

3-[4-(5-Methoxy-pyridin-3-yl)-[1,2,3]triazol-1-yl]-4-methyl-benzoic acid was prepared from 3-azido-4-methyl benzoic acid and 5-ethynyl-3-methoxy pyridine in the same manner as 3-[4-(6-chloro-pyridin-3-yl)-1,2,3-triazol-1-yl]-4-methyl-benzoic acid (Example 1).

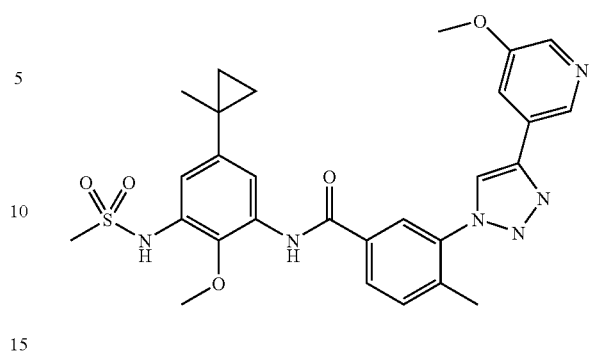

Example 12 was prepared by coupling 3-[4-(5-methoxy-pyridin-3-yl)-[1,2,3]triazol-1-yl]-4-methyl-benzoic acid with N-[3-amino-2-methoxy-5-(1-methyl-cyclopropyl)-phenyl]-methanesulfonamide (U.S. Ser. No. 04/102,492) in the same manner as Example 1. ESI MS m/z 563 $[C_{28}H_{30}N_6O_5S+H]^+$.

Example 13

N-(5-tert-Butyl-3-methanesulfonylamino-2-methoxy-phenyl)-4-methyl-3-[4-(6-morpholin-4-ylmethyl-pyridin-3-yl)-[1,2,3]triazol-1-yl]-benzamide

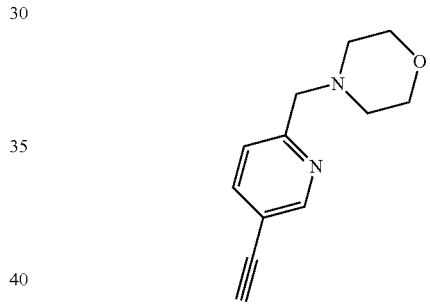

4-(5-Ethynyl-pyridin-2-ylmethyl)-morpholine was prepared from 4-(5-bromo-pyridine-2-ylmethyl)-morpholine (U.S. Pat. No. 6,358,945) in the same manner as 2-methyl-5-ethynyl pyridine (Example 7).

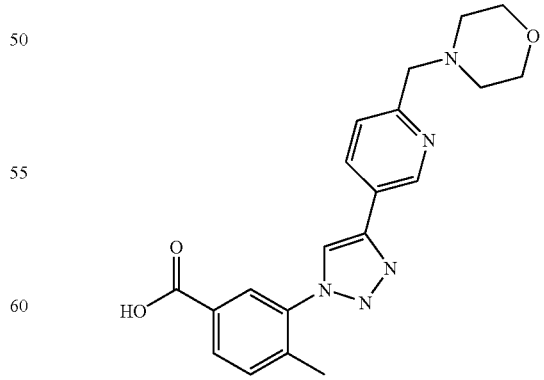

A suspension of 87.5 mg (0.494 mmol) of 3-azido-4-methyl-benzoic acid and 100 mg (0.494 mmol) of 4-(5-ethynyl-pyridin-2-ylmethyl)-morpholine were suspended in 200 μL of EtOH and heated to 140° C. for 1 h in a microwave reactor. After cooling, the mixture was concentrated to provide 150 mg of 4-methyl-3-[4-(6-morpholin-4-ylmethyl-pyridin-3-yl)-1,2,3-triazol-1-yl]-benzoic acid, and its triazole isomer 4-methyl-3-[5-(6-morpholin-4-ylmethyl-pyridin-3-yl)-1,2,3-triazol-1-yl]-benzoic acid in a 2:1 ratio

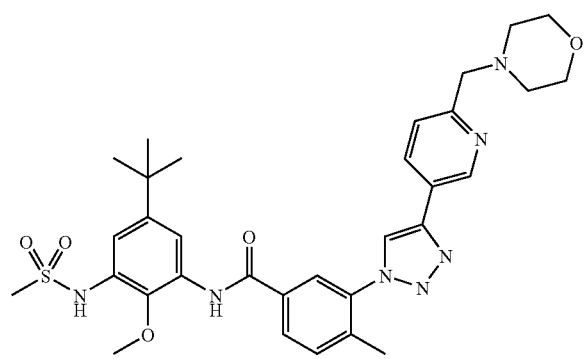

Example 13 was prepared by coupling 4-methyl-3-[4-(6-morpholin-4-ylmethyl-pyridin-3-yl)-[1,2,3]triazol-1-yl]-benzoic acid (2:1 with 4-methyl-3-[5-(6-morpholin-4-ylmethyl-pyridin-3-yl)-1,2,3-triazol-1-yl]-benzoic acid) with N-(3-amino-5-tert-butyl-2-methoxy-phenyl)-methane-sulfonamide in the same manner as Example 1. Chromatography separated the triazole isomers. ESI MS m/z 635 $[C_{32}H_{39}N_7O_5S+H]^+$.

Example 14

N-(5-tert-butyl-3-methanesulfonylamino-2-methoxy-phenyl)-4-methyl-3-(4-pyridin-3-yl-[1,2,3]triazol-1-yl)-benzamide

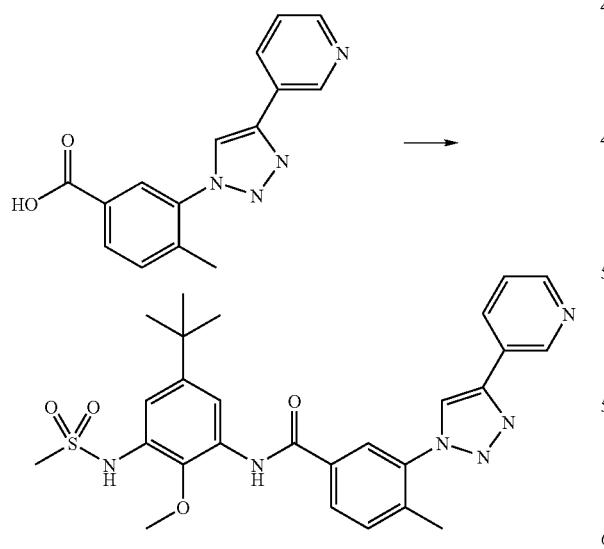

4-Methyl-3-(4-pyridin-3-yl-1,2,3-triazol-1-yl)-benzoic acid (76.3 mg; 0.272 mmol) was suspended in 5 mL of CH$_2$Cl$_2$, and 1 mL of THF, and 0.04 mL (0.4 mmol) of oxalyl chloride was added. One drop of DMF was then added to the stirring suspension, and the mixture was stirred for 2 h. The resulting cloudy solution was concentrated to dryness and suspended in CH$_2$Cl$_2$. N-(3-Amino-5-tert-butyl-2-methoxy-phenyl)-methane-sulfonamide (81 mg; 0.30 mmol) was added, then 0.06 mL (0.5 mmol) of 2,6-lutidine, and the resulting solution was stirred overnight. The mixture was then washed with 1M NaHSO$_4$, saturated NaHCO$_3$, and brine. The organic portion was dried with Na$_2$SO$_4$, filtered, and concentrated. Chromatography (0–6.5% MeOH in CH$_2$Cl$_2$), with careful selection of only the pure fractions, provided 80 mg (0.15 mmol; 55%) of Example 14. ESI MS m/z 535 $[C_{27}H_{30}N_6O_4S+H]^+$.

Example 15

3-[4-(6-amino-pyridin-3-yl)-[1,2,3]triazol-1-yl]-N-(5-tert-butyl-3-methanesulfonylamino-2-methoxy-phenyl)-4-methyl-benzamide

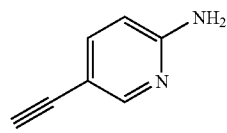

2-Amino-4-bromopyridine (Aldrich; 500 mg, 2.89 mmol), (PhCN)$_2$PdCl$_2$ (66 mg, 0.17 mmol), (t-Bu)$_3$P.BF$_4$ (101 mg, 0.345 mmol), and CuI (28 mg, 0.15 mmol) under N$_2$, were added 10 mL of dioxane, 1.02 mL (7.03 mmol) of Me$_3$SiCCH, and 0.49 mL (3.5 mmol) of i-Pr$_2$NH. The mixture was heated to 80° C. under and N$_2$ atmosphere overnight. The mixture was then diluted with EtOAc and filtered through Celite. The filtrate was washed with NH$_4$Cl and brine. The organic phase was dried with Na$_2$SO$_4$, filtered, and concentrated. The dark-brown residue was crystallized from hexanes to provide 2-amino-4-(trimethylsilyl)ethynyl pyridine (157 mg, 1.88 mmol, 65%). ESI MS m/z 191 $[C_{10}H_{14}N_2Si+H]^+$. The above trimethylsilylalkyne (340 mg, 1.79 mmol) was dissolved in 3.6 mL of cold THF and 3.6 mL of 1.0 M TBAF in THF was slowly added to the stirring mixture. After 2 h, the mixture was concentrated and partitioned between Et$_2$O and water. The ether layer was washed with brine, and the washes were extracted once with Et$_2$O. The extracts were combined, dried with MgSO$_4$, filtered, and concentrated to provide 191 mg of 2-amino-5-ethynyl pyridine (1.61 mmol, 91%).

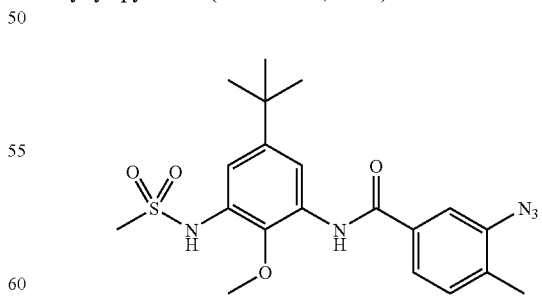

3-Azido-4-methyl benzoic acid (240 mg, 1.24 mmoL) was suspeneded in 3 mL of CH$_2$Cl$_2$ and 3 mL of THF. Oxalyl choride (0.14 mL, 1.5 mmol) was added, followed by 1 drop of 10% DMF in THF. The mixture was stirred for 1 h and then concentrated.

The residue was redissolved in dry CH$_2$Cl$_2$ (5mL) and 391 mg (1.27 mmol) of N-(3-amino-5-tert-butyl-2-methoxyphenyl)-methane-sulfonamide was added followed by 0.4 ml (2.5 mmol) of DIPEA. The mixture became homogeneous, and was stirred for 4 h, and then was washed with 1M NaHSO$_4$ and saturated NaHCO$_3$. The washes were extracted once with CH$_2$Cl$_2$ and the extracts were combined, dried with Na$_2$SO$_4$, filtered, and concentrated to provide 516 mg (93%) of 3-azido-N-(5-tert-butyl-3-methanesulfonylamino-2-methoxy-phenyl)-4-methyl-benzamide as a tan powder.

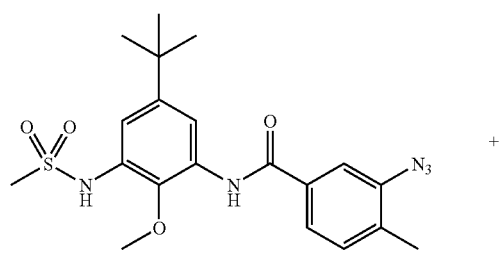

+

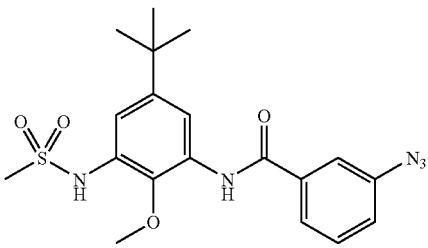

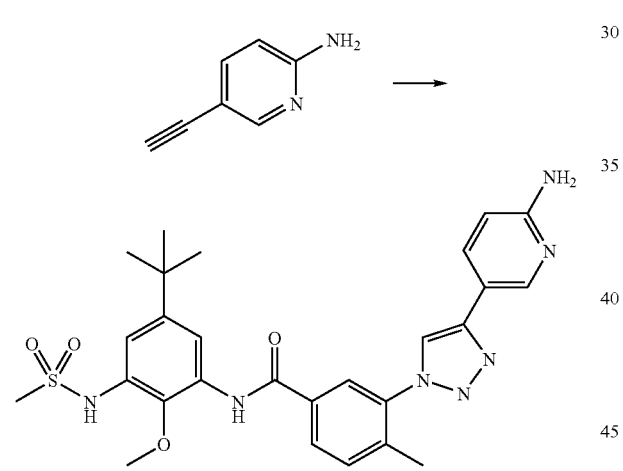

To a stirring suspension of 310 mg (0.719 mmol) of 3-azido-N-(5-tert-butyl-3-methanesulfonylamino-2-methoxy-phenyl)-4-methyl-benzamide in 2 mL of EtOH and 2 mL of water was added dropwise 4M NaOH until the mixture became homogeneous. A solution of 142 mg (0.719 mmol) of sodium ascorbate in 0.5 mL of water was added, followed by 100 mg (0.719 mmol) 2-amino-4-ethynyl pyridine in 1 mL of EtOH. Finally 0.72 mL of 0.1 M CuSO$_4$ was added, and the resulting mixture was stirred vigorously for 14 h. The mixture was then diluted with 40 mL of water and HOAc was added until a precipitate formed and the pH was about 6. The precipitate was filtered and washed with water and hexanes. The solids were chromatographed (0–5% MeOH/0.5% NH$_4$OH in CH$_2$Cl$_2$) to provide 321 mg (0.584 mmol; 81%) of the title compound. ESI MS m/z 548 [C$_{27}$H$_{31}$N$_7$O$_4$S—H]$^-$.

Example 16

N-(5-tert-Butyl-3-methanesulfonylamino-2-methoxy-phenyl)-3-(4-pyridin-3-yl-[1,2,3]triazol-1-yl)-benzamide

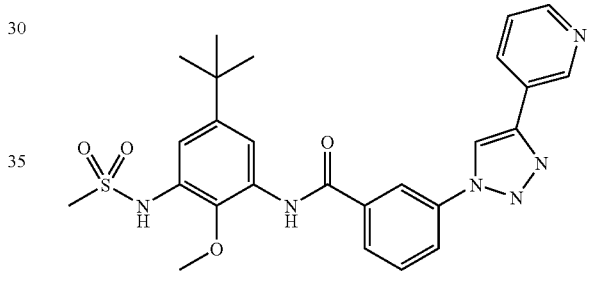

3-Azido-N-(5-tert-butyl-3-methanesulfonylamino-2-methoxy-phenyl)-benzamide was prepared from 3-azido benzoic acid and N-(3-amino-5-tert-butyl-2-methoxy-phenyl)-methane-sulfonamide in the same manner as 3-azido-N-(5-tert-butyl-3-methanesulfonylamino-2-methoxy-phenyl)-4-methyl-benzamide (Example 15). 3-Azido benzoic acid was prepared from 3-amino benzoic acid in the same manner as 3-azido-4-methyl benzoic acid.

Example 16 was prepared from 3-azido-N-(5-tert-butyl-3-methanesulfonylamino-2-methoxy-phenyl)-benzamide and 3-ethynyl pyridine in the same manner as Example 15. ESI MS m/z 521 [C$_{26}$H$_{28}$N$_6$O$_4$S+H]$^+$.

Example 17

N-(5-tert-Butyl-3-methanesulfonylamino-2-methoxy-phenyl)-4-methyl-3-(4-pyridin-4-yl-[1,2,3]triazol-1-yl)-benzamide

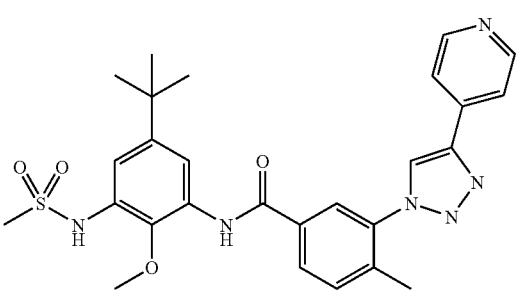

Example 17 was prepared from 3-azido-N-(5-tert-butyl-3-methanesulfonylamino-2-methoxy-phenyl)-4-methylbenzamide and 4-ethynyl pyridine hydrochloride (Aldrich) in the same manner as Example 15. ESI MS m/z 535 $[C_{27}H_{30}N_6O_4S+H]^+$.

Example 18

N-(5-tert-Butyl-3-methanesulfonylamino-2-methoxy-phenyl)-4-methyl-3-[4-(3-methyl-3H-imidazol-4-yl)-[1,2,3]triazol-1-yl]-benzamide

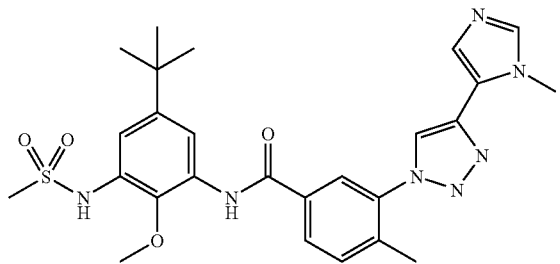

Example 18 was prepared from 3-azido-N-(5-tert-butyl-3-methanesulfonylamino-2-methoxy-phenyl)-4-methyl-benzamide and 5-ethynyl-1-methyl-1H-imidazole (Aldrich) in the same manner as Example 15. ESI MS m/z 538 $[C_{26}H_{31}N_7O_4S+H]^+$.

Example 19

N-(5-tert-Butyl-3-methanesulfonylamino-2-methoxy-phenyl)-4-methyl-3-[4-(6-methylamino-pyridin-3-yl)-[1,2,3]triazol-1-yl]-benzamide

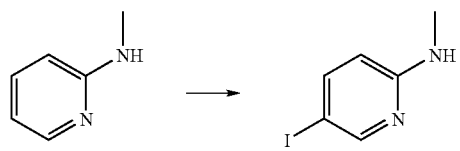

To a solution of 2-methylaminopyridine (Aldrich; 1.00 g, 9.25 mmol) in 10 mL of 1:1 HOAc and water was added 2.35 g (9.25 mmol) of $I_2$. The resulting brown solution was heated to 80° C. for 3 h. After cooling to room temperature, the mixture was neutralized with saturated $NaHCO_3$ and extracted with $Et_2O$. The extract was washed with water and brine, dried with $MgSO_4$, filtered, and concentrated to provide 540 mg of (5-iodo-pyridin-2-yl)-methyl-amine.

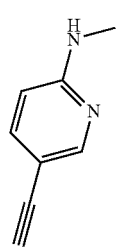

(5-Ethynyl-pyridin-2-yl)-methyl-amine was prepared from (5-iodo-pyridin-2-yl)-methyl-amine in the same manner as 2-chloro-5-ethynyl-pyridine (Example 1).

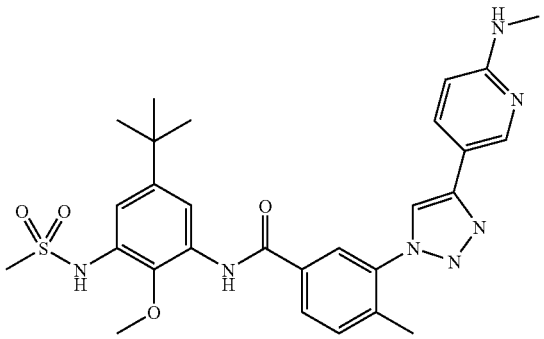

Example 19 was prepared from 3-azido-N-(5-tert-butyl-3-methanesulfonylamino-2-methoxy-phenyl)-4-methyl-benzamide and (5-ethynyl-pyridin-2-yl)-methyl-amine in the same manner as Example 15. ESI MS m/z 564 $[C_{28}H_{33}N_7O_4S+H]^+$.

Example 20

N-(5-tert-Butyl-3-methanesulfonylamino-2-methoxy-phenyl)-4-methyl-3-[4-(4-methyl-pyridin-3-yl)-[1,2,3]triazol-1-yl]-benzamide

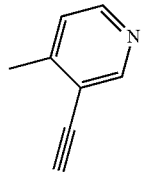

3-Ethynyl-4-methyl-pyridine was prepared from 3-bromo-4-methyl-pyridine in the same manner as 2-amino-3-ethynyl pyridine (Example 15).

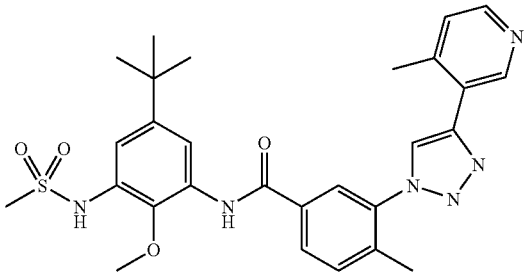

Example 20 was prepared from 3-azido-N-(5-tert-butyl-3-methanesulfonylamino-2-methoxy-phenyl)-4-methyl-benzamide and 3-ethynyl-4-methyl-pyridine in the same manner as Example 15. ESI MS m/z 549 $[C_{28}H_{32}N_6O_4S+H]^+$.

Example 21

N-(5-tert-Butyl-3-methanesulfonylamino-2-methoxy-phenyl)-3-fluoro-4-methyl-5-(4-pyridin-3-yl-[1,2,3]triazol-1-yl)-benzamide

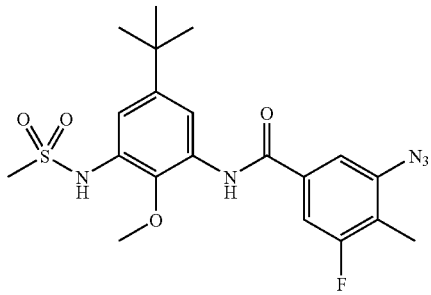

3-Azido-N-(5-tert-butyl-3-methanesulfonylamino-2-methoxy-phenyl)-5-fluoro-4-methyl-benzamide was prepared from 3-azido-5-fluoro-4-methyl benzoic acid (U.S. Ser. No. 04/102,492) and N-(3-amino-5-tert-butyl-2-methoxy-phenyl)-methane-sulfonamide in the same manner as 3-azido-N-(5-tert-butyl-3-methanesulfonylamino-2-methoxy-phenyl)-4-methyl-benzamide (Example 15).

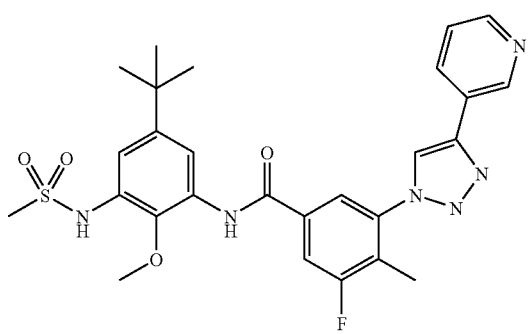

Example 21 was prepared from 3-azido-N-(5-tert-butyl-3-methanesulfonylamino-2-methoxy-phenyl)-5-fluoro-4-methyl-benzamide and 3-ethynyl-pyridine in the same manner as Example 15. ESI MS m/z 553 $[C_{27}H_{29}FN_6O_4S+H]^+$.

Example 22

N-(5-tert-Butyl-3-methanesulfonylamino-2-methoxy-phenyl)-3-[4-(6-methoxy-pyridin-3-yl)-[1,2,3]triazol-1-yl]-4-methyl-benzamide

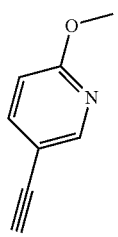

5-Ethynyl-2-methoxy pyridine was prepared from 5-bromo-2-methoxy-pyridine (Aldrich) in the same manner as 2-chloro-5-ethynyl-pyridine (Example 1).

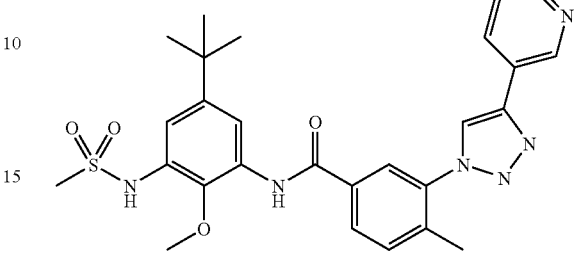

Example 22 was prepared from 3-azido-N-(5-tert-butyl-3-methanesulfonylamino-2-methoxy-phenyl)-4-methyl-benzamide and 5-ethynyl-2-methoxy-pyridine in the same manner as Example 15. ESI MS m/z 565 $[C_{28}H_{32}N_6O_5S+H]^+$.

Example 23

N-(5-tert-Butyl-3-methanesulfonylamino-2-methoxy-phenyl)-3-[4-(5-methoxy-pyridin-3-yl)-1,2,3-triazol-1-yl]-4-methyl-benzamide

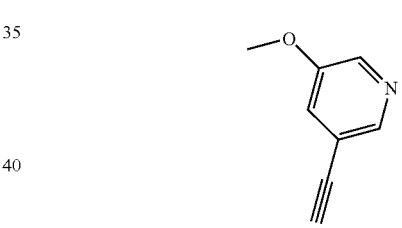

5-Ethynyl-3-methoxy pyridine was prepared from 5-bromo-3-methoxy-pyridine (Frontier) in the same manner as 2-chloro-5-ethynyl-pyridine (Example 1).

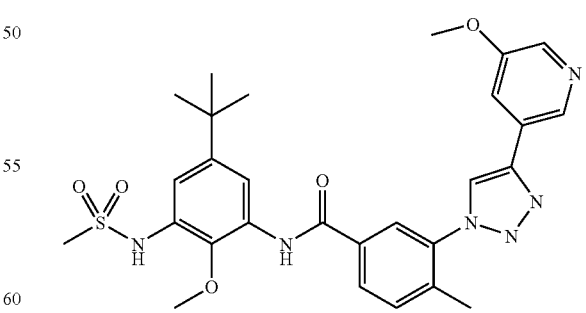

Example 23 was prepared from 3-azido-N-(5-tert-butyl-3-methanesulfonylamino-2-methoxy-phenyl)-4-methyl-benzamide and 5-ethynyl-3-methoxy-pyridine ( ) in the same manner as Example 15. ESI MS m/z 565 $[C_{28}H_{32}N_6O_5S+H]^+$.

Example 24

N-(5-tert-Butyl-3-methanesulfonylamino-2-methoxy-phenyl)-3-[4-(6-dimethylamino-pyridin-3-yl)-[1,2,3]triazol-1-yl]-4-methyl-benzamide

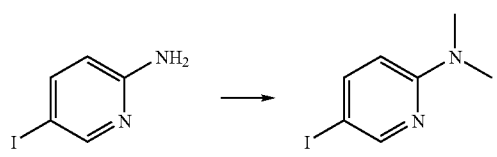

To a solution of 2-amino-5-iodopyridine (1.00 g; 4.55 mmol) in 10 mL of DMF was added 545 mg of 60% NaH (13.6 mmol) and 0.85 mL of iodomethane (13.6 mmol). The mixture was stirred for 14 h, and the mixture was neutralized with 1M HOAc. The mixture was extracted with Et₂O, the extract was washed with water and brine, dried with MgSO₄, filtered, and concentrated. Chromatography (0–25% EtOAc in hexanes) provided 700 mg (2.82 mmol) of (5-iodo-pyridin-2-yl)-dimethyl-amine.

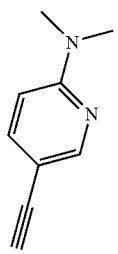

(5-Ethynyl-pyridin-2-yl)-dimethyl-amine was prepared from (5-iodo-pyridin-2-yl)-dimethyl-amine in the same manner as 2-chloro-5-ethynyl-pyridine (Example 1).

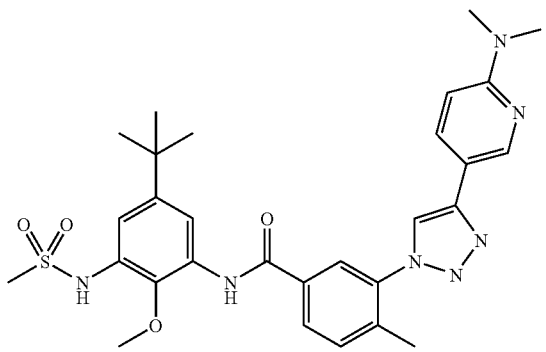

Example 24 was prepared from 3-azido-N-(5-tert-butyl-3-methanesulfonylamino-2-methoxy-phenyl)-4-methyl-benzamide and (5-ethynyl-pyridin-2-yl)-dimethyl-amine in the same manner as Example 15. ESI MS m/z 578 $[C_{29}H_{35}N_7O_4S+H]^+$.

Example 25

N-(5-tert-Butyl-3-methanesulfonylamino-2-methoxy-phenyl)-4-methyl-3-[4-(3-methyl-2-methylsulfanyl-3H-imidazol-4-yl)-[1,2,3]triazol-1-yl]-benzamide

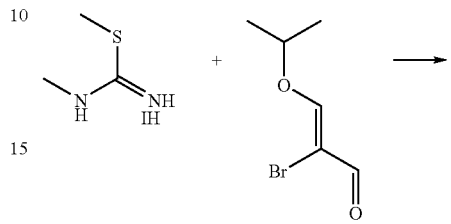

To a mixture of 2.65 g (11.4 mmol) of 1,2-dimethyl-isothiourea hydroiodide and 1.00 g (10.4 mmol) of 2-bromo-3-isopropoxy-propenal 8 mL of MeCN was added 1.58 g (11.4 mmol) of K₂CO₃ (Shilcrat, S. C. et al. *J. Org. Chem.*, 1997, 62, 8449–8454). The mixture was stirred at 35° C. under N₂ for 16 h, water (20 ml) was added, and the mixture was extracted with CH₂Cl₂ (200 mL). The extract was dried over MgSO₄, filtered, concentrated, and chromatographed (0 to 100% EtOAc in hexanes) to provide 1.09 g of 3-methyl-2-methylsulfanyl-3H-imidazole-4-carbaldehyde and 284 mg of 1-methyl-2-methylsulfanyl-1H-imidazole-4-carbaldehyde.

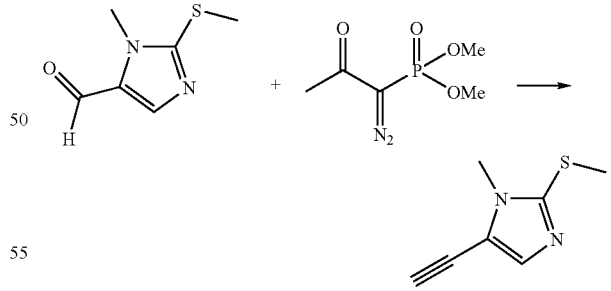

To a mixture of 850 mg (5.44 mmol) of 3-methyl-2-methylsulfanyl-3H-imidazole-4-carbaldehyde and 1.34 g (7.00 mmol) of dimethyl 2-oxo-1-diazopropylphosphinate in 15 mL of MeOH was added 1.52 g (11.0 mmol) of K₂CO₃. The mixture was stirred at room temperature for 28 hours. The mixture was diluted with saturated K₂CO₃ (10 mL) and and extracted with CH₂Cl₂ (3×75 mL). The combined extracts were dried over MgSO₄, concentrated, and chromatographed (0 to 100% EtOAc in hexanes) to give the 5-ethynyl-1-methyl-2-methylsulfanyl-1H-imidazole (600 mg, 72%) as a colorless liquid.

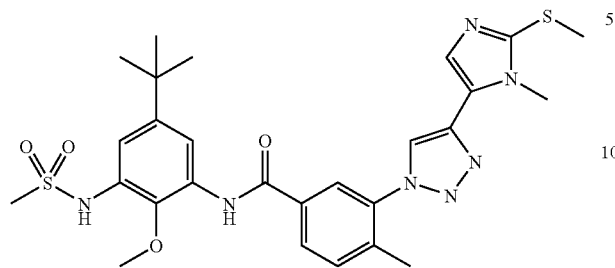

Example 25 was prepared from 3-azido-N-(5-tert-butyl-3-methanesulfonylamino-2-methoxy-phenyl)-4-methyl-benzamide and 5-ethynyl-1-methyl-2-methylsulfanyl-1H-imidazole in the same manner as Example 15. ESI MS m/z 584 [C$_{27}$H$_{33}$N$_7$O$_4$S+H]$^+$.

Example 26

N-(5-tert-Butyl-3-methanesulfonylamino-2-methoxy-phenyl)-3-[4-(6-cyclopropylamino-pyridin-3-yl)-[1,2,3]triazol-1-yl]-4-methyl-benzamide

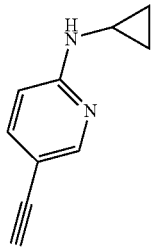

Cyclopropyl-(5-ethynyl-pyridin-2-yl)-amine was prepared from cyclopropyl-(5-iodo-pyridin-2-yl)-amine in the same manner as 2-chloro-5-ethynyl-pyridine (Example 1). Cyclopropyl-(5-iodo-pyridin-2-yl)-amine was prepared from 2-chloro-5-iodo-pyridine and cyclopropyl amine in the same manner as cyclopropylmethyl-(5-iodo-pyridin-2-yl)-amine (Example 2).

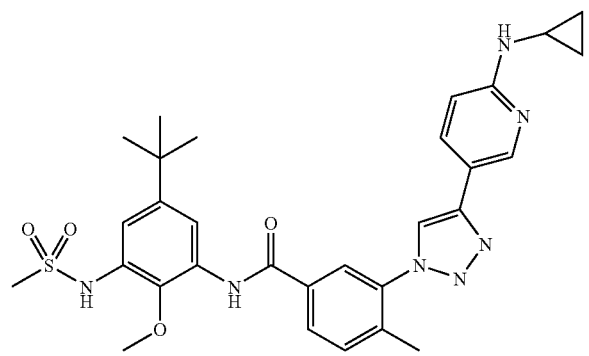

Example 26 was prepared from 3-azido-N-(5-tert-butyl-3-methanesulfonylamino-2-methoxy-phenyl)-4-methyl-benzamide and cyclopropyl-(5-ethynyl-pyridin-2-yl)-amine in the same manner as Example 15. ESI MS m/z 590 [C$_{30}$H$_{35}$N$_7$O$_4$S+H]$^+$.

Example 27

N-(5-tert-Butyl-3-methanesulfonylamino-2-methoxy-phenyl)-3-{4-[2-(1-hydroxy-1-methyl-ethyl)-3-methyl-3H-imidazol-4-yl]-[1,2,3]triazol-1-yl}-4-methyl-benzamide

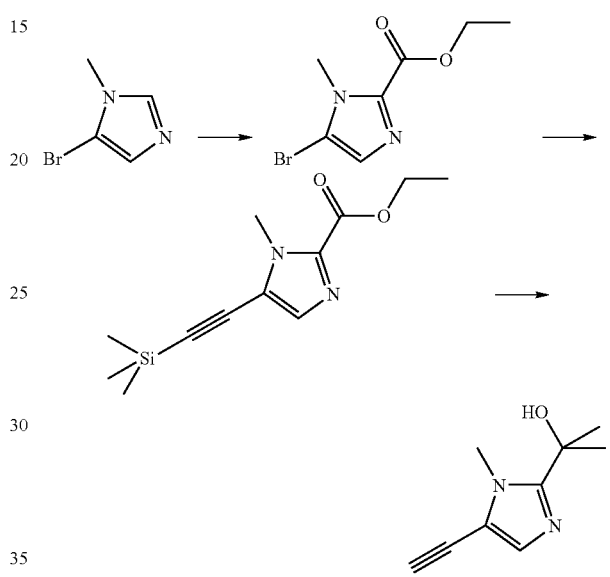

Ethyl chloroformate (1.19 mL, 12.4 mmol) in MeCN (5 mL) was added dropwise to a 1.00 g (6.21 mmol) of 5-bromo-1-methyl-1H-imidazole (Aldrich) in 30 mL of MeCN under N$_2$. The mixture was stirred and allowed to warm to rt overnight. The mixture was concentrated and the residue was treated with 2M NaOH (100 mL) and extratcted with CH$_2$Cl$_2$ (3×100 mL). The combined extracts were washed with brine, dried with MgSO$_4$, filtered, concentrated, and chromatographed (0–50% EtOAc in hexanes) to give the 5-bromo-1-methyl-1H-imidazole-2-carboxylic acid ethyl ester as a yellow oil (800 mg).

To a solution of 800 mg (3.43 mmol) of 5-bromo-1-methyl-1H-imidazole-2-carboxylic acid ethyl ester in Et$_3$N (10 mL) and THF (10 mL) was added 33 mg (0.17 mmol) of CuI and 120 mg (0.10 mmol) of Pd(PPh$_3$)$_4$. Trimethylsilylacetylene (0.48 mL, 3.4 mmol) was then added and the reaction was heated at 70° C. under N$_2$. After 12 h, the mixture was cooled and filtered though a pad of celite, and then concentrated and chromatographed (0–50% EtOAc in hexanes) to give 1-methyl-5-trimethylsilanylethynyl-1H-imidazole-2-carboxylic acid ethyl ester as a brown oil (205 mg).

A solution of 0.67 mL of 3M MeMgBr in ether (2.0 mmol) was added to a stirring 0° C. solution of 200 mg of 1-methyl-5-trimethylsilanylethynyl-1H-imidazole-2-carboxylic acid ethyl ester (0.80 mmol) in 5 mL of THF over 15 min. The mixture was allowed to warm to rt and stirred overnight. Water (20 mL) was added and the mixture was extracted with EtOAc (3×100 mL). The combined extracts were washed with brine and dried with MgSO₄, filtered, concentrated and chromatographed (10–100 EtOAc in hexanes) to give 2-(1-methyl-5-trimethylsilanylethynyl-1H-imidazol-2-yl)-propan-2-ol as a yellow oil (110 mg).

To 2-(1-Methyl-5-trimethylsilanylethynyl-1H-imidazol-2-yl)-propan-2-ol (100 mg, 0.42 mmol) in 5 mL of THF was added IM TBAF in THF (1.3 mL, 1.3 mmol). The reaction was stirred at rt overnight, and then was diluted with 50 mL of water and extracted with EtOAc (3×50 mL). The combined extracts were washed with brine and dried with MgSO₄, filtered, and concentrated to provide 58 mg of 2-(5-ethynyl-1-methyl-1H-imidazol-2-yl)-propan-2-ol.

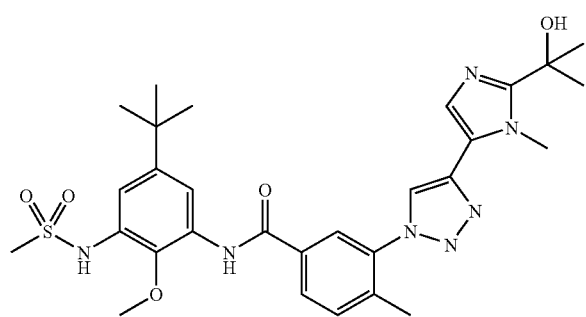

Example 27 was prepared from 3-azido-N-(5-tert-butyl-3-methanesulfonylamino-2-methoxy-phenyl)-4-methyl-benzamide and 2-(5-ethynyl-1-methyl-1H-imidazol-2-yl)-propan-2-ol in the same manner as Example 15. ESI MS m/z 596 $[C_{29}H_{37}N_7O_5S+H]^+$.

Example 28

N-(5-tert-Butyl-3-methanesulfonylamino-2-methoxy-phenyl)-3-{4-[6-(cyclopropylmethyl-amino)-pyridin-3-yl]-[1,2,3]triazol-1-yl}-4-methyl-benzamide

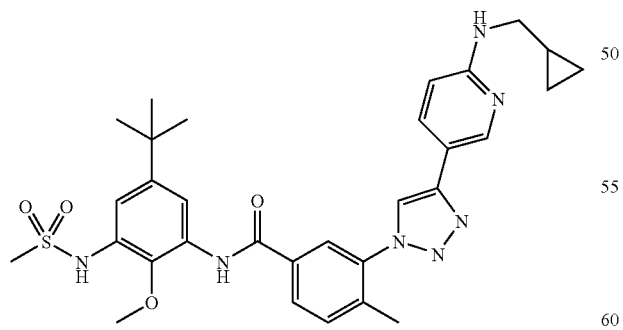

Example 28 was prepared from 3-azido-N-(5-tert-butyl-3-methanesulfonylamino-2-methoxy-phenyl)-4-methyl-benzamide and cyclopropylmethyl-(5-trimethylsilanyl-ethynyl-pyridin-2-yl)-amine in the same manner as Example 15. ESI MS m/z 604 $[C_{31}H_{37}N_7O_4S+H]^+$.

Example 29

N-(5-tert-Butyl-3-methanesulfonylamino-2-methoxy-phenyl)-4-methyl-3-[4-(3-methyl-2-morpholin-4-yl-3H-imidazol-4-yl)-[1,2,3]triazol-1-yl]-benzamide

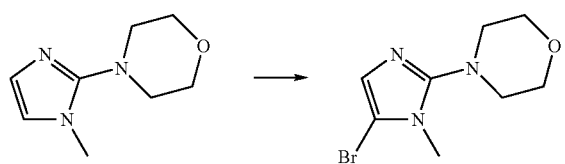

4-(1-Methyl-1H-imidazol-2-yl)-morpholine (Nagarajan, K. et al. Indian J. Chem. Sect. B, 21, 10, 1982, 949–952) (1.02 g, 6.08 mmol) was dissolved in 35 mL of 1,4-dioxane under and N₂ atmosphere. The mixture was heated to 60° C. and a solution of 0.34 mL (6.4 mmol) of Br₂ in 10 mL of dichloroethane was added slowly. The mixture was heated for 1 h, then cooled. The mixture was concentrated and the residue was partitioned between 6.5 mL of 1 N NaOH and 25 mL of EtOAc. The NaOH solution was extracted twice more with EtOAc, and the extracts were washed with NaHCO₃ and brine, dried with Na₂SO₄, filtered, concentrated, and chromatographed (0–4% MeOH (0.5% NH₄OH) in CH₂Cl₂) to provide 464 mg of 4-(5-bromo-1-methyl-1H-imidazol-2-yl)-morpholine.

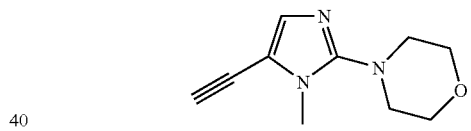

4-(5-Ethynyl-1-methyl-1H-imidazol-2-yl)-morpholine was prepared from 4-(5-bromo-1-methyl-1H-imidazol-2-yl)-morpholine in the same manner as 2-chloro-5-ethynyl-pyridine (Example 1).

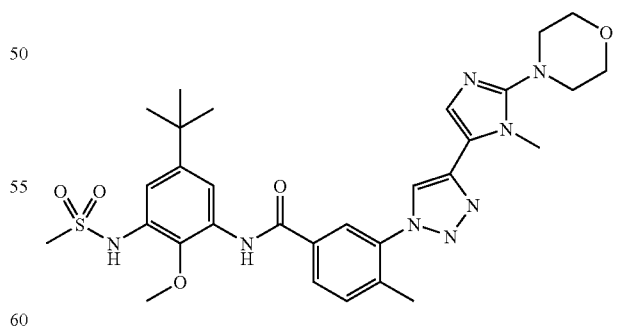

Example 29 was prepared from 3-azido-N-(5-tert-butyl-3-methanesulfonylamino-2-methoxy-phenyl)-4-methyl-benzamide and 4-(5-ethynyl-1-methyl-1H-imidazol-2-yl)-morpholine in the same manner as Example 15. ESI MS m/z 623 $[C_{30}H_{38}N_8O_5S+H]^+$.

Example 30

N-(5-tert-Butyl-3-methanesulfonylamino-2-methoxy-phenyl)-3-{4-[2-(2,2-dimethyl-propionyl)-3-methyl-3H-imidazol-4-yl]-[1,2,3]triazol-1-yl}-4-methyl-benzamide

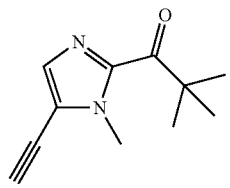

Preparation of 1-(5-ethynyl-1-methyl-1H-imidazol-2-yl)-2,2-dimethyl-propan-1-one was prepared from 5-bromo-1-methyl imidazole and pivaloyl chloride in the same manner as 1-methyl-5-ethynyl-1H-imidazole-2-carboxylic acid ethyl ester (Example 27).

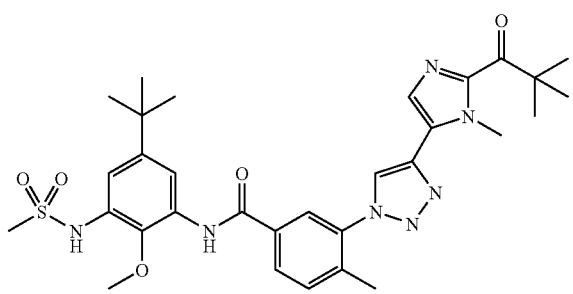

Example 30 was prepared from 3-azido-N-(5-tert-butyl-3-methanesulfonylamino-2-methoxy-phenyl)-4-methyl-benzamide and 1-(5-ethynyl-1-methyl-1H-imidazol-2-yl)-2,2-dimethyl-propan-1-one in the same manner as Example 15. ESI MS m/z 622 $[C_{31}H_{39}N_7O_5S+H]^+$.

Example 30

N-(5-tert-Butyl-3-methanesulfonylamino-2-methoxy-phenyl)-3-[4-(2-tert-butylsulfanyl-3-methyl-3H-imidazol-4-yl)-[1,2,3]triazol-1-yl]-4-methyl-benzamide

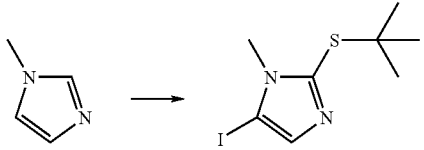

A 1.6 M solution of n-BuLi in hexanes (16.2 ml; 25.9 mmol) was added over the course of 5 minutes to 2.06 g (25.9 mmol) of 1-methyl-1H-imidazole in 100 mL of THF at −78° C. After stirring for 30 minutes, 5.00 mL (25.9 mmol) of t-butyldisulfide was added and reaction was warmed to rt and stirred for 30 min. The solution was cooled to −78° C. and an additional 16.2 mL (25.9 mmol) of n-BuLi was added over 5 minutes. The mixture was stirred cold for 1 h when 6.57 g (25.9 mmol) of $I_2$ was added. The mixture was warmed to rt and stirred for 15 minutes. Saturated NaHSO$_3$ (20 mL) was added and mixture was extracted with ether (4×100 mL). The extracts were combined and dried over MgSO$_4$, filtered, concentrated, and chromatographed (0 to 40% EtOAc in hexanes) to give 2-tert-butylsulfanyl-5-iodo-1-methyl-1H-imidazole as a tan semi-solid (421 mg).

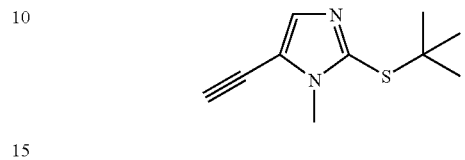

2-tert-Butylsulfanyl-5-iodo-1-methyl-1H-imidazole was prepared from 2-tert-butylsulfanyl-5-iodo-1-methyl-1H-imidazole in the same manner as 2-chloro-5-ethynyl-pyridine (Example 1).

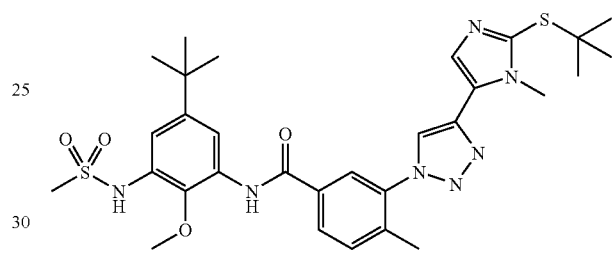

Example 30 was prepared from 3-azido-N-(5-tert-butyl-3-methanesulfonylamino-2-methoxy-phenyl)-4-methyl-benzamide and 2-tert-butylsulfanyl-5-ethynyl-1-methyl-1H-imidazole in the same manner as Example 15. ESI MS m/z 626 $[C_{30}H_{39}N_7O_4S_2+H]^+$.

Example 32

N-(5-tert-Butyl-3-methanesulfonylamino-2-methoxy-phenyl)-3-{4-[6-(cyclopropylmethyl-amino)-5-methoxy-pyridin-3-yl]-[1,2,3]triazol-1-yl}-4-methyl-benzamide

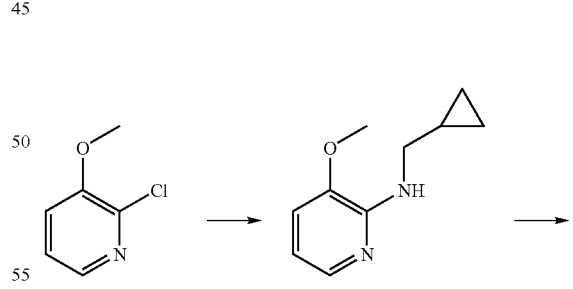

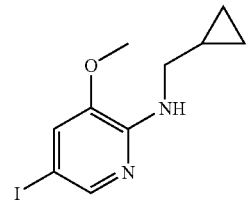

A mixture of 2.00 g (13.9 mmol) of 2-chloro-3-methoxy-pyridine (Lancaster) in 13.3 mL of aminomethylcyclopropane was heated at 125° C. in a sealed tube for 4 days. The mixture was then cooled to room temperature and partitioned between Et$_2$O and water. The aqueous layer was washed with Et$_2$O, and the combined extracts were washed with brine, dried with MgSO$_4$, filtered, and concentrated. The residue was passed through a plug of silica gel with CH$_2$Cl$_2$ to provide 1.25 g (7.01 mmol; 50%) of 2-cyclopropylmethylamino-3-methoxypyridine. To a mixture of 2-cyclopropyl-methylamino-3-methoxypyridine (430 mg; 2.41 mmol) in 7.5 mL of 2:1 HOAc and water was added 612 mg (2.41 mmol) of I$_2$. The mixture was heated to 100° C. for 4 h, and an additional 320 mg of I$_2$ was added. The mixture was heated for 2 h, then cooled to room temperature and stirred for 12 h. Saturated NaHCO$_3$ (20 mL) and water (20 mL) were added and the suspension was extracted with EtOAc. The extract was then washed with 10% Na$_2$S$_2$O$_3$, water, and brine, dried with MgSO$_4$, filtered, and concentrated. The pure fractions from chromatography (1–4% MeOH in CH$_2$Cl$_2$) were concentrated to provide 145 mg of 2-cyclopropylmethylamino-3-methoxy-5-iodopyridine.

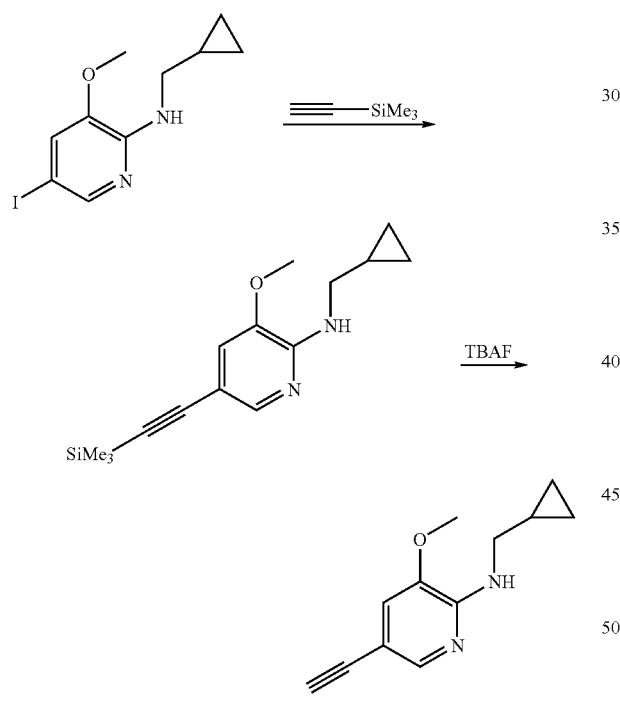

To a mixture of 2-cyclopropylmethylamino-3-methoxy-5-iodopyridine (145 mg; 0.477 mmol), (Ph$_3$P)$_2$PdCl$_2$ (17 mg; 0.024 mmol), and CuI (5 mg; 0.02 mmol) under N$_2$ was added 2 mL of Et$_3$N and 75 µL of Me$_3$SiCCH (0.525 mmol). The resulting green suspension was stirred for 30 min at 50° C. The mixture was cooled to room temperature and partitioned between EtOAc and water. The organic extract was washed with water, washed with brine, dried with MgSO$_4$, filtered, and concentrated. Chromatography (0–1% MeOH in CH$_2$Cl$_2$) provided 130 mg of 2-cyclopropanemethylamino-3-methoxy-5-(trimethylsilyl)ethynylpyridine contaminated with a small amount of Ph$_3$P.

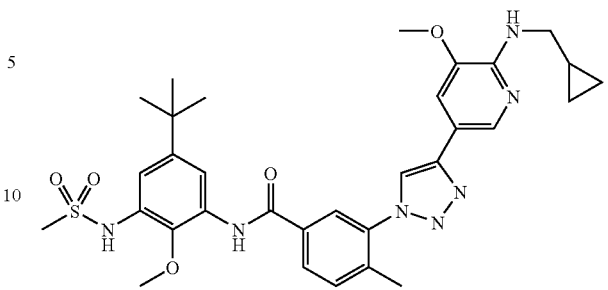

Example 32 was prepared from 3-azido-N-(5-tert-butyl-3-methanesulfonylamino-2-methoxy-phenyl)-4-methyl-benzamide and 2-cyclopropanemethylamino-3-methoxy-5-(trimethylsilyl)ethynylpyridine in the same manner as Example 15. ESI MS m/z 634 [C$_{32}$H$_{39}$N$_7$O$_5$S+H]$^+$.

Example 33

3-{4-[2-(Hydroxy-phenyl-methyl)-3-methyl-3H-imidazol-4-yl]-[1,2,3]triazol-1-yl}-N-[3-methane-sulfonylamino-2-methoxy-5-(1-methyl-cyclopropyl)-phenyl]-4-methyl-benzamide

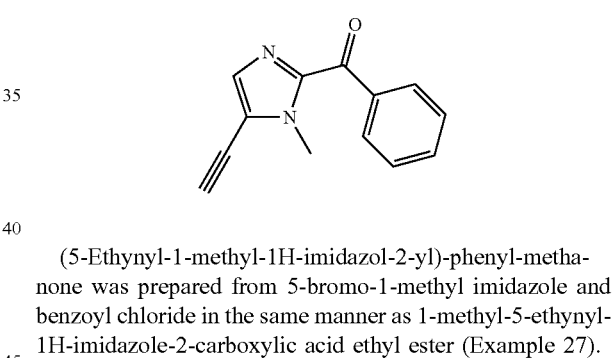

(5-Ethynyl-1-methyl-1H-imidazol-2-yl)-phenyl-methanone was prepared from 5-bromo-1-methyl imidazole and benzoyl chloride in the same manner as 1-methyl-5-ethynyl-1H-imidazole-2-carboxylic acid ethyl ester (Example 27).

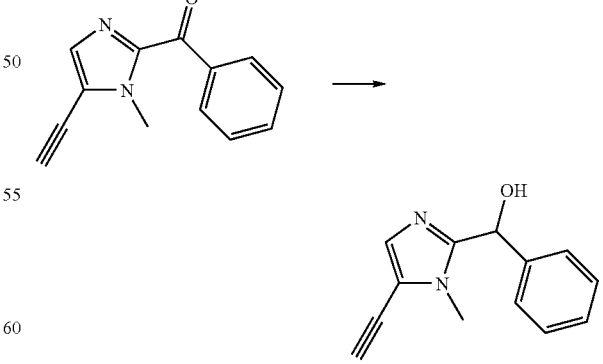

A solution of 200 mg (0.951 mmol) of (5-ethynyl-1-methyl-1H-imidazol-2-yl)-phenyl-methanone in 1 mL of MeOH was added dropwise to a 0° C. solution of 54 mg (1.43 mmol) of NaBH$_4$ in 5 mL of MeOH. After stirring for 2 h, 10 mL of water was added and the mixture was extracted with CH$_2$Cl$_2$ (3×50 mL). The combined extracts were washed with brine, dried with MgSO$_4$, filtered, concentrated, and chromatographed (0–80% EtOAc in hexanes) to give (5-ethynyl-1-methyl-1H-imidazol-2-yl)-phenyl-methanol as a white solid (75 mg).

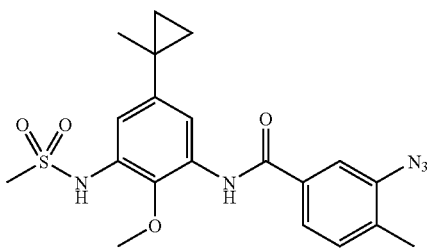

3-Azido-N-[3-methanesulfonylamino-2-methoxy-5-(1-methyl-cyclopropyl)-phenyl]-4-methyl-benzamide was prepared from 3-azido-4-methyl benzoic acid and N-[3-amino-2-methoxy-5-(1-methyl-cyclopropyl)-phenyl]-methanesulfonamide in the same manner as 3-azido-N-(5-tert-butyl-3-methanesulfonylamino-2-methoxy-phenyl)-4-methyl-benzamide (Example 15).

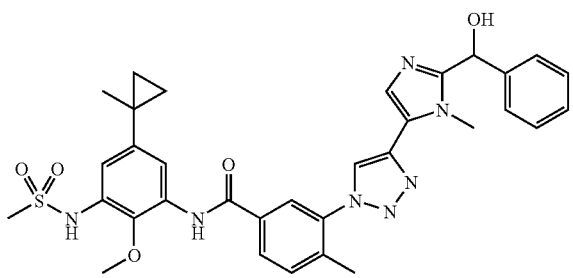

Example 33 was prepared from 3-azido-N-[3-methanesulfonylamino-2-methoxy-5-(1-methyl-cyclopropyl)-phenyl]-4-methyl-benzamide and 5-ethynyl-1-methyl-1H-imidazol-2-yl)-phenyl-methanol in the same manner as Example 15. ESI MS m/z 642 [C$_{33}$H$_{35}$N$_7$O$_5$S+H]$^+$.

Example 34

3-[4-(2-Benzoyl-3-methyl-3H-imidazol-4-yl)-[1,2,3]triazol-1-yl]-N-[3-methanesulfonylamino-2-methoxy-5-(1-methyl-cyclopropyl)-phenyl]-4-methyl-benzamide

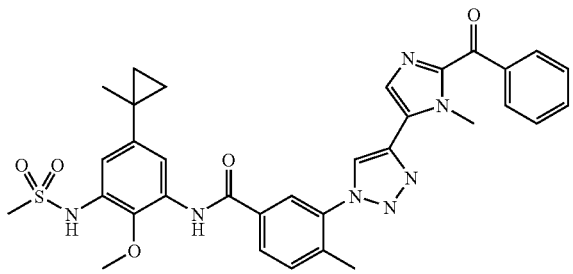

Example 34 was prepared from (5-ethynyl-1-methyl-1H-imidazol-2-yl)-phenyl-methanone (Example 33) and 3-azido-N-[3-methanesulfonylamino-2-methoxy-5-(1-methyl-cyclopropyl)-phenyl]-4-methyl-benzamide (Example 33) in the same manner as Example 15. ESI MS m/z 640 [C$_{33}$H$_{33}$N$_7$O$_5$S+H]$^+$.

Example 35

3-[4-(2-Benzoyl-3-methyl-3H-imidazol-4-yl)-[1,2,3]triazol-1-yl]-N-(5-tert-butyl-3-methanesulfonylamino-2-methoxy-phenyl)-4-methyl-benzamide

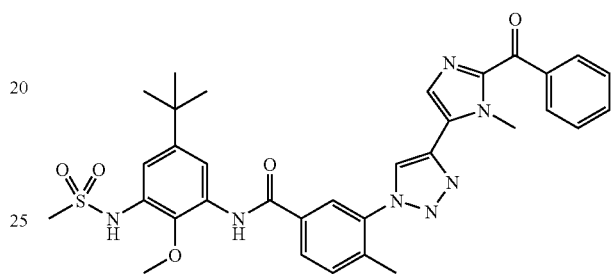

Example 35 was prepared from (5-ethynyl-1-methyl-1H-imidazol-2-yl)-phenyl-methanone (Example 33) and 3-azido-N-(5-tert-butyl-3-methanesulfonylamino-2-methoxy-phenyl)-4-methyl-benzamide in the same manner as Example 15. ESI MS m/z 642 [C$_{33}$H$_{35}$N$_7$O$_5$S+H]$^+$.

Example 36

3-[4-(2-Benzenesulfonyl-3-methyl-3H-imidazol-4-yl)-[1,2,3]triazol-1-yl]-N-(5-tert-butyl-3-methanesulfonylamino-2-methoxy-phenyl)-4-methyl-benzamide

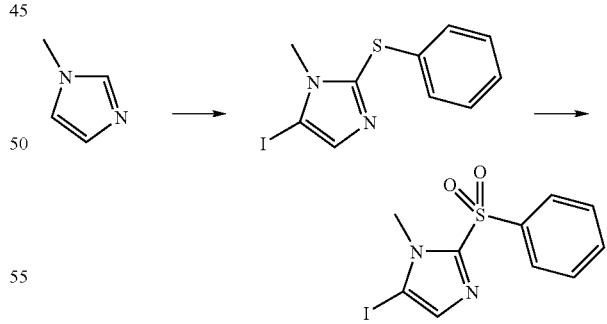

1-Methylimidazole (4.0 mL, 50.3 mmol) was dissolved in dry THF (250 mL) under a N$_2$ atmosphere. The solution was cooled to −78° C. and n-BuLi (2.5 M in hexanes, 20.1 mL, 50.3 mmol) was added slowly. After 15 min phenyl disulfide (11.0 g, 50.3 mmol) was added and the reaction was warmed to room temperature and stirred for 30 min. The reaction was then cooled to −78° C. and a second portion of n-BuLi (20.1 mL, 50.3 mmol) was added. After 30 min, iodine (13.4 g, 50.3 mmol) was added. The reaction was warmed to room temperature and Et$_2$O (400 mL) and 1 M sodium bisulfite (250 mL) was added. The layers were separated and the organic layer washed with brine, dried over MgSO$_4$, and filtered. The solution was concentrated and hexanes were added to the resulting precipitate. The precipitate was collected by vacuum filtration, washed with hexanes, and dried under vacuum to provide 5-iodo-1-methyl-2-phenylsulfanyl-1H-imidazole (4.0 g, 25%) as a white solid: ESI MS m/z 317 [C$_{10}$H$_9$IN$_2$S+H]$^+$.

5-Iodo-1-methyl-2-phenylsulfanyl-1H-imidazole (2.0 g, 6.3 mmol) was dissolved in CH$_2$Cl$_2$ (50 mL). m-CPBA (2.8 g, 12.6 mmol) was added and the reaction stirred for 1 h during which time a white precipitate formed. An additional portion of m-CPBA (1.0 g) was added and the reaction stirred 1 h. Saturated NaHCO$_3$ was added and the layers were separated. The aqueous layer was extracted with CH$_2$Cl$_2$ and the combined extracts were washed with saturated NaHCO$_3$ and brine, dried over Na$_2$SO$_4$, filtered, and concentrated. The residue was dissolved in MeOH (60 mL) with a small amount of CH$_2$Cl$_2$. The mixture was boiled until homogeneous, allowed to cool to room temperature and then cooled in ice. The resulting needles were collected by vacuum filtration, washed with MeOH and hexanes, and then dried under vacuum to provide benzenesulfonyl-5-iodo-1-methyl-1H-imidazole (1.23 g, 56%) as a white solid.

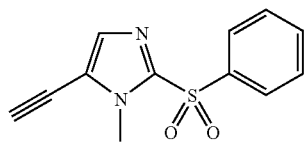

2-benzenesulfonyl-5-ethynyl-1-methyl-1H-imidazole was prepared from 2-benzenesulfonyl-5-iodo-1-methyl-1H-imidazole in the same manner as 2-chloro-5-ethynyl pyridine (Example 1).

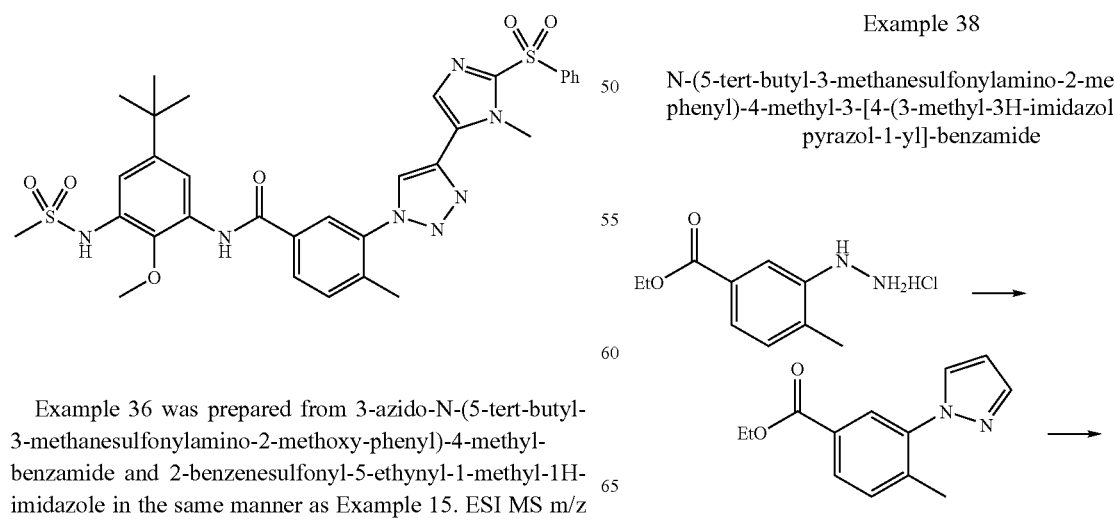

Example 36 was prepared from 3-azido-N-(5-tert-butyl-3-methanesulfonylamino-2-methoxy-phenyl)-4-methyl-benzamide and 2-benzenesulfonyl-5-ethynyl-1-methyl-1H-imidazole in the same manner as Example 15. ESI MS m/z 678 [C$_{32}$H$_{35}$N$_7$O$_6$S+H]$^+$.

Example 37

N-(5-tert-butyl-3-methanesulfonylamino-2-methoxy-phenyl)-3-{4-[6-(2-dimethylamino-ethylamino)-pyridin-3-yl]-[1,2,3]triazol-1-yl}-4-methyl-benzamide

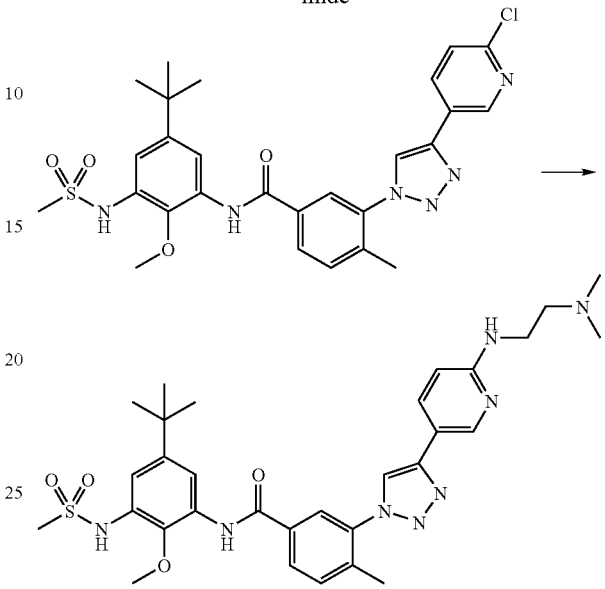

To a suspension of Example 1 (100 mg; 0.176 mmol), Pd$_2$dba$_3$ (13 mg; 0.014 mmol), and t-BuOK (68 mg; 0.70 mmol) in 1.5 mL of toluene stirring under N$_2$ was added N,N-dimethylaminoethylamine (31 mg; 0.35 mmol) and 2,8,9-triisobutyl-2,5,8,9-tetraaza-1-phosphabicyclo[3.3.3]undecane (9.0 mg; 0.026 mmol). The resulting suspension was heated to 100° C. for 14 h. The reaction was then cooled to room temperature and partitioned between EtOAc and water. The layers were separated, with the organic portion being washed twice with water and once with brine. The solution was dried with MgSO$_4$, filtered, and concentrated. The pure fractions isolated from chromatography (2–7% MeOH (0.5% NH$_4$OH in CH$_2$Cl$_2$) were combined and concentrated to provide 10 mg of Example 37. ESI MS m/z 621 [C$_{31}$H$_{40}$N$_8$O$_4$S+H]$^+$.

Example 38

N-(5-tert-butyl-3-methanesulfonylamino-2-methoxy-phenyl)-4-methyl-3-[4-(3-methyl-3H-imidazol-4-yl)-pyrazol-1-yl]-benzamide

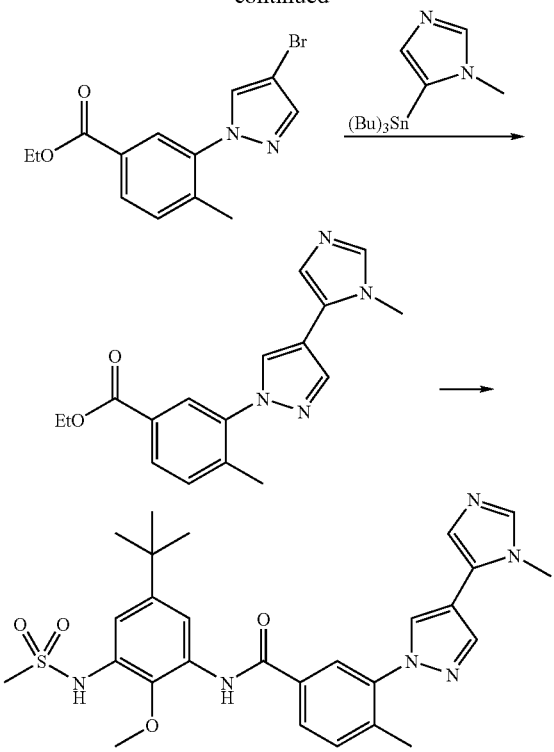

Butyllithium (3.75 mL, 9.40 mmol) and TMEDA (2.24 mL, 14.85 mmol) were stirred at −20° C. in hexanes (7 mL) in an ethanol/dry ice/water bath for 30 minutes. 1-Methylimidazole (0.5 mL, 6.27 mmol) was added and the mixture stirred at room temperature for 1 h. After cooling to −20° C., Bu₃SnCl (1.70 mL, 15.67 mmol) was added dropwise. The reaction stirred for 15 minutes at −20° C. then at room temperature overnight before being quenched with 1:1 EtOAc/water (20 mL). The layers were separated and the aqueous layer extracted with EtOAc (3×). The combined organics were washed with water, dried over Na₂SO₄, concentrated, and chromatographed (4:96 MeOH/EtOAc) to give 1-methyl-5-tributylstannanyl-1H-imidazole (0.486 g).

A solution of 3-hydrazino-4-methyl benzoic acid (See U.S. provisional application 60/570,284) (1.0 g, 4.93 mmol), malonaldehyde(bismethylacetate) (0.82 mL, 4.93 mmol), and concentrated HCl (1 mL) in EtOH (20 mL) was heated to reflux for 4 h. After cooling to room temperature, the reaction was poured into ice water, neutralized with 2N NaOH, and extracted with CH₂Cl₂ (3×). The organic layers were dried over Na₂SO₄, filtered and concentrated to afford 4-methyl-3-pyrazol-1-yl-benzoic acid ethyl ester (536 mg, 47%) as a yellow oil. A solution of the pyrazole (536 mg, 2.33 mmol) and bromine (0.167mL, 3.26 mmol) in CHCl₃ (15 mL) was refluxed for 4.5 h then cooled and concentrated. Chromatography (1:1 EtOAc/hexanes) yielded 3-(4-bromo-pyrazol-1-yl)-4-methyl-benzoic acid ethyl ester (0.739 g, 99%). The bromopyrazole (366 mg, 1.18 mmol) was dissolved in dioxane (2 mL) and flushed with N₂. 1-Methyl-5-tributylstannanyl-1H-imidazole (366 mg, 0.986 mmol) was added to the reaction flask in dioxane (0.5 mL) then the flask was purged with N₂. After Pd(PPh₃)₄ (85 mg, 0.074 mmol) was added, the reaction was heated to 100° C. in a sealed tube. The reaction mixture was stirred with a 10% KF solution for 30 min then diluted with EtOAc. The layers were separated and the aqueous layer extracted with EtOAc (3×). The organic layers were combined, dried over Na₂SO₄, and concentrated. The resulting residue was purified by chromatography on silica gel (5% MeOH/CH₂Cl₂) to give 4-methyl-3-[4-(3-methyl-3H-imidazol-4-yl)-pyrazol-1-yl]-benzoic acid ethyl ester (81 mg, 22%).

A solution of N-(3-amino-5-tert-butyl-2-methoxy-phenyl)-methane-sulfonamide (81 mg, 0.261 mmol) in THF (4 mL) was stirred in a bath cooled to −78° C., and n-BuLi (0.22 mL, 0.548 mmol) was added slowly. The cold bath was removed, and the reaction was allowed to stir for 30 min. LHMDS (0.261 mmol) was then added slowly. The suspension was transferred dropwise to a stirring solution of compound 4-methyl-3-[4-(3-methyl-3H-imidazol-4-yl)-pyrazol-1-yl]-benzoic acid ethyl ester (81 mg, 0.261 mmol) in THF at 0° C. After 30 min cole MeOH was added and the mixture was partitioned between saturated NH₄Cl and EtOAc, then extracted with EtOAc (3×). The organic combined extracts were washed with brine, dried over Na₂SO₄, filtered, and concentrated, and chromatographed (1% MeOH (with 5% NH₄OH)/CH₂Cl₂ to 5% MeOH (with 5% NH₄H)/CH₂Cl₂) to afford N-(5-tert-butyl-3-methanesulfonylamino-2-methoxy-phenyl)-4-methyl-3-[4-(3-methyl-3H-imidazol-4-yl)-pyrazol-1-yl]-benzamide (47 mg, 33%) as an orange foam: ESI MS m/z=537 [C₂₇H₃₂N₆O₄S+H]⁺.

Example 39

N-(5-tert-butyl-3-methanesulfonylamino-2-methoxy-phenyl)-3-(4-furan-3-yl-[1,2,3]triazol-1-yl)-4-methyl-benzamide

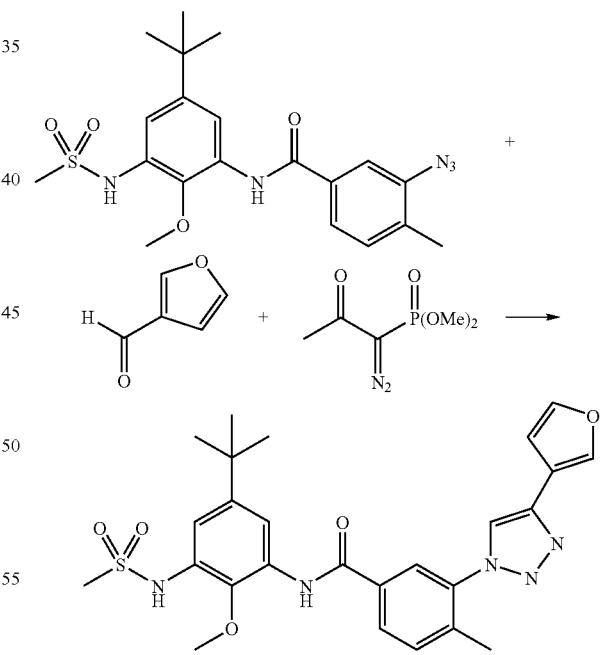

To a solution of 96 mg (0.20 mmol) of furan-3-carbaldehyde (Aldrich) and dimethyl 2-oxo-1-diazopropylphosphinate (46 mg; 0.24 mmol) in 1.5 mL of MeOH was added 55.6 mg (0.402 mmol) of K₂CO₃. The mixture was stirred for 4 h and 58 mg (0.134 mmol) of 3-azido-N-(5-tert-butyl-3-methanesulfonylamino-2-methoxy-phenyl)-4-methyl-benzamide was then added followed by an additional 1 mL of MeOH and 27 mg of sodium ascorbate in 0.2 mL of water.

The mixture was vigorously stirred and 0.13 mL (0.013 mmol) of 0.1 M CuSO₄ was added. The head space was purged with N₂, and the vessel was sealed for 20 h. The mixture was then partitioned between EtOAc and 1M HCl, and the extract was washed with saturated NaHCO₃ and brine. The extract was then dried with Na₂SO₄, filtered, concentrated, and chromatographed (10–50% EtOAc in hexanes) to provide 57 mg (0.11 mmol; 81%) of Example 39. ES MS m/z 524 $[C_{26}H_{29}N_5O_5S+H]^+$.

Example 40

N-(5-tert-Butyl-3-methanesulfonylamino-2-methoxy-phenyl)-4-methyl-3-[4-(tetrahydro-furan-3-yl)-[1,2,3]triazol-1-yl]-benzamide

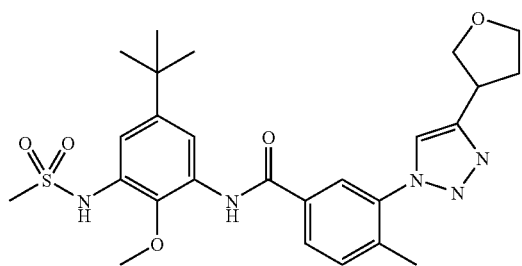

Example 40 was prepared from tetrahydro-furan-3-carbaldehyde (Aldrich) and 3-azido-N-(5-tert-butyl-3-methanesulfonylamino-2-methoxy-phenyl)-4-methyl-benzamide in the same manner as Example 39. ESI MS )/z 528 $[C_{26}H_{33}N_5O_5S+H]^+$.

Example 41

N-(5-tert-Butyl-3-methanesulfonylamino-2-methoxy-phenyl)-4-methyl-3-(4-pyrimidin-5-yl-[1,2,3]triazol-1-yl)-benzamide

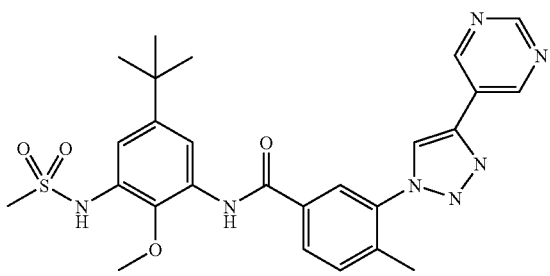

Example 41 was prepared from pyrimidine-3-carbaldehyde (Matrix) and 3-azido-N-(5-tert-butyl-3-methanesulfonylamino-2-methoxy-phenyl)-4-methyl-benzamide in the same manner as Example 39. ESI MS m/z 536 $[C_{26}H_{29}N_7O_4S+H]^+$.

Example 42

N-(5-tert-Butyl-3-methanesulfonylamino-2-methoxy-phenyl)-4-methyl-3-(4-thiazol-5-yl-[1,2,3]triazol-1-yl)-benzamide

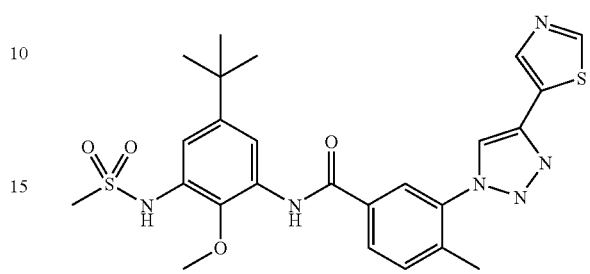

Example 42 was prepared from thiazole-5-carbaldehyde (Matrix) and 3-azido-N-(5-tert-butyl-3-methanesulfonylamino-2-methoxy-phenyl)-4-methyl-benzamide in the same manner as Example 39. ESI MS m/z 541 $[C_{25}H_{28}N_6O_4S_2+H]^+$.

Example 43

N-(5-tert-Butyl-3-methanesulfonylamino-2-methoxy-phenyl)-3-[4-(1,5-dimethyl-1H-pyrazol-4-yl)-[1,2,3]triazol-1-yl]-4-methyl-benzamide

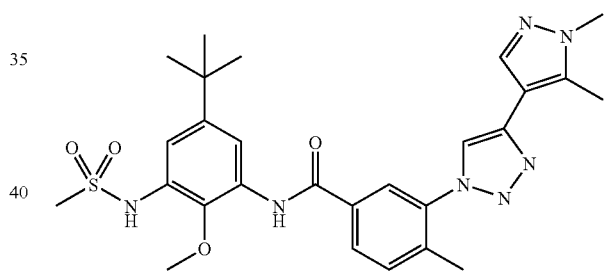

Example 43 was prepared from 1,5-dimethyl-1H-pyrazole-4-carbaldehyde (Matrix) and 3-azido-N-(5-tert-butyl-3-methanesulfonylamino-2-methoxy-phenyl)-4-methylbenzamide in the same manner as Example 39. ESI MS m/z 552 $[C_{27}H_{33}N_7O_4S+H]^+$.

Example 44

N-(5-tert-Butyl-3-methanesulfonylamino-2-methoxy-phenyl)-3-[4-((S)-2,2-dimethyl-[1,3]dioxolan-4-yl)-[1,2,3]triazol-1-yl]-4-methyl-benzamide

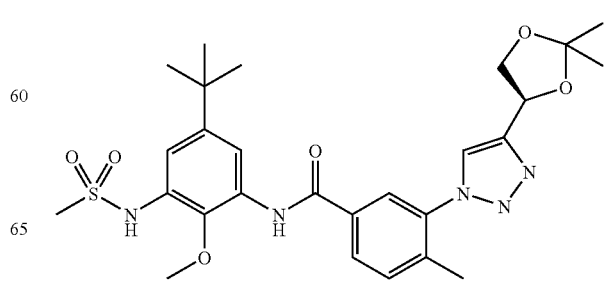

Example 44 was prepared from (S)-2,2-dimethyl-[1,3]dioxolane-4-carbaldehyde (Matrix) and 3-azido-N-(5-tert-butyl-3-methanesulfonylamino-2-methoxy-phenyl)-4-methyl-benzamide in the same manner as Example 39. ESI MS m/z 558 $[C_{27}H_{35}N_5O_6S+H]^+$.

Example 45

N-(5-tert-Butyl-3-methanesulfonylamino-2-methoxy-phenyl)-3-[4-(3-cyclopropyl-2-methyl-3H-imidazol-4-yl)-[1,2,3]triazol-1-yl]-4-methyl-benzamide

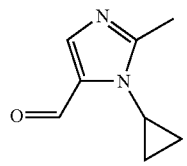

Ethyl acetimidate hydrochloride (5.0 g, 40 mmol) and cyclopropylamine (2.3 mL, 40 mL) were dissolved in 45 mL of EtOH and heated to 85° C. in a sealed pressure vessel overnight. The mixture was cooled and concentrated to provide N-cylcopropyl-acetamidine hydrochloride as a viscous oil. N-Cyclopropyl-acetamidine hydrochloride (1.00 g, 7.43 mmol) and 2-bromo-3-isopropoxy-propenal (Shilcrat, S. C. et al. *J. Org. Chem.*, 1997, 62, 8449–8454) (1.45 g, 7.50 mmol) were dissolved in 13 mL of CHCl$_3$ and 1.6 mL of water. Then K$_2$CO$_3$ (1.5 g, 11 mmol) was added and the mixture was stirred overnight. The reaction was partitioned between CH$_2$Cl$_2$ (60 mL) and water (30 mL). The layers were separated and the aqueous portion was extracted with CH$_2$Cl$_2$ (40 mL). The combined organic layers were washed with brine (30 mL), dried (MgSO$_4$), filtered, concentrated, and chromatographed to provide 400 mg of 3-cyclopropyl-2-methyl-3H-imidazole-4-carbaldehyde.

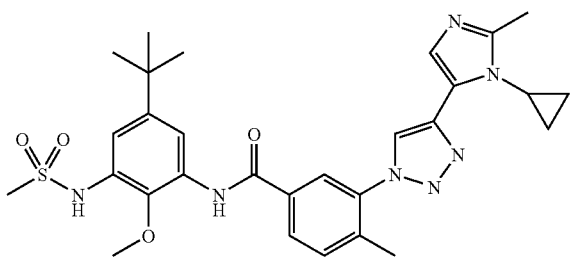

Example 45 was prepared from 3-cyclopropyl-2-methyl-3H-imidazole-4-carbaldehyde and 3-azido-N-(5-tert-butyl-3-methanesulfonylamino-2-methoxy-phenyl)-4-methyl-benzamide in the same manner as Example 39. ESI MS m/z 578 $[C_{29}H_{35}N_7O_4S+H]^+$.

Example 46

N-(5-tert-Butyl-3-methanesulfonylamino-2-methoxy-phenyl)-3-[4-(2-cyclopropyl-3-methyl-3H-imidazol-4-yl)-[1,2,3]triazol-1-yl]-4-methyl-benzamide

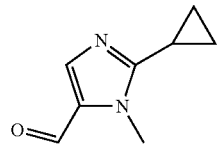

In 50 mL of Et$_2$O were stirred 1.70 g (20.0 mmol) of cyclopropyl carboxamide and 2.9 g (20 mmol) of trimethyloxonium tetrafluoroborate for 16 h. The resulting suspension was chilled to 0° C., and the ether was decanted. The solids were washed with 20 mL of cold Et$_2$O, and the residue was dried under a stream of N$_2$. Then 10 mL of EtOH was added, followed by the 2.5 mL of a 33% MeNH$_2$ solution in EtOH. The reaction vessel was sealed and heated to 80° C. overnight. The mixture was cooled and concentrated to provide 3.7 g of N-methyl-cyclopropanecarboxamidine tetrafluoroborate as a gummy solid.

To a solution of 2.32 g (12.5 mmol) of N-methyl-cyclopropanecarboxamidine tetrafluoroborate in 4 mL of MeCN were added 2.41 g (12.5 mmol) of 2-bromo-3-isopropoxy-propenal, 5.1 g (37 mmol) of K$_2$CO$_3$, and 0.17 g (0.62 mmol) of 18-crown-6. The mixture was stirred at rt overnight, and then was concentrated and redissolved in EtOAc. Water was added to dissolve the salts, the layers were separated, and the aqueous phase was extracted twice with EtOAc. The combined extracts were washed with a small amount of water and brine, dried over Na$_2$SO$_4$, filtered, concentrated, and chromatographed (35–85% EtOAc in hexanes) to provide 646 mg of 2-cyclopropyl-3-methyl-3H-imidazole-4-carbaldehyde as a pale yellow oil.

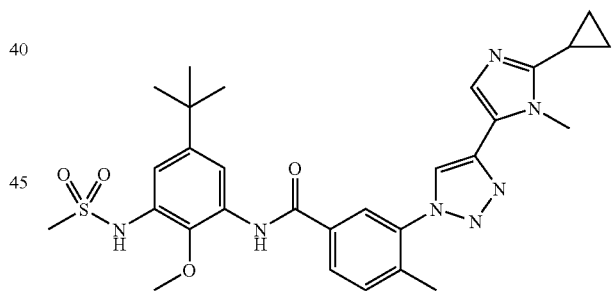

Example 46 was prepared from 2-cyclopropyl-3-methyl-3H-imidazole-4-carbaldehyde and 3-azido-N-(5-tert-butyl-3-methanesulfonylamino-2-methoxy-phenyl)-4-methyl-benzamide in the same manner as Example 39. ESI MS m/z 578 $[C_{29}H_{35}N_7O_4S+H]^+$.

Example 47

N-(5-tert-Butyl-3-methanesulfonylamino-2-methoxy-phenyl)-3-[4-(2-cyclopropyl-1-methyl-1H-imidazol-4-yl)-[1,2,3]triazol-1-yl]-4-methyl-benzamide

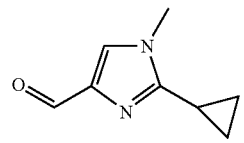

N-methyl-cyclopropanecarboxamidine tetrafluoroborate (0.19 g, 1.0 mmol) and 2-bromo-3-isopropoxy-propenal (Shilcrat, S. C. et al. *J. Org. Chem.*, 1997, 62, 8449–8454) (0.19 g, 1.0 mmol) were dissolved in 1.3 mL of CHCl$_3$ and 0.16 mL of water. Then K$_2$CO$_3$ (0.45 g, 3.3 mmol) was added and the mixture was stirred overnight. The reaction was partitioned between CH$_2$Cl$_2$ and water. The layers were separated and the aqueous portion was extracted with CH$_2$Cl$_2$. The combined organic layers were washed with brine, dried (MgSO$_4$), filtered, concentrated, and chromatographed to provide 0.15 g of a 1:1 mixture of 2-cyclopropyl-1-methyl-1H-imidazole-4-carbaldehyde and 2-cyclopropyl-3-methyl-3H-imidazole-4-carbaldehyde.

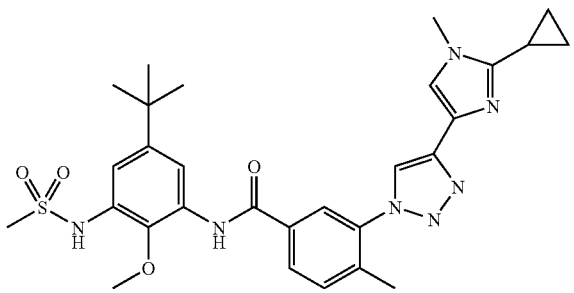

Example 47 was prepared from 2-cyclopropyl-1-methyl-1H-imidazole-4-carbaldehyde (as a 1:1 mixture with 2-cyclopropyl-3-methyl-3H-imidazole-4-carbaldehyde) and 3-azido-N-(5-tert-butyl-3-methanesulfonylamino-2-methoxy-phenyl)-4-methyl-benzamide in the same manner as Example 39. Chromatography allowed separation of Example 47 from Example 46. ESI MS m/z 578 [C$_{29}$H$_{35}$N$_7$O$_4$S+H]$^+$.

Example 48

N-(5-tert-Butyl-3-methanesulfonylamino-2-methoxy-phenyl)-4-methyl-3-[4-(5,6,7,8-tetrahydro-imidazo[1,2-a]pyridin-3-yl)-[1,2,3]triazol-1-yl]-benzamide

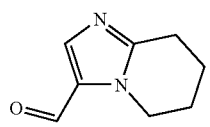

5,6,7,8-Tetrahydro-imidazo[1,2-a]pyridine-3-carbaldehyde (2:1 with 5,6,7,8-Tetrahydro-imidazo[1,2-a]pyridine-2-carbaldehyde) was prepared from piperidin-2-ylideneamine hydrochloride (Aldrich) and 2-bromo-3-isopropoxy-propenal in the same manner as cyclopropyl-2-methyl-3H-imidazole-4-carbaldehyde (Example 45).

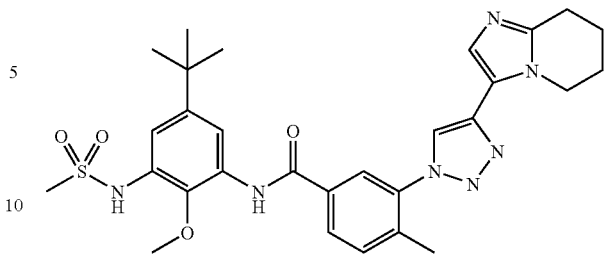

Example 48 was prepared from 5,6,7,8-tetrahydro-imidazo[1,2-a]pyridine-3-carbaldehyde and 3-azido-N-(5-tert-butyl-3-methanesulfonylamino-2-methoxy-phenyl)-4-methyl-benzamide in the same manner as Example 39. ESI MS t/z 578 [C$_{29}$H$_{35}$N$_7$O$_4$S+H]$^+$.

Example 49

N-(5-tert-Butyl-3-methanesulfonylamino-2-methoxy-phenyl)-3-[4-(5-cyclopropyl-1-isopropyl-1H-pyrazol-4-yl)-[1,2,3]triazol-1-yl]-4-methyl-benzamide

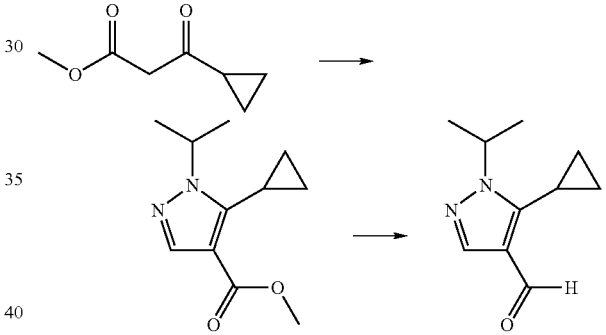

3-Cyclopropyl-3-oxo-propionic acid methyl ester (1.25 g, 8.79 mmol) was dissovled in 6.25 mL of CHCl$_3$ and 1.17 mL (8.79 mmol) of dimethylformamide dimethyl acetal was added. The mixture was heated to 60° C. in a sealed vessel overnight. The mixuture was then cooled and concentrated to provide 1.67 g of 2-cyclopropanecarbonyl-3-dimethylamino-acrylic acid methyl ester.

In 10 mL of EtOH was combined 544 mg (2.76 mmol) of 2-cyclopropanecarbonyl-3-dimethylamino-acrylic acid methyl ester, 305 mg (2.76 mmol) of isopropylhydrazine hydrochloride, and 226 (2.76 mmol) of sodium acetate. The mixture was heated to 60° C. for 12 h. The mixture was then partitioned between water and EtOAc and the extract was washed with brine. The washes were extracted twice more with EtOAc and the extracts were combined, dried with Na$_2$SO$_4$, filtered, and concentrated to provide 442 mg of an 85:15 mixture of 5-cyclopropyl-1-isopropyl-1H-pyrazole-4-carboxylic acid methyl ester and 5-Cyclopropyl-1-isopropyl-1H-pyrazole-3-carbaldehyde.

To an ice-cold solution of 5-cyclopropyl-1-isopropyl-1H-pyrazole-4-carboxylic acid methyl ester (442 mg, 2.12 mmol) in THF was slowly added 8.48 mL of 1 M DIBAL-H in CH$_2$Cl$_2$. After 2 h 1 mL of EtOAc, was added followed by saturated aqueous Na$_2$SO$_4$ with very rapid stirring. After stirring for 10 min, the resulting slurry was diluted with EtOAc until it freely stirred and MgSO₄ was added. The resulting suspension was stirred an additional 30 min, and then was filtered through celite. The filter cake was washed with EtOAc and the combined filtrate was concentrated to provide 337 mg of 5-cyclopropyl-1-isopropyl-1H-pyrazol-4-yl)-methanol.

To a solution of 337 mg (1.87 mmol) of 5-cyclopropyl-1-isopropyl-1H-pyrazol-4-yl)-methanol was added 813 mg (9.35 mmol) of activated MnO₂. The slurry was stirred overnight, and then was filtered through celite (rinsed with CH₂Cl₂) and the filtrate was concentrated to provide an off-white solid. The solid was washed with with hexanes to provide 170 mg of 5-cyclopropyl-1-isopropyl-1H-pyrazole-4-carbaldehyde.

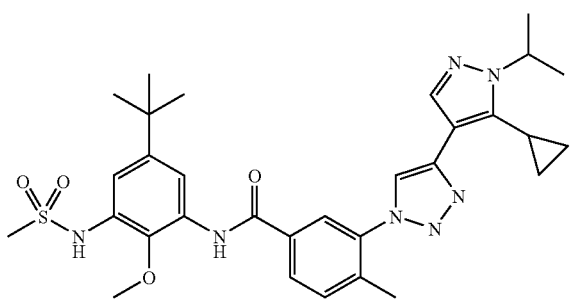

Example 49 was prepared from 5-cyclopropyl-1-isopropyl-1H-pyrazole-4-carbaldehyde and 3-azido-N-(5-tert-butyl-3-methanesulfonylamino-2-methoxy-phenyl)-4-methyl-benzamide in the same manner as Example 39. ESI MS m/z 606 $[C_{31}H_{39}N_7O_4S+H]^+$.

Example 50

N-(5-tert-Butyl-3-methanesulfonylamino-2-methoxy-phenyl)-3-[4-(1-cyclopropyl-5-methyl-1H-pyrazol-4-yl)-[1,2,3]triazol-1-yl]-4-methyl-benzamide

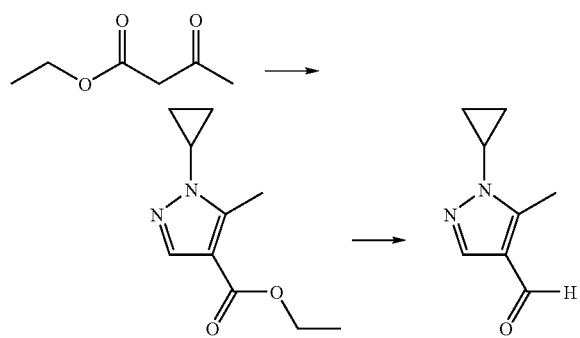

1-Cyclopropyl-5-methyl-1H-pyrazole-4-carbaldehyde was prepared with ethyl acetoacetate and cylclopropyl hydrazine oxalate (Gever, G. and Hayes, K. *J. Org. Chem*, 1949, 14, 813–818) in the same manner as 5-cyclopropyl-1-isopropyl-1H-pyrazole-4-carbaldehyde (Example 49).

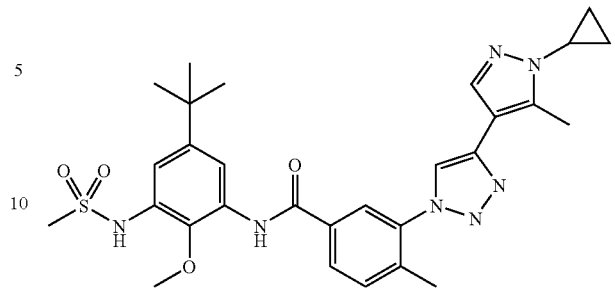

Example 50 was prepared from 1-cyclopropyl-5-methyl-1H-pyrazole-4-carbaldehyde and 3-azido-N-(5-tert-butyl-3-methanesulfonylamino-2-methoxy-phenyl)-4-methyl-benzamide in the same manner as Example 39. ESI MS m/z 578 $[C_{29}H_{35}N_7O_4S+H]^+$.

Example 51

N-(5-tert-Butyl-3-methanesulfonylamino-2-methoxy-phenyl)-3-[4-(2,3-diethyl-3H-imidazol-4-yl)-[1,2,3]triazol-1-yl]-4-methyl-benzamide

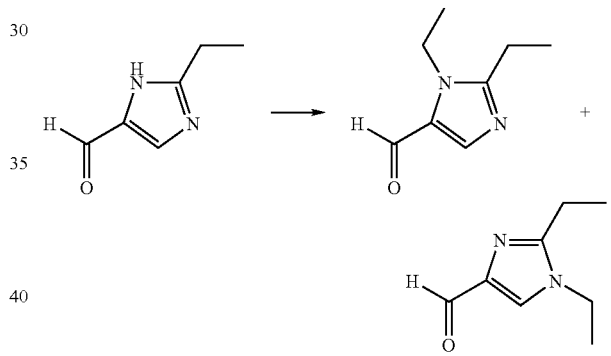

To 2-ethyl-5-formylimidazole (200 mg; 1.611 mmol) in 2 mL of DMF was added 0.132 mL (1.65 mmol) of EtI and 224 mg (1.62 mmol) of K₂CO₃. The mixture was stirred for 12 h, and then it was poured into water and extracted twice with EtOAc. The organic extracts were washed with brine, dried over Na₂SO₄, filtered and concentrated. Chromatography (0.5–2.0% MeOH in CH₂Cl₂) provided 46 mg (0.30 mmol; 19%) of 1,2-diethyl-5-formyl-1H-imidazole and 106 mg (0.69 mmol; 43%) of 1,2-diethyl-4-formyl-1H-imidazole.

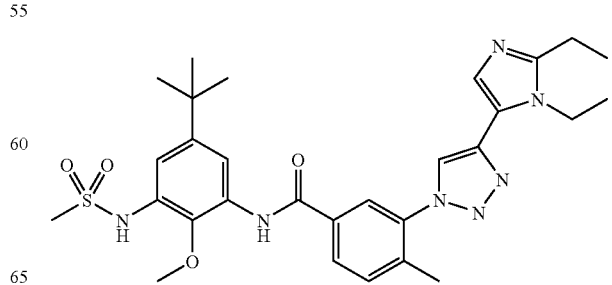

Example 51 was prepared from 1,2-diethyl-5-formyl-1H-imidazole and 3-azido-N-(5-tert-butyl-3-methanesulfonylamino-2-methoxy-phenyl)-4-methyl-benzamide in the same manner as Example 39. ESI MS m/z 580 [C$_{29}$H$_{37}$N$_{7}$O$_{4}$S+H]$^{+}$.

Example 52

N-(5-tert-Butyl-3-methanesulfonylamino-2-methoxy-phenyl)-3-[4-(1,2-diethyl-1H-imidazol-4-yl)-1,2,3-triazol-1-yl]-4-methyl-benzamide

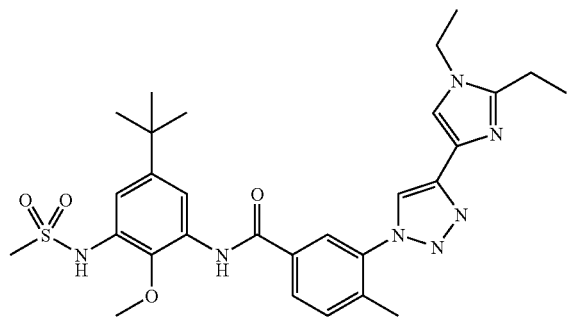

Example 52 was prepared from 1,2-diethyl-4-formyl-1H-imidazole (Example 51) and 3-azido-N-(5-tert-butyl-3-methanesulfonylamino-2-methoxy-phenyl)-4-methyl-benzamide in the same manner as Example 39. ESI MS m/z 580 [C$_{29}$H$_{37}$N$_{7}$O$_{4}$S+H]$^{+}$.

Example 53

N-(5-tert-Butyl-3-methanesulfonylamino-2-methoxy-phenyl)-3-[4-(2-isopropyl-3-methyl-3H-imidazol-4-yl)-[1,2,3]triazol-1-yl]-4-methyl-benzamide

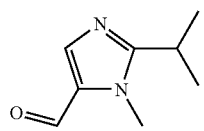

2-Isopropyl-3-methyl-3H-imidazole-4-carbaldehyde was prepared from isobutyramide in the same manner as 2-cyclopropyl-3-methyl-3H-imidazole-4-carbaldehyde (Example 46).

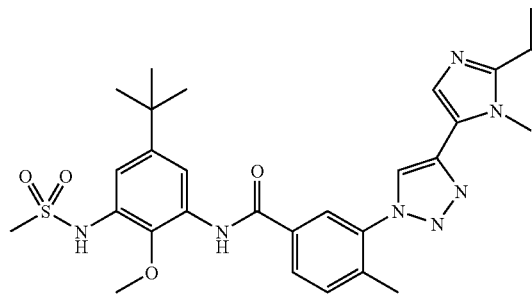

Example 53 was prepared from 2-isopropyl-3-methyl-3H-imidazole-4-carbaldehyde and 3-azido-N-(5-tert-butyl-3-methanesulfonylamino-2-methoxy-phenyl)-4-methyl-benzamide in the same manner as Example 39. ESI MS m/z 580 [C$_{29}$H$_{37}$N$_{7}$O$_{4}$S+H]$^{+}$.

Example 54

N-(5-tert-Butyl-3-methanesulfonylamino-2-methoxy-phenyl)-3-[4-(3-isopropyl-2-methyl-3H-imidazol-4-yl)-[1,2,3]triazol-1-yl]-4-methyl-benzamide

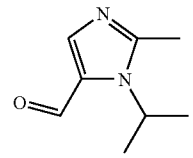

3-Isopropyl-2-methyl-3H-imidazole-4-carbaldehyde was prepared from ethyl acetimidate hydrochloride and isopropylamine in the same manner as 3-cyclopropyl-2-methyl-3H-imidazole-4-carbaldehyde (Example 45).

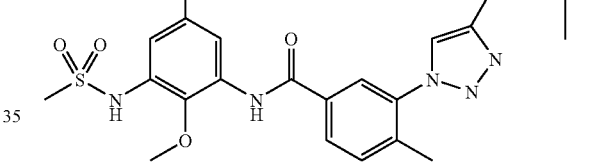

Example 54 was prepared from 3-isopropyl-2-methyl-3H-imidazole-4-carbaldehyde and 3-azido-N-(5-tert-butyl-3-methanesulfonylamino-2-methoxy-phenyl)-4-methyl-benzamide in the same manner as Example 39. ESI MS m/z 580 [C$_{29}$H$_{37}$N$_{7}$O$_{4}$S+H]$^{+}$.

Example 55

N-(5-tert-Butyl-3-methanesulfonylamino-2-methoxy-phenyl)-3-[4-(1-isopropyl-5-methyl-1H-pyrazol-4-yl)-[1,2,3]triazol-1-yl]-4-methyl-benzamide

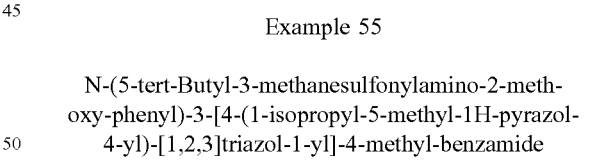

1-Isopropyl-5-methyl-1H-pyrazole-4-carbaldehyde was prepared with methyl acetoacetate and isopropyl hydrazine hydrochloride in the same manner as 5-cyclopropyl-1-isopropyl-1H-pyrazole-4-carbaldehyde (Example 49).

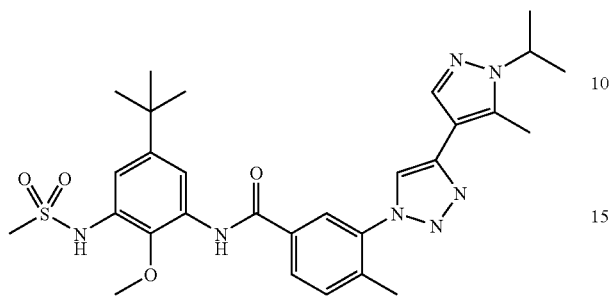

Example 55 was prepared from 1-isopropyl-5-methyl-1H-pyrazole-4-carbaldehyde and 3-azido-N-(5-tert-butyl-3-methanesulfonylamino-2-methoxy-phenyl)-4-methyl-benzamide in the same manner as Example 39. ESI MS m/z 580 $[C_{29}H_{37}N_7O_4S+H]^+$.

Example 56

3-[4-(3-tert-Butyl-3H-imidazol-4-yl)-[1,2,3]triazol-1-yl]-N-(5-tert-butyl-3-methanesulfonylamino-2-methoxy-phenyl)-4-methyl-benzamide

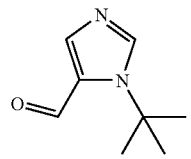

3-tert-Butyl-3H-imidazole-4-carbaldehyde was prepared from ethyl formimidate hydrochloride (Aldrich) and tert-butylamine in the same manner as 3-cyclopropyl-2-methyl-3H-imidazole-4-carbaldehyde (Example 45).

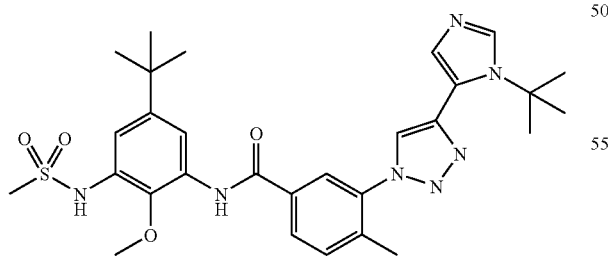

Example 56 was prepared from 3-tert-butyl-3H-imidazole-4-carbaldehyde and 3-azido-N-(5-tert-butyl-3-methanesulfonylamino-2-methoxy-phenyl)-4-methyl-benzamide in the same manner as Example 39. ESI MS m/z 580 $[C_{29}H_{37}N_7O_4S+H]^+$.

Example 57

3-{4-[2-(4-Benzyl-piperazin-1-yl)-3-methyl-3H-imidazol-4-yl]-[1,2,3]triazol-1-yl}-N-(5-tert-butyl-3-methanesulfonylamino-2-methoxy-phenyl)-4-methyl-benzamide Example 58

3-{4-[2-(4-Benzyl-piperazin-1-yl)-1-methyl-1H-imidazol-4-yl]-[1,2,3]triazol-1-yl}-N-(5-tert-butyl-3-methanesulfonylamino-2-methoxy-phenyl)-4-methyl-benzamide

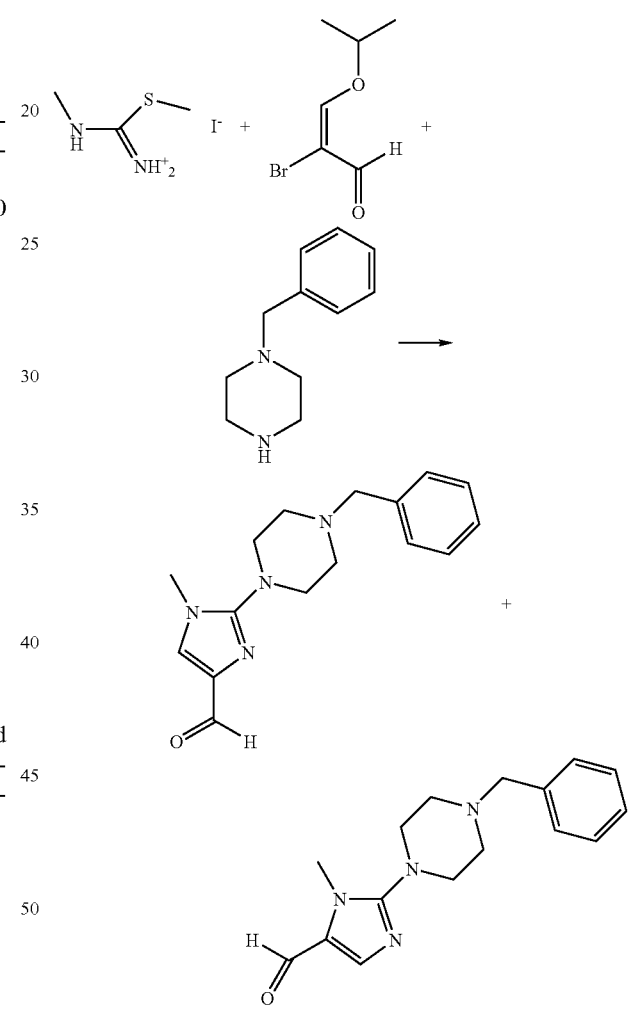

To 15 mL of MeCN was added 880 mg (4.99 mmol) of N-benzyl-piperazine and 1.16 g (5.00 mmol) of 1,2-dimethyl-isothiourea hydroiodide. The mixture was heated at reflux overnight. Then, 970 mg (5.02 mmol) of 2-bromo-3-isopropoxy-propenal and 2.07 g (15.0 mmol) of $K_2CO_3$, and 250 mg of 18-crown-6 were added and the mixture was heated to reflux overnight. The mixture was cooled, concentrated, and dissolved in EtOAc with a small amount of water to dissolve salts. The aqueous phase was extracted twice with EtOAc, and the combined the organics were washed with water and brine, dried over $MgSO_4$, concentrated, and chromatographed to provide 250 mg of 2-(4- benzyl-piperazin-1-yl)-3-methyl-3H-imidazole-4-carbalde-hyde and 2-(4-benzyl-piperazin-1-yl)-1-methyl-1H-imidazole-4-carbaldehyde as a 1:1 mixture of isomers.

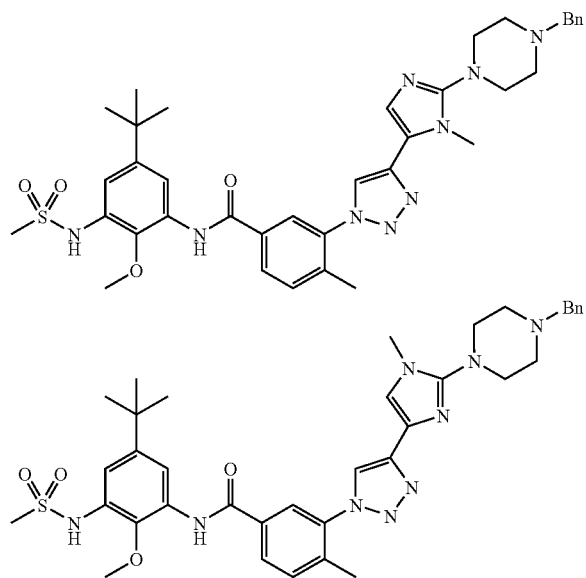

Example 57 and Example 58 were prepared from a mixture of 2-(4-benzyl-piperazin-1-yl)-3-methyl-3H-imidazole-4-carbaldehyde and 2-(4-benzyl-piperazin-1-yl)-1-methyl-1H-imidazole-4-carbaldehyde in the same manner as Example 39. The isomers were separated by chromatography (4% EtOH in $CH_2Cl_2$ with 0.5% $NH_4OH$).

Example 57: ESI MS m/z 712 $[C_{37}H_{45}N_9O_4S+H]^+$.

Example 58: ESI MS m/z 712 $[C_{37}H_{45}N_9O_4S+H]^+$.

Example 59

N-(5-tert-Butyl-3-methanesulfonylamino-2-methoxy-phenyl)-3-[4-(2-dimethylamino-3-methyl-3H-imidazol-4-yl)-[1,2,3]triazol-1-yl]-4-methyl-benzamide Example 60

N-(5-tert-Butyl-3-methanesulfonylamino-2-methoxy-phenyl)-3-[4-(2-dimethylamino-1-methyl-1H-imidazol-4-yl)-[1,2,3]triazol-1-yl]-4-methyl-benzamide

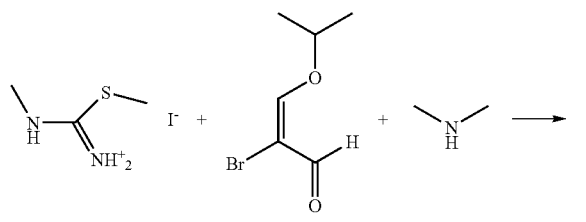

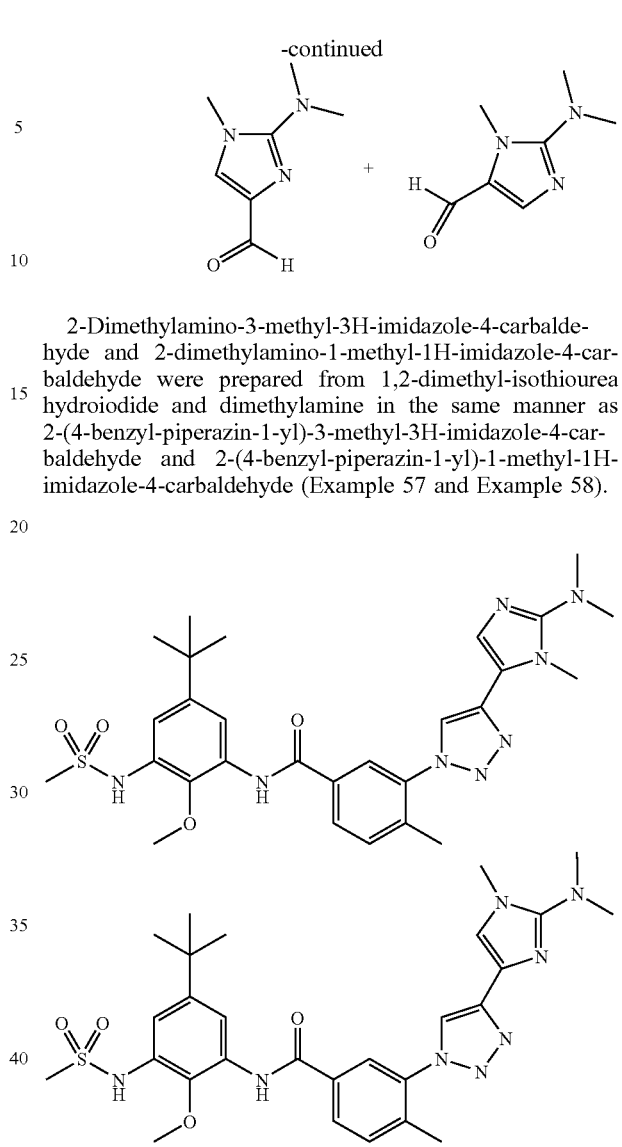

2-Dimethylamino-3-methyl-3H-imidazole-4-carbaldehyde and 2-dimethylamino-1-methyl-1H-imidazole-4-carbaldehyde were prepared from 1,2-dimethyl-isothiourea hydroiodide and dimethylamine in the same manner as 2-(4-benzyl-piperazin-1-yl)-3-methyl-3H-imidazole-4-carbaldehyde and 2-(4-benzyl-piperazin-1-yl)-1-methyl-1H-imidazole-4-carbaldehyde (Example 57 and Example 58).

Example 59 and Example 60 were prepared from a mixture of 2-dimethylamino-3-methyl-3H-imidazole-4-carbaldehyde and 2-dimethylamino-1-methyl-1H-imidazole-4-carbaldehyde in the same manner as Example 39. The isomers were separated by chromatography (4% EtOH in $CH_2Cl_2$ with 0.5% $NH_4OH$).

Example 59: ESI MS m/z 581 $[C_{28}H_{36}N_8O_4S+H]^+$.
Example 60: ESI MS m/z 581 $[C_{28}H_{36}N_8O_4S+H]^+$.

Example 61

N-(5-tert-Butyl-3-methanesulfonylamino-2-methoxy-phenyl)-3-[4-(2,3-dihydro-imidazo[2,1-b]thiazol-5-yl)-[1,2,3]triazol-1-yl]-4-methyl-benzamide

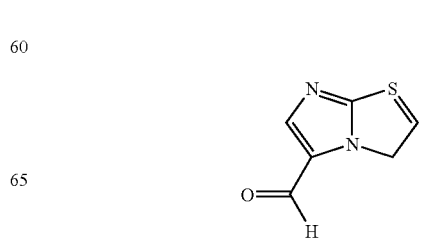

2,3-Dihydro-imidazo[2,1-b]thiazole-5-carbaldehyde was prepared from 4,5-dihydro-thiazol-2-ylamine and and 2-bromo-3-isopropoxy-propenal in the same manner as cyclopropyl-2-methyl-3H-imidazole-4-carbaldehyde (Example 45).

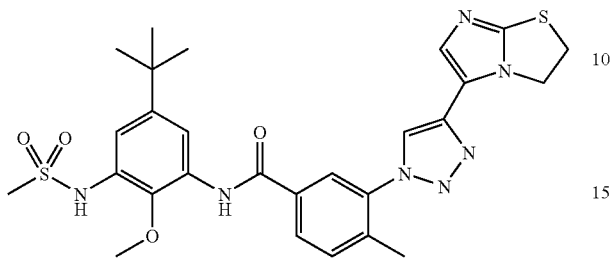

Example 61 was prepared from 2,3-Dihydro-imidazo[2,1-b]thiazole-5-carbaldehyde and 3-azido-N-(5-tert-butyl-3-methanesulfonylamino-2-methoxy-phenyl)-4-methyl-benzamide in the same manner as Example 39. ESI MS m/z 582 $[C_{27}H_{31}N_7O_4S_2+H]^+$.

Example 62

N-(5-tert-Butyl-3-methanesulfonylamino-2-methoxy-phenyl)-3-[4-(2-cyclobutyl-3-methyl-3H-imidazol-4-yl)-1,2,3-triazol-1-yl]-4-methyl-benzamide

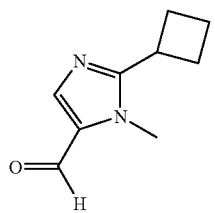

2-Cyclobutyl-3-methyl-3H-imidazole-4-carbaldehyde may be prepared from cyclobutane carboxamide in the same manner as 2-cyclopropyl-3-methyl-3H-imidazole-4-carbaldehyde (Example 46).

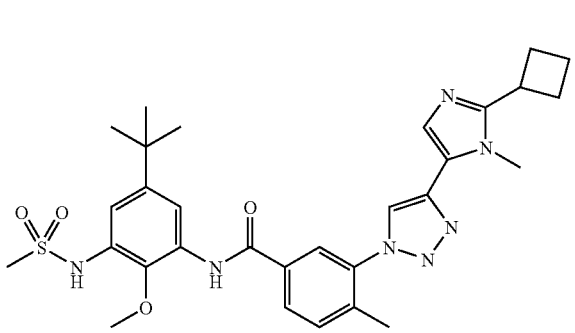

Example 62 may be prepared from 2-cyclobutyl-3-methyl-3H-imidazole-4-carbaldehyde and 3-azido-N-(5-tert-butyl-3-methanesulfonylamino-2-methoxy-phenyl)-4-methyl-benzamide in the same manner as Example 39

Example 63

N-(5-tert-Butyl-3-methanesulfonylamino-2-methoxy-phenyl)-4-methyl-3-{4-[3-methyl-2-(1-methyl-cyclopropyl)-3H-imidazol-4-yl]-[1,2,3]triazol-1-yl}-benzamide

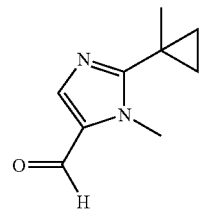

3-Methyl-2-(1-methyl-cyclopropyl)-3H-imidazole-4-carbaldehyde was prepared from 1-methyl-cyclopropyl carboxamide in the same manner as 2-cyclopropyl-3-methyl-3H-imidazole-4-carbaldehyde (Example 46).

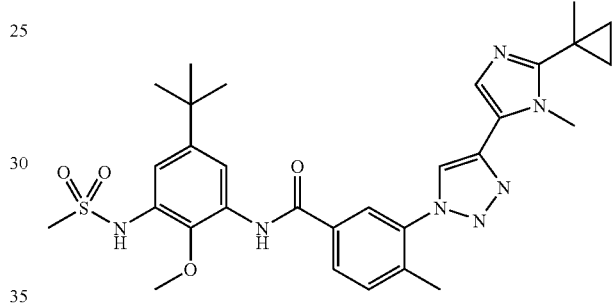

Example 63 was prepared from 3-methyl-2-(1-methyl-cyclopropyl)-3H-imidazole-4-carbaldehyde and 3-azido-N-(5-tert-butyl-3-methanesulfonylamino-2-methoxy-phenyl)-4-methyl-benzamide in the same manner as Example 39. ESI MS m/z 592 $[C_{30}H_{37}N_7O_4S+H]^+$.

Example 64

N-(5-tert-Butyl-3-methanesulfonylamino-2-methoxy-phenyl)-3-[4-(1-cyclopropyl-5-ethyl-1H-pyrazol-4-yl)-[1,2,3]triazol-1-yl]-4-methyl-benzamide

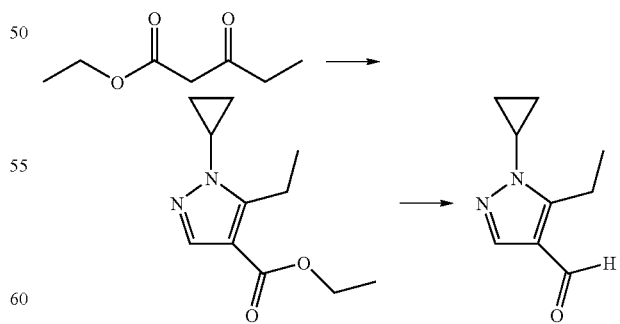

1-Cyclopropyl-5-ethyl-1H-pyrazole-4-carbaldehyde was prepared with ethyl 3-oxopentanoate and cyclopropyl hydrazine oxalate (Gever, G. and Hayes, K. *J. Org. Chem*, 1949, 14, 813–818) in the same manner as 5-cyclopropyl-1-isopropyl-1H-pyrazole-4-carbaldehyde (Example 49).

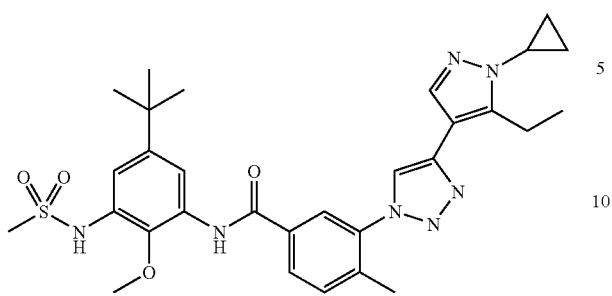

Example 64 was prepared from 1-cyclopropyl-5-ethyl-1H-pyrazole-4-carbaldehyde and 3-azido-N-(5-tert-butyl-3-methanesulfonylamino-2-methoxy-phenyl)-4-methyl-benzamide in the same manner as Example 39. ESI MS m/z 592 $[C_{30}H_{37}N_7O_4S+H]^+$.

Example 65

N-(5-tert-Butyl-3-methanesulfonylamino-2-methoxy-phenyl)-3-[4-(5,5-dimethyl-6,7-dihydro-5H-pyrrolo[1,2-a]imidazol-3-yl)-[1,2,3]triazol-1-yl]-4-methyl-benzamide

5,5-Dimethyl-6,7-dihydro-5H-pyrrolo[1,2-a]imidazole-3-carbaldehyde was prepared from 5,5-dimethyl-pyrrolidin-2-ylideneamine (Buckley, et al. *J. Chem. Soc.* 1947, 1507.) and 2-bromo-3-isopropoxy-propenal in the same manner as cyclopropyl-2-methyl-3H-imidazole-4-carbaldehyde (Example 45).

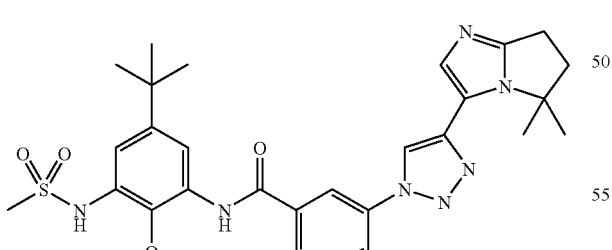

Example 65 was prepared from 5,5-dimethyl-6,7-dihydro-5H-pyrrolo[1,2-a]imidazole-3-carbaldehyde and 3-azido-N-(5-tert-butyl-3-methanesulfonylamino-2-methoxy-phenyl)-4-methyl-benzamide in the same manner as Example 39. ESI MS m/z 592 $[C_{30}H_{37}N_7O_4S+H]^+$.

Example 66

N-(5-tert-Butyl-3-methanesulfonylamino-2-methoxy-phenyl)-3-[4-(7,7-dimethyl-6,7-dihydro-5H-pyrrolo[1,2-a]imidazol-3-yl)-1,2,3-triazol-1-yl]-4-methyl-benzamide

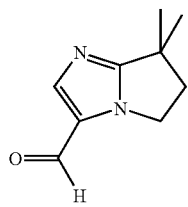

7,7-Dimethyl-6,7-dihydro-5H-pyrrolo[1,2-a]imidazole-3-carbaldehyde may be prepared from 3,3-dimethyl-pyrrolidin-2-one (Reddy, P. A. et al. *J. Med. Chem.* 1996, 1898.) and 2-bromo-3-isopropoxy-propenal in the same manner as cyclopropyl-2-methyl-3H-imidazole-4-carbaldehyde (Example 45)

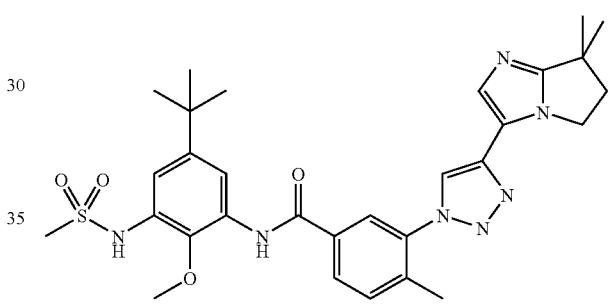

Example 66 may be prepared from 7,7-dimethyl-6,7-dihydro-5H-pyrrolo[1,2-a]imidazole-3-carbaldehyde and 3-azido-N-(5-tert-butyl-3-methanesulfonylamino-2-methoxy-phenyl)-4-methyl-benzamide in the same manner as Example 39.

Example 67

N-(5-tert-Butyl-3-methanesulfonylamino-2-methoxy-phenyl)-3-[4-(2-tert-butyl-3-methyl-3H-imidazol-4-yl)-[1,2,3]triazol-1-yl]-4-methyl-benzamide

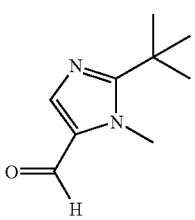

2-tert-Butyl-3-methyl-3H-imidazole-4-carbaldehyde was prepared from trimethyl acetamide in the same manner as 2-cyclopropyl-3-methyl-3H-imidazole-4-carbaldehyde (Example 46).

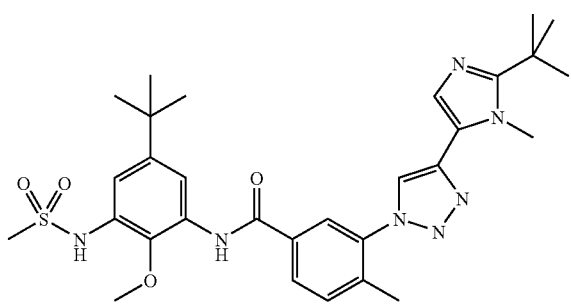

Example 67 was prepared from 2-tert-butyl-3-methyl-3H-imidazole-4-carbaldehyde and 3-azido-N-(5-tert-butyl-3-methanesulfonylamino-2-methoxy-phenyl)-4-methyl-benzamide in the same manner as Example 39. ESI MS m/z 594 $[C_{30}H_{39}N_7O_4S+H]^+$.

Example 68

N-(5-tert-Butyl-3-methanesulfonylamino-2-methoxy-phenyl)-3-[4-(3-tert-butyl-2-methyl-3H-imidazol-4-yl)-[1,2,3]triazol-1-yl]-4-methyl-benzamide

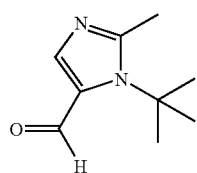

3-tert-Butyl-2-methyl-3H-imidazole-4-carbaldehyde was prepared from ethyl acetimidate hydrochloride and tert-butylamine in the same manner as 3-cyclopropyl-2-methyl-3H-imidazole-4-carbaldehyde (Example 45).

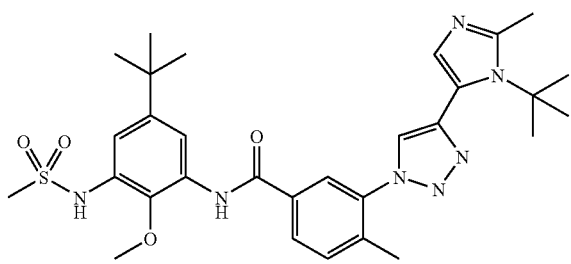

Example 68 was prepared from 3-tert-butyl-2-methyl-3H-imidazole-4-carbaldehyde and 3-azido-N-(5-tert-butyl-3-methanesulfonylamino-2-methoxy-phenyl)-4-methyl-benzamide in the same manner as Example 39. ESI MS m/z 594 $[C_{30}H_{39}N_7O_4S+H]^+$.

Example 69

N-(5-tert-Butyl-3-methanesulfonylamino-2-methoxy-phenyl)-3-[4-(1-tert-butyl-5-methyl-1H-pyrazol-4-yl)-[1,2,3]triazol-1-yl]-4-methyl-benzamide

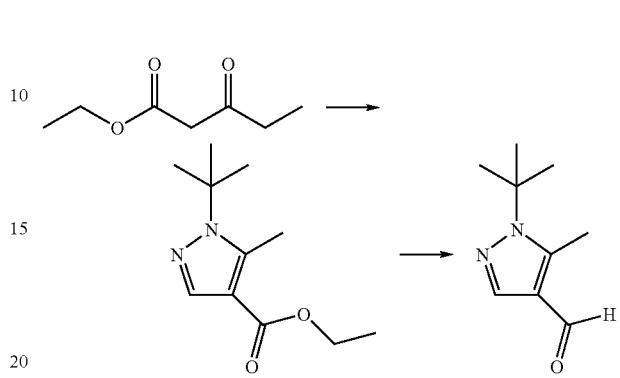

1-tert-Butyl-5-methyl-1H-pyrazole-4-carbaldehyde was prepared with ethyl acetoacetate and tert-butyl hydrazine hydrochloride in the same manner as 5-cyclopropyl-1-isopropyl-1H-pyrazole-4-carbaldehyde (Example 49).

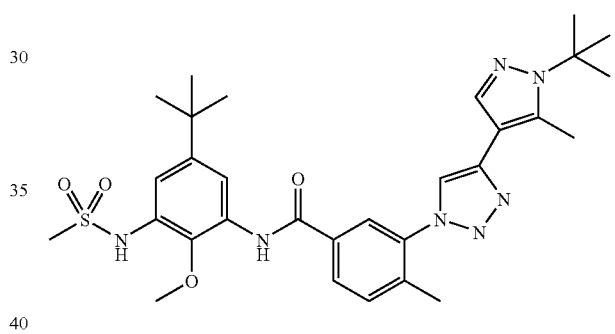

Example 69 was prepared from 1-tert-butyl-5-methyl-1H-pyrazole-4-carbaldehyde and 3-azido-N-(5-tert-butyl-3-methanesulfonylamino-2-methoxy-phenyl)-4-methyl-benzamide in the same manner as Example 39. ESI MS m/z 594 $[C_{30}H_{39}N_7O_4S+H]^+$.

Example 70

N-(5-tert-Butyl-3-methanesulfonylamino-2-methoxy-phenyl)-3-[4-(5-ethyl-1-isopropyl-1H-pyrazol-4-yl)-[1,2,3]triazol-1-yl]-4-methyl-benzamide

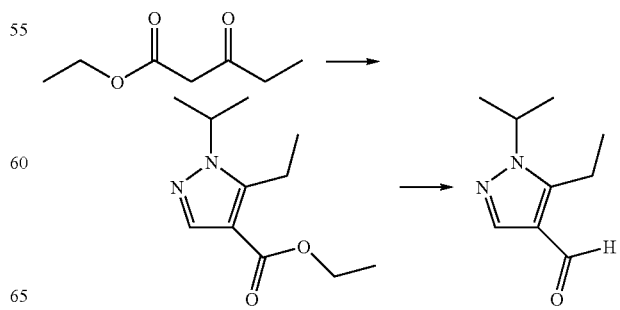

5-Ethyl-1-isopropyl-1H-pyrazole-4-carbaldehyde was prepared with ethyl 3-oxopentanoate and isopropyl hydrazine hydrochloride in the same manner as 5-cyclopropyl-1-isopropyl-1H-pyrazole-4-carbaldehyde (Example 49).

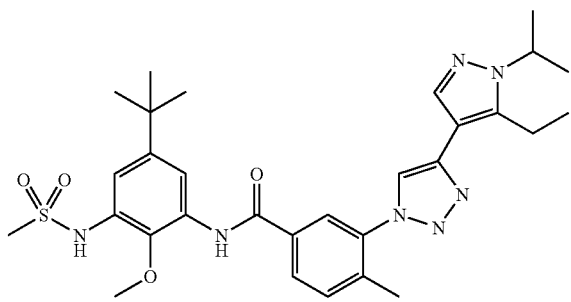

Example 70 was prepared from 5-ethyl-1-isopropyl-1H-pyrazole-4-carbaldehyde and 3-azido-N-(5-tert-butyl-3-methanesulfonylamino-2-methoxy-phenyl)-4-methyl-benzamide in the same manner as Example 39. ESI MS m/z 594 $[C_{30}H_{39}N_7O_4S+H]^+$.

Example 71

N-(5-tert-Butyl-3-methanesulfonylamino-2-methoxy-phenyl)-4-methyl-3-[4-(6-trifluoromethyl-pyridin-3-yl)-[1,2,3]triazol-1-yl]-benzamide

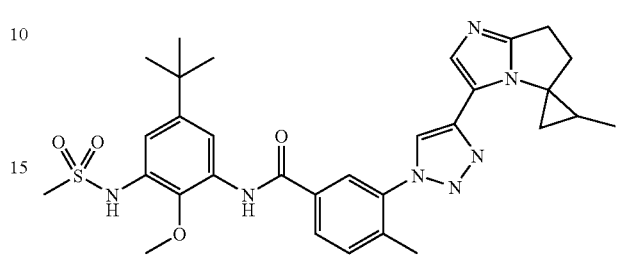

Example 71 was prepared from 6-trifluoromethyl-pyridine-3-carbaldehyde (Matrix) and 3-azido-N-(5-tert-butyl-3-methanesulfonylamino-2-methoxy-phenyl)-4-methyl-benzamide in the same manner as Example 39. ESI MS m/z 603 $[C_{28}H_{29}F_3N_6O_4S+H]^+$.

Example 72

N-(5-tert-Butyl-3-methanesulfonylamino-2-methoxy-phenyl)-4-methyl-3-[4-[spiro(6,7-dihydro-5H-pyrrolo[1,2-a]imidazol-3-yl-5-(2'-methyl-cyclopoane))]-[1,2,3]triazol-1-yl]-benzamide

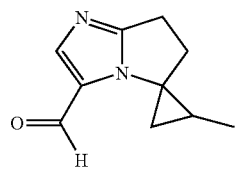

Spiro[6,7-dihydro-5H-pyrrolo[1,2-a]imidazole-5-(2'-methyl-cyclopropane)]-3-carboxaldehyde was prepared from 1-methyl-4-aza-spiro[2.4]heptan-5-one (Bertus, P.; Szymoniak, J. SYNLETT, 2, 2003, 265–267) and 2-bromo-3-isopropoxy-propenal in the same manner as 2-cyclopropyl-3-methyl-3H-imidazole-4-carbaldehyde (Example 46).

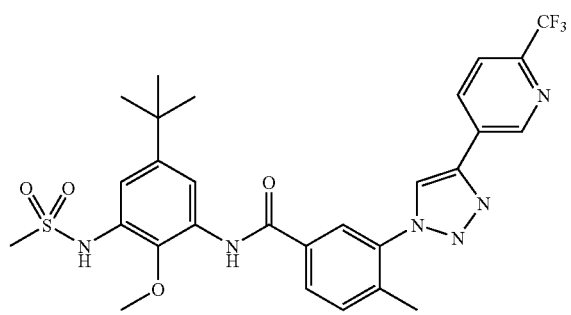

Example 72 was prepared from spiro[6,7-dihydro-5H-pyrrolo[1,2-a]imidazole-5-(2'-methyl-cyclopropane)]-3-carboxaldehyde and 3-azido-N-(5-tert-butyl-3-methanesulfonylamino-2-methoxy-phenyl)-4-methyl-benzamide in the same manner as Example 39. ESI MS m/z 604 $[C_{31}H_{37}N_7O_4S+H]^+$.

Example 73

N-(5-tert-Butyl-3-methanesulfonylamino-2-methoxy-phenyl)-3-[4-(3-cyclopropyl-2-isopropyl-3H-imidazol-4-yl)-[1,2,3]triazol-1-yl]-4-methyl-benzamide

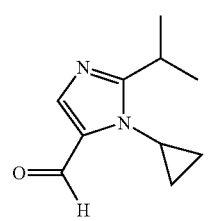

3-Cyclopropyl-2-isopropyl-3H-imidazole-4-carbaldehyde was prepared from isobutyramide and cyclopropylamine in the same manner as 2-cyclopropyl-3-methyl-3H-imidazole-4-carbaldehyde (Example 46).

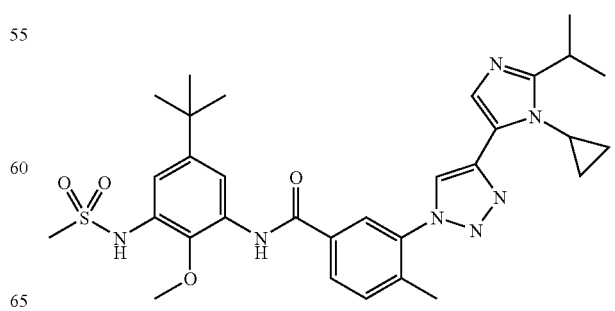

Example 73 was prepared from 3-cyclopropyl-2-isopropyl-3H-imidazole-4-carbaldehyde and 3-azido-N-(5-tert-butyl-3-methanesulfonylamino-2-methoxy-phenyl)-4-methyl-benzamide in the same manner as Example 39. ESI MS m/z 606 $[C_{31}H_{39}N_7O_4S+H]^+$.

Example 74

N-(5-tert-Butyl-3-methanesulfonylamino-2-methoxy-phenyl)-3-[4-(2-cyclopropyl-3-isopropyl-3H-imidazol-4-yl)-[1,2,3]triazol-1-yl]-4-methyl-benzamide

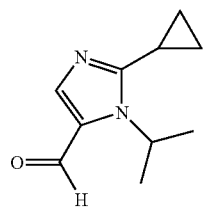

2-Cyclopropyl-3-isopropyl-3H-imidazole-4-carbaldehyde was prepared from cyclopropane carboxamide and isopropylamine in the same manner as 2-cyclopropyl-3-methyl-3H-imidazole-4-carbaldehyde (Example 46).

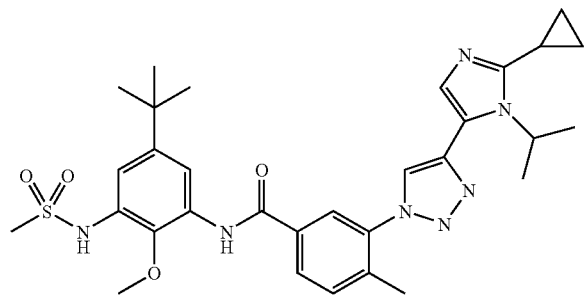

Example 74 was prepared from 2-cyclopropyl-3-isopropyl-3H-imidazole-4-carbaldehyde and 3-azido-N-(5-tert-butyl-3-methanesulfonylamino-2-methoxy-phenyl)-4-methyl-benzamide in the same manner as Example 39. ESI MS m/z 606 $[C_{31}H_{39}N_7O_4S+H]^+$.

Example 75

N-(5-tert-Butyl-3-methanesulfonylamino-2-methoxy-phenyl)-3-[4-(1-cyclopropyl-5-isopropyl-1H-pyrazol-4-yl)-[1,2,3]triazol-1-yl]-4-methyl-benzamide

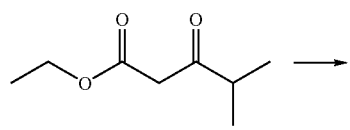

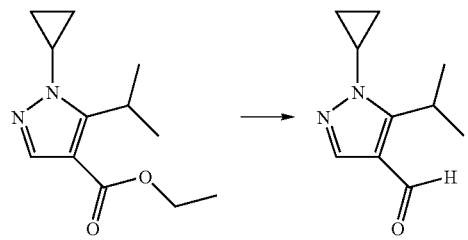

1-Cyclopropyl-5-isopropyl-1H-pyrazole-4-carbaldehyde was prepared from ethyl 4-methyl-3-oxopentanoate and cyclopropyl hydrazine hydrochloride in the same manner as 5-cyclopropyl-1-isopropyl-1H-pyrazole-4-carbaldehyde (Example 49).

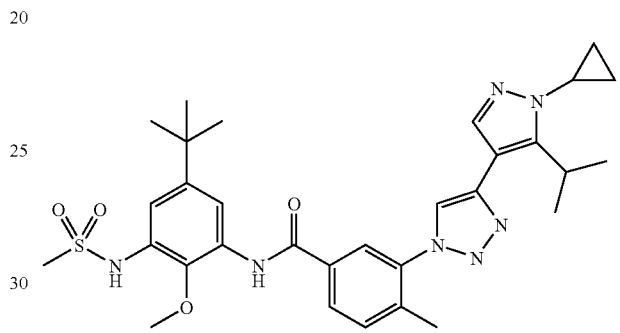

Example 75 benzamide was prepared from 1-cyclopropyl-5-isopropyl-1H-pyrazole-4-carbaldehyde and 3-azido-N-(5-tert-butyl-3-methanesulfonylamino-2-methoxy-phenyl)-4-methyl-benzamide in the same manner as Example 39. ESI MS m/z 606 $[C_{31}H_{39}N_7O_4S+H]^+$.

Example 76

N-(5-tert-Butyl-3-methanesulfonylamino-2-methoxy-phenyl)-3-[4-(1,5-diisopropyl-1H-pyrazol-4-yl)-[1,2,3]triazol-1-yl]-4-methyl-benzamide

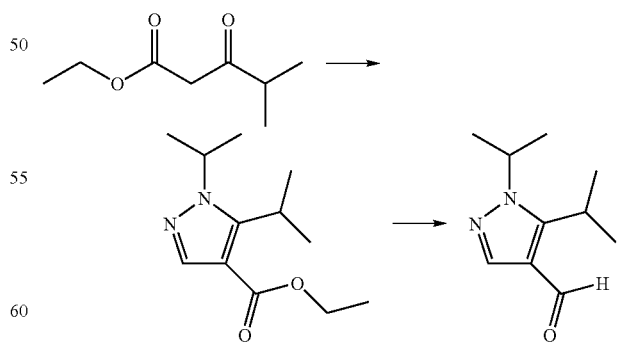

1,5-Diisoopropyl-1H-pyrazole-4-carbaldehyde was prepared from ethyl 4-methyl-3-oxopentanoate and isopropyl hydrazine hydrochloride in the same manner as 5-cyclopropyl-1-isopropyl-1H-pyrazole-4-carbaldehyde (Example 49).

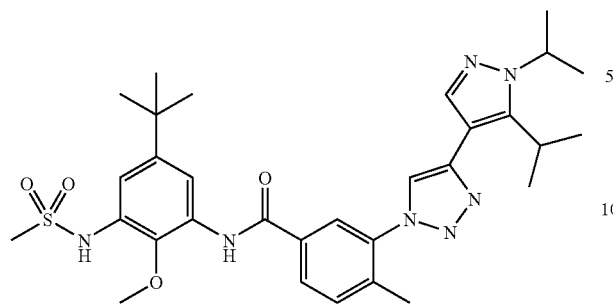

Example 76 was prepared from 1,5-diisopropyl-1H-pyrazole-4-carbaldehyde and 3-azido-N-(5-tert-butyl-3-methanesulfonylamino-2-methoxy-phenyl)-4-methyl-benzamide in the same manner as Example 39. ESI MS m/z 608 [$C_{31}H_{41}N_7O_4S$+H]$^+$.

Example 77

N-(5-tert-Butyl-3-methanesulfonylamino-2-methoxy-phenyl)-4-methyl-3-[4-(5-methyl-1-phenyl-1H-pyrazol-4-yl)-[1,2,3]triazol-1-yl]-benzamide

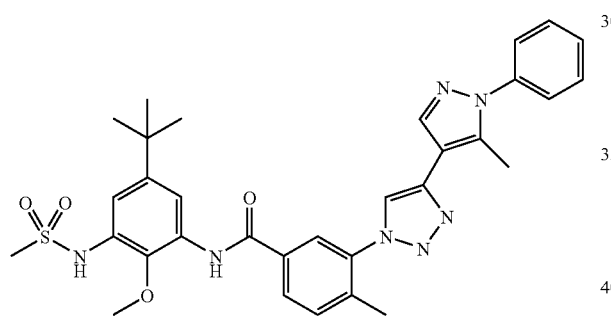

Example 77 was prepared from 5-methyl-1-phenyl-1H-pyrazole-4-carbaldehyde (Maybridge) and 3-azido-N-(5-tert-butyl-3-methanesulfonylamino-2-methoxy-phenyl)-4-methyl-benzamide in the same manner as Example 39. ESI MS m/z 614 [$C_{32}H_{35}N_7O_4S$+H]$^+$.

Example 78

N-(5-tert-Butyl-3-methanesulfonylamino-2-methoxy-phenyl)-4-methyl-3-[4-(3-methyl-2-phenyl-3H-imidazol-4-yl)-[1,2,3]triazol-1-yl]-benzamide

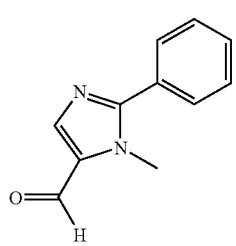

3-Methyl-2-phenyl-3H-imidazole-4-carbaldehyde was prepared from benzene carboxamide in the same manner as 2-cyclopropyl-3-methyl-3H-imidazole-4-carbaldehyde (Example 46).

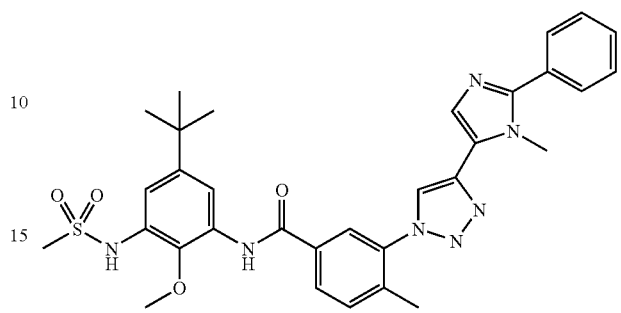

Example 78 was prepared from 3-methyl-2-phenyl-3H-imidazole-4-carbaldehyde and 3-azido-N-(5-tert-butyl-3-methane-sulfonylamino-2-methoxy-phenyl)-4-methyl-benzamide in the same manner as Example 39. ESI MS m/z 614 [$C_{32}H_{35}N_7O_4S$+H]$^+$.

Example 79

N-(5-tert-Butyl-3-methanesulfonylamino-2-methoxy-phenyl)-4-methyl-3-[4-(3-methyl-2-pyridin-4-yl-3H-imidazol-4-yl)-[1,2,3]triazol-1-yl]-benzamide

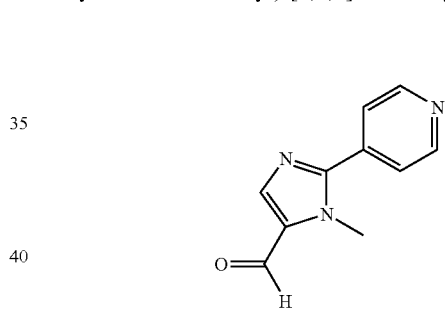

3-Methyl-2-pyridin-4-yl-3H-imidazole-4-carbaldehyde was prepared from pyridine-4-carboxamide in the same manner as 2-cyclopropyl-3-methyl-3H-imidazole-4-carbaldehyde (Example 46).

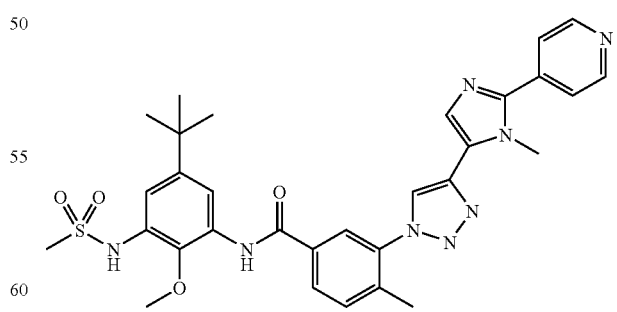

Example 79 was prepared from 3-methyl-2-pyridin-4-yl-3H-imidazole-4-carbaldehyde and 3-azido-N-(5-tert-butyl-3-methanesulfonylamino-2-methoxy-phenyl)-4-methyl-benzamide in the same manner as Example 39. ESI MS m/z 615 [$C_{31}H_{34}N_8O_4S$+H]$^+$.

Example 80

N-(5-tert-Butyl-3-methanesulfonylamino-2-methoxy-phenyl)-4-methyl-3-[4-(5-methyl-1-pyridin-2-yl-1H-pyrazol-4-yl)-[1,2,3]triazol-1-yl]-benzamide

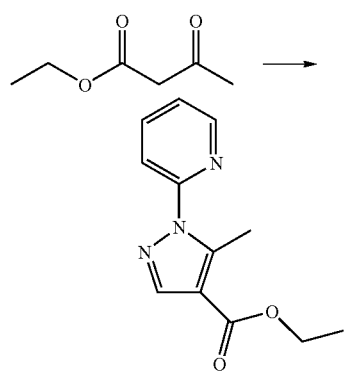

5-Methyl-1-pyridin-2-yl-1H-pyrazole-4-carbaldehyde was prepared from ethyl acetoacetate and 2-pyridyl hydrazine in the same manner as 5-cyclopropyl-1-isopropyl-1H-pyrazole-4-carbaldehyde (Example 49).

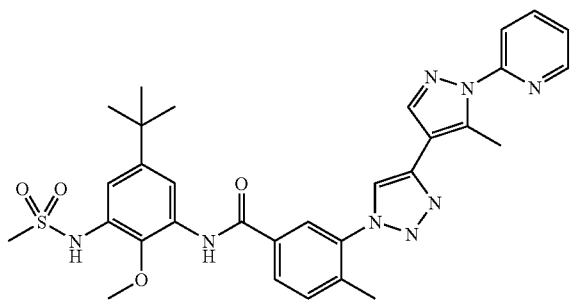

Example 80 was prepared from 5-methyl-1-pyridin-2-yl-1H-pyrazole-4-carbaldehyde and 3-azido-N-(5-tert-butyl-3-methane-sulfonylamino-2-methoxy-phenyl)-4-methyl-benzamide in the same manner as Example 39. ESI MS m/z 615 $[C_{31}H_{34}N_8O_4S+H]^+$.

Example 81

N-(5-tert-Butyl-3-methanesulfonylamino-2-methoxy-phenyl)-4-methyl-3-{4-[2-methyl-3-(2,2,2-trifluoro-ethyl)-3H-imidazol-4-yl]-[1,2,3]triazol-1-yl}-benzamide

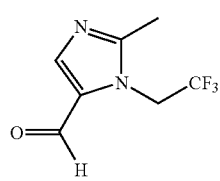

2-Methyl-3-(2,2,2-trifluoro-ethyl)-3H-imidazole-4-carbaldehyde was prepared from ethyl acetimidate hydrochloride and 2,2,2-trifluoroethylamine in the same manner as 3-cyclopropyl-2-methyl-3H-imidazole-4-carbaldehyde (Example 45).

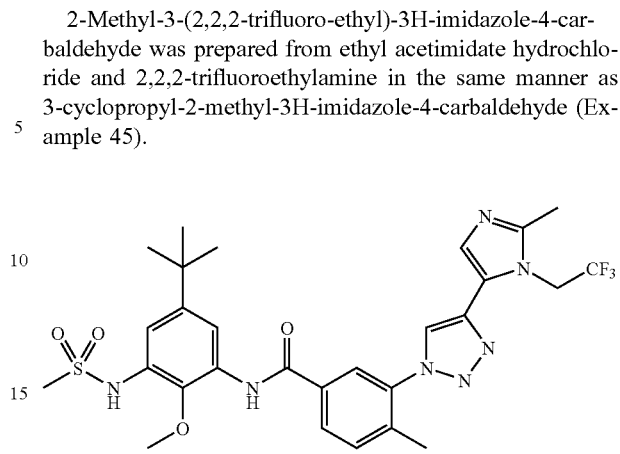

Example 81 was prepared from 2-methyl-3-(2,2,2-trifluoro-ethyl)-3H-imidazole-4-carbaldehyde and 3-azido-N-(5-tert-butyl-3-methanesulfonylamino-2-methoxy-phenyl)-4-methyl-benzamide in the same manner as Example 39. ESI MS m/z 620 $[C_{28}H_{32}F_3N_7O_4S+H]^+$.

Example 82

3-[4-(3-tert-Butyl-2-cyclopropyl-3H-imidazol-4-yl)-[1,2,3]triazol-1-yl]-N-(5-tert-butyl-3-methanesulfonylamino-2-methoxy-phenyl)-4-methyl-benzamide

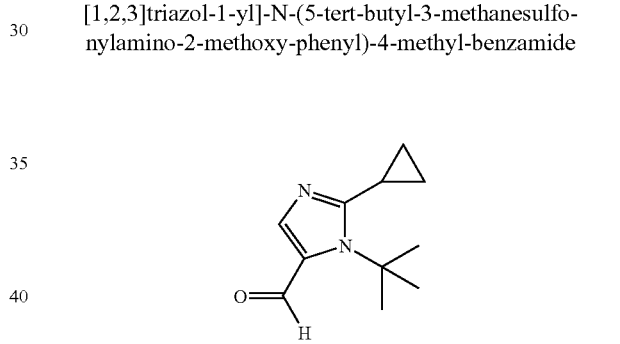

3-tert-Butyl-2-cyclopropyl-3H-imidazole-4-carbaldehyde was prepared from cyclopropyl carboxamide and tert-butylamine in the same manner as 2-cyclopropyl-3-methyl-3H-imidazole-4-carbaldehyde (Example 46).

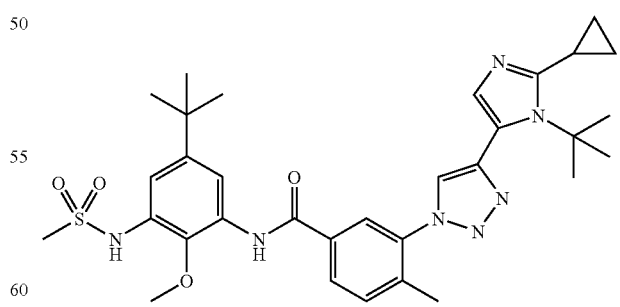

Example 82 benzamide was prepared from 3-tert-butyl-2-cyclopropyl-3H-imidazole-4-carbaldehyde and 3-azido-N-(5-tert-butyl-3-methanesulfonylamino-2-methoxy-phenyl)-4-methyl-benzamide in the same manner as Example 39. ESI MS m/z 620 $[C_{32}H_{41}N_7O_4S+H]^+$.

Example 83

N-(5-tert-Butyl-3-methanesulfonylamino-2-methoxy-phenyl)-3-[4-(1-cyclohexyl-5-methyl-1H-pyrazol-4-yl)-[1,2,3]triazol-1-yl]-4-methyl-benzamide

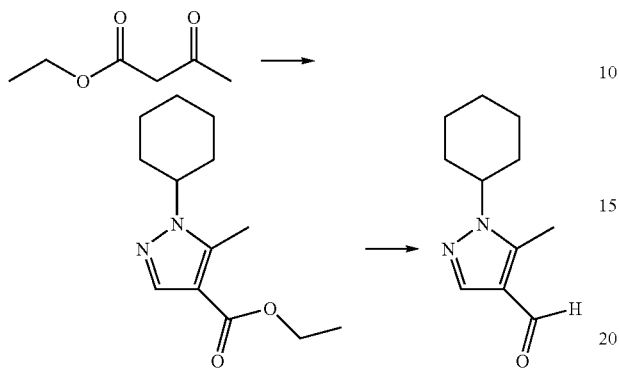

1-Cyclohexyl-5-methyl-1H-pyrazole-4-carbaldehyde was prepared from ethyl acetoacetate and cyclohexyl hydrazine (TCI) in the same manner as 5-cyclopropyl-1-isopropyl-1H-pyrazole-4-carbaldehyde (Example 49).

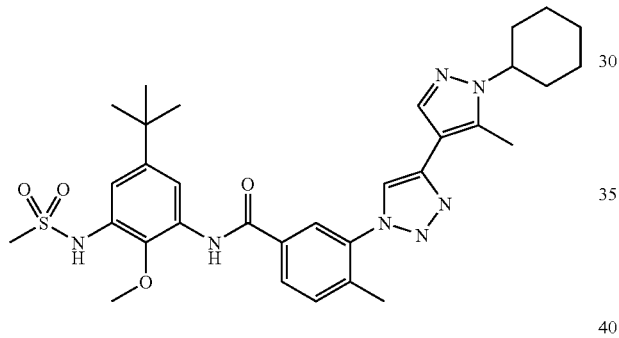

Example 83 was prepared from 1-cyclohexyl-5-methyl-1H-pyrazole-4-carbaldehyde and 3-azido-N-(5-tert-butyl-3-methane-sulfonylamino-2-methoxy-phenyl)-4-methyl-benzamide in the same manner as Example 39. ESI MS m/z 620 $[C_{32}H_{41}N_7O_4S+H]^+$.

Example 84

N-(5-tert-Butyl-3-methanesulfonylamino-2-methoxy-phenyl)-4-methyl-3-[4-(2-morpholin-4-yl-thiazol-5-yl)-[1,2,3]triazol-1-yl]-benzamide

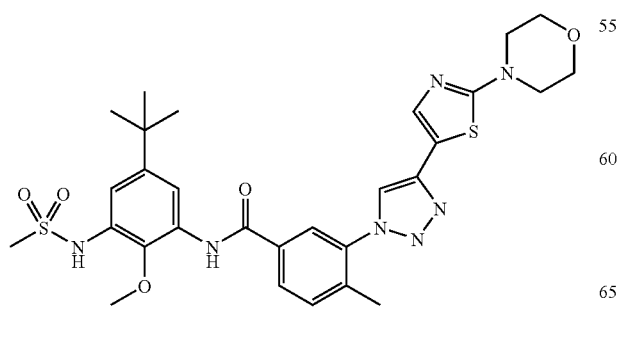

Example 84 was prepared from 2-morpholin-4-yl-thiazole-5-carbaldehyde (Bionet) and 3-azido-N-(5-tert-butyl-3-methane-sulfonylamino-2-methoxy-phenyl)-4-methyl-benzamide in the same manner as Example 39. ESI MS m/z 626 $[C_{29}H_{35}N_7O_5S_2+H]^+$.

Example 85

N-(5-tert-Butyl-3-methanesulfonylamino-2-methoxy-phenyl)-4-methyl-3-[4-(3-ethyl-2-phenyl-3H-imidazol-4-yl)-[1,2,3]triazol-1-yl]-benzamide

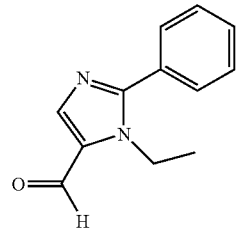

3-Ethyl-2-phenyl-3H-imidazole-4-carbaldehyde was prepared from benzene carboxamide and ethylamine in the same manner as 2-cyclopropyl-3-methyl-3H-imidazole-4-carbaldehyde (Example 46).

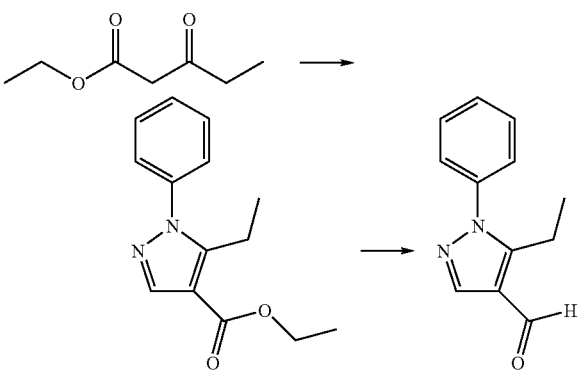

Example 85 was prepared from 3-ethyl-2-phenyl-3H-imidazole-4-carbaldehyde and 3-azido-N-(5-tert-butyl-3-methane-sulfonylamino-2-methoxy-phenyl)-4-methyl-benzamide in the same manner as Example 39. ESI MS m/z 628 $[C_{33}H_{37}N_7O_4S+H]^+$.

Example 86

N-(5-tert-Butyl-3-methanesulfonylamino-2-methoxy-phenyl)-3-[4-(5-ethyl-1-phenyl-1H-pyrazol-4-yl)-[1,2,3]triazol-1-yl]-4-methyl-benzamide

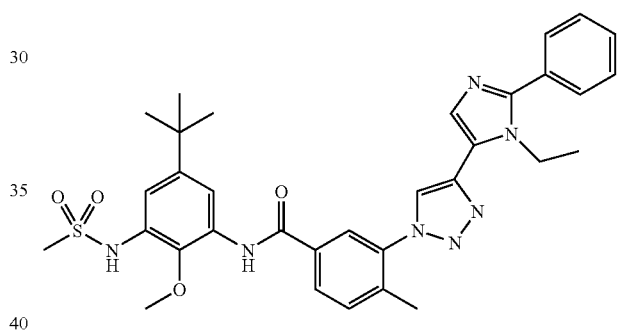

5-Ethyl-1-phenyl-1H-pyrazole-4-carbaldehyde was prepared from ethyl 3-oxo-pentanoate and phenyl hydrazine in the same manner as 5-cyclopropyl-1-isopropyl-1H-pyrazole-4-carbaldehyde (Example 49).

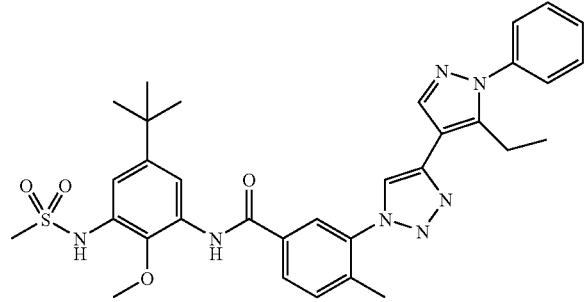

Example 86 was prepared from 5-ethyl-1-phenyl-1H-pyrazole-4-carbaldehyde and 3-azido-N-(5-tert-butyl-3-methane-sulfonylamino-2-methoxy-phenyl)-4-methyl-benzamide in the same manner as Example 39. ESI MS m/z 628 $[C_{33}H_{37}N_7O_4S+H]^+$

Example 87

3-[4-(2-Benzyl-3-methyl-3H-imidazol-4-yl)-[1,2,3]triazol-1-yl]-N-(5-tert-butyl-3-methanesulfonylamino-2-methoxy-phenyl)-4-methyl-benzamide

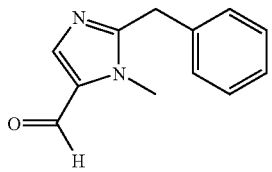

2-Benzyl-3-methyl-3H-imidazole-4-carbaldehyde was prepared from 2-phenyl-acetamide in the same manner as 2-cyclopropyl-3-methyl-3H-imidazole-4-carbaldehyde (Example 46).

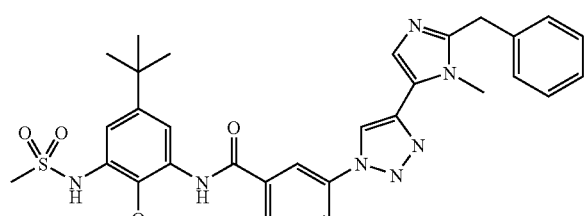

Example 87 was prepared from 2-benzyl-3-methyl-3H-imidazole-4-carbaldehyde and 3-azido-N-(5-tert-butyl-3-methane-sulfonylamino-2-methoxy-phenyl)-4-methyl-benzamide in the same manner as Example 39. ESI MS m/z 628 $[C_{33}H_{37}N_7O_4S+H]^+$.

Example 88

N-(5-tert-Butyl-3-methanesulfonylamino-2-methoxy-phenyl)-3-[4-(5-ethyl-1-pyridin-2-yl-1H-pyrazol-4-yl)-1,2,3-triazol-1-yl]-4-methyl-benzamide

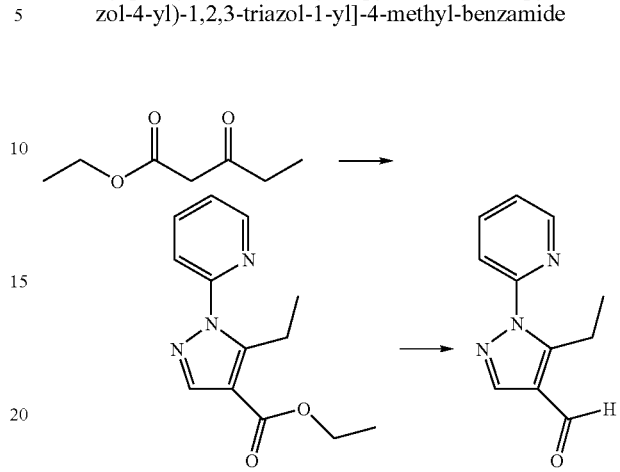

5-Ethyl-1-pyridin-2-yl-1H-pyrazole-4-carbaldehyde was prepared from ethyl 3-oxo-pentanoate and 2-pyridyl hydrazine in the same manner as 5-cyclopropyl-1-isopropyl-1H-pyrazole-4-carbaldehyde (Example 49).

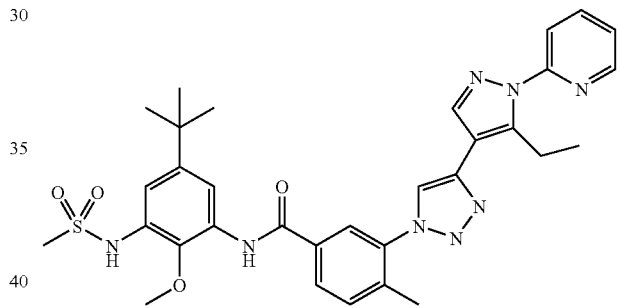

Example 88 was prepared from 5-ethyl-1-pyridin-2-yl-1H-pyrazole-4-carbaldehyde and 3-azido-N-(5-tert-butyl-3-methane-sulfonylamino-2-methoxy-phenyl)-4-methyl-benzamide in the same manner as Example 39. ESI MS n/z 629 $[C_{32}H_{36}N_8O_4S+H]^+$.

Example 89

N-(5-tert-Butyl-3-methanesulfonylamino-2-methoxy-phenyl)-4-methyl-3-[4-[spiro(6,7-dihydro-5H-pyrrolo[1,2-a]imidazol-3-yl-5-cyclohexane)]-[1,2,3]triazol-1-yl]-benzamide

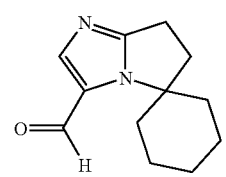

Spiro[6,7-dihydro-5H-pyrrolo[1,2-a]imidazole-5-cyclohexane]-3-carbaldehyde was prepared from 1-aza-spiro[4.5]

dec-2-ylideneamine (Buckley, et al. *J. Chem. Soc.* 1947, 1507.) and 2-bromo-3-isopropoxy-propenal in the same manner as cyclopropyl-2-methyl-3H-imidazole-4-carbaldehyde (Example 45).

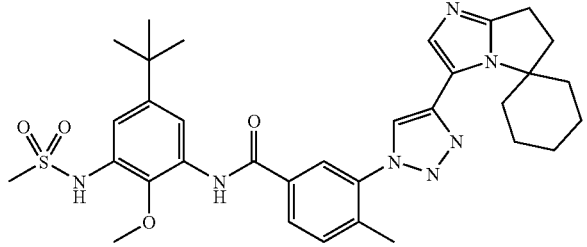

Example 89 was prepared from spiro[6,7-dihydro-5H-pyrrolo[1,2-a]imidazole-5-cyclohexane]-3-carbaldehyde and 3-azido-N-(5-tert-butyl-3-methanesulfonylamino-2-methoxy-phenyl)-4-methyl-benzamide in the same manner as Example 39. ESI MS m/z 592 $[C_{30}H_{37}N_7O_4S+H]^+$.

Example 90

N-(5-tert-Butyl-3-methanesulfonylamino-2-methoxy-phenyl)-3-{4-[1-(4-fluoro-phenyl)-5-methyl-1H-pyrazol-4-yl]-[1,2,3]triazol-1-yl}-4-methyl-benzamide

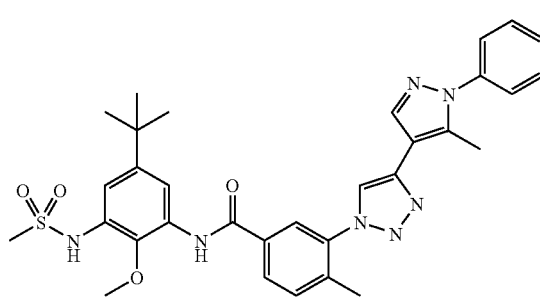

Example 90 was prepared from 1-(4-fluoro-phenyl)-5-methyl-1H-pyrazole-4-carbaldehyde (Maybridge) and 3-azido-N-(5-tert-butyl-3-methane-sulfonylamino-2-methoxy-phenyl)-4-methyl-benzamide in the same manner as Example 39. ESI MS m/z 632 $[C_{32}H_{34}FN_7O_4S+H]^+$.

Example 91

N-(5-tert-Butyl-3-methanesulfonylamino-2-methoxy-phenyl)-3-[4-(1-cyclohexyl-5-ethyl-1H-pyrazol-4-yl)-[1,2,3]triazol-1-yl]-4-methyl-benzamide

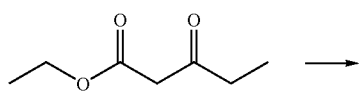

-continued

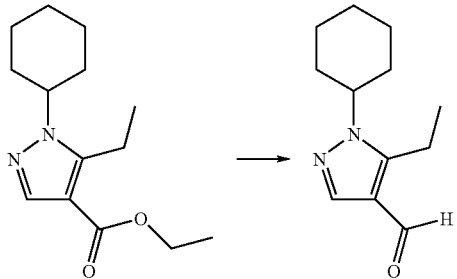

1-Cyclohexyl-5-ethyl-1H-pyrazole-4-carbaldehyde was prepared from ethyl 3-oxo-pentanoate and cyclohexyl hydrazine (TCI) in the same manner as 5-cyclopropyl-1-isopropyl-1H-pyrazole-4-carbaldehyde (Example 49).

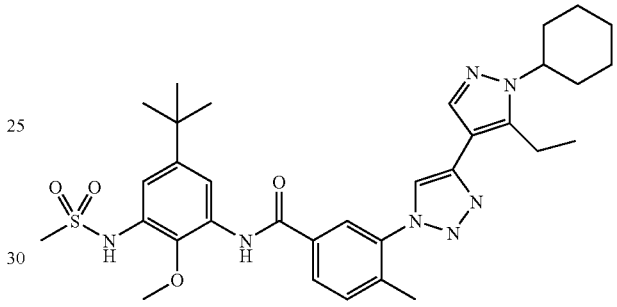

Example 91 was prepared from 1-cyclohexyl-5-ethyl-1H-pyrazole-4-carbaldehyde and 3-azido-N-(5-tert-butyl-3-methane-sulfonylamino-2-methoxy-phenyl)-4-methyl-benzamide in the same manner as Example 39. ESI MS m/z 634 $[C_{33}H_{43}N_7O_4S+H]^+$.

Example 92

N-(5-tert-Butyl-3-methanesulfonylamino-2-methoxy-phenyl)-4-methyl-3-{4-[5-methyl-1-(1-methyl-piperidin-4-yl)-1H-pyrazol-4-yl]-[1,2,3]triazol-1-yl}-benzamide

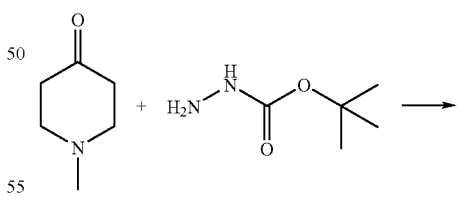

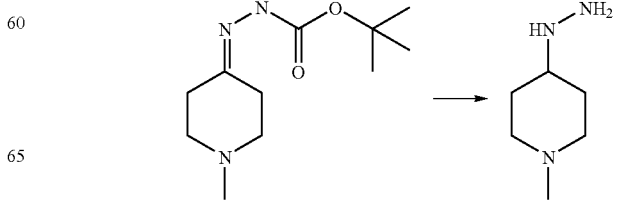

A solution of 11.2 g (99.0 mmol) of 1-methyl-piperid-4-one and 13.0 g (100 mmol) of Boc-hydrazine in 150 mL of hexanes was refluxed for 30 minutes. The hot solution was dried over MgSO$_4$, filtered, and allowed to cool. The resulting crystals were isolated and recrystallized from Et$_2$O to provide 7.2 g of tert-butyl N'-(1-Methyl-piperidin-4-ylidene)-hydrazinecarboxylate as a white solid.

A solution of 1 M borane in THF (30 mL) was added to solid 2.80 g (12.3 mmol) of tert-butyl N'-(1-Methyl-piperidin-4-ylidene)-hydrazinecarboxylate. The mixture was stirred under N$_2$ for 16 h when 40 mL of 6M HCl was carefully added. The mixture was heated to 60° C. for 30 min. The mixture was concentrated in vacuo at ambient temperature for 2 days. Petroleum ether (200 mL) and powdered NaOH (5 g) were added, and the mixture was stirred manually for 30 min. The mixture was dried with MgSO$_4$, filtered, and carefully concentrated to give 1.3 g of (1-methyl-piperidin-4-yl)-hydrazine.

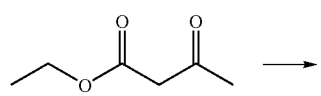

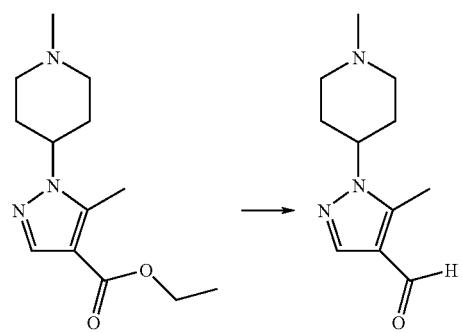

5-Methyl-1-(1-methyl-piperidin-4-yl)-1H-pyrazole-4-carbaldehyde was prepared from ethyl acetoacetate and (1-methyl-piperidin-4-yl)-hydrazine in the same manner as 5-cyclopropyl-1-isopropyl-1H-pyrazole-4-carbaldehyde (Example 49).

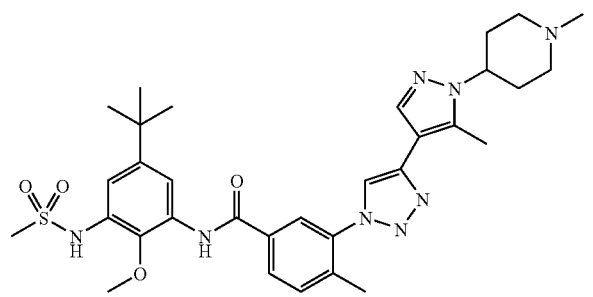

Example 92 was prepared from 5-methyl-1-(1-methyl-piperidin-4-yl)-1H-pyrazole-4-carbaldehyde and 3-azido-N-(5-tert-butyl-3-methanesulfonylamino-2-methoxy-phenyl)-4-methyl-benzamide in the same manner as Example 39. ESI MS m/z 635 [C$_{32}$H$_{42}$N$_8$O$_4$S+H]$^+$.

Example 93

N-(5-tert-Butyl-3-methanesulfonylamino-2-methoxy-phenyl)-3-[4-(5-cyclopropyl-1-phenyl-1H-pyrazol-4-yl)-[1,2,3]triazol-1-yl]-4-methyl-benzamide

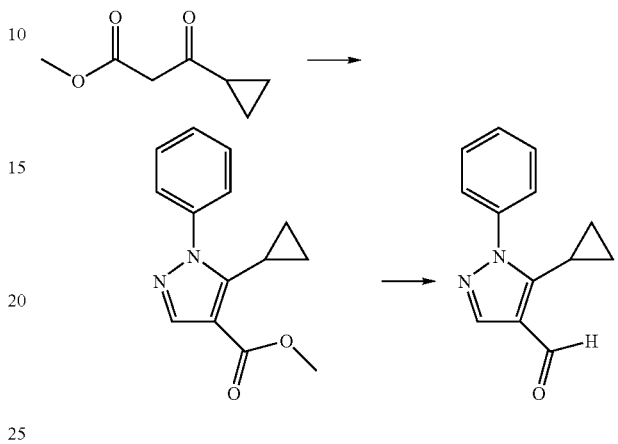

5-Cyclopropyl-1-phenyl-1H-pyrazole-4-carbaldehyde was prepared from methyl 3-cyclopropyl-3-oxo-propionate and phenyl hydrazine in the same manner as 5-cyclopropyl-1-isopropyl-1H-pyrazole-4-carbaldehyde (Example 49).

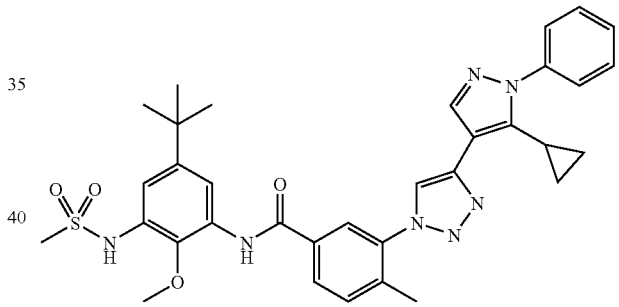

Example 93 was prepared from 5-cyclopropyl-1-phenyl-1H-pyrazole-4-carbaldehyde and 3-azido-N-(5-tert-butyl-3-methane-sulfonylamino-2-methoxy-phenyl)-4-methyl-benzamide in the same manner as Example 39. ESI MS m/z 640 [C$_{34}$H$_{37}$N$_7$O$_4$S+H]$^+$.

Example 94

N-(5-tert-Butyl-3-methanesulfonylamino-2-methoxy-phenyl)-3-[4-(1-cyclopropyl-5-pyridin-2-yl-1H-pyrazol-4-yl)-[1,2,3]triazol-1-yl]-4-methyl-benzamide

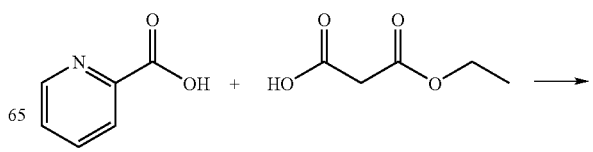

-continued

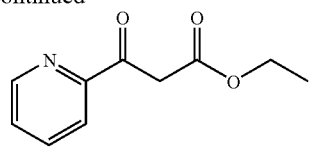

A solution of isopropylmagnesium bromide (2M in Et$_2$O; 36.5 mL, 73.0 mmol) was added to 4.36 mL (36.6 mmol) of malonic acid monoethyl ester in 30 mL of THF under N$_2$ at 0° C. The reaction was stirred at 0° C. for 30 min, at room temperature for 30 min, and then at 40° C. for 30 min. The mixture was subsequently cooled to 0° C. and a imidazol-1-yl-pyridin-2-yl-methanone solution (prepared by stirring 3.00 g (24.3 mmol) of pyridine-2-carboxylic acid with 4.7 g (29 mmol) of CDI in 30 mL of THF for 12 h) was slowly added. The reaction was allowed to warm to room temperature and stirred for 12 h. The mixture was then poured into ice cold 1M H$_3$PO$_4$ (150 mL). Solid NaHCO$_3$ was added to the mixture until the pH reached 7. The mixture was extracted with EtOAc (3×100 mL). The combined organic extracts were washed with NaHCO$_3$ (100 mL) and brine, dried with MgSO$_4$, filtered, and concentrated to provide 2.5 g ethyl 3-oxo-3-pyridin-2-yl-propionate as an oil.

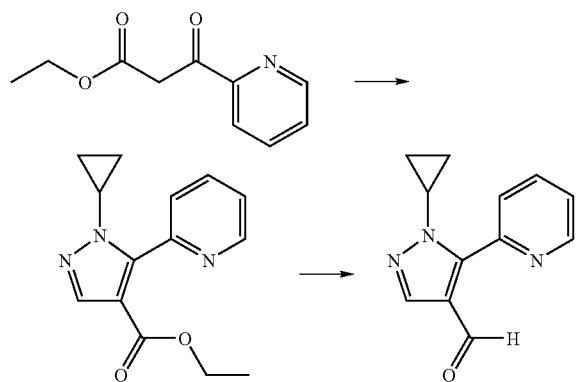

1-Cyclopropyl-5-pyridin-2-yl-1H-pyrazole-4-carbaldehyde was prepared from ethyl 3-oxo-3-pyridin-2-yl-propionate and cyclopropyl hydrazine oxalate in the same manner as 5-cyclopropyl-1-isopropyl-1H-pyrazole-4-carbaldehyde (Example 49).

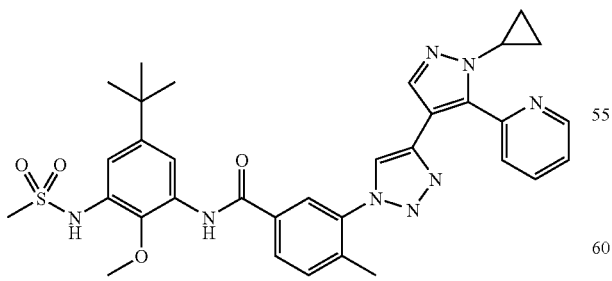

Example 94 was prepared from 1-cyclopropyl-5-pyridin-2-yl-1H-pyrazole-4-carbaldehyde and 3-azido-N-(5-tert-butyl-3-methane-sulfonylamino-2-methoxy-phenyl)-4-methyl-benzamide in the same manner as Example 39. ESI MS m/z 641 [C$_{33}$H$_{36}$N$_8$O$_4$S+H]$^+$.

Example 95

3-[4-(3-Benzyl-2-ethyl-3H-imidazol-4-yl)-[1,2,3]triazol-1-yl]-N-(5-tert-butyl-3-methanesulfonylamino-2-methoxy-phenyl)-4-methyl-benzamide

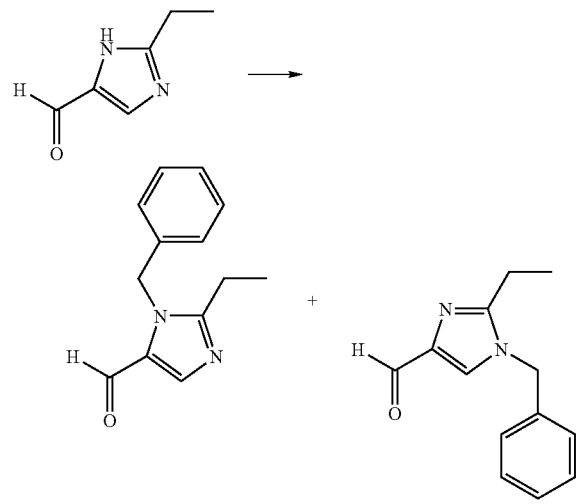

3-Benzyl-2-ethyl-3H-imidazole-4-carbaldehyde and 1-benzyl-2-ethyl-1H-imidazole-4-carbaldehyde were prepared in the same manner as 1,2-diethyl-5-formylimidazole and 1,2-diethyl-4-formylimidazole (Example 51).

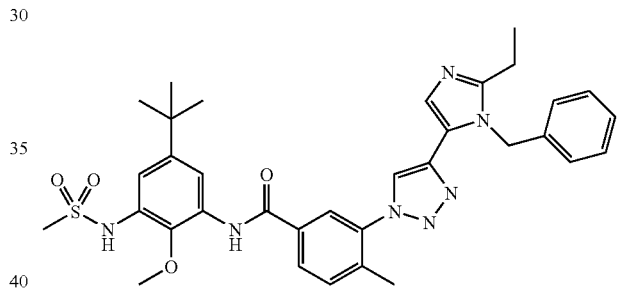

Example 95 was prepared from 3-benzyl-2-ethyl-3H-imidazole-4-carbaldehyde and 3-azido-N-(5-tert-butyl-3-methanesulfonylamino-2-methoxy-phenyl)-4-methyl-benzamide in the same manner as Example 39. ESI MS m/z 642 [C$_{34}$H$_{39}$N$_7$O$_4$S+H]$^+$.

Example 96

3-[4-(1-Benzyl-2-ethyl-1H-imidazol-4-yl)-[1,2,3]triazol-1-yl]-N-(5-tert-butyl-3-methanesulfonylamino-2-methoxy-phenyl)-4-methyl-benzamide

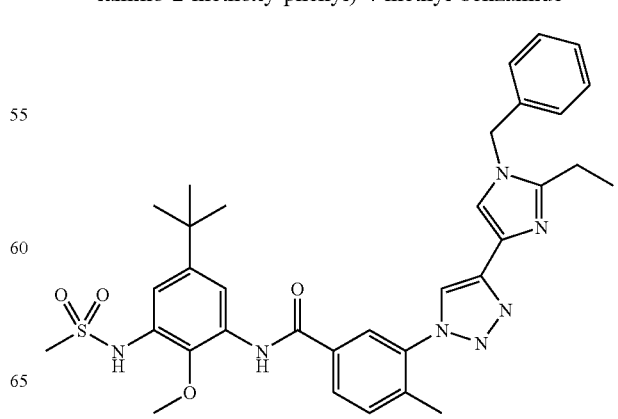

Example 96 was prepared from 1-benzyl-2-ethyl-1H-imidazole-4-carbaldehyde (Example 95) and 3-azido-N-(5-tert-butyl-3-methanesulfonylamino-2-methoxy-phenyl)-4-methyl-benzamide in the same manner as Example 39. ESI MS m/z 642 $[C_{34}H_{39}N_7O_4S+H]^+$.

Example 97

N-(5-tert-Butyl-3-methanesulfonylamino-2-methoxy-phenyl)-3-[4-(5-isopropyl-1-phenyl-1H-pyrazol-4-yl)-[1,2,3]triazol-1-yl]-4-methyl-benzamide

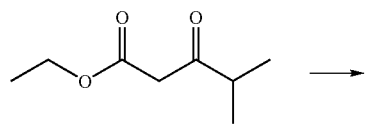

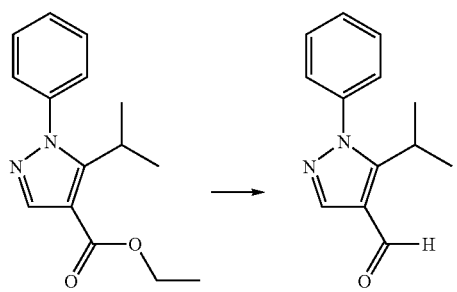

5-Isopropyl-1-phenyl-1H-pyrazole-4-carbaldehyde was prepared from ethyl 3-oxo-3-methyl-pentanoate and phenyl hydrazine in the same manner as 5-cyclopropyl-1-isopropyl-1H-pyrazole-4-carbaldehyde (Example 49).

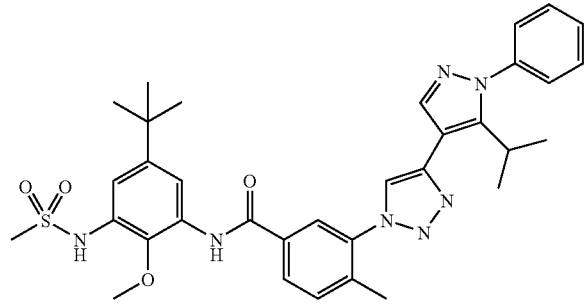

Example 97 was prepared from 5-isopropyl-1-phenyl-1H-pyrazole-4-carbaldehyde and 3-azido-N-(5-tert-butyl-3-methane-sulfonylamino-2-methoxy-phenyl)-4-methyl-benzamide in the same manner as Example 39. ESI MS m/z 642 $[C_{34}H_{39}N_7O_4S+H]^+$.

Example 98

N-(5-tert-Butyl-3-methanesulfonylamino-2-methoxy-phenyl)-3-{4-[1-(4-methoxy-phenyl)-5-methyl-1H-pyrazol-4-yl]-1,2,3-triazol-1-yl}-4-methyl-benzamide

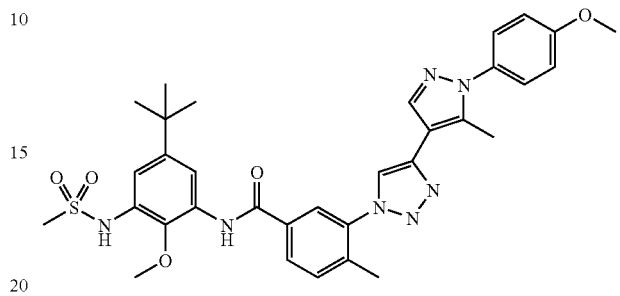

Example 98 was prepared from 1-(4-methoxy-phenyl)-5-methyl-1H-pyrazole-4-carbaldehyde (Maybridge) and 3-azido-N-(5-tert-butyl-3-methane-sulfonylamino-2-methoxy-phenyl)-4-methyl-benzamide in the same manner as Example 39. ESI MS m/z 644 $[C_{33}H_{37}N_7O_5S+H]^+$ Example 99

N-(5-tert-Butyl-3-methanesulfonylamino-2-methoxy-phenyl)-3-{4-[2-cyclopropyl-3-(2,2,2-trifluoro-ethyl)-3H-imidazol-4-yl]-[1,2,3]triazol-1-yl}-4-methyl-benzamide

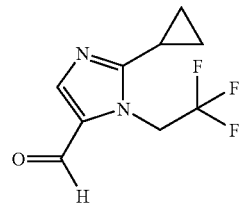

2-Cyclopropyl-3-(2,2,2-trifluoro-ethyl)-3H-imidazole-4-carbaldehyde was prepared from cyclopropyl carboxamide and 2,2,2-trifluoroethylamine in the same manner as 2-cyclopropyl-3-methyl-3H-imidazole-4-carbaldehyde (Example 46).

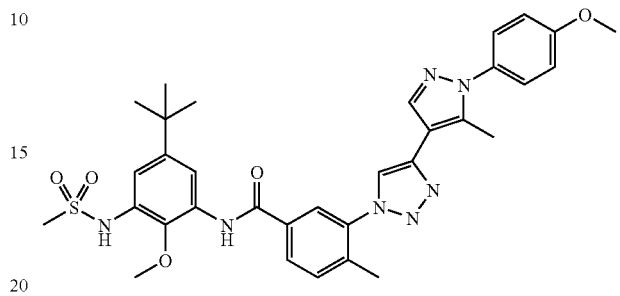

Example 99 was prepared from 2-cyclopropyl-3-(2,2,2-trifluoro-ethyl)-3H-imidazole-4-carbaldehyde and 3-azido-N-(5-tert-butyl-3-methanesulfonylamino-2-methoxy-phenyl)-4-methyl-benzamide in the same manner as Example 39. ESI MS m/z 646 [C$_{30}$H$_{34}$F$_3$N$_7$O$_4$S+H]$^+$.

Example 100

N-(5-tert-Butyl-3-methanesulfonylamino-2-methoxy-phenyl)-4-methyl-3-[4-(3-methyl-2-phenylsulfanyl-3H-imidazol-4-yl)-[1,2,3]triazol-1-yl]-benzamide

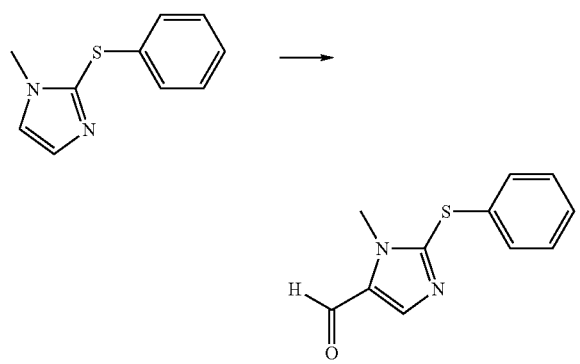

1-Methyl-2-thiophenyl-1H-imidazole (Ohta, S. et al. Bioorg. Med. Chem. Lett. 1992, 40, 2681–2685) (500 mg; 2.63 mmol) was dissolved in 5 mL THF and chilled to −78° C., then n-BuLi (3.29 mL of a 1.6 M solution in hexanes; 5.26 mmol) was added dropwise. The solution was stirred at −78° C. for 15 min, and then a solution of DMF (1.02 mL; 13.1 mmol) in 2 mL THF was added dropwise. After stirring 10 min, the mixture was warmed to room temperature. After stirring 1 h, the reaction was quenched with saturated aqueous NH$_4$Cl and diluted with EtOAc (30 mL) and water (20 mL). The layers were separated and the organic portion was washed with water (20 mL), brine (20 mL), dried (MgSO$_4$), filtered, concentrated, and chromatographed (0–5% MeOH in CH$_2$Cl$_2$) to provide 458 mg (2.1 0 mmol; 80%) of 1-methyl-2-phenylsulfanyl-1H-imidazole-4-carboxaldehyde.

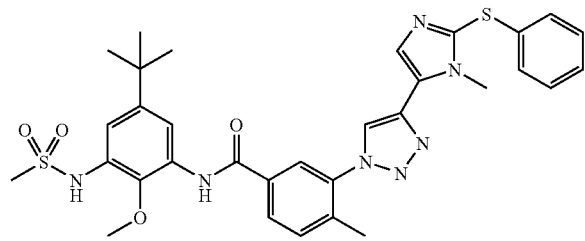

Example 100 was prepared from 1-methyl-2-phenylsulfanyl-1H-imidazole-4-carboxaldehyde and 3-azido-N-(5-tert-butyl-3-methanesulfonylamino-2-methoxy-phenyl)-4-methyl-benzamide in the same manner as Example 39. ESI MS m/z 646 [C$_{32}$H$_{35}$N$_7$O$_4$S$_2$+H]$^+$.

Example 101

N-(5-tert-Butyl-3-methanesulfonylamino-2-methoxy-phenyl)-4-methyl-3-{4-[3-methyl-2-(1-methyl-1-phenyl-ethyl)-3H-imidazol-4-yl]-[1,2,3]triazol-1-yl}-benzamide

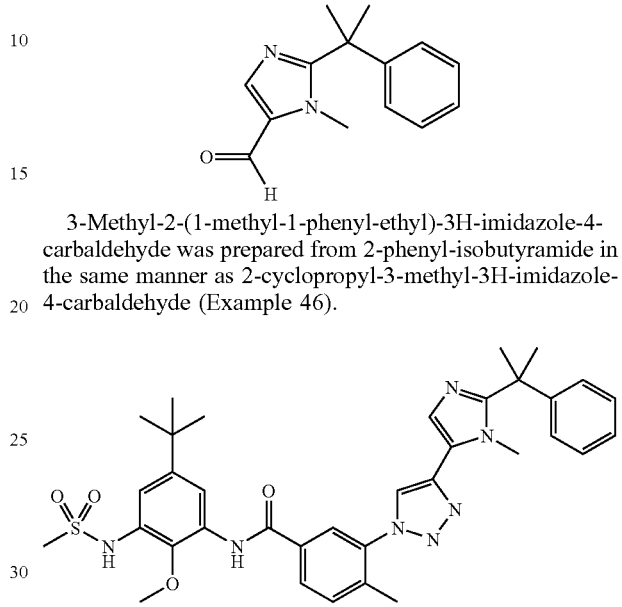

3-Methyl-2-(1-methyl-1-phenyl-ethyl)-3H-imidazole-4-carbaldehyde was prepared from 2-phenyl-isobutyramide in the same manner as 2-cyclopropyl-3-methyl-3H-imidazole-4-carbaldehyde (Example 46).

Example 101 was prepared from 3-methyl-2-(1-methyl-1-phenyl-ethyl)-3H-imidazole-4-carbaldehyde and 3-azido-N-(5-tert-butyl-3-methane-sulfonylamino-2-methoxy-phenyl)-4-methyl-benzamide in the same manner as Example 39. ESI MS m/z 656 [C$_{35}$H$_{41}$N$_7$O$_4$S+H]$^+$.

Example 102

3-[4-(2-Benzyloxymethyl-3-methyl-3H-imidazol-4-yl)-[1,2,3]triazol-1-yl]-N-(5-tert-butyl-3-methane-sulfonylamino-2-methoxy-phenyl)-4-methyl-benzamide

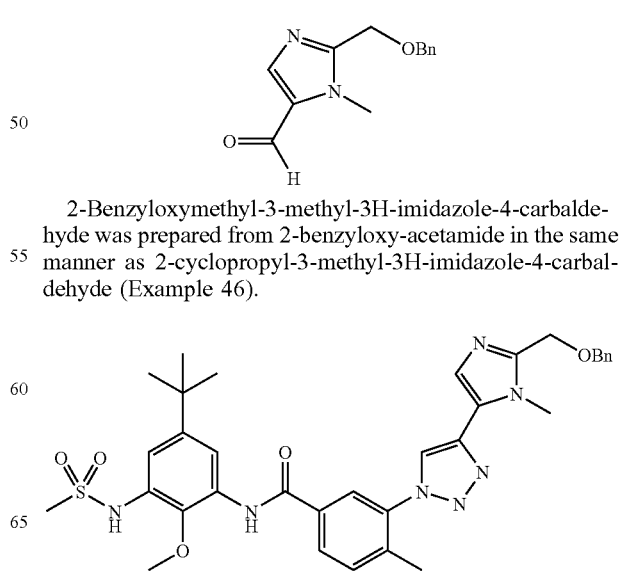

2-Benzyloxymethyl-3-methyl-3H-imidazole-4-carbaldehyde was prepared from 2-benzyloxy-acetamide in the same manner as 2-cyclopropyl-3-methyl-3H-imidazole-4-carbaldehyde (Example 46).

Example 102 was prepared from 2-benzyloxymethyl-3-methyl-3H-imidazole-4-carbaldehyde and 3-azido-N-(5-tert-butyl-3-methane-sulfonylamino-2-methoxy-phenyl)-4-methyl-benzamide in the same manner as Example 39. ESI MS m/z 658 $[C_{34}H_{39}N_7O_5S+H]^+$.

Example 103

N-(5-tert-Butyl-3-methanesulfonylamino-2-methoxy-phenyl)-4-methyl-3-[4-(1-phenyl-5-trifluoromethyl-1H-pyrazol-4-yl)-[1,2,3]triazol-1-yl]-benzamide

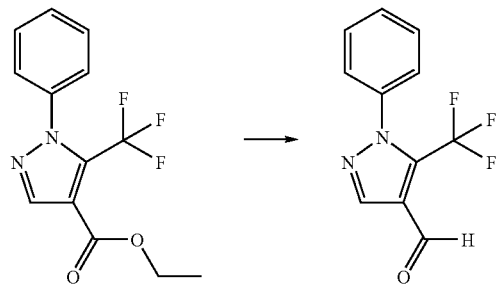

1-Phenyl-5-trifluoromethyl-1H-pyrazole-4-carbaldehyde was prepared from 1-phenyl-5-trifluoromethyl-1H-pyrazole-4-carboxylic acid ethyl ester (Maybridge) in the same manner as 5-cyclopropyl-1-isopropyl-1H-pyrazole-4-carbaldehyde (Example 49).

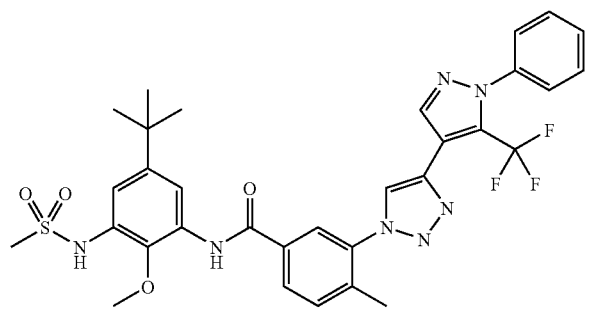

Example 103 was prepared from 1-phenyl-5-trifluoromethyl-1H-pyrazole-4-carbaldehyde and 3-azido-N-(5-tert-butyl-3-methane-sulfonylamino-2-methoxy-phenyl)-4-methyl-benzamide in the same manner as Example 39. ESI MS m/z 668 $[C_{32}H_{32}F_3N_7O_4S+H]^+$.

Example 104

N-(5-tert-Butyl-3-methanesulfonylamino-2-methoxy-phenyl)-3-{4-[1-(1-tert-butyl-piperidin-4-yl)-5-methyl-1H-pyrazol-4-yl]-[1,2,3]triazol-1-yl}-4-methyl-benzamide

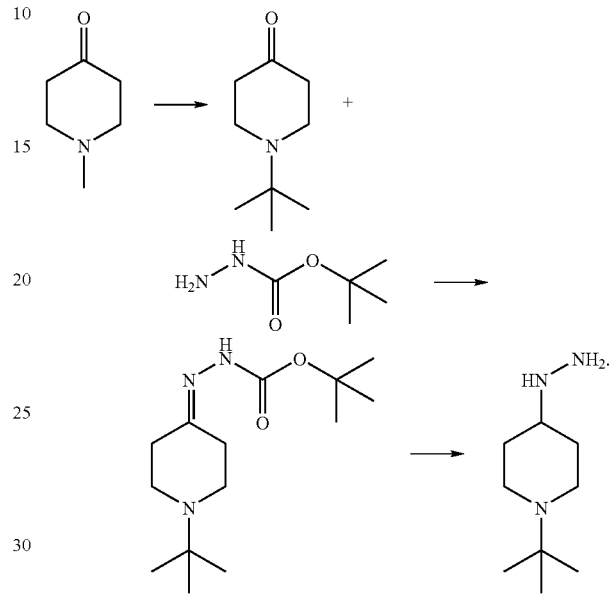

To 45.0 g (398 mmol) of 1-methyl-piperid-4-one in 500 mL of acetone was added dropwise 60.0 g (423 mmol) of MeI over 1 h. The mixture was stirred for 3 h, cooled to 0° C., and filtered. The solids were washed with cold acetone, and dried to provide 1,1-dimethyl-4-oxo-piperidinium iodide as a pale yellow solid (95.3 g).

A suspension of 64.5 g (253 mmol) of 1,1-dimethyl-4-oxo-piperidinium iodide in 50 mL of water and 90 mL (860 mmol) of tert-butylamine was stirred for 15 min when 1.0 mL of 40% Triton B in MeOH was added. The mixture was refluxed for 2 hr under $N_2$, and then it was extracted with $Et_2O$ (4×100 mL). The aqueous phase was basified with 20 g of NaOH in 20 mL of water, and then it was extracted further with $Et_2O$ (4×100 mL). The combined organic extracts were washed with brine, dried over $MgSO_4$, filtered, and concentrated. The residual oil was shaken with 1.5 L of petroleum ether, which was decanted and concentrated. The residue was distilled under vacuum to provide 1.8 g of 1-tert-butyl-piperid-4-one.

To 1.8 g (11.6 mmol) of 1-tert-butyl-piperid-4-one in 10 mL of hexanes was added Boc-hydrazine (1.59 g, 12.0 mmol) in 75 mL of hexanes. The mixture was refluxed for 30 minutes, dried hot with $MgSO_4$, filtered while hot, and then concentrated to provide 3.0 g of N'-(1-tert-Butyl-piperidin-4-ylidene)-hydrazinecarboxylic acid tert-butyl.

A 1M solution borane in THF (28.7 mL, 28.7 mmol) was added to N'-(1-tert-Butyl-piperidin-4-ylidene)-hydrazinecarboxylic acid tert-butyl ester. The mixture was stirred for 16 h, and then 40 mL of 6M HCl was added. The mixture was heated to 60° C. for 30 min. The mixture was concentrated and 200 mL of petroleum ether was added, followed by powdered NaOH (5 g). The slurry was stirred manually for 30 min, and then the mixture was dried with $MgSO_4$, filtered, and concentrated to give 1.21 g of (1-tert-butyl-piperidin-4-yl)-hydrazine (1.21 g).

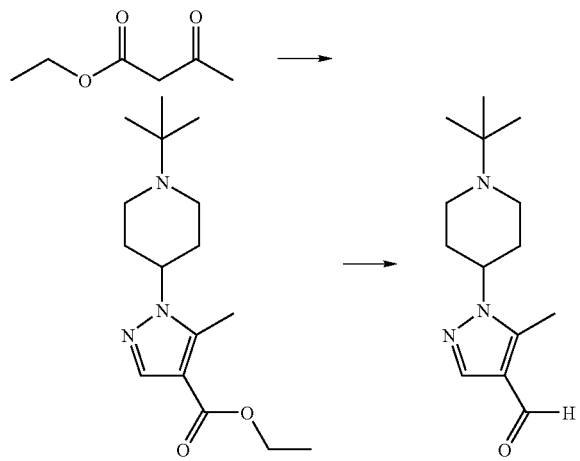

1-(1-tert-Butyl-piperidin-4-yl)-5-methyl-1H-pyrazole-4-carbaldehyde was prepared from ethyl acetoacetate and (1-tert-butyl-piperidin-4-yl)-hydrazine in the same manner as 5-cyclopropyl-1-isopropyl-1H-pyrazole-4-carbaldehyde (Example 49).

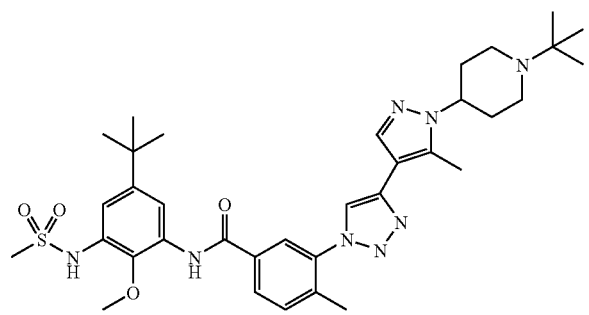

Example 104 was prepared from 1-(1-tert-butyl-piperidin-4-yl)-5-methyl-1H-pyrazole-4-carbaldehyde and 3-azido-N-(5-tert-butyl-3-methanesulfonylamino-2-methoxy-phenyl)-4-methyl-benzamide in the same manner as Example 39. ESI MS m/z 677 $[C_{35}H_{48}N_8O_4S+H]^+$.

Example 105

3-{4-[2-(1-Benzyloxy-cyclopropyl)-3-methyl-3H-imidazol-4-yl]-[1,2,3]triazol-1-yl}-N-(5-tert-butyl-3-methanesulfonylamino-2-methoxy-phenyl)-4-methyl-benzamide

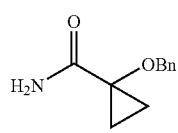

1-Hydroxy-cyclopropanecarboxylic acid methyl ester (Acros; 1.00 g, 8.61 mmol) in 24 mL of THF was stirred with 516 mg (12.9 mmol) of NaH (60% in mineral oil) for 10 min. Benzyl bromide (1.13 mL, 9.37 mmol) and Bu$_4$I (0.32 g, 0.85 mmol) were then added, and the mixture was stirred overnight. The mixture was diluted with EtOAc and washed with saturated NH$_4$Cl. The wash was extracted once with EtOAc, and the combined extracts were washed with brine, dried with Na$_2$SO$_4$, filtered, concentrated, and chromatographed (0–50% EtOAc in hexanes) to provide 774 mg (3.75 mmol) of 1-benzyloxy-cyclopropanecarboxylic acid methyl ester that was dissolved in 14 mL of 1:1 Is EtOH/THF. Sodium hydroxide (1M, 5.63 mL) was added, and the mixture was stirred for 4 h. After concentrating, 5 mL of water was added and the solution was extracted once with Et$_2$O. The aqueous layer was then adjusted to pH 3 with HCl, and the suspension was extracted twice with EtOAc. The extracts were washed with brine, dried with Na$_2$SO$_4$, filtered, and concentrated to provide 723 mg of 1-Benzyloxy-cyclopropanecarboxylic acid. To the above acid (3.76 mmol) in 10 mL of CH$_2$Cl$_2$ was added 2.82 mL (5.64 mmol) of 2M oxalyl chloride in CH$_2$Cl$_2$ and one drop of DMF. After stirring for 15 min, the mixture was concentrated and redissolved in 4 mL of MTBE and 0.15 mL of CH$_2$Cl$_2$ and chilled to 0° C. Ammonium hydroxide (28% in water; 0.78 mL) was added, and the mixture was stirred for 15 min when 1 mL of saturated NaHCO$_3$ was added. The mixture was extracted twice with EtOAc, and the extracts were combined, washed with brine, dried with Na$_2$SO$_4$, filtered, and concentrated to provide 550 mg of 1-benzyloxy-cyclopropanecarboxylic acid amide as a yellow oil.

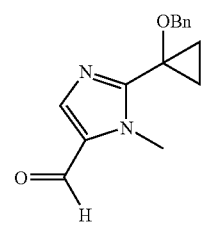

2-(1-Benzyloxy-cyclopropyl)-3-methyl-3H-imidazole-4-carbaldehyde was prepared from 1-benzyloxy-cyclopropanecarboxylic acid amide in the same manner as 2-cyclopropyl-3-methyl-3H-imidazole-4-carbaldehyde (Example 46).

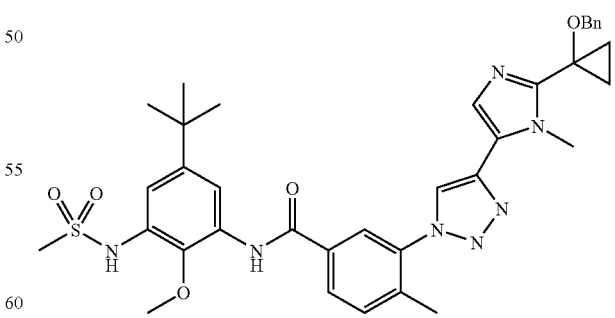

Example 105 was prepared from 2-(1-benzyloxy-cyclopropyl)-3-methyl-3H-imidazole-4-carbaldehyde and 3-azido-N-(5-tert-butyl-3-methane-sulfonylamino-2-methoxy-phenyl)-4-methyl-benzamide in the same manner as Example 39. ESI MS m/z 684 $[C_{36}H_{41}N_7O_5S+H]^+$.

Example 106

3-{4-[2-(2-Benzyloxy-1,1-dimethyl-ethyl)-3-methyl-3H-imidazol-4-yl]-[1,2,3]triazol-1-yl}-N-(5-tert-butyl-3-methanesulfonylamino-2-methoxy-phenyl)-4-methyl-benzamide

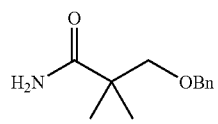

3-Hydroxy-2,2-dimethyl-propionic acid methyl ester (3.00 g, 22.7 mmol) in 40 mL of THF at 0° C. was treated with 1.0 g (25 mmol) of 60% NaH in mineral oil for 20 min. Benzyl bromide (2.97 mL, 25.0 mmol) was added dropwise over 10 minutes. The mixture was stirred overnight, 30 mL of water was added, and the mixture was extracted with EtOAc (3×100 mL). The combined extracts were washed with brine, dried with MgSO$_4$, filtered, and concentrated. The residue was dissolved in 40 mL of EtOH, 28 mL of 2M NaOH was added, and the mixture was heated to 80° C. for 12 h. The mixture was cooled, neutralized with 2M HCl, and extracted with EtOAc (3×100 mL). The combined extracts were washed with brine, dried with MgSO$_4$, filtered, concentrated, and chromatographed (10–100% EtOAc in hexanes) to provide 2.4 g of 3-benzyloxy-2,2-dimethyl-propionic acid.

To a 0° C. solution of 2.4 g (11.4 mmol) of 3-benzyloxy-2,2-dimethyl-propionic acid and 1.65 ml (11.5 mmol) of Et$_3$N in 80 mL of chloroform was added 1.04 mL (11.5 mmol) of ethyl chloroformate. After stirring for 15 min, NH$_3$ gas was passed through the solution for 5 minutes. The resulting suspension was removed from the ice bath and allowed to stir overnight. The suspension was filtered and the filtrate was concentrated to near dryness. The resulting residue was crystallized from benzene/hexanes (16 mL/40 mL) mixture to provide 2.3 g of 3-benzyloxy-2,2-dimethyl-propionamide.

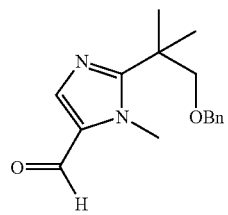

2-(2-Benzyloxy-1,1-dimethyl-ethyl)-3-methyl-3H-imidazole-4-carbaldehyde was prepared from 3-benzyloxy-2,2-dimethyl-propionamide in the same manner as 2-cyclopropyl-3-methyl-3H-imidazole-4-carbaldehyde (Example 46).

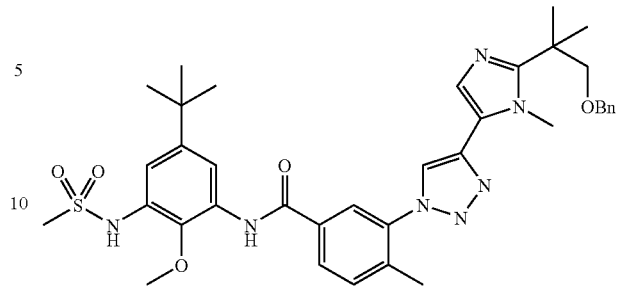

Example 106 was prepared from 2-(2-benzyloxy-1,1-dimethyl-ethyl)-3-methyl-3H-imidazole-4-carbaldehyde and 3-azido-N-(5-tert-butyl-3-methane-sulfonylamino-2-methoxy-phenyl)-4-methyl-benzamide in the same manner as Example 39. ESI MS m/z 700 [C$_{37}$H$_{45}$N$_7$O$_5$S+H]$^+$.

Example 107

3-{4-[1-(1-Benzyl-piperidin-4-yl)-5-methyl-1H-pyrazol-4-yl]-[1,2,3]triazol-1-yl}-N-(5-tert-butyl-3-methanesulfonylamino-2-methoxy-phenyl)-4-methyl-benzamide

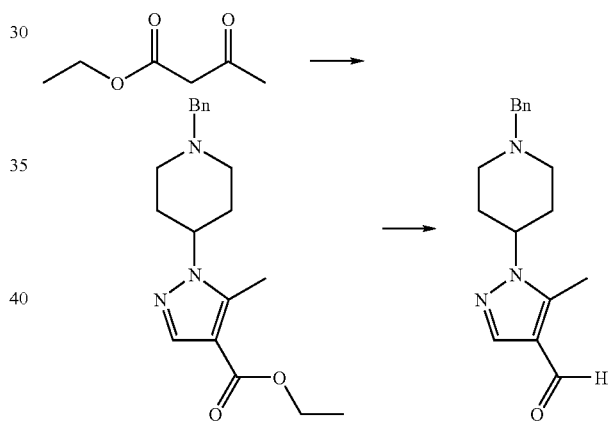

1-(1-Benzyl-piperidin-4-yl)-5-methyl-1H-pyrazole-4-carbaldehyde was prepared from ethyl acetoacetate and (1-benzyl-piperidin-4-yl)-hydrazine in the same manner as 5-cyclopropyl-1-isopropyl-1H-pyrazole-4-carbaldehyde (Example 49). (1-Benzyl-piperidin-4-yl)-hydrazine was prepared from 1-benzyl-piperidin-4-one in the same manner as (1-methyl-piperidin-4-yl)-hydrazine (Example 92).

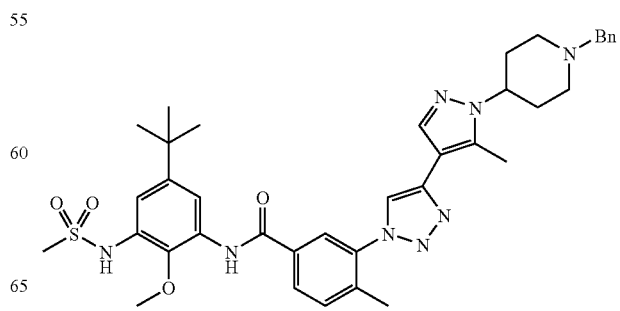

Example 107 was prepared from 1-(1-benzyl-piperidin-4-yl)-5-methyl-1H-pyrazole-4-carbaldehyde and 3-azido-N-(5-tert-butyl-3-methanesulfonylamino-2-methoxy-phenyl)-4-methyl-benzamide in the same manner as Example 39. ESI MS m/z 711 $[C_{38}H_{46}N_8O_4S+H]^+$.

Example 108

4-(4-{1-[5-(5-tert-Butyl-3-methanesulfonylamino-2-methoxy-phenylcarbamoyl)-2-methyl-phenyl]-1H-[1,2,3]triazol-4-yl}-2-cyclopropyl-2H-pyrazol-3-yl)-piperidine-1-carboxylic acid tert-butyl ester

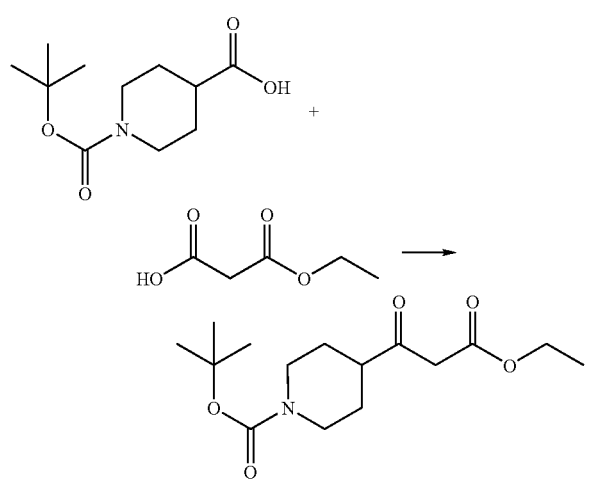

N-Boc-4-(2-Ethoxycarbonyl-acetyl)-piperidine was prepared from N-Boc-piperidine-4-carboxylic acid in the same manner as ethyl 3-oxo-3-pyridin-2-yl-propionate (Example 94).

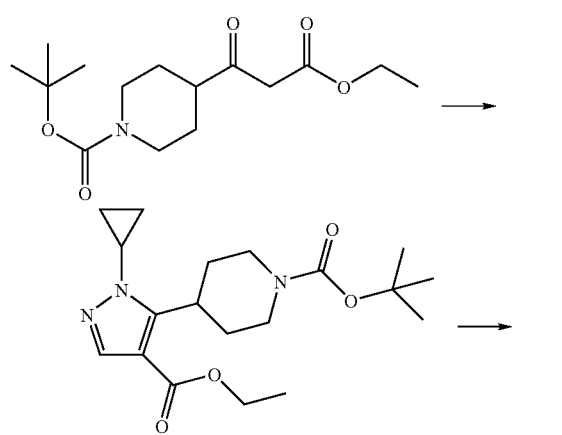

N-Boc-4-(2-Cyclopropyl-4-ethoxycarbonyl-2H-pyrazol-3-yl)-piperidine was prepared from N-Boc-4-(2-ethoxycarbonyl-acetyl)-piperidine and cyclopropyl hydrazine oxalate in the same manner as 5-cyclopropyl-1-isopropyl-1H-pyrazole-4-carboxylic acid ethyl ester (Example 49).

A solution of 1.71 mL (3.42 mmol) of 2M NaOH was added to 0.540 g (1.49 mmol) N-Boc-4-(2-cyclopropyl-4-ethoxycarbonyl-2H-pyrazol-3-yl)-piperidine in 15 mL of EtOH. After stirring at 60° C. for 18 h, the solution was concentrated and dissolved in 100 mL of EtOAc (100 mL) and 10 mL of 5% HCl (10 mL). The extract was washed with 50 mL of brine (50 mL), dried over MgSO$_4$, filtered, concentrated, and chromatographed (0–100% EtOAc in hexanes) to give 330 mg of N-Boc-4-(4-carboxy-2-cyclopropyl-2H-pyrazol-3-yl)-piperidine as a white powder.

The above acid (300 mg, 0.894 mmol) was dissolved in 5 mL of THF. To this solution was added 3.58 mL (3.58 mmol) of 1M borane in THF. After stirring for 5 h, the mixture was poured into 15 mL of 5% HCl. The solution was extracted with 200 mL of EtOAc, and the extract was washed with saturated NaHCO$_3$ and brine, dried over MgSO$_4$, filtered, concentrated, and chromatographed (10–100 EtOAc in hexanes) to give 120 mg of N-Boc-4-(2-cyclopropyl-4-hydroxymethyl-2H-pyrazol-3-yl)-piperidine. This alcohol (100 mg, 0.31 mmol) was stirred overnight in 10 mL of THF with 270 mg (3.1 mmol) of activated MnO$_2$. The mixture was filtered and concentrated to provide 70 mg of N-Boc-4-(2-cyclopropyl-4-formyl-2H-pyrazol-3-yl)-piperidine.

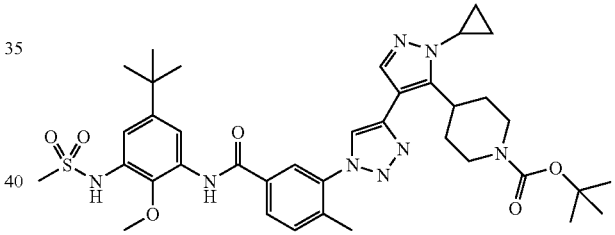

Example 108 was prepared from N-Boc-4-(2-cyclopropyl-4-formyl-2H-pyrazol-3-yl)-piperidine and 3-azido-N-(5-tert-butyl-3-methane-sulfonylamino-2-methoxy-phenyl)-4-methyl-benzamide in the same manner as Example 39. ESI MS m/z 747 $[C_{38}H_{50}N_8O_6S+H]^+$.

Example 109

[[2-(4-{1-[5-(5-tert-Butyl-3-methanesulfonylamino-2-methoxy-phenylcarbamoyl)-2-methyl-phenyl]-1H-[1,2,3]triazol-4-yl}-2-phenyl-2H-pyrazol-3-yl)-ethyl]-carbamic acid benzyl ester

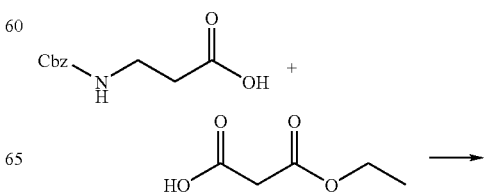

-continued

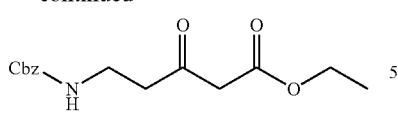

Ethyl 5-benzyloxycarbonylamino-3-oxo-pentanoate was prepared from N-Cbz-β-alanine in the same manner as ethyl 3-oxo-3-pyridin-2-yl-propionate (Example 94).

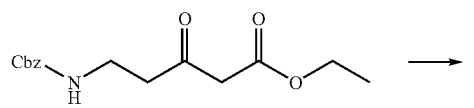

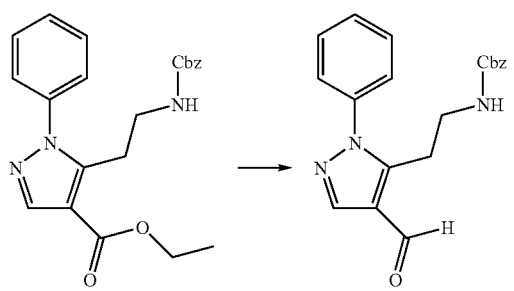

[2-(4-Formyl-2-phenyl-2H-pyrazol-3-yl)-ethyl]-carbamic acid benzyl ester was prepared from ethyl 5-benzyloxycarbonylamino-3-oxo-pentanoate in the same manner as N-Boc-4-(2-cyclopropyl-4-formyl-2H-pyrazol-3-yl)-piperidine (Example 108).

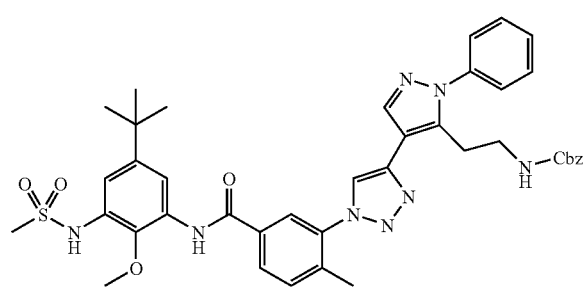

Example 109 was prepared from [2-(4-formyl-2-phenyl-2H-pyrazol-3-yl)-ethyl]-carbamic acid benzyl ester and 3-azido-N-(5-tert-butyl-3-methane-sulfonylamino-2-methoxy-phenyl)-4-methyl-benzamide in the same manner as Example 39. ESI MS m/z 777 $[C_{41}H_{44}N_8O_6S+H]^+$.

Example 110

N-(5-tert-Butyl-2-methoxy-phenyl)-3-[4-(2-cyclopropyl-3-methyl-3H-imidazol-4-yl)-[1,2,3]triazol-1-yl]-4-methyl-benzamide

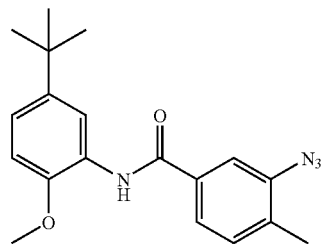

3-Azido-N-(5-tert-butyl-2-methoxy-phenyl)-4-methyl-benzamide was prepared from 3-azido-4-methyl benzoic acid (U.S. Ser. No. 04/102,492) and 5-tert-butyl-2-methoxy-phenylamine in the same manner as 3-azido-N-(5-tert-butyl-3-methanesulfonylamino-2-methoxy-phenyl)-4-methyl-benzamide (Example 15).

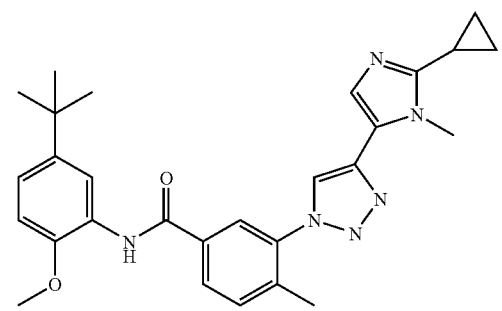

Example 110 was prepared from 2-cyclopropyl-3-methyl-3H-imidazole-4-carbaldehyde (Example 46) and 3-azido-N-(5-tert-butyl-2-methoxy-phenyl)-4-methyl-benzamide in the same manner as Example 39. ESI MS m/z 485 $[C_{28}H_{32}N_6O_2+H]^+$.

Example 111

N-(5-tert-Butyl-3-cyano-2-methoxy-phenyl)-3-[4-(2-cyclopropyl-3-methyl-3H-imidazol-4-yl)-[1,2,3]triazol-1-yl]-4-methyl-benzamide

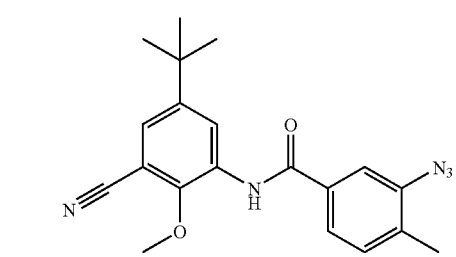

3-Azido-N-(5-tert-butyl-3-cyano-2-methoxy-phenyl)-4-methyl-benzamide was prepared from 3-azido-4-methyl benzoic acid (U.S. Ser. No. 04/102,492) and 3-amino-5-tertbutyl-2-methoxy-benzonitrile in the same manner as 3-azido-N-(5-tert-butyl-3-methanesulfonylamino-2-methoxy-phenyl)-4-methyl-benzamide (Example 15).

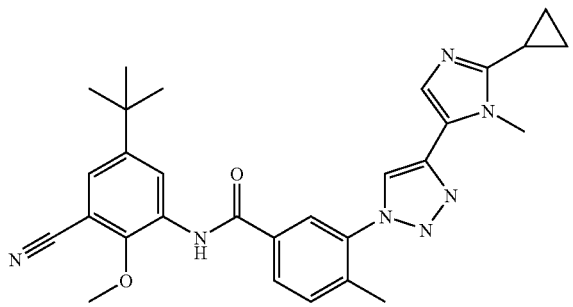

Example 111 was prepared from 2-cyclopropyl-3-methyl-3H-imidazole-4-carbaldehyde (Example 46) and 3-azido-N-(5-tert-butyl-3-cyano-2-methoxy-phenyl)-4-methyl-benzamide in the same manner as Example 39. ESI MS m/z 510 $[C_{29}H_{31}N_7O_2+H]^+$.

Example 112

N-(5-tert-Butyl-2-methanesulfinyl-phenyl)-3-[4-(2-cyclopropyl-3-methyl-3H-imidazol-4-yl)-[1,2,3]triazol-1-yl]-4-methyl-benzamide

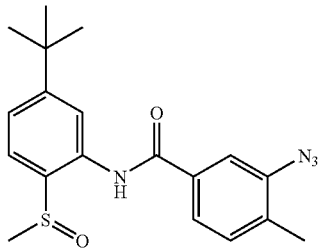

3-Azido-N-(5-tert-butyl-2-methanesulfinyl-phenyl)-4-methyl-benzamide was prepared from 3-azido-4-methyl benzoic acid (U.S. Ser. No. 04/102,492) and 5-tert-butyl-2-methanesulfinyl-phenylamine in the same manner as 3-azido-N-(5-tert-butyl-3-methanesulfonylamino-2-methoxy-phenyl)-4-methyl-benzamide (Example 15).

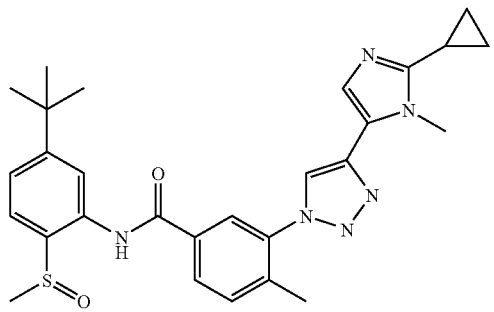

Example 112 was prepared from 2-cyclopropyl-3-methyl-3H-imidazole-4-carbaldehyde (Example 46) and 3-azido-N-(5-tert-butyl-2-methanesulfinyl-phenyl)-4-methyl-benzamide in the same manner as Example 39. ESI MS m/z 517 $[C_{28}H_{32}N_6O_2S+H]^+$.

Example 113

N-(5-tert-Butyl-3-methanesulfonylamino-2-methyl-phenyl)-3-[4-(2-cyclopropyl-3-methyl-3H-imidazol-4-yl)-[1,2,3]triazol-1-yl]-4-methyl-benzamide

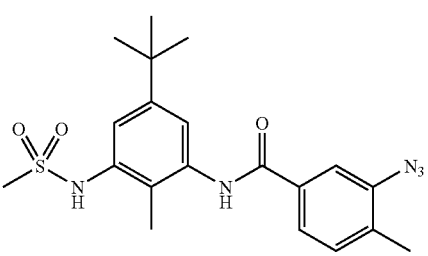

3-Azido-N-(5-tert-butyl-3-methanesulfonylamino-2-methyl-phenyl)-4-methyl-benzamide was prepared from 3-azido-4-methyl benzoic acid (U.S. Ser. No. 04/102,492) and N-(3-Amino-5-tert-butyl-2-methyl-phenyl)-methanesulfonamide in the same manner as 3-azido-N-(5-tert-butyl-3-methanesulfonylamino-2-methoxy-phenyl)-4-methyl-benzamide (Example 15).

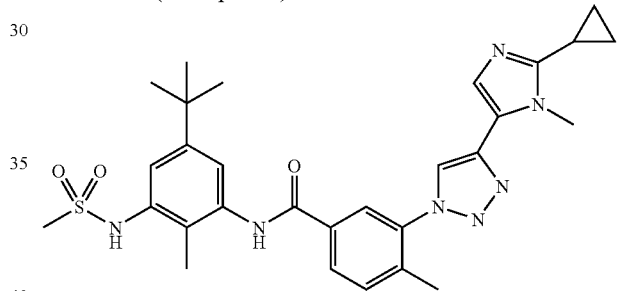

Example 113 was prepared from 2-cyclopropyl-3-methyl-3H-imidazole-4-carbaldehyde (Example 46) and 3-azido-N-(5-tert-butyl-3-methanesulfonylamino-2-methyl-phenyl)-4-methyl-benzamide in the same manner as Example 39. ESI MS m/z 562 $[C_{29}H_{35}N_7O_3S+H]^+$.

Example 114

N-[3-Methanesulfonylamino-2-methoxy-5-(1-methyl-cyclopropyl)-phenyl]-4-methyl-3-[4-(5-methyl-1-phenyl-1H-pyrazol-4-yl)-[1,2,3]triazol-1-yl]-benzamide

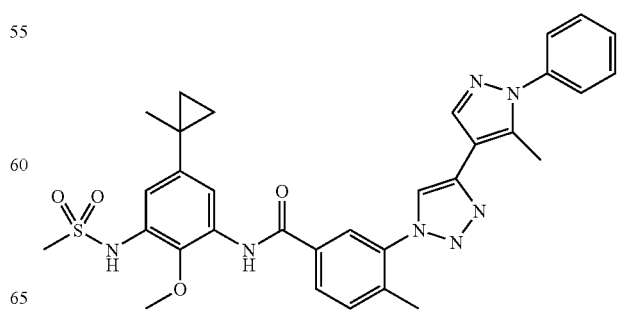

Example 114 was prepared from 5-methyl-1-phenyl-1H-pyrazole-4-carbaldehyde (Maybridge) and 3-azido-N-[3-methanesulfonylamino-2-methoxy-5-(1-methyl-cyclopropyl)-phenyl]-4-methyl-benzamide (Example 33) in the same manner as Example 39. ESI MS m/z 612 [$C_{32}H_{33}N_7O_4S$+H]$^+$.

Example 115

3-[4-(3-tert-Butyl-3H-imidazol-4-yl)-[1,2,3]triazol-1-yl]-N-[3-methanesulfonylamino-2-methoxy-5-(1-methyl-cyclopropyl)-phenyl]-4-methyl-benzamide

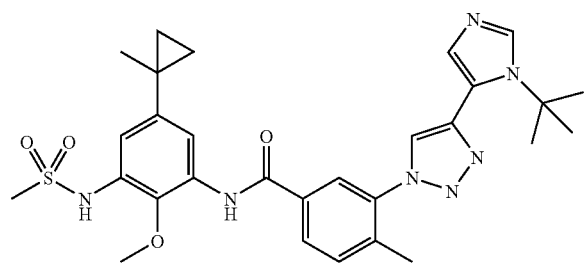

Example 115 was prepared from 3-tert-butyl-3H-imidazole-4-carbaldehyde (Example 56) and 3-azido-N-[3-methanesulfonylamino-2-methoxy-5-(1-methyl-cyclopropyl)-phenyl]-4-methyl-benzamide (Example 33) in the same manner as Example 39. ESI MS m/z 578 [$C_{29}H_{35}N_7O_4S$+H]$^+$.

Example 116

3-[4-(1-Isopropyl-5-methyl-1H-pyrazol-4-yl)-[1,2,3]triazol-1-yl]-N-[3-methanesulfonylamino-2-methoxy-5-(1-methyl-cyclopropyl)-phenyl]-4-methyl-benzamide

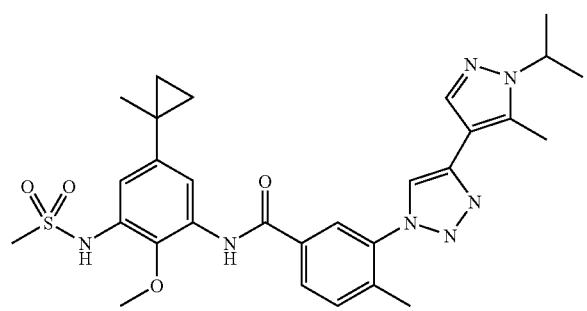

Example 116 was prepared from 1-isopropyl-5-methyl-1H-pyrazole-4-carbaldehyde (Example 55) and 3-azido-N-[3-methanesulfonylamino-2-methoxy-5-(1-methyl-cyclopropyl)-phenyl]-4-methyl-benzamide (Example 33) in the same manner as Example 39. ESI MS m/z 578 [$C_{29}H_{35}N_7O_4S$+H]$^+$.

Example 117

3-[4-(2-Isopropyl-3-methyl-3H-imidazol-4-yl)-[1,2,3]triazol-1-yl]-N-[3-methanesulfonylamino-2-methoxy-5-(1-methyl-cyclopropyl)-phenyl]-4-methyl-benzamide

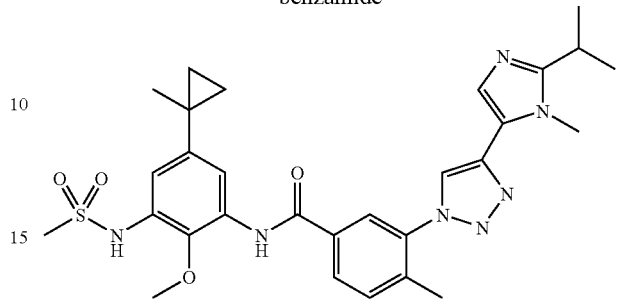

Example 117 was prepared from 2-isopropyl-3-methyl-3H-imidazole-4-carbaldehyde (Example 53) and 3-azido-N-[3-methanesulfonylamino-2-methoxy-5-(1-methyl-cyclopropyl)-phenyl]-4-methyl-benzamide (Example 33) in the same manner as Example 39. ESI MS m/z 578 [$C_{29}H_{35}N_7O_4S$+H]$^+$.

Example 118

3-[4-(2-Cyclopropyl-3-methyl-3H-imidazol-4-yl)-[1,2,3]triazol-1-yl]-N-[3-methanesulfonylamino-2-methoxy-5-(1-methyl-cyclopropyl)-phenyl]-4-methyl-benzamide

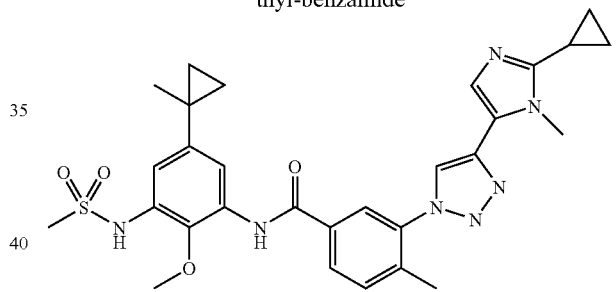

Example 118 was prepared from 2-cyclopropyl-3-methyl-3H-imidazole-4-carbaldehyde (Example 46) and 3-azido-N-[3-methanesulfonylamino-2-methoxy-5-(1-methyl-cyclopropyl)-phenyl]-4-methyl-benzamide (Example 33) in the same manner as Example 39. ESI MS m/z 576 [$C_{29}H_{33}N_7O_4S$+H]$^+$.

Example 119

3-[4-(2-Cyclobutyl-3-methyl-3H-imidazol-4-yl)-1,2,3-triazol-1-yl]-N-[3-methanesulfonylamino-2-methoxy-5-(1-methyl-cyclopropyl)-phenyl]-4-methyl-benzamide

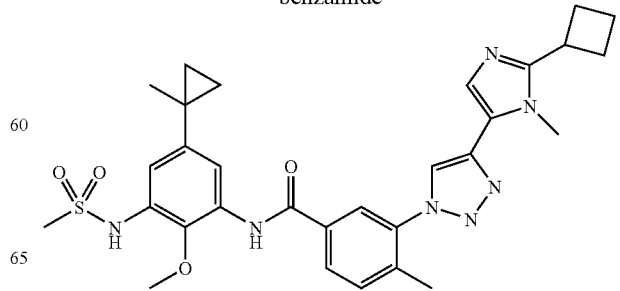

Example 119 may be prepared from 2-cyclobutyl-3-methyl-3H-imidazole-4-carbaldehyde and 3-azido-N-[3-methanesulfonylamino-2-methoxy-5-(1-methyl-cyclopropyl)-phenyl]-4-methyl-benzamide (Example 33) in the same manner as Example 39.

Example 120

N-[3-Methanesulfonylamino-2-methoxy-5-(1-methyl-cyclopropyl)-phenyl]-4-methyl-3-{4-[3-methyl-2-(1-methyl-cyclopropyl)-3H-imidazol-4-yl]-[1,2,3]triazol-1-yl}-benzamide

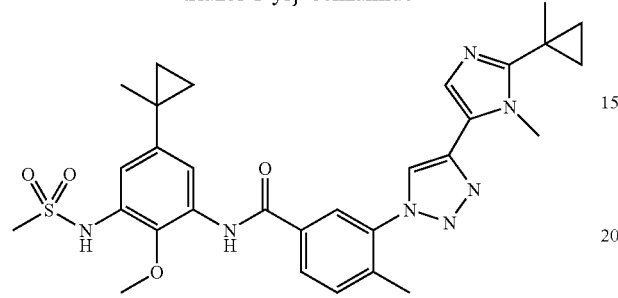

Example 120 was prepared from 3-methyl-2-(1-methyl-cyclopropyl)-3H-imidazole-4-carbaldehyde (Example 63) and 3-azido-N-[3-methanesulfonylamino-2-methoxy-5-(1-methyl-cyclopropyl)-phenyl]-4-methyl-benzamide (Example 33) in the same manner as Example 39. ESI MS m/z 590 $[C_{30}H_{35}N_7O_4S+H]^+$.

Example 121

3-[4-(1-Cyclopropyl-5-ethyl-1H-pyrazol-4-yl)-[1,2,3]triazol-1-yl]-N-[3-methanesulfonylamino-2-methoxy-5-(1-methyl-cyclopropyl)-phenyl]-4-methyl-benzamide

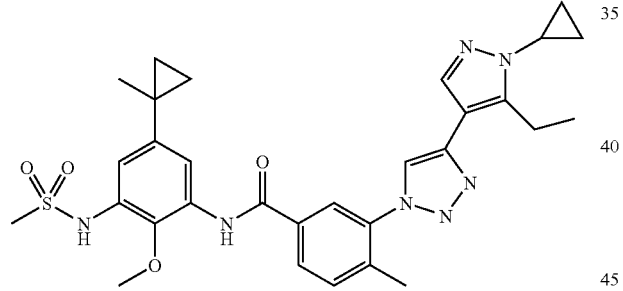

Example 121 was prepared from 1-cyclopropyl-5-ethyl-1H-pyrazole-4-carbaldehyde (Example 64) and 3-azido-N-[3-methanesulfonylamino-2-methoxy-5-(1-methyl-cyclopropyl)-phenyl]-4-methyl-benzamide (Example 33) in the same manner as Example 39. ESI MS m/z 590 $[C_{30}H_{35}N_7O_4S+H]^+$.

Example 122

3-[4-(1-tert-Butyl-5-methyl-1H-pyrazol-4-yl)-[1,2,3]triazol-1-yl]-N-[3-methanesulfonylamino-2-methoxy-5-(1-methyl-cyclopropyl)-phenyl]-4-methyl-benzamide

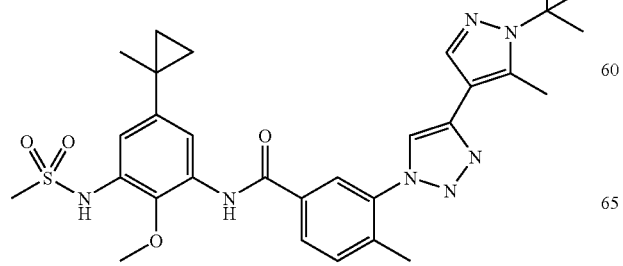

Example 122 was prepared from 1-tert-butyl-5-methyl-1H-pyrazole-4-carbaldehyde (Example 69) and 3-azido-N-[3-methanesulfonylamino-2-methoxy-5-(1-methyl-cyclopropyl)-phenyl]-4-methyl-benzamide (Example 33) in the same manner as Example 39. ESI MS m/z 592 $[C_{30}H_{37}N_7O_4S+H]^+$.

Example 123

3-[4-(3-tert-Butyl-2-methyl-3H-imidazol-4-yl)-[1,2,3]triazol-1-yl]-N-[3-methanesulfonylamino-2-methoxy-5-(1-methyl-cyclopropyl)-phenyl]-4-methyl-benzamide

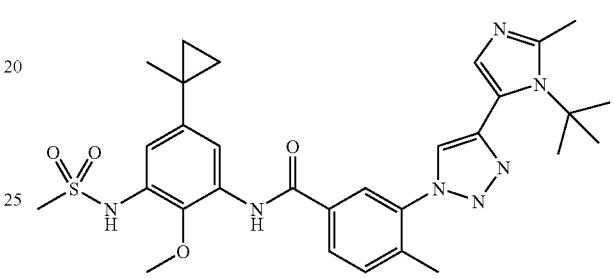

Example 123 was prepared from 3-tert-butyl-2-methyl-3H-imidazole-4-carbaldehyde (Example 68) and 3-azido-N-[3-methanesulfonylamino-2-methoxy-5-(1-methyl-cyclopropyl)-phenyl]-4-methyl-benzamide (Example 33) in the same manner as Example 39. ESI MS m/z 592 $[C_{30}H_{37}N_7O_4S+H]^+$.

Example 124

3-[4-(2-tert-Butyl-3-methyl-3H-imidazol-4-yl)-[1,2,3]triazol-1-yl]-N-[3-methanesulfonylamino-2-methoxy-5-(1-methyl-cyclopropyl)-phenyl]-4-methyl-benzamide

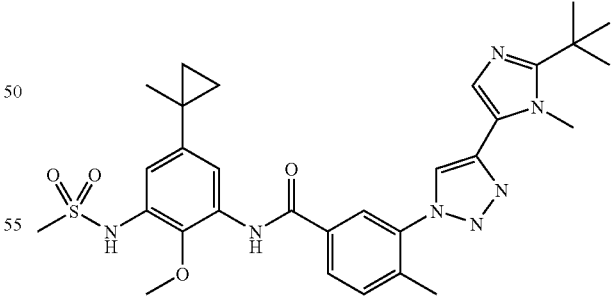

Example 124 was prepared from 2-tert-butyl-3-methyl-3H-imidazole-4-carbaldehyde (Example 67) and 3-azido-N-[3-methanesulfonylamino-2-methoxy-5-(1-methyl-cyclopropyl)-phenyl]-4-methyl-benzamide (Example 33) in the same manner as Example 39. ESI MS m/z 592 $[C_{30}H_{37}N_7O_4S+H]^+$.

Example 125

3-[4-(5-Ethyl-1-phenyl-1H-pyrazol-4-yl)-[1,2,3]triazol-1-yl]-N-[3-methanesulfonylamino-2-methoxy-5-(1-methyl-cyclopropyl)-phenyl]-4-methyl-benzamide

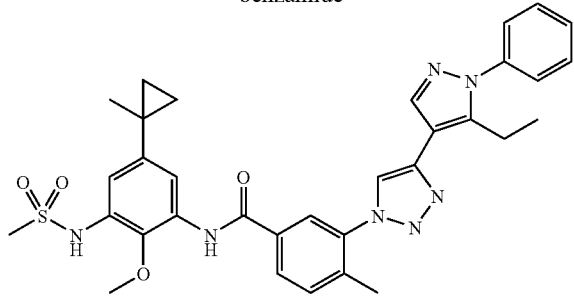

Example 125 was prepared from 5-ethyl-1-phenyl-1H-pyrazole-4-carbaldehyde (Example 86) and 3-azido-N-[3-methanesulfonylamino-2-methoxy-5-(1-methyl-cyclopropyl)-phenyl]-4-methyl-benzamide (Example 33) in the same manner as Example 39. ESI MS m/z 626 $[C_{33}H_{35}N_7O_4S+H]^+$.

Example 126

3-[4-(3-Ethyl-2-phenyl-3H-imidazol-4-yl)-[1,2,3]triazol-1-yl]-N-[3-methanesulfonylamino-2-methoxy-5-(1-methyl-cyclopropyl)-phenyl]-4-methyl-benzamide

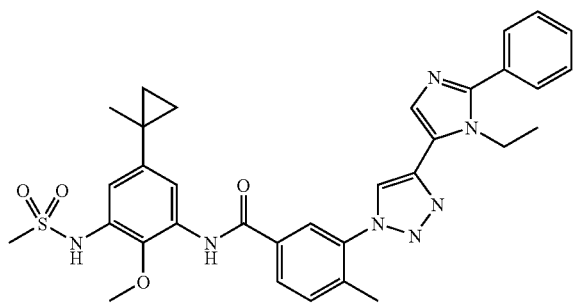

Example 126 was prepared from 3-ethyl-2-phenyl-3H-imidazole-4-carbaldehyde (Example 85) and 3-azido-N-[3-methanesulfonylamino-2-methoxy-5-(1-methyl-cyclopropyl)-phenyl]-4-methyl-benzamide (Example 33) in the same manner as Example 39. ESI MS m/z 626 $[C_{33}H_{35}N_7O_4S+H]^+$.

Example 127

N-[3-Methanesulfonylamino-2-methoxy-5-(1-methyl-cyclopropyl)-phenyl]-4-methyl-3-{4-[3-methyl-2-(1-methyl-1-phenyl-ethyl)-3H-imidazol-4-yl]-[1,2,3]triazol-1-yl}-benzamide

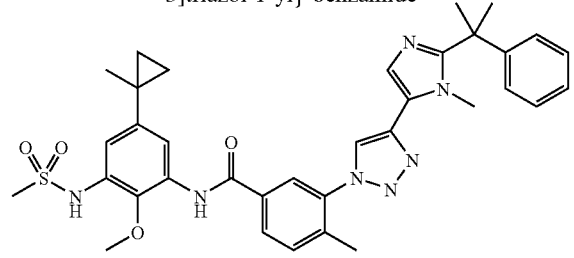

Example 127 was prepared from 3-methyl-2-(1-methyl-1-phenyl-ethyl)-3H-imidazole-4-carbaldehyde (Example 101) and 3-azido-N-[3-methanesulfonylamino-2-methoxy-5-(1-methyl-cyclopropyl)-phenyl]-4methyl-benzamide (Example 33) in the same manner as Example 39. ESI MS m/z 655 $[C_{35}H_{39}N_7O_4S+H]^+$.

Example 128

N-(5-tert-Butyl-3-methanesulfonylamino-2-methoxy-phenyl)-3-[4-(2-hydroxymethyl-3-methyl-3H-imidazol-4-yl)-1,2,3-triazol-1-yl]-4-methyl-benzamide

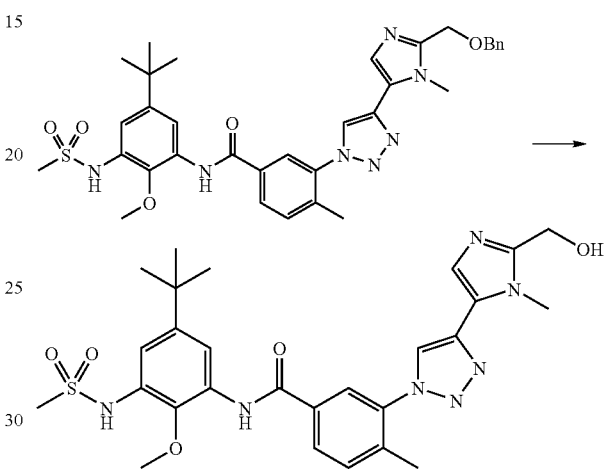

A mixture of 386 mg (0.587 mmol) of Example 102, 185 mg (2.94 mmol) of ammonium formate, 40 mg of Pd/C in 20 mL MeOH (20 mL) with 0.1 mL (1.2 mmol) of formic acid was stirred at rt for 12 h. The mixture was filtered through celite and concentrated to provide 280 mg of Example 128. ESI MS m/z 568 $[C_{27}H_{33}N_7O_5S+H]^+$.

Example 129

N-(5-tert-Butyl-3-methanesulfonylamino-2-methoxy-phenyl)-3-[4-(2-formyl-3-methyl-3H-imidazol-4-yl)-1,2,3-triazol-1-yl]-4-methyl-benzamide

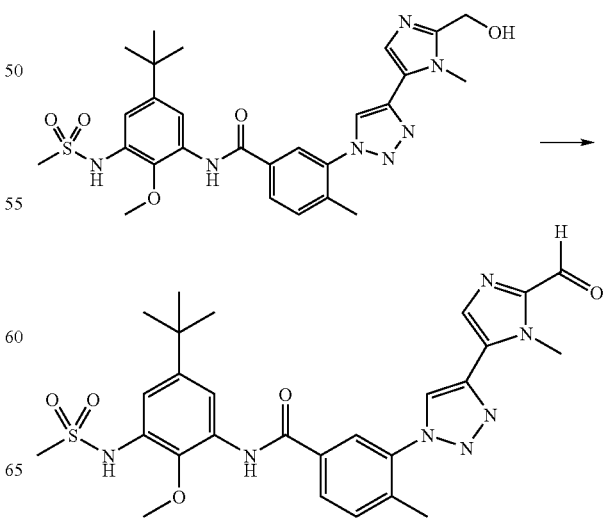

Example 128 (400 mg, 0.705 mmol) was dissolved in THF (20 mL) and 308 mg of activated MnO$_2$ was added. The reaction was stirred for 12 h and was then filtered through celite and concentrated. The residue was dissolved in EtOAc and washed with water and brine, dried with MgSO$_4$, filtered, concentrated, and chromatographed (10–100% EtOAc in hexanes) to provide 200 mg of Example 129. ESI MS m/z 567 [C$_{27}$H$_{31}$N$_7$O$_5$S+H]$^+$.

Example 130

N-(5-tert-Butyl-3-methanesulfonylamino-2-methoxy-phenyl)-3-{4-[2-(1-hydroxy-ethyl)-3-methyl-3H-imidazol-4-yl]-1,2,3-triazol-1-yl}-4-methyl-benzamide

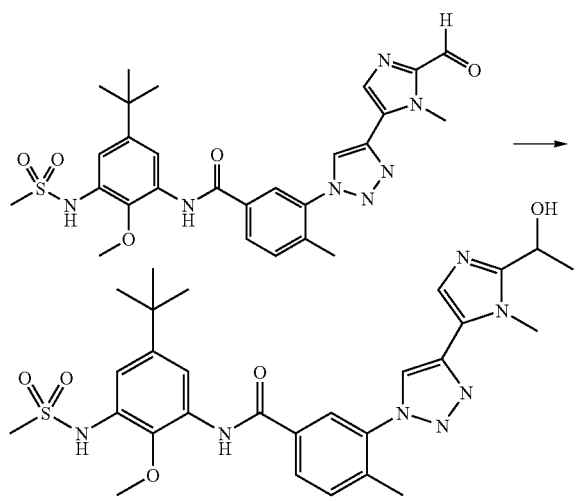

To a 0° C. solution of 45 mg (0.080 mmol) of Example 129 in 10 mL of THF was slowly added 0.11 mL (0.32 mmol) of 3M MeMgBr in Et$_2$O. The mixture was allowed to warm to rt with stirring overnight. A 10% HCl solution was added, and the mixture was extracted with EtOAc (3×50 mL) and the combined organics were washed with brine, dried with MgSO$_4$, concentrated, and chromatographed (0–10% MeOH in CH$_2$Cl$_2$) to provide Example 129 (45 mg). ESI MS m/z 582 [C$_{28}$H$_{35}$N$_7$O$_5$S]$^+$.

Example 131

N-(5-tert-Butyl-3-methanesulfonylamino-2-methoxy-phenyl)-3-{4-[2-(cyclopropyl-hydroxy-methyl)-3-methyl-3H-imidazol-4-yl]-1,2,3-triazol-1-yl}-4-methyl-benzamide

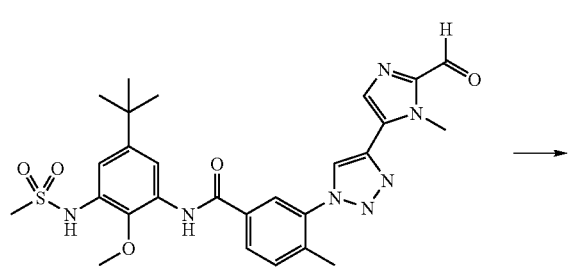

-continued

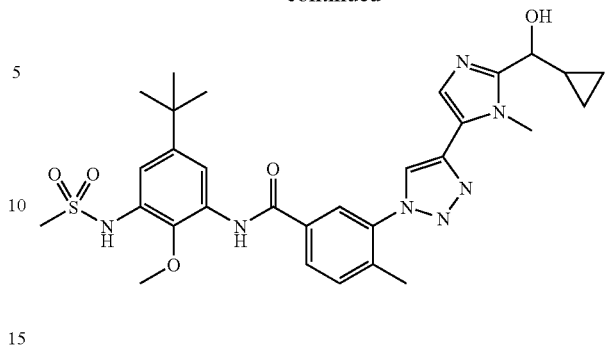

To a 0° C. solution of 50 mg (0.088 mmol) of Example 129 in 5 mL of THF was slowly added 0.88 mL (0.44 mmol) of cyclopropylmagnesium bromide (0.5 M in THF). The mixture was allowed to warm to rt with stirring overnight. Water (50 mL) was added, and the mixture was extracted with EtOAc (3×50 mL), the combined organics were washed with brine, dried with MgSO$_4$, concentrated, and chromatographed (0–10% MeOH in CH$_2$Cl$_2$) to provide Example 131 (15 mg). ESI MS m/z 609 [C$_{30}$H$_{37}$N$_7$O$_5$S+H]$^+$.

Example 132

3-[4-(2-Acetyl-3-methyl-3H-imidazol-4-yl)-1,2,3-triazol-1-yl]-N-(5-tert-butyl-3-methanesulfonylamino-2-methoxy-phenyl)-4-methyl-benzamide

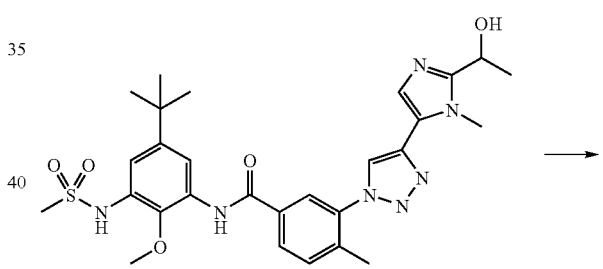

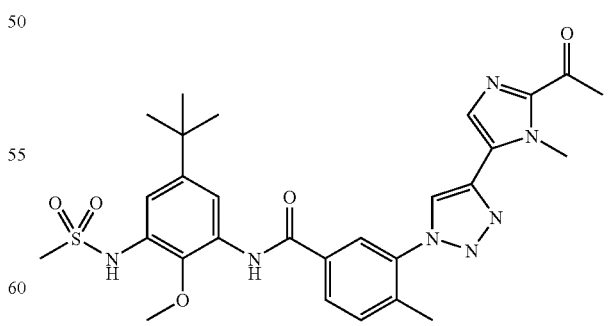

To 15 mg (0.026 mmol) of Example 130 in 5 mL of THF was added 7.6 mg (0.13 mmol) of activated MnO$_2$. The reaction stirred at overnight, then was filtered through celite and concentrated to provide 10 mg of Example 132. ESI MS m/z 580 [C$_{28}$H$_{33}$N$_7$O$_5$S+H]$^+$.

Example 133

3-[4-(2-Cyclopropyl-3-methyl-3H-imidazol-4-yl)-1,2,3-triazol-1-yl]-N-[5-(2-hydroxy-1,1-dimethyl-ethyl)-3-methanesulfonylamino-2-methoxy-phenyl]-4-methyl-benzamide

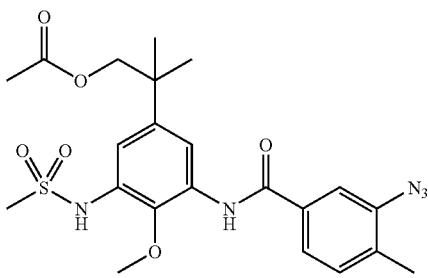

A solution of TMSCHCN$_2$ (1.0 M) was added to 4.28 g (17.3 mmol) of (4-hydroxy-3,5-dinitro-phenyl)-acetic acid in 63 mL of MeCN and 7 mL of MeOH. After 2 h, 0.8 mL of acetic acid was added. After stirring an additional 30 min, the solution was concentrated and partitioned between saturated NaHCO$_3$ and EtOAc. The organic portion was washed with brine, dried with Na$_2$SO$_4$, filtered, and concentrated to provide (4-methoxy-3,5-dinitro-phenyl)-acetic acid methyl ester (3.22 g).

Methyl iodide (3.36 mL, 54.0 mmol) was added to 3.65 g (13.5 mmol) of (4-methoxy-3,5-dinitro-phenyl)-acetic acid methyl ester in 40 mL of DMF at 0° C. Sodium hydride (60%; 1.62 g, 40.5 mmol) was carefully added in portions. The mixture was allowed to warm to rt, then it was diluted with water and extracted with EtOAc. The aqueous layer was extracted twice with EtOAc, and the extracts were washed with water and brine. The extracts were combined, dried with Na$_2$SO$_4$, filtered, and concentrated to provide a brown oil. Hexanes was added, swirled around the flask, and decanted. This procedure was repeated twice, and the resulting residue was dried in vacuo to provide 2.96 g of 2-(4-methoxy-3,5-dinitro-phenyl)-2-methyl-propionic acid methyl ester.

To a 0° C. solution of 1.30 g (4.35 mmol) of 2-(4-methoxy-3,5-dinitro-phenyl)-2-methyl-propionic acid methyl ester in 30 mL of THF was added dropwise 17 mL (17 mmol) of 1.0 M DIBAL in CH$_2$Cl$_2$. After stirring an additional 4 h, 2 mL of MeOH and then saturated Na$_2$SO$_4$ (2 mL) were slowly added. The resulting suspension was rapidly stirred for 20 min then 40 mL of EtOAc was added followed by MgSO$_4$. The resulting mixture was then stirred at rt for an additional 30 min. The mixture was filtered through celite, and the filter cake was washed with EtOAc. The filtrate was concentrated to provide 580 mg of 2-(4-methoxy-3,5-dinitro-phenyl)-2-methyl-propan-1-ol.

2-(4-Methoxy-3,5-dinitro-phenyl)-2-methyl-propan-1-ol was dissolved in 5 mL of CH$_2$Cl$_2$. Acetic anhydride was added followed by DMAP. The mixture was stirred overnight, then diluted in 15 mL of CH$_2$Cl$_2$ and washed with 1 M NaSO$_4$, saturated NaHCO$_3$, and brine. The CH$_2$Cl$_2$ solution was then dried with Na$_2$SO$_4$, filtered, and concentrated to provide acetic acid 2-(4-methoxy-3,5-dinitro-phenyl)-2-methyl-propyl ester (628 mg) as a brown oil.

Acetic acid 2-(4-methoxy-3,5-dinitro-phenyl)-2-methyl-propyl ester (625 mg, 2.00 mmol) was dissolved in 10 mL MeOH. Ethyl acetate (10 mL), ammonium formate (1.26 g, 20.0 mmol), and Pd/C (56 mg) were added and the mixture was heated to 40° C. overnight. The mixture was then filtered through celite and partitioned between sat'd NaHCO$_3$ and EtOAc. The EtOAc extract was washed with brine. The washes were extracted once more with EtOAc. The extracts were combined, dried with Na$_2$SO$_4$, filtered, and concentrated to provide 500 mg of acetic acid 2-(3,5-diamino-4-methoxy-phenyl)-2-methyl-propyl ester.

To a solution of 500 mg (1.99 mmol) of acetic acid 2-(3,5-diamino-4-methoxy-phenyl)-2-methyl-propyl ester in 10 mL of MTBE was added 0.16 mL (2.0 mmol) of methansulfonyl chloride and 0.35 mL (2.0 mmol) of DIPEA. The mixture was stirred overnight, and then was washed with saturated NH$_4$Cl, saturated NaHCO$_3$, and brine. The ether layer was dried with Na$_2$SO$_4$, filtered, concentrated, and chromatographed (0–2.5% MeOH (0.05% NH$_4$OH) in CH$_2$Cl$_2$) to provide 265 mg of 2-(3-amino-5-methanesulfonylamino-4-methoxy-phenyl)-2-methyl-propyl ester.

Oxalyl chloride (0.11 mL, 1.3 mmol) was added to a stirring suspension of 148 mg (0.84 mmol) of 3-azido-4-methyl benzoic acid in 5 mL of 1:1 CH$_2$Cl$_2$/THF followed by 1 drop of 10% DMF in THF. After stirring for 1 h, the now homogeneous mixture was concentrated to provide a dark oil. The acid chloride was dissolved in 5 mL of CH$_2$Cl$_2$ and 185 mg (0.56 mmol) of acetic acid 2-(3-amino-5-methanesulfonylamino-4-methoxy-phenyl)-2-methyl-propyl ester was added along with 0.2 mL (1.7 mmol) of 2,6-lutidine. The mixture was stirred overnight, then was diluted with 10 mL of CH$_2$Cl$_2$, and washed with 1 M NaHSO$_4$ (2×), saturated NaHCO$_3$, and brine. The organic portion was dried with Na$_2$SO$_4$, filtered, and concentrated to provide acetic acid 2-[3-(3-azido-4-methyl-benzoylamino)-5-methanesulfonylamino-4-methoxy-phenyl]-2-methyl-propyl ester (238 mg).

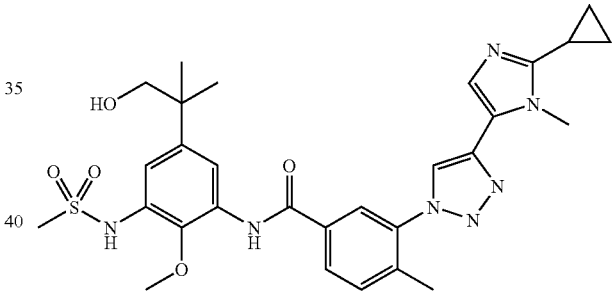

To a stirring suspension of 49 mg (0.10 mmol) of acetic acid 2-[3-(3-azido-4-methyl-benzoylamino)-5-methanesulfonylamino-4-methoxy-phenyl]-2-methyl-propyl ester in 1 mL of EtOH was added 4N NaOH dropwise until the solids dissolved. 2-Cyclopropyl-5-ethynyl-1-methyl-1H-imidazole (125 mg, 0.855 mmol) was added followed by 20mg (0.1 mmol) of sodium ascorbate in water. The mixture was stirred under N$_2$ and CuSO$_4$ (0.1 M; 0.1 mL, 0.010 mmol) was added. The suspension was stirred overnight, then was was diluted with half-saturated NH$_4$Cl, and extracted with EtOAc. The extract was washed with brine, and the washes were extract once more wtih EtOAc. The extracts were combined, dried with Na$_2$SO$_4$, filtered, and concentrated. Chromatography (0–4% MeOH (0.5% NH$_4$OH) in CH$_2$Cl$_2$) provided the desired product with a slight blue-green color. The product was then redissolved in EtOAc and washed again with NH$_4$Cl with a few drops of NH$_4$OH added. The aqueous layer became blue, and the organic layer was washed once more with NH$_4$Cl/NH$_4$OH, and once with brine. The organic layer was then dried with Na$_2$SO$_4$, filtered, and concentrated to provide Example 133 (83 mg). ESI MS m/z 594 [C$_{29}$H$_{35}$N$_7$O$_5$S+H]$^+$.

Example 134

N-[5-(2-Hydroxy-1,1-dimethyl-ethyl)-3-methane-sulfonylamino-2-methoxy-phenyl]-4-methyl-3-{4-[3-methyl-2-(1-methyl-cyclopropyl)-3H-imidazol-4-yl]-1,2,3-triazol-1-yl}-benzamide

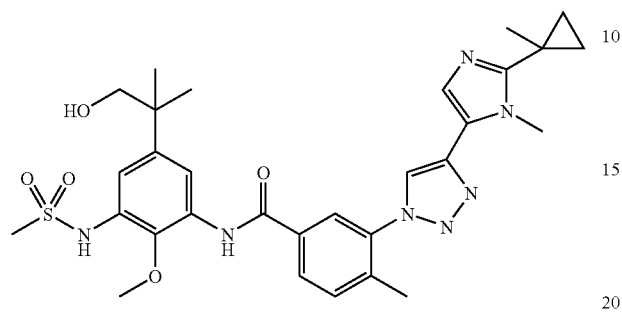

Example 134 was prepared in the same manner as 3-[4-(2-cyclopropyl-3-methyl-3H-imidazol-4-yl)-1,2,3-triazol-1-yl]-N-[5-(2-hydroxy-1,1-dimethyl-ethyl)-3-methane-sulfonylamino-2-methoxy-phenyl]-4-methyl-benzamide (Example 133) with 1.5 equivalents of 5-ethynyl-1-methyl-2-(1-methyl-cyclopropyl)-1H-imidazole. ESI MS m/z 608 $[C_{30}H_{37}N_7O_5S+H]^+$.

Example 135

N-(5-tert-Butyl-3-methanesulfonylamino-2-methoxy-phenyl)-4-methyl-3-[4-(5-methyl-1-piperidin-4-yl-1H-pyrazol-4-yl)-1,2,3-triazol-1-yl]-benzamide

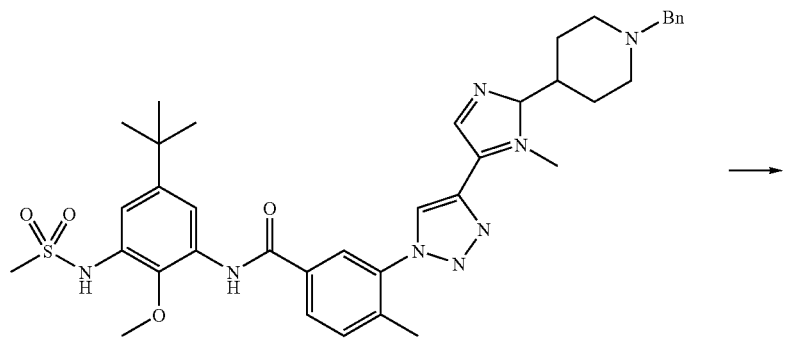

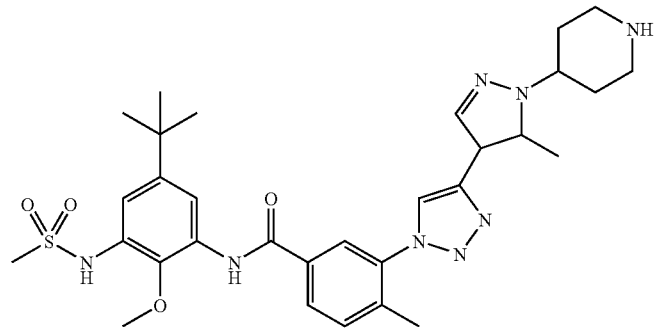

Example 107 (210 mg; 0.30 mmol) and 10% Pd/C (65 mg) were stirred in 6 mL of MeOH with 1 g of ammonium formate for 8 h. The mixture was then filtered through Celite and concentrated. The resulting residue was partitioned between water (5 mL) and EtOAc (100 mL). Brine (20 mL) and saturated NaHCO$_3$ were added and the organic layer was separated and the aqueous layer was extracted with EtOAc (2×25 mL). The extracts were combined, washed with brine, dried over MgSO$_4$, and concentrated to give Example 135 (125 mg; 68%). ESI MS m/z 621 [C$_{31}$H$_{40}$N$_8$O$_4$S+H]$^+$.

Example 136

N-(5-tert-Butyl-3-methanesulfonylamino-2-methoxy-phenyl)-4-methyl-3-[4-(3-methyl-2-piperazin-1-yl-3H-imidazol-4-yl)-1,2,3-triazol-1-yl]-benzamide

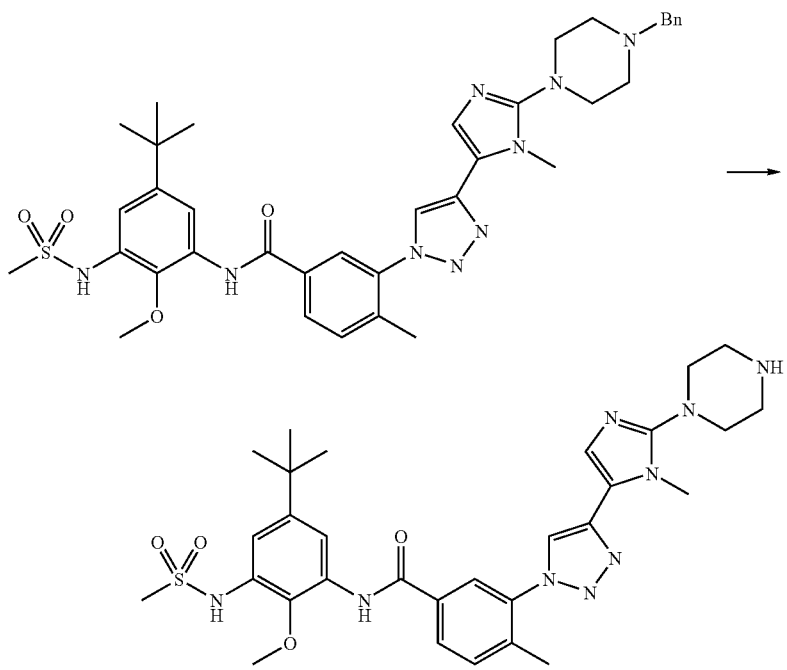

A mixture of Example 57 (100 mg, 0.14 mmol) and 40 mg of Pd(OH)$_2$ in 10 mL of MeOH was stirred under and H$_2$ atmosphere for 72 h. The mixture was filtered through Celite and concentrated to provide Example 136. MS m/z 622 [C$_{30}$H$_{39}$N$_9$O$_4$S+H]$^+$.

Example 137

N-(5-tert-Butyl-3-methanesulfonylamino-2-methoxy-phenyl)-4-methyl-3-[4-(1-methyl-2-piperazin-1-yl-1H-imidazol-4-yl)-[1,2,3]triazol-1-yl]-benzamide

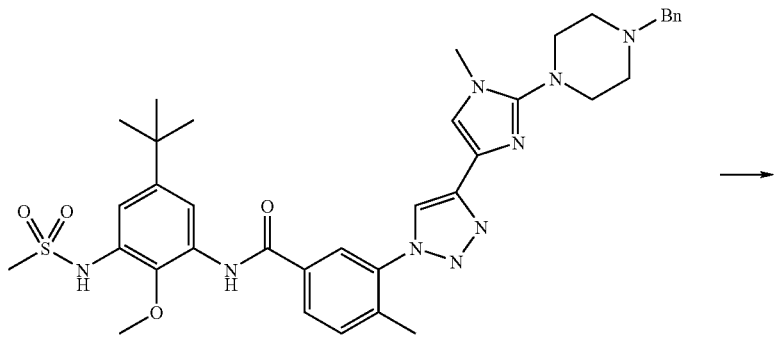

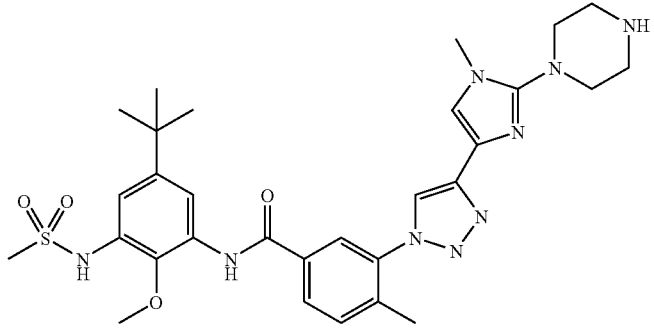

Example 137 was prepared from Example 58 in the same manner as Example 136. ESI MS m/z 622 [$C_{30}H_{39}N_9O_4S$+H]$^+$.

Example 138

N-(5-tert-Butyl-3-methanesulfonylamino-2-methoxy-phenyl)-3-{4-[2-(1-hydroxy-cyclopropyl)-3-methyl-3H-imidazol-4-yl]-1,2,3-triazol-1-yl}-4-methyl-benzamide

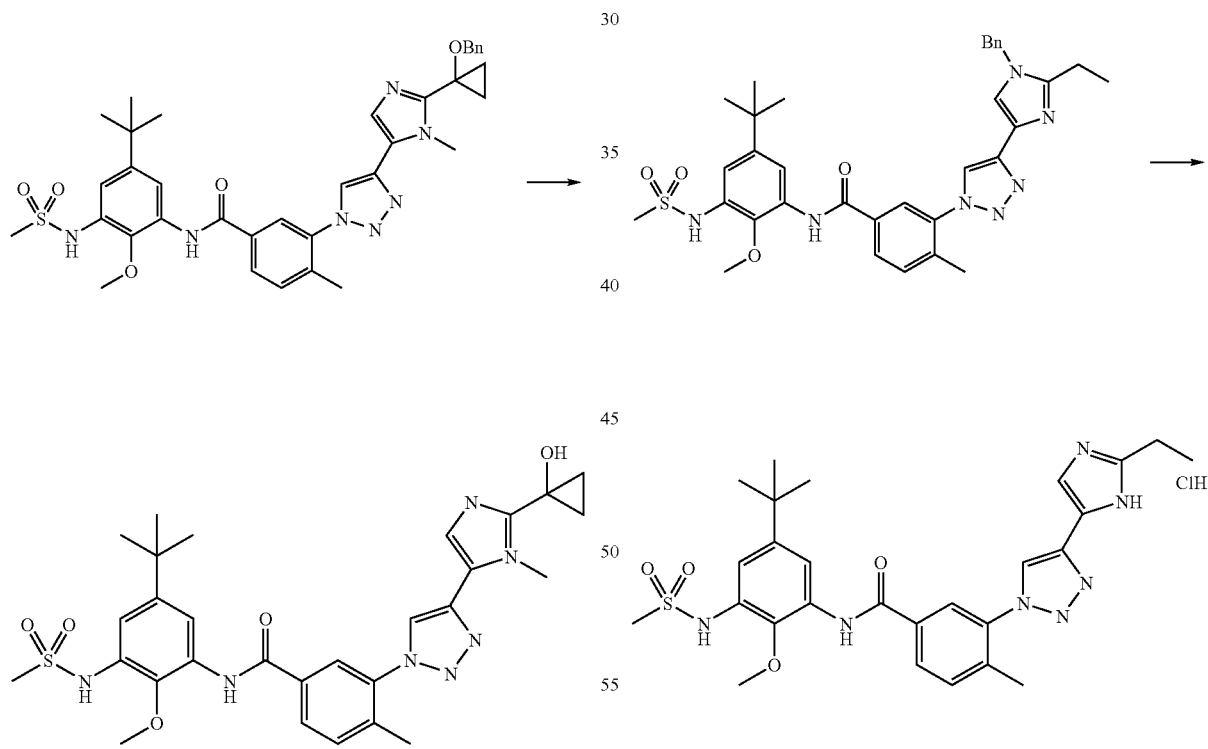

A solution of 190 mg (0.28 mmol) of Example 105 in 2 mL of EtOH was stirred over 30 mg of Pd/C under and H$_2$ atmosphere for 3.5 h. Concentrated HCl (0.027 mL, 0.33 mmol) was added to the mixture, the temperature was warmed to 40° C., and the mixture was stirred overnight. The mixture was cooled and filtered through celite. The filter cake was washed with CH$_2$Cl$_2$, and the combined filtrates were washed with saturated NaHCO$_3$ and brine. The organics were dried with Na$_2$SO$_4$, filtered, and concentrated to provide Example 138 (130 mg). ESI MS m/z 594 [$C_{29}H_{35}N_7O_4S$+H]$^+$.

Example 139

N-(5-tert-butyl-3-methanesulfonylamino-2-methoxy-phenyl)-3-[4-(2-ethyl-3H-imidazol-4-yl)-[1,2,3]triazol-1-yl]-4-methyl-benzamide hydrochloride Example 96 (120 mg; 0.187 mmol) was stirred with 15 mL of MeOH, 4 drops of concentrated HCl, and 25 mg of Pd/C. The mixture was then stirred for 20 h under an H$_2$ atmosphere at 50° C. The mixture was filtered through diatomaceous earth and concentrated. The residue was crystallized from MeOH/Et$_2$O to provide 93 mg (0.16 mmol; 85%) of Example 138 as the hydrochloride salt. ESI MS m/z 552 [$C_{27}H_{33}N_7O_4S$+H]$^+$.

Example 139

N-(5-tert-Butyl-3-methanesulfonylamino-2-methoxy-phenyl)-3-[4-(2-methanesulfonyl-3-methyl-3H-imidazol-4-yl)-1,2,3-triazol-1-yl]-4-methyl-benzamide

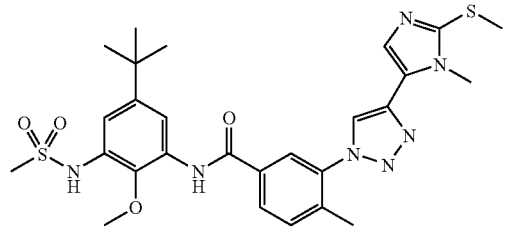

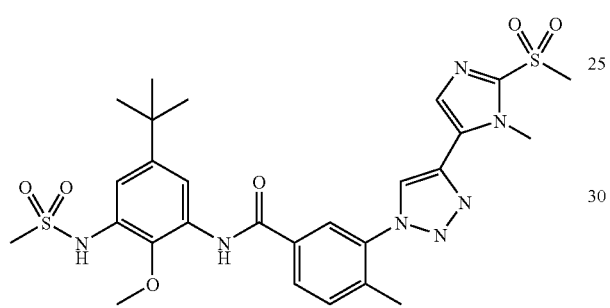

To Example 25 (250 mg, 0.43 mmol) in 10 mL of MeOH (10 mL) was added 790 mg (2.6 mmol) of oxone in 10 mL of water. The mixture was stirred for 16 h before being partitioned between CHCl$_3$ (10 mL) and water (10 mL) with 3 mL of NH$_4$OH. The mixture was extracted with chloroform (3×60 mL), dried over MgSO$_4$, concentrated, and chromatographed (25 to 100% EtOAc in hexanes) to provide Example 139 (216 mg). ESI MS m/z 616 [C$_{27}$H$_{33}$N$_7$O$_6$S$_2$+H]$^+$.

Example 140

N-(5-tert-Butyl-3-methanesulfonylamino-2-methoxy-phenyl)-4-methyl-3-{4-[3-methyl-2-(2-methyl-propane-2-sulfonyl)-3H-imidazol-4-yl]-1,2,3-triazol-1-yl}-benzamide

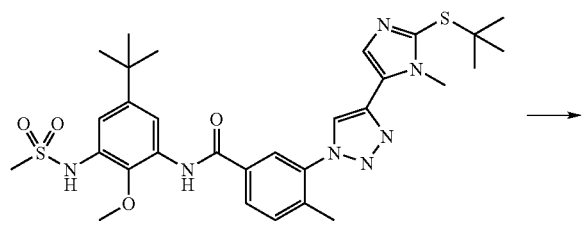

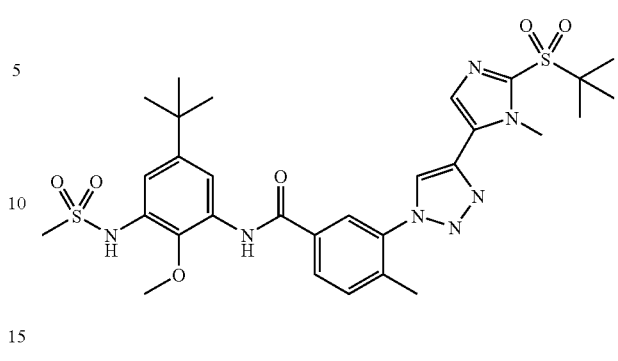

Example 140 was prepared from Example 30 in the same manner as Example 139. ESI MS m/z 658 [C$_{30}$H$_{39}$N$_7$O$_6$S$_2$+H]$^+$.

Example 141

N-(5-tert-Butyl-3-methanesulfonylamino-2-methoxy-phenyl)-3-[4-(2-methanesulfinyl-3-methyl-3H-imidazol-4-yl)-1,2,3-triazol-1-yl]-4-methyl-benzamide

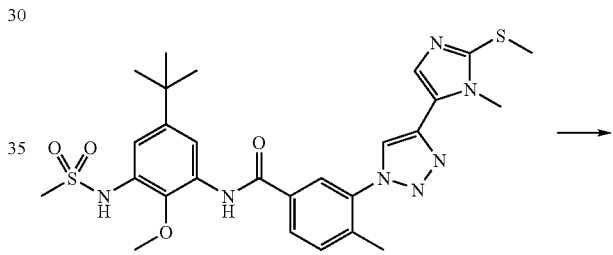

To Example 25 (410 mg, 0.69 mmol) in 10 mL of MeOH (10 mL) was added 370 mg (1.2 mmol) of oxone in 10 mL of water. The mixture was stirred at 0° C. for 22 h before being partitioned between CHCl$_3$ (10 mL) and water (10 mL) with 3 mL of NH$_4$OH. The mixture was extracted with chloroform (3×60 mL), dried over MgSO$_4$, concentrated, and chromatographed (85 to 100% EtOAc in hexanes) to provide Example 141 (360 mg). ESI MS m/z 601 [C$_{27}$H$_{33}$N$_7$O$_5$S$_2$+H]$^+$.

Example 142

N-(5-tert-Butyl-3-methanesulfonylamino-2-methoxy-phenyl)-3-{4-[2-(hydroxy-phenyl-methyl)-3-methyl-3H-imidazol-4-yl]-1,2,3-triazol-1-yl}-4-methyl-benzamide

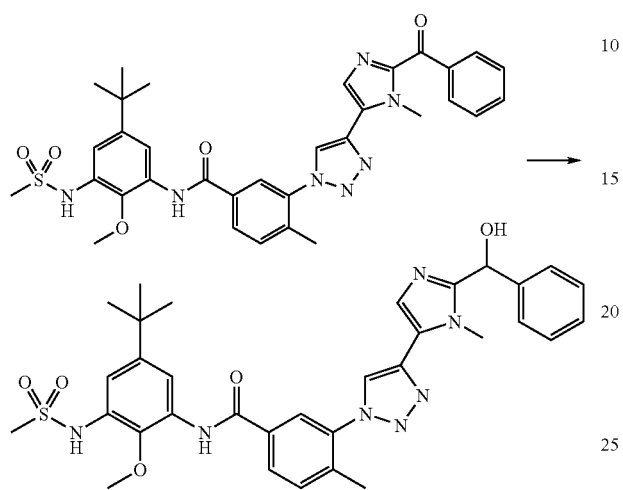

To a solution of 30 mg (0.047 mmol) of Example 35 in 2 mL of EtOH was added 7 mg (0.18 mmol) of NaBH$_4$. After stirring for 2 h, 2 mL of water was added and the mixture was extracted with CH$_2$Cl$_2$ (3×20 mL). The combined organics were washed with brine, dried with MgSO$_4$, and concentrated to provide 17 mg of Example 142. ESI MS m/z 645 [C$_{33}$H$_{37}$N$_7$O$_5$S+H]$^+$.

Example 143

N-(5-tert-Butyl-3-methanesulfonylamino-2-methoxy-phenyl)-3-{4-[2-(1-hydroxy-2,2-dimethyl-propyl)-3-methyl-3H-imidazol-4-yl]-1,2,3-triazol-1-yl}-4-methyl-benzamide

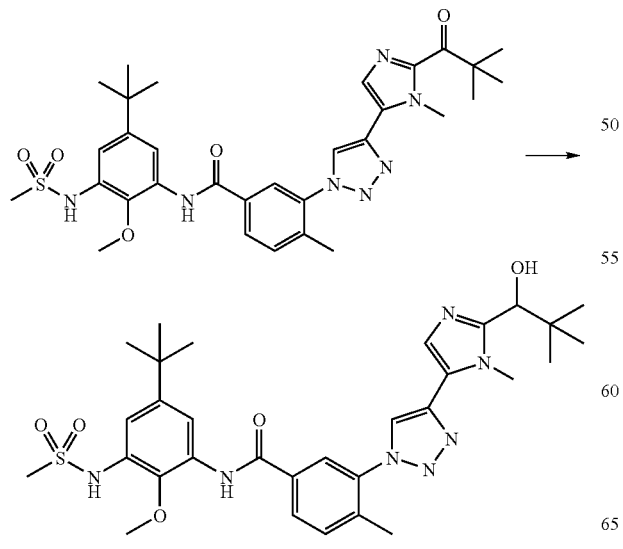

Example 143 was prepared from Example 30 in the same manner as Example 142. ESI MS m/z 624 [C$_{31}$H$_{41}$N$_7$O$_5$S+H]$^+$.

Example 144

N-(5-tert-Butyl-3-methanesulfonylamino-2-methoxy-phenyl)-3-[4-(1-cyclopropyl-5-piperidin-4-yl-1H-pyrazol-4-yl)-1,2,3-triazol-1-yl]-4-methyl-benzamide

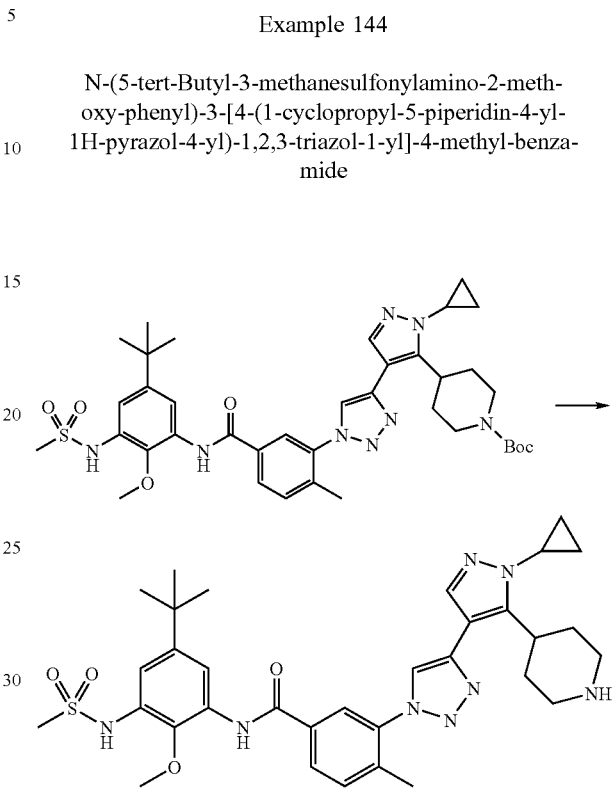

To a solution of Example 108 (50 mg, 0.067 mmol) in 2 mL of MeOH was added 2M HCl (5 mL). The mixture was stirred at for 12 h. Solvent removed under vacuum and the resulting residue was dissolved in CH$_2$Cl$_2$ (50 mL) and washed with satd NaHCO$_3$ (50 mL), brine (50 mL) and dried with MgSO$_4$. The mixture was filtered, concentrated, and chromatographed (10:1 CH$_2$Cl$_2$:MeOH with 1% Et$_3$N) to give Example 144 (10 mg). MS m/z 647 [C$_{33}$H$_{42}$N$_8$O$_4$S+H]$^+$.

Example 145

N-(5-tert-Butyl-3-methanesulfonylamino-2-methoxy-phenyl)-3-{4-[2-(2-hydroxy-1,1-dimethyl-ethyl)-3-methyl-3H-imidazol-4-yl]-1,2,3-triazol-1-yl}-4-methyl-benzamide

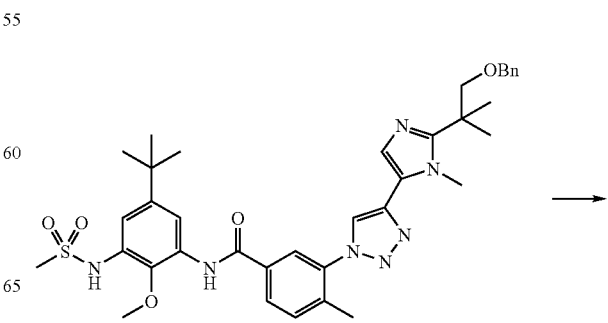

-continued

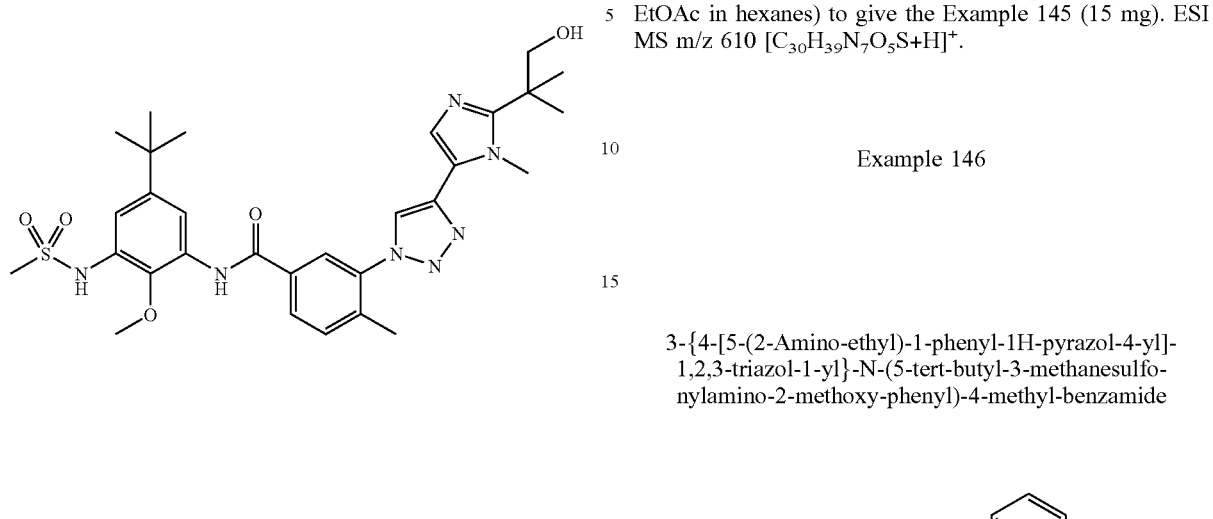

Example 106 (250 mg, 0.36 mmol) and 50 mg of Pd/C (5%) were stirred in 10 mL of MeOH under an $H_2$ atmosphere for 12 h. The mixture was filtered through a pad of celite, concentrated, and chromatogrpahed (10–100% EtOAc in hexanes) to give the Example 145 (15 mg). ESI MS m/z 610 $[C_{30}H_{39}N_7O_5S+H]^+$.

Example 146

3-{4-[5-(2-Amino-ethyl)-1-phenyl-1H-pyrazol-4-yl]-1,2,3-triazol-1-yl}-N-(5-tert-butyl-3-methanesulfonylamino-2-methoxy-phenyl)-4-methyl-benzamide

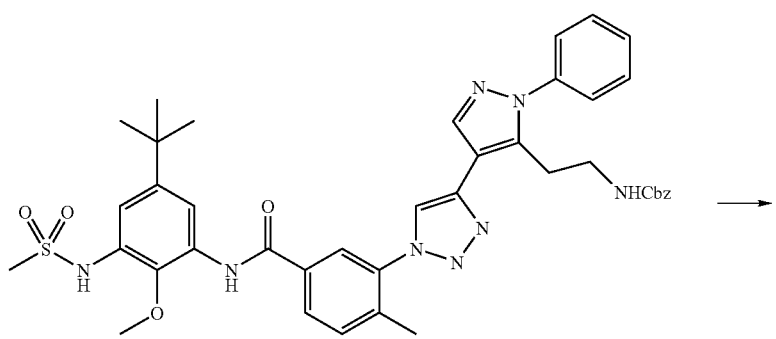

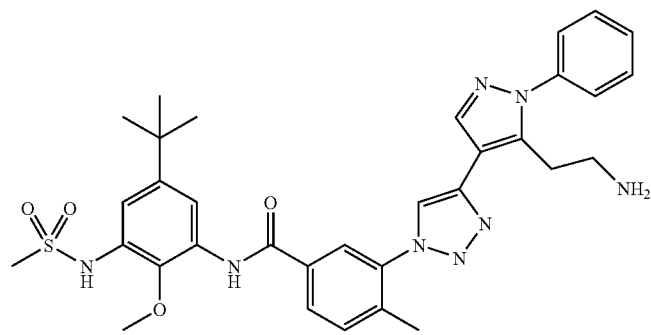

To a solution of 800 mg (1.03 mmol) of Example 109 in MeOH (40 mL) was added 3.6 g of $NH_4CO_2$ and 150 mg of Pd/C. The mixture was stirred at room temperature for 3 h, filtered through celite, and concentrated. The resulting residue was taken up in EtOAc (250 mL) and washed with a solution of water (10 mL) saturated $NaHCO_3$ (50 mL) and brine (20 mL). The organic layer was washed with brine (50 mL), dried over $MgSO_4$, and concentrated to give the 655 mg of Example 146 (1.01 mmol). MS m/z 643 $[C_{33}H_{38}N_8O_4S+H]^+$.

Example 147

N-(5-tert-Butyl-3-methanesulfonylamino-2-methoxy-phenyl)-3-{4-[5-(2-dimethylamino-ethyl)-1-phenyl-1H-pyrazol-4-yl]-1,2,3-triazol-1-yl}-4-methyl-benzamide

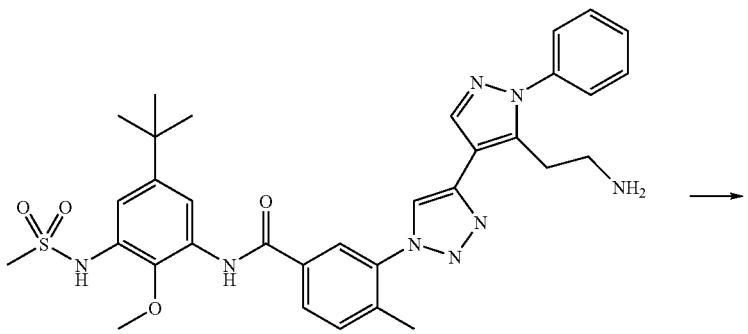

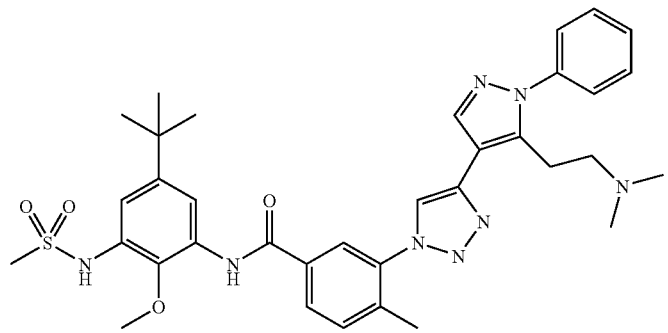

Example 146 (250 mg, 0.389 mmol) was dissolved in 10 mL of MeOH. Formalin (0.6 mL of 37% aqueous formaldehyde) and 200 mg of Pd/C were added. The mixture was stirred under 1 atm $H_2$ for 48 h, filtered through Celite, concentrated, and purified by chromatography (0 to 10% MeOH in $CH_2Cl_2$; 0.5% $NH_4OH$) to give Example 147 (120 mg). MS m/z 671 $[C_{35}H_{42}N_8O_4S+H]^+$.

Example 148

N-(5-tert-Butyl-3-methanesulfonylamino-2-methoxy-phenyl)-4-methyl-3-{4-[5-(2-morpholin-4-yl-ethyl)-1-phenyl-1H-pyrazol-4-yl]-1,2,3-triazol-1-yl}-benzamide

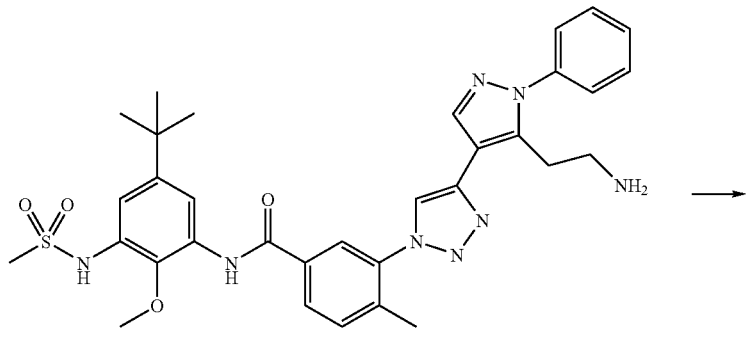

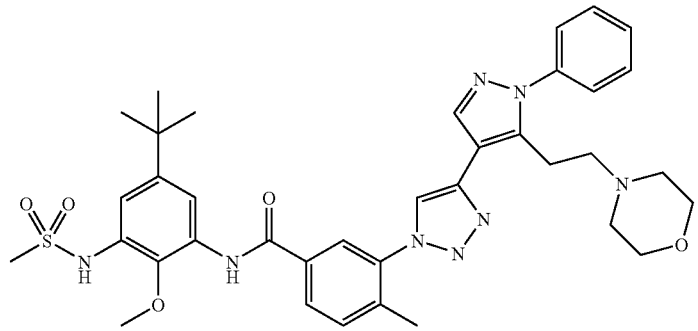

Example 146 (270 mg, 0.42 mmol) was dissolved in 8 mL of DMF followed by 0.25 mL (2.1 mmol) of 2,6-lutidine and 600 mg (2.3 mmol) of 1-bromo-2-(2-bromo-ethoxy)-ethane. The mixture was stirred at 80° C. for 12 h, then was dissolved in EtOAc (300 mL) and washed with sat NaHCO$_3$, water, and brine. The organic portion was dried over MgSO$_4$, filtered, concentrated, and chromatographed (0 to 10% MeOH in CH$_2$Cl$_2$; 0.5% NH$_4$OH) to give Example 148 (52 mg). MS m/z 713 [C$_{37}$H$_{44}$N$_8$O$_5$S+H]$^+$.

Example 149

N-(5-tert-butyl-3-methanesulfonylamino-2-methoxy-phenyl)-4-methyl-3-[4-(5-methyl-1-phenyl-1H-pyrazol-4-yl)-imidazol-1-yl]-benzamide

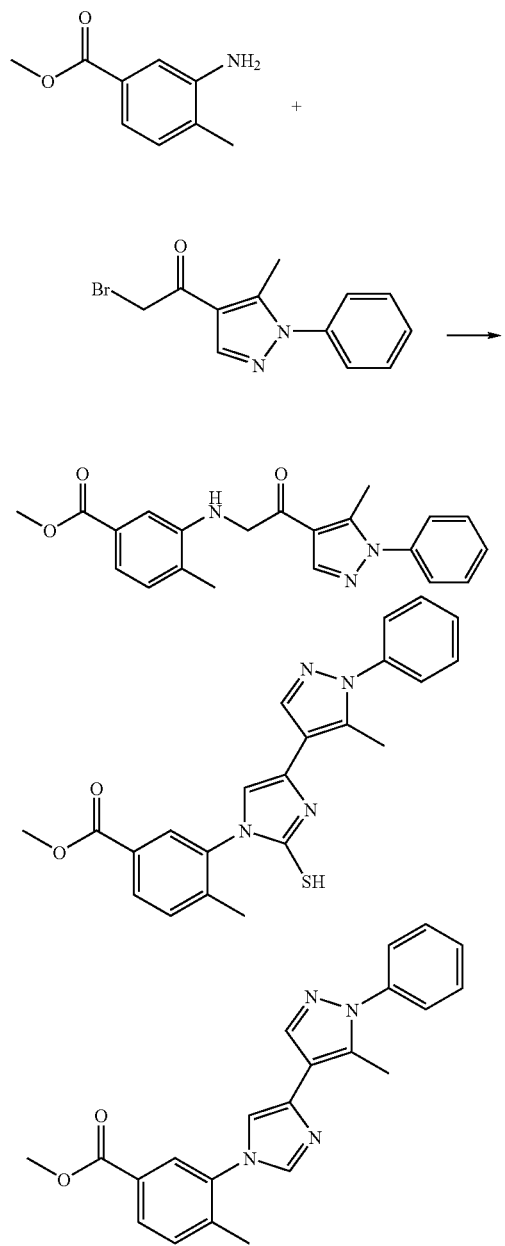

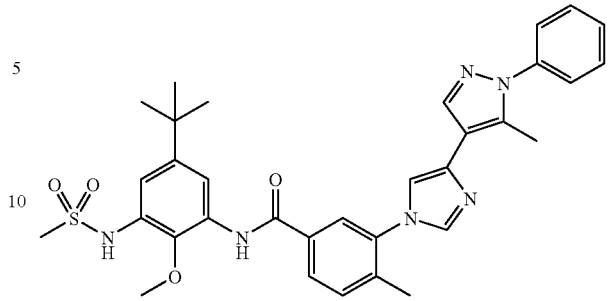

A solution of 2-bromo-1-(5-methyl-1-phenyl-1H-pyrazol-4-yl)-ethanone (829 mg; 2.97 mmol) and 3-amino-4-methyl benzoic acid methyl ester in 6 mL of EtOH was stirred at 75° C., for 6 h. The mixture was cooled, and the resulting precipitate was filtered and washed with cold EtOH to provide 564 mg (1.55 mmol; 52%) of 4-methyl-3-[2-(5-methyl-1-phenyl-1H-pyrazol-4-yl)-2-oxo-ethylamino]-benzoic acid methyl ester as a white powder.

A suspension of 380 mg (1.05 mmol) of 4-methyl-3-[2-(5-methyl-1-phenyl-1H-pyrazol-4-yl)-2-oxo-ethylamino]-benzoic acid methyl ester and 203 mg (2.09 mmol) of KSCN in 4 mL of HOAc was stirred at 100° C. for 4 h, when a precipitate formed. The mixture was cooled to room temperature, filtered, and washed with cold MeOH to provide 283 mg of 3-[2-mercapto-4-(5-methyl-1-phenyl-1H-pyrazol-4-yl)-imidazol-1-yl]-4-methyl-benzoic acid methyl ester (0.70 mmol; 67%). ESI MS m/z 405 [C$_{22}$H$_{20}$N$_4$O$_2$S+H]$^+$.

To 1 mL of 20% HNO$_3$ was added 28 mg of HNO$_2$. This mixture was then added to 3-[2-mercapto-4-(5-methyl-1-phenyl-1H-pyrazol-4-yl)-imidazol-1-yl]-4-methyl-benzoic acid methyl ester (280 mg; 0.69 mmol) suspended in 5 mL of rapidly stirring HOAc over 15 min. After stirring an additional 5 min, the solution was poured into ice-cold water. The pH was adjusted to about 7 with NaHCO$_3$, and the mixture was extracted with EtOAc. The extract was washed once with brine, dried with Na$_2$SO$_4$, filtered, and concentrated. The resulting residue was chromatographed (5–60% EtOAc in hexanes) to provide 210 mg (0.56 mmol; 82%) of 4-methyl-3-[4-(5-methyl-1-phenyl-1H-pyrazol-4-yl)-imidazol-1-yl]-benzoic acid methyl ester. ESI MS m/z 373 [C$_{22}$H$_{20}$N$_4$O$_2$+H]$^+$.

To 119 mg (0.32 mmol) of N-(3-amino-5-tert-butyl-2-methoxy-phenyl)-methane-sulfonamide in 4 mL of THF at −78° C. was added slowly 0.42 mL of 1.6 M n-BuLi in hexanes (0.67 mmol). The cold bath was removed, the mixture was stirred for 30 min., and 0.34 mL of 1M LHMDS in THF (0.34 mmol) was added to the resulting purple solution. THF was added as necessary to facilitate stirring and the purple suspension was slowly transferred via syringe to a rapidly stirring solution of 4-methyl-3-[4-(5-methyl-1-phenyl-1H-pyrazol-4-yl)-imidazol-1-yl]-benzoic acid methyl ester in 2 mL of THF at 0° C. After 20 min, cold MeOH was added, and the solution was partitioned between half saturated NH$_4$Cl and EtOAc. The EtOAc layer was then washed with brine. The washes were extracted once with EtOAc, and the extracts were combined, dried with Na$_2$SO$_4$, filtered, and concentrated. Chromatography (0–3.5% (MeOH with 5% NH4OH) in CH$_2$Cl$_2$) provided Example 149. ESI MS m/z 613 [C$_{33}$H$_{36}$N$_6$O$_4$S+H]$^+$.

Example 150

N-(5-tert-Butyl-3-methanesulfonylamino-2-methoxy-phenyl)-3-[4-(1-isopropyl-5-methyl-1H-pyrazol-4-yl)-imidazol-1-yl]-4-methyl-benzamide

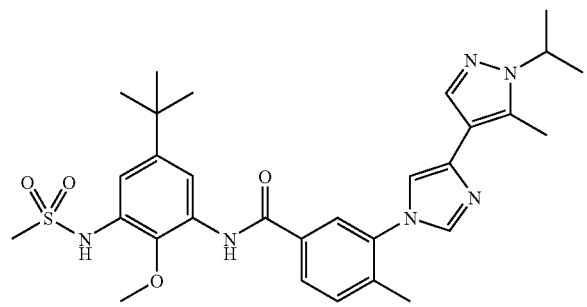

Example 150 was prepared from 2-tosyloxy-1-(5-methyl-1-isopropyl-1H-pyrazol-4-yl)-ethanone (Singh, S. P. et al, *J. Indian Chem. Soc.*, 1997, 74, 940–942) in the same manner as Example 149. ESI MS m/z 579 [$C_{30}H_{38}N_6O_4S+H$]$^+$.

Example 151

3-[4-(5-Ethyl-1-phenyl-1H-pyrazol-4-yl)-imidazol-1-yl]-N-[3-methanesulfonylamino-2-methoxy-5-(1-methyl-cyclopropyl)-phenyl]-4-methyl-benzamide

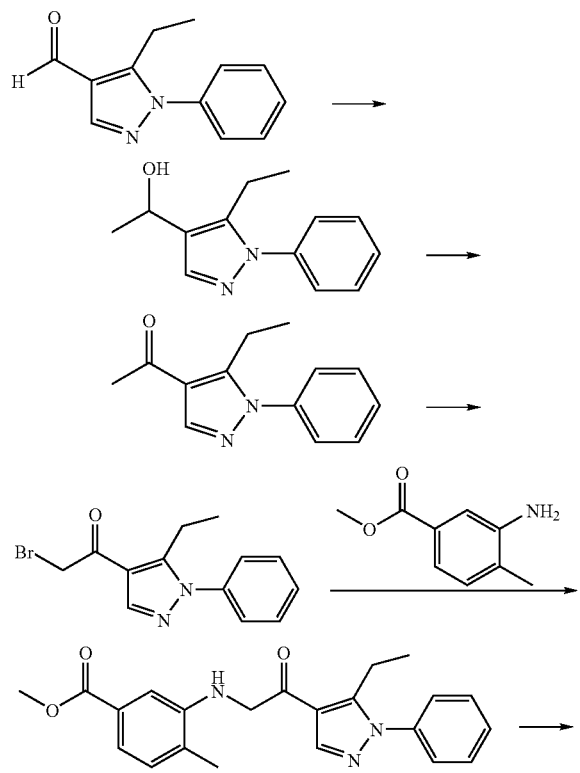

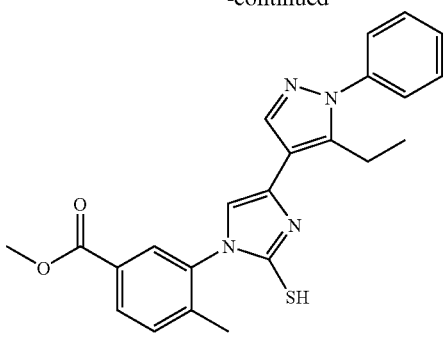

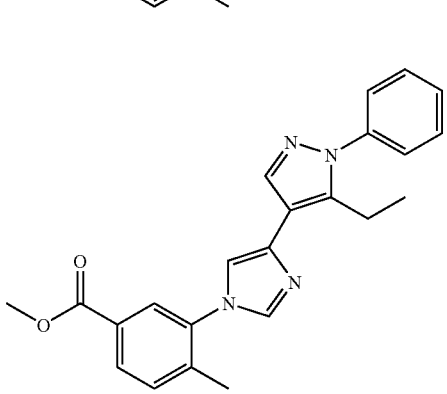

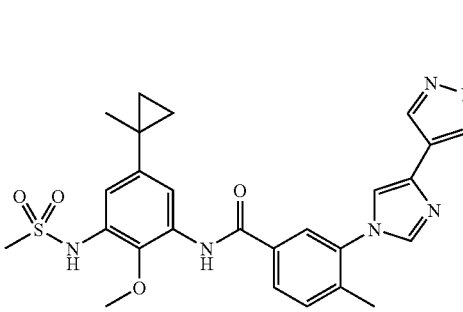

To a 0° C. solution of 7.55 (37.7 mmol) of 5-ethyl-1-phenyl-1H-pyrazole-4-carbaldehyde (Example 86) in anhydrous THF (100 mL) under $N_2$ was added over 5 minutes 15.7 (47.1 mmol) of 3.0 M MeMgBr in $Et_2O$. The mixture was warmed to room temperature and stirred for 16 h, then 25 mL of 5% $NH_4Cl$ was added and the mixture was extracted with $CH_2Cl_2$ (70 mL), and the extract was washed with saturated NaCl (15 mL). The organic layer separated, dried over $MgSO_4$, and concentrated to give 1-(5-ethyl-1-phenyl-1H-pyrazol-4-yl)-ethanol (7.91 g). ESI MS m/z 217 [$C_{13}H_{16}N_2O+H$]$^+$.

A solution of 7.9 g (36.5 mmol) of 1-(5-ethyl-1-phenyl-1H-pyrazol-4-yl)-ethanol in 100 mL THF was stirred at rt over 24 g of activated $MnO_2$ for 23 h. The mixture was filtered through Celite and concentrated to give 1-(5-ethyl-1-phenyl-1H-pyrazol-4-yl)-ethanone (7.71 g). ESI MS m/z 215 [$C_{13}H_{14}N_2O^+H$]$^+$.

To a solution of 5.40 g (25.3 mmol) of 1-(5-ethyl-1-phenyl-1H-pyrazol-4-yl)-ethanone in HOAc (30 mL) was added HBr in HOAc (30 mL). Bromine (1.42 ml, 27.7 mmol) was added dropwise and the mixture was stirred at rt for 45 minutes and was poured into ice water (500 mL). The liquid was decanted and remaining residue was washed with water, then dissolved in $CH_2Cl_2$ (500 mL) and washed with sat NaHCO₃, dried over MgSO₄, and concentrated to give 7.20 g of 2-bromo-1-(5-ethyl-1-phenyl-1H-pyrazol-4-yl)-ethanone.

A solution of 7.20 g (24.6 mmol) of 2-bromo-1-(5-ethyl-1-phenyl-1H-pyrazol-4-yl)-ethanone and 8.52 g (51.6 mmol) of 3-amino-4-methyl benzoic acid methyl ester in EtOH (30 mL) was heated to 75° C. for 16 h. The solution was cooled and allowed to stand at rt for 6 h. The solids were filtered off and washed with cold EtOH to provide 3-[2-(5-ethyl-1-phenyl-1H-pyrazol-4-yl)-2-oxo-ethylamino]-4-methyl-benzoic acid methyl ester as a white powder (3.75 g). ESI MS m/z 378 [C$_{22}$H$_{23}$N$_3$O$_3$+H]⁺.

A suspension of 3.75 g (9.94 mmol) of 3-[2-(5-ethyl-1-phenyl-1H-pyrazol-4-yl)-2-oxo-ethylamino]-4-methyl-benzoic acid methyl ester and 2.9 g (30 mmol) of KSCN in 25 mL of HOAc was stirred at 100° C. for 4 h. The mixture was allowed to cool overnight before being filtered and washed with cold MeOH. The solids were dried to provide 2.65 g of 3-[4-(5-ethyl-1-phenyl-1H-pyrazol-4-yl)-2-mercapto-imidazol-1-yl]-4-methyl-benzoic acid methyl ester as an off-white solid. ESI MS m/z 419 [C$_{23}$H$_{22}$N$_4$O$_2$S+H]⁺.

The above thioimidazole (2.65 g, 6.33 mmol) was suspended in 5 mL of HOAc and 0.63 mL of water and heated to 35° C. Hydrogen peroxide (2.36 g, 20.8 mmol) was added over 15 minutes. After heating at 40° C. for 35 minutes, the mixture was cooled to 25° C. and quenched with 10% Na$_x$SO$_3$ (1 mL). After 15 min, concentrated NH$_4$OH (20 mL) added and the resulting gummy orange solid was washed with water, then dissolved in EtOAc and washed with brine, dried over MgSO$_4$, concentrated, and chromatographed (10 to 80% EtOAc in hexanes). The desired fractions were stirred in DCM with PS-TBD resin and decolorizing charcoal, filtered through Celite, and concentrated to give 1.85 g of 3-[4-(5-ethyl-1-phenyl-1H-pyrazol-4-yl)-imidazol-1-yl]-4-methyl-benzoic acid methyl ester. ESI MS m/z 387 [C$_{23}$H$_{22}$N$_4$O$_2$+H]⁺.

To a solution of 70 mg (0.25 mmol) of N-[3-amino-2-methoxy-5-(1-methyl-cyclopropyl)-phenyl]-methanesulfonamide in 5 mL of THF under N$_2$ was added 1.04 mL of LHMDS (1.0 M). The mixture was stirred at rt for 15 minutes when a solution of 3-[4-(5-ethyl-1-phenyl-1H-pyrazol-4-yl)-imidazol-1-yl]-4-methyl-benzoic acid methyl ester (100 mg, 0.026 mmol) in 5 mL of THF (5 mL) was added. After stirring for 45 minutes, 10 mL of saturated NaHCO$_3$ was added. The mixture was extracted with CH$_2$Cl$_2$ (100 ml), dried with Na$_2$SO$_4$, filtered, concentrated, and chromatographed (30 to 100% EtOAc in hexanes) to give Example 151 (69 mg). ESI MS m/z 625 [C$_{34}$H$_{36}$N$_6$O$_4$S+H]⁺.

Example 152

N-(5-tert-Butyl-2-methyl-pyridin-3-yl)-3-[4-(5-ethyl-1-phenyl-1H-pyrazol-4-yl)-imidazol-1-yl]-4-methyl-benzamide

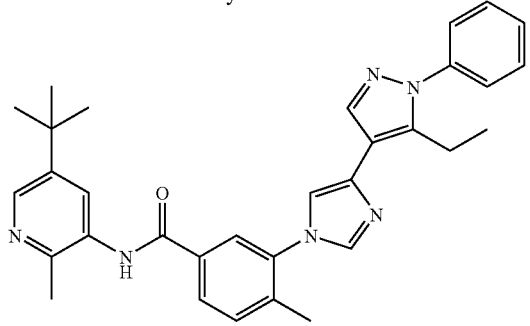

Example 152 was prepared from 5-tert-butyl-2-methyl-pyridin-3-ylamine (see U.S. provisional application 60/567,693) and 3-[4-(5-ethyl-1-phenyl-1H-pyrazol-4-yl)-imidazol-1-yl]-4-methyl-benzoic acid methyl ester (Example 151) in the same manner as Example 151. ESI MS m/z 519 [C$_{32}$H$_{34}$N$_6$O+H]⁺.

Example 153

N-(5-tert-Butyl-2-methoxy-phenyl)-3-[4-(5-ethyl-1-phenyl-1H-pyrazol-4-yl)-imidazol-1-yl]-4-methyl-benzamide

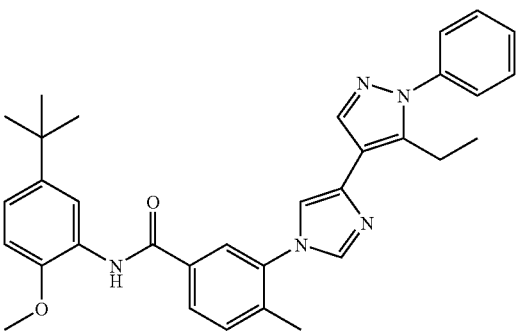

Example 153 was prepared from 5-tert-butyl-2-methoxy-phenylamine and 3-[4-(5-ethyl-1-phenyl-1H-pyrazol-4-yl)-imidazol-1-yl]-4-methyl-benzoic acid methyl ester (Example 151) in the same manner as Example 151. ESI MS m/z 534 [C$_{33}$H$_{35}$N$_5$O$_2$+H]⁺.

Example 154

3-[4-(5-Ethyl-1-phenyl-1H-pyrazol-4-yl)-imidazol-1-yl]-N-(2-methoxy-5-trifluoromethyl-phenyl)-4-methyl-benzamide

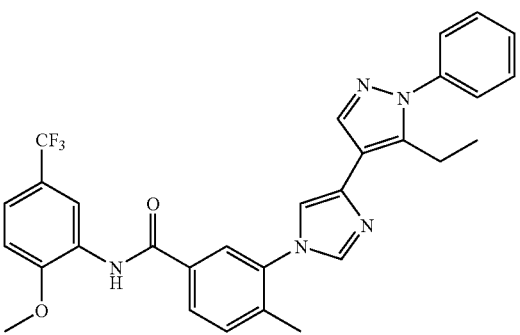

Example 154 was prepared from 2-methoxy-5-trifluoromethyl-phenylamine and 3-[4-(5-ethyl-1-phenyl-1H-pyrazol-4-yl)-imidazol-1-yl]-4-methyl-benzoic acid methyl ester (Example 151) in the same manner as Example 151. ESI MS m/z 546 [C$_{30}$H$_{26}$F$_3$N$_5$O$_2$+H]⁺.

Example 155

N-(5-tert-Butyl-3-cyano-2-methoxy-phenyl)-3-[4-(5-ethyl-1-phenyl-1H-pyrazol-4-yl)-imidazol-1-yl]-4-methyl-benzamide

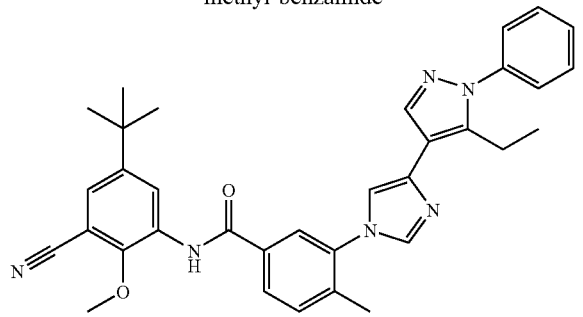

Example 155 was prepared from 3-amino-5-tert-butyl-2-methoxy-benzonitrile and 3-[4-(5-ethyl-1-phenyl-1H-pyrazol-4-yl)-imidazol-1-yl]-4-methyl-benzoic acid methyl ester (Example 151) in the same manner as Example 151. ESI MS m/z 559 $[C_{34}H_{34}N_6O_2+H]^+$.

Example 156

N-(5-tert-Butyl-2-methanesulfinyl-phenyl)-3-[4-(5-ethyl-1-phenyl-1H-pyrazol-4-yl)-imidazol-1-yl]-4-methyl-benzamide

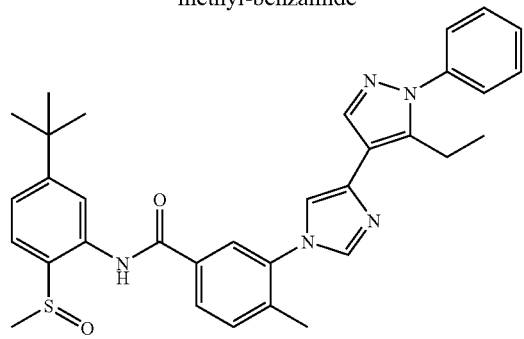

Example 156 was prepared from 5-tert-butyl-2-methanesulfinyl-phenylamine and 3-[4-(5-ethyl-1-phenyl-1H-pyrazol-4-yl)-imidazol-1-yl]-4-methyl-benzoic acid methyl ester (Example 151) in the same manner as Example 151. ESI MS m/z 566 $[C_{33}H_{35}N_5O_2S+H]^+$.

Example 157

N-(5-tert-Butyl-3-methanesulfonylamino-2-methyl-phenyl)-3-[4-(5-ethyl-1-phenyl-1H-pyrazol-4-yl)-imidazol-1-yl]-4-methyl-benzamide

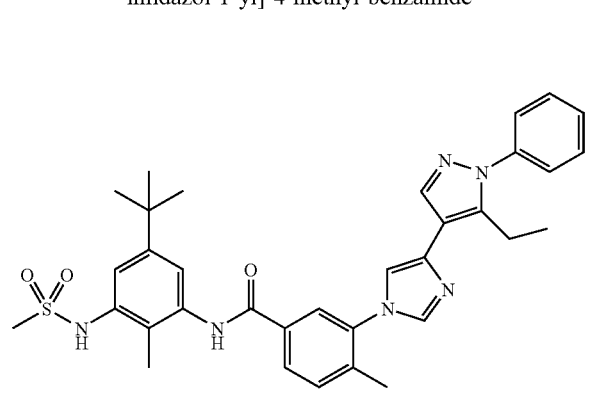

Example 157 was prepared from N-(3-amino-5-tert-butyl-2-methyl-phenyl)-methanesulfonamide and 3-[4-(5-ethyl-1-phenyl-1H-pyrazol-4-yl)-imidazol-1-yl]-4-methyl-benzoic acid methyl ester (Example 151) in the same manner as Example 151. ESI MS m/z 611 $[C_{34}H_{38}N_6O_3S+H]^+$.

Example 158

N-(5-tert-Butyl-3-methanesulfonylamino-2-methoxy-phenyl)-3-[4-(5-ethyl-1-phenyl-1H-pyrazol-4-yl)-imidazol-1-yl]-4-methyl-benzamide

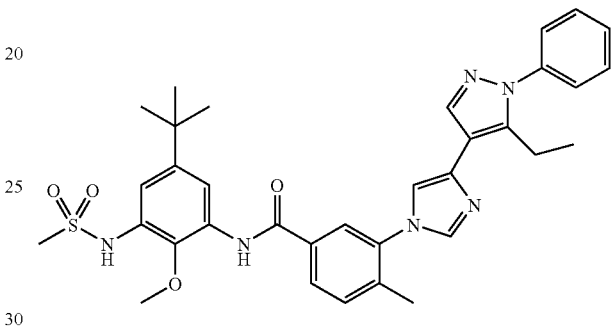

Example 158 was prepared from N-(3-amino-5-tert-butyl-2-methoxy-phenyl)-methanesulfonamide and 3-[4-(5-ethyl-1-phenyl-1H-pyrazol-4-yl)-imidazol-1-yl]-4-methyl-benzoic acid methyl ester (Example 151) in the same manner as Example 151. ESI MS m/z 627 $[C_{34}H_{38}N_6O_4S+H]^+$.

Example 159

3-[4-(5-Ethyl-1-phenyl-1H-pyrazol-4-yl)-imidazol-1-yl]-N-(3-methanesulfonylamino-2-methoxy-5-trifluoromethyl-phenyl)-4-methyl-benzamide

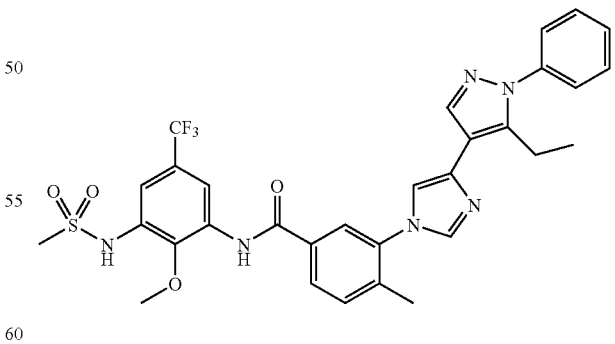

Example 159 was prepared from N-(3-amino-2-methoxy-5-trifluoromethyl-phenyl)-methanesulfonamide and 3-[4-(5-ethyl-1-phenyl-1H-pyrazol-4-yl)-imidazol-1-yl]-4-methyl-benzoic acid methyl ester (Example 151) in the same manner as Example 151. ESI MS m/z 639 $[C_{31}H_{29}F_3N_6O_4S+H]^+$.

Example 160

N-(5-tert-butyl-3-methanesulfonylamino-2-methoxy-phenyl)-4-methyl-3-(4-pyridin-3-yl-imidazol-1-yl)-benzamide

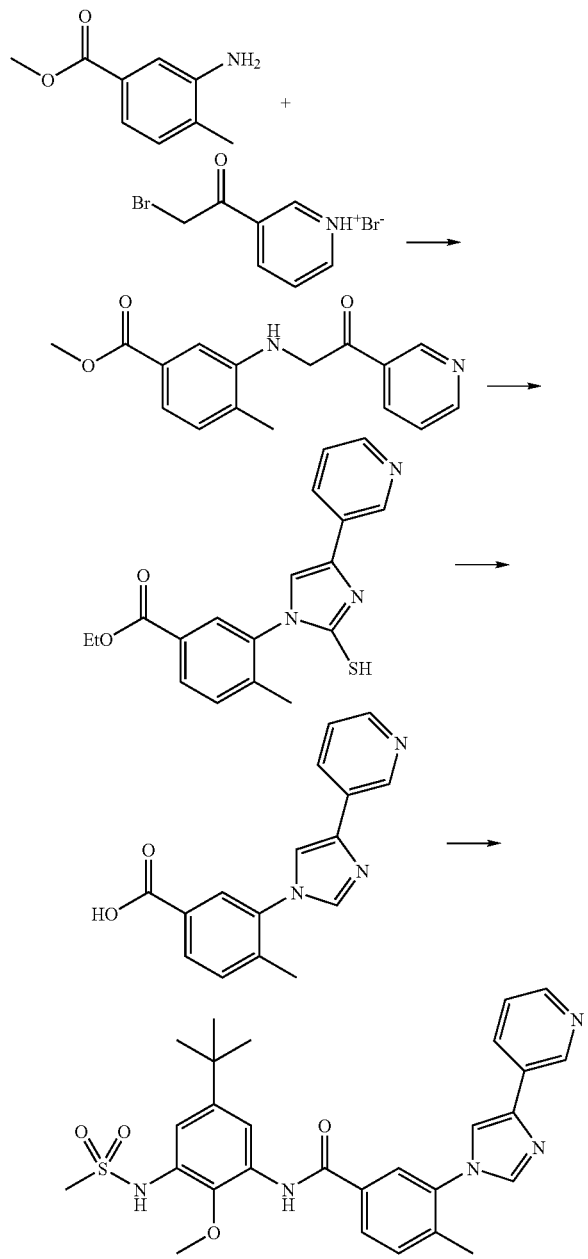

To a solution of 2-bromo-1-pyridin-3-yl-ethanone hydrobromide (Barlin, G. B. et al. *Australian J. Chem*, 1989, 1735) (500 mg, 1.78 mmol) in 2 ml of EtOH was added 3-amino-4-methyl-benzoic acid methyl ester (Lancaster; 294 mg, 1.78 mmol) and NaHCO$_3$ (750 mg, 8.9 mmol), and the mixture was stirred for 2 h. The mixture was then filtered and washded with MeOH, then the filtrated was concentrated to a small volume and dissolved in EtOAc. The EtOAc slurry was washed with water and brine, and the washes were extracted once more with EtOAc. The combined organic portions were dried with Na$_2$SO$_4$, filtered, concentrated, and chromatographed (0–5% MeOH in dichloromethane) to provide 84.5 mg of 4-methyl-3-(2-oxo-2-pyridin-3-yl-ethylamino)-benzoic acid methyl ester.

A mixture of 4-methyl-3-(2-oxo-2-pyridin-3-yl-ethylamino)-benzoic acid methyl ester (84.5 mg; 0.297 mmol) and KSCN (58 mg; 0.59 mmol) in 1.5 mL of HOAc were heated to 100° C. for 2 h. The mixture was then poured into water and carefully brought to pH 8 with NaOH. The mixture was immediately extracted with EtOAc, and the extract washed with brine. The washes were extracted once more with EtOAc, and the combined extracts were dried with Na$_2$SO$_4$, filtered, and concentrated to provide 3-(2-mercapto-4-pyridin-3-yl-imidazol-1-yl)-4-methyl-benzoic acid methyl ester (90 mg; 0.28 mmol; 93%). ESI MS m/z 326 [C$_{17}$H$_{15}$N$_3$O$_2$S+H]$^+$.

To a suspension of 85 mg (0.261 mmol) of 3-(2-mercapto-4-pyridin-3-yl-imidazol-1-yl)-4-methyl-benzoic acid methyl ester in 1.8 mL of water was added 0.68 mL of concentrated HNO$_3$ and 2 mg of NaNO$_2$. After 2 h, the mixture was cooled to 0° C. and 4N NaOH was added until the pH reached about 10. The mixture was stirred for 30 min then HOAc was added until the pH reached about 6. The resulting precipitate was filtered, washed with water and dried to provide 16 mg (0.057 mmol; 22%) of 4-methyl-3-(4-pyridin-3-yl-imidazol-1-yl)-benzoic acid.

4-Methyl-3-(4-pyridin-3-yl-imidazol-1-yl)-benzoic acid (15 mg; 0.054 mmol), N-(3-amino-5-tert-butyl-2-methoxyphenyl)-methane-sulfonamide (29 mg; 0.11), and HATU (49 mg; 0.11 mmol) were dissolved in 1 mL of DMF, and the mixture was chilled to 0° C. Diisopropylethylamine (19 μL; 0.11 mmol) was then added, the cold-bath was removed, and the mixture was stirred overnight. The mixture was then poured into water and extracted with EtOAc. The organic portion was washed with NaHCO$_3$ and brine, and the washes were extracted once with EtOAc. The extracts were combined, dried with Na$_2$SO$_4$, filtered, and concentrated. Chromatography (0–6.5% MeOH/0.5% NH$_4$OH in CH$_2$Cl$_2$) provided 23 mg (0.043 mmol; 80%) of Example 160. ESI MS m/z 534 [C$_{28}$H$_{31}$N$_5$O$_4$S+H]$^+$.

Example 161

N-(5-tert-Butyl-3-methanesulfonylamino-2-methoxy-phenyl)-4-methyl-3-{4-[6-(2-morpholin-4-yl-ethyl)-pyridin-3-yl]-1,2,3-triazol-1-yl}-benzamide

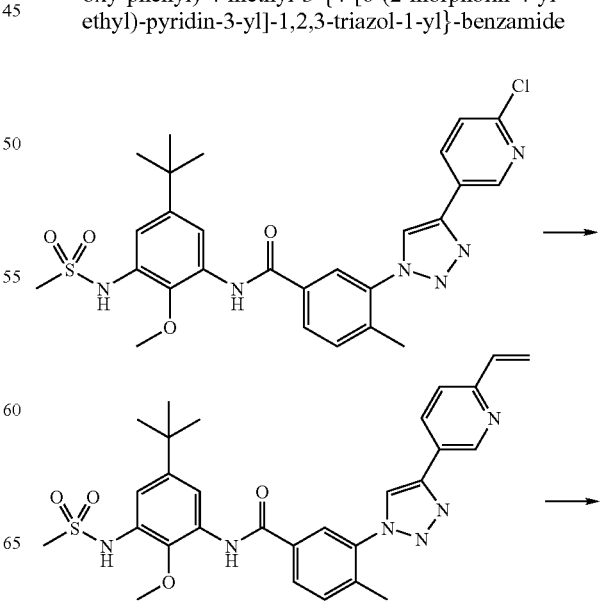

-continued

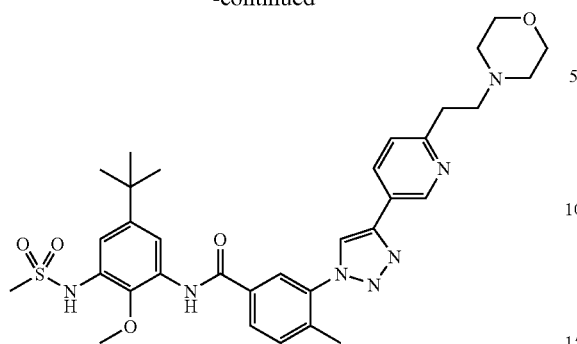

Example 1 (500 mg, 0.88 mmol), Ph₃As (27 mg, 0.088 mmol), and CsF (295 mg, 1.93 mmol) were combined in NMP (2.5 mL) and degassed by the freeze-pump-thaw method. 2,6-Di-tert-butyl-4-methylphenol (few crystals), Pd$_2$(dba)$_3$ (20 mg, 0.022 mmol), and tributyl vinyl tin (310 μL, 1.06 mmol) were added and the reaction was heated at 70° C. overnight. Additional Ph₃As (27 mg, 0.088 mmol) and Pd$_2$(dba)$_3$ (20 mg, 0.022 mmol) were added and the reaction heated at 70° C. overnight. Water and EtOAc were added and the layers were separated. The organic layer was dried over sodium sulfate, filtered, and evaporated. The product, N-(5-tert-butyl-3-methanesulfonylamino-2-methoxy-phenyl)-4-methyl-3-[4-(6-vinyl-pyridin-3-yl)-1,2,3-triazol-1-yl]-benzamide, was used without purification for the next step. ESI MS m/z 561 [C$_{29}$H$_{32}$N$_6$O$_4$S+H]⁺.

The above impure vinylpyridine (300 mg) was dissolved in EtOH (5 mL). Morpholine (120 microL) and HOAc (3 drops) were added and the mixture was heated in a sealed tube at 50° C. overnight. The reaction was evaporated and chromatographed (3% ammonium hydroxide, 10% MeOH, 20% chloroform, 67% EtOAc) and the product containing fractions evaporated. The residue was further purified by semi-prep HPLC to provide Example 161 (21 mg). ESI MS m/z 648 [C$_{33}$H$_{41}$N$_7$O$_5$S+H]⁺.

Example 162

N-(5-tert-Butyl-3-methanesulfonylamino-2-methoxy-phenyl)-4-methyl-3-{4-[6-(2-methylamino-ethyl)-pyridin-3-yl]-[1,2,3]triazol-1-yl}-benzamide

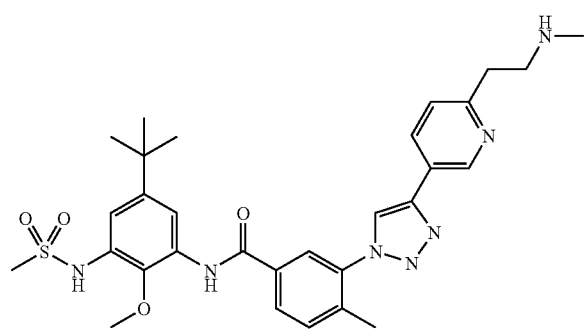

Example 162 was prepared from N-(5-tert-butyl-3-methanesulfonylamino-2-methoxy-phenyl)-4-methyl-3-[4-(6-vinyl-pyridin-3-yl)-1,2,3-triazol-1-yl]-benzamide (Example 151) and methylamine in the same manner as Example 151. ESI MS m/z 592 [C$_{30}$H$_{37}$N$_7$O$_4$S+H]⁺.

Example 163

N-(5-tert-Butyl-3-methanesulfonylamino-2-methoxy-phenyl)-3-{4-[6-(2-dimethylamino-ethyl)-pyridin-3-yl]-[1,2,3]triazol-1-yl}-4-methyl-benzamide

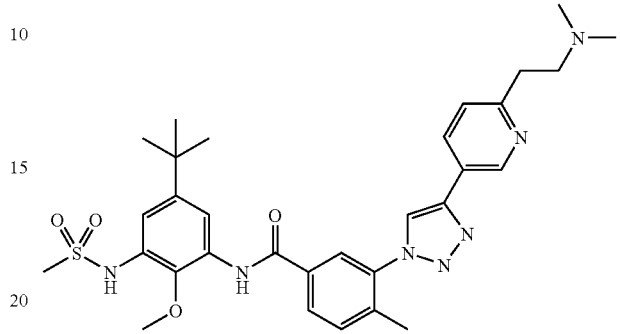

Example 163 was prepared from N-(5-tert-butyl-3-methanesulfonylamino-2-methoxy-phenyl)-4-methyl-3-[4-(6-vinyl-pyridin-3-yl)-1,2,3-triazol-1-yl]-benzamide (Example 151) and dimethylamine in the same manner as Example 151. ESI MS m/z 606 [C$_{31}$H$_{39}$N$_7$O$_4$S+H]⁺.

Methods of Use

In accordance with the invention, there are provided novel methods of using the compounds of the formula (I). The compounds disclosed therein effectively block inflammatory cytokine production from cells. The inhibition of cytokine production is an attractive means for preventing and treating a variety of cytokine mediated diseases or conditions associated with excess cytokine production, e.g., diseases and pathological conditions involving inflammation. Thus, the compounds are useful for the treatment of diseases and conditions as described in the Background section, including the following conditions and diseases:

osteoarthritis, atherosclerosis, contact dermatitis, bone resorption diseases, reperfusion injury, asthma, multiple sclerosis, Guillain-Barre syndrome, Crohn's disease, ulcerative colitis, psoriasis, graft versus host disease, systemic lupus erythematosus and insulin-dependent diabetes mellitus, rheumatoid arthritis, toxic shock syndrome, Alzheimer's disease, diabetes, inflammatory bowel diseases, acute and chronic pain as well as symptoms of inflammation and cardiovascular disease, stroke, myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, syndromes associated with hemodialysis, leukopherisis, granulocyte transfusion associated syndromes, and necrotizing entrerocolitis, complications including restenosis following percutaneous transluminal coronary angioplasty, traumatic arthritis, sepsis, chronic obstructive pulmonary disease and congestive heart failure. The compounds of the invention may also be useful for anticoagulant or fibrinolytic therapy (and the diseases or conditions related to such therapy) as described in the provisional application No. 60/403,422.

The compounds of the invention are also p38 MAP kinase inhibitors. Activity can be demonstrated by using methods known in the art. See for example Branger et al., (2002) *J Immunol.* 168: 4070–4077. As disclosed in the Background of the Invention, the compounds of the invention will therefore be useful for treating, in addition to inflammatory diseases, oncological diseases. These diseases include but are not limited to solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma and mesothelioma.

Examples of brain cancers include, but are not limited to brain stem, optic and hypophtalmic glioma, cerebella and cerebral astrocytoma, medulloblastoma, ependymoma, as well as pituitary, neuroectodermal and pineal tumor.

Examples of peripheral nervous system tumors include, but are not limited to neuroblastoma, ganglioneuroblastoma, and peripheral nerve sheath tumors.

Examples of tumors of the endocrine and exocrine system include, but are not limited to thyroid carcinoma, adrenocortical carcinoma, pheochromocytoma, and carcinoid tumors.

Tumors of the male reproductive organs include, but are not limited to prostate and testicular cancer.

Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallblader, gastric, pancreatic, rectal, small-intestine, and salivary gland cancers.

Tumors of the urinary tract include, but are not limited to bladder, penile, kidney, renal pelvis, ureter, and urethral cancers.

Eye cancers include, but are not limited to intraocular melanoma and retinoblastoma.

Examples of liver cancers include, but are not limited to hepatocellular carcinoma (liver cell carcinomas with or without fibrolamellar variant), hepatoblastoma, cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal/hypopharyngeal/nasopharyngeal/oropharyngeal cancer, and lip and oral cavity cancer.

Lymphomas include, but are not limited to AIDS-related lymphoma, non-Hodgkin's lymphoma, Hodgkins lymphoma, cutaneous T-cell lymphoma, and lymphoma of the central nervous system.

Sarcomas include, but are not limited to sarcoma of the soft tissue, osteosarcoma, Ewings sarcoma, malignant fibrous histiocytoma, lymphosarcoma, angiosarcoma, and rhabdomyosarcoma. Leukemias include, but are not limited to acute myeloid leukemia, acute lymphoblastic leukemia, chronic lymphocytic leukemia, chronic myelogenous leukemia, and hairy cell leukemia.

Plasma cell dyscrasias include, but are not limited to multiple myeloma, and Waldenstrom's macroglobulinemia.

These disorders have been well characterized in man, but also exist with a similar etiology in other mammals, and can be treated by pharmaceutical compositions of the present invention.

For therapeutic use, the compounds may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds may be administered alone or in combination with adjuvants that enhance stability of the inhibitors, facilitate administration of pharmaceutic compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. The above described compounds may be physically combined with the conventional therapeutics or other adjuvants into a single pharmaceutical composition. Reference is this regard may be made to Cappola et al.: U.S. patent application Ser. No. 09/902,822, PCT/US 01/21860 and U.S. application Ser. No. 10/214,782, each incorporated by reference herein in their entirety. Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of the invention may vary and is within the purview of those skilled in the art. Alternatively, the compounds may be administered separately (either serially or in parallel). Separate dosing allows for greater flexibility in the dosing regime.

As mentioned above, dosage forms of the compounds described herein include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (1990)). Dosage levels and requirements are well-recognized in the art and may be selected by those of ordinary skill in the art from available methods and techniques suitable for a particular patient. In some embodiments, dosage levels range from about 1–1000 mg/dose for a 70 kg patient. Although one dose per day may be sufficient, up to 5 doses per day may be given. For oral doses, up to 2000 mg/day may be required. Reference in this regard may also be made to U.S. provisional application No. 60/339,249. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

Biological Assays

Inhibition of TNF Production in THP Cells

The inhibition of cytokine production can be observed by measuring inhibition of TNFα in lipopolysaccharide stimulated THP cells (for example, see W. Prichett et al., 1995, *J. Inflammation*, 45, 97). All cells and reagents were diluted in RPMI 1640 with phenol red and L-glutamine, supplemented with additional L-glutamine (total: 4 mM), penicillin and streptomycin (50 units/ml each) and fetal bovine serum (FBS, 3%) (GIBCO, all conc. final). Assay was performed under sterile conditions; only test compound preparation was nonsterile. Initial stock solutions were made in DMSO followed by dilution into RPMI 1640 2-fold higher than the desired final assay concentration. Confluent THP.1 cells ($2 \times 10^6$ cells/ml, final conc.; American Type Culture Company, Rockville, Md.) were added to 96 well polypropylene round bottomed culture plates (Costar 3790; sterile) containing 125 μl test compound (2 fold concentrated) or DMSO vehicle (controls, blanks). DMSO concentration did not exceed 0.2% final. Cell mixture was allowed to preincubate for 30 min, 37° C., 5% $CO_2$ prior to stimulation with lipopolysaccharide (LPS; 1 μg/ml final; Siga L-2630, from *E. coli* serotype 0111.B4; stored as 1 mg/ml stock in endotoxin screened distilled $H_2O$ at −80° C.). Blanks (unstimulated) received $H_2O$ vehicle; final incubation volume was 250 μl. Overnight incubation (18–24 hr) proceeded as described above. Assay was terminated by centrifuging plates 5 min, room temperature, 1600 rpm (400×g); supernatants were transferred to clean 96 well plates and stored −80° C. until analyzed for human TNFα by a commercially available ELISA kit (Biosource #KHC3015, Camarillo, Calif.). Data was analyzed by non-linear regression (Hill equation) to generate a dose response curve using SAS Software System (SAS institute, Inc., Cary, N.C.).

The calculated $IC_{50}$ value is the concentration of the test compound that caused a 50% decrease in the maximal TNFα production.

Preferred compounds have an $IC_{50} < 1$ uM in this assay.

Inhibition of Other Cytokines

By similar methods using peripheral blood monocytic cells, appropriate stimuli, and commercially available ELISA kits (or other method of detection such as radioimmunoassay), for a particular cytokine, inhibition of IL-1beta, GM-CSF, IL-6 and IL-8 can be demonstrated for preferred compounds (for example, see J. C. Lee et al., 1988, *Int. J. Immunopharmacol.*, 10, 835).

All references disclosed in this application including patents, patent publications and literature citations are incorporated herein by reference in their entirety.

What is claimed is:
1. A compound of the formula (I)

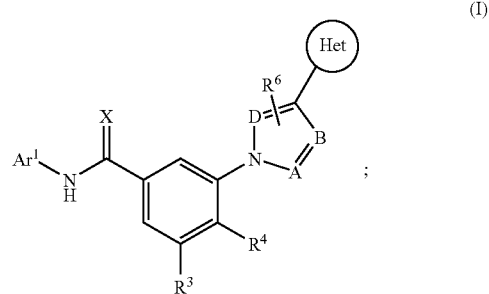

wherein:
Ar$^1$ is chosen from (i), (ii) and (iii) below:
(i) a carbocycle substituted by R$^1$, R$^2$ and R$^x$,

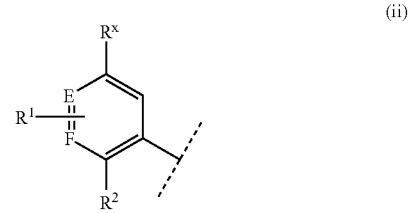

wherein one of E or F is nitrogen and the other is carbon, R$^1$ is covalently attached to either E or F, and when nitrogen is N—R$^1$ the double bond between E and F is not present;

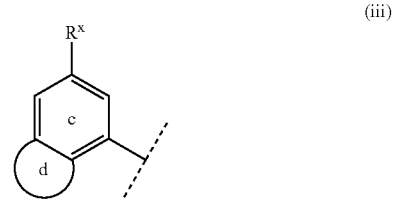

wherein c is a benzo ring fused to ring d which is a 5–7 membered heterocyclic ring optionally substituted by an oxo (═O) group and one to two R groups each independently being H or C1–3 alkyl;
R$^1$ is chosen from hydrogen, NO$_2$, —N(R$^c$)$_2$, J-C(O)—N(R$^c$)—, J-S(O)$_m$—N(R$^c$)—, C1–6 alkylS(O)$_m$—,
or R$^1$ is chosen from C1–6 alkyl, C3–7 cylcoalkyl, C1–5 alkoxyl or C3–7 cycloalkoxyl, C1–5 alkylthiol or C3–7 cycloalkylthiol, C1–5 acyl, C1–5 alkoxycarbonyl, C1–5 acyloxy, C1–5 acylamino, C2–5 alkenyl, C2–5 alkynyl, heterocycle, heterocycleC1–6 alkyl, heteroaryl, heteroarylC1–6 alkyl and nitrile; each of the aforementioned where possible are optionally partially or fully halogenated or are optionally further substituted with alkylsulfonylamino, aminocarboxyl, alkoxyl, amino, alkylamino, dialkylamino, hydroxyl, oxo, nitro or nitrile;
R$^2$ is chosen from:
hydrogen, halogen, nitrile, C1–5 alkylS(O)$_m$—, arylS(O)$_m$, J-O—C(O)—O—, N(R$^c$)$_2$—C(O)—(CH$_2$)$_n$—, C1–6 acetyl, aroyl, C1–6alkoxycarbonyl, C1–6 alkyl, C3–7cycloalkyl, C1–6 alkoxy, C3–5cycloalkoxy, C1–5 alkylC1–5 alkoxy, hydroxy, hydroxy C1–5 alkyl, and amino optionally mono- or di-substituted by C1–5 alkyl, aryl or aryl C1–5 alkyl; each of the aforementioned where possible are optionally partially or fully halogenated or are optionally further substituted with C1–3 alkyl, alkylsulfonylamino, alkoxyl, amino, alkylamino, dialkylamino, hydroxyl, oxo, nitro or nitrile;

each $R^x$ is chosen from C1–6 alkyl or C3–7 cycloalkyl each being optionally substituted by C1–3 alkyl and optionally partially or fully halogenated, C1–4 acyl, aroyl, C1–4 alkoxy, C1–5alkylS(O)$_m$—, each may optionally be partially or fully halogenated, halogen, C1–6 alkoxycarbonyl, carbocyclesulfonyl;

each $R^c$ is independently hydrogen or C1–5 alkyl;

D, A and B in

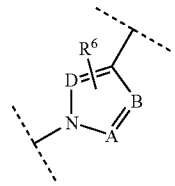

of the formula (I) are each independently chosen from N or CH wherein the hydrogen atom is optionally replaced by $R^6$;

Het is a heterocyclic or heteroaryl ring wherein Het is optionally substituted by one to three $R^5$;

m is 0,1 or 2;

J is chosen from C1–10 alkyl and C3–7cycloalkyl each optionally substituted by $R^b$;

$R^3$, $R^4$, $R^6$, $R^7$ and $R^8$ are each independently chosen from hydrogen, halogen, C1–5 alkyl, C1–5 alkoxy, C1–5 alkylC1–5 alkoxy, hydroxy, hydroxy C1–5 alkyl or amino optionally mono- or di-substituted by C1–5 alkyl, aryl or aryl C1–5 alkyl;

$R^5$ is:
$R^a$, —O—$R^a$, —S(O)$_m$—$R^a$, —N($R^a$)$_2$, —C(O)—$R^a$, —NH(CR$^7$R$^8$)$_n$—$R^a$, N($R^a$)$_2$—(CH$_2$)$_{1-2}$— —(CR$^7$R$^8$)$_n$—$R^a$, —O(CR$^7$R$^8$)$_n$—$R^a$, —C(O)—O (CR$^7$R$^8$)$_n$—$R^a$, —C(O)(CR$^7$R$^8$)$_n$—$R^a$—C(O)C(O)$R^a$, —C(O)C(O)O$R^a$, —C(O)NH$R^a$, or —C(O)NH (CR$^7$R$^8$)$_n$—, each optionally substituted by C1–3 alkyl, halogen or hydroxy, wherein n is 1–5;

or $R^5$ is aryl, heteroaryl or heterocyclyl each optionally substituted by $R^a$;

$R^a$ and $R^b$ are each independently chosen from hydrogen, C1–6 alkyl, hydroxyC1–5 alkyl, C2–5 alkenyl, C2–5 alkynyl, carbocycle, carbocycleC0–2 alkyl, aryl, heterocycle, heteroaryl, C1–5 alkoxy, C1–5 alkylthio, amino, C1–5 alkylamino, C1–5 dialkylamino, arylamino, aryl C1–5 alkylamino, diarylamino, C1–5 acyl, C1–5 alkoxycarbonyl, C1–5 acyloxy, C1–5 acylamino, each of the aforementioned are optionally partially or fully halogenated, or $R^a$ and $R^b$ are chosen from C1–5 alkylsulphonylamino, hydroxy, oxo, halogen, —CF$_3$, —CH$_2$—CF$_3$, nitro and nitrile, wherein each carbocycle, heterocycle or heteroaryl for $R^a$ and $R^b$ is optionally substituted by amino, C1–3 alkyl, halogen or hydroxy; and X is O or S or the pharmaceutically acceptable salts thereof.

2. The compound according to claim 1 wherein

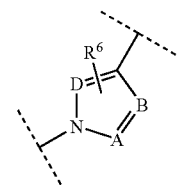

of the formula (I) is chosen from:

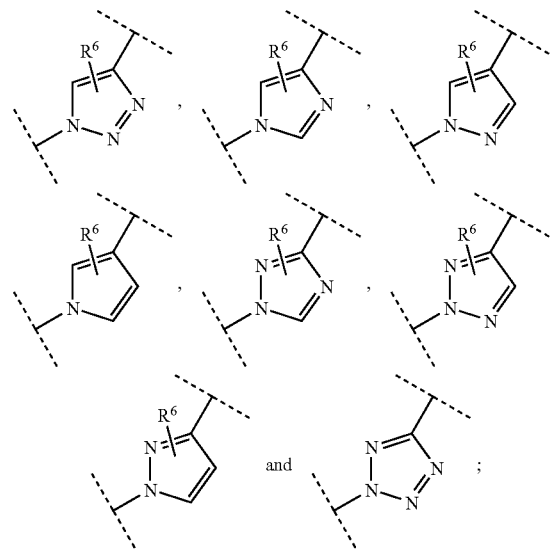

Het is

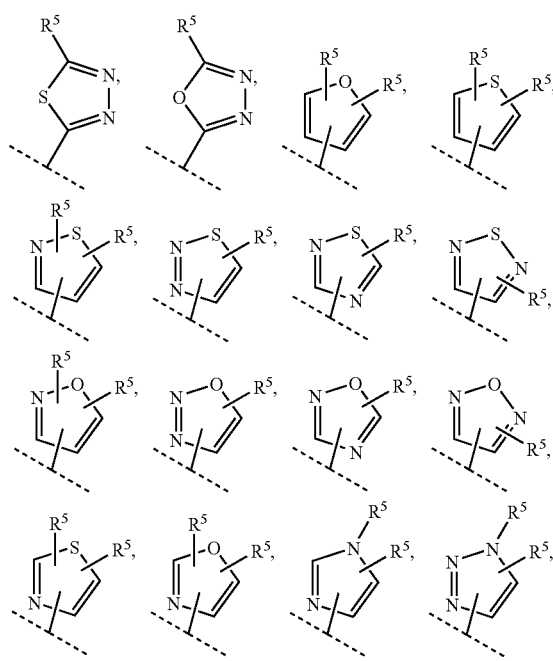

-continued

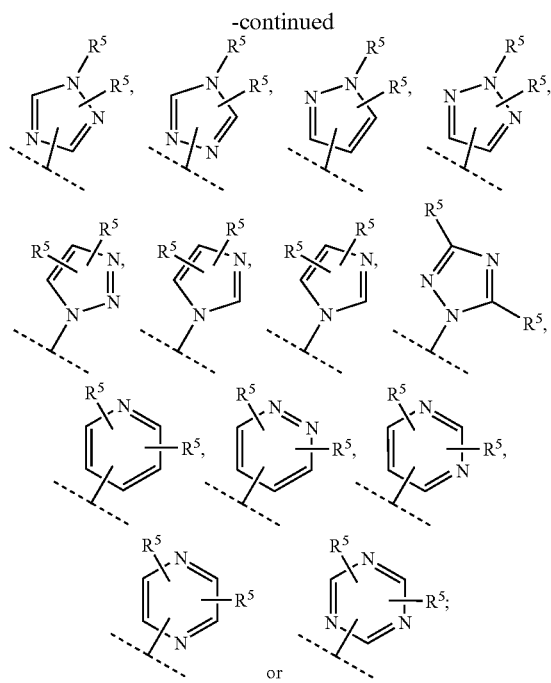

J is chosen from C1–10 alkyl, aryl and C3–7 cycloalkyl each optionally substituted by $R^b$;

$R^2$ is independently chosen from hydrogen, J-O—C(O)—O—, C1–6 alkoxy, C1–6 alkyl, C1–6 acetyl, aroyl, halogen, methoxycarbonyl, phenylsulfonyl, C1–5 alkylS(O)$_m$— and C3–7 cycloalkyl optionally substituted by C1–3 alkyl, each $R^2$ where possible may be optionally partially or fully halogenated;

$R^1$ is chosen from H, C1–6 alkyl, C1–5 alkylS(O)$_m$—, J-S(O)$_m$—N($R^c$)—, C1–5 alkoxyl, C1–5 alkylthiol, NH$_2$—C(O)—(CH$_2$)$_n$—, ($R^c$)$_2$N C1–6 alkyl, C1–5acylNH—, —NH$_2$, —NO$_2$, heteroaryl chosen from pyrazole, triazole, imidazole and tetrazole, and nitrile;

ring d is a 5–6 membered heterocyclic ring such that rings c and d fuse to form the following:

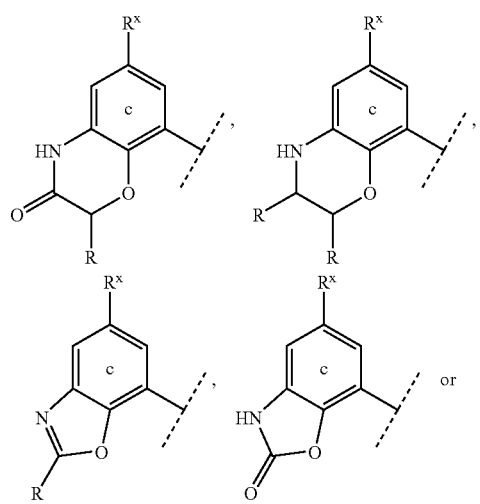

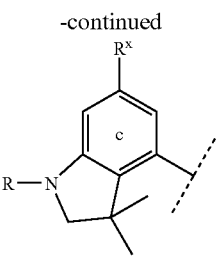

where each R is independently H or C1–3 alkyl;

$R^3$ and $R^4$ are each independently chosen from hydrogen, C1–3 alkoxy, C1–3 alkyl and halogen;

n is 1–4;

$R^a$ and $R^b$ are each independently chosen from hydrogen, C1–6 alkyl, C2–5 alkenyl, C2–5 alkynyl, C3–8 cycloalkylC0–2 alkyl, aryl, C1–5 alkoxy, C1–5 alkylthio, amino, C1–5 alkylamino, C1–5 dialkylamino, arylamino, C1–5 acyl, C1–5 alkoxycarbonyl, C1–5 acyloxy, C1–5 acylamino, aryl C1–5alkylamino, C1–5 alkylsulphonylamino, hydroxy, halogen, —CF$_3$, —CH$_2$—CF$_3$ nitro, nitrile, or $R^a$ and $R^b$ are chosen from; heterocycle chosen from pyrrolidinyl, pyrrolinyl, morpholinyl, thiomorpholinyl, thiomorpholinyl sulfoxide, thiomorpholinyl sulfone, dioxalanyl, piperidinyl, piperazinyl, homopiperazinyl, tetrahydrofuranyl, tetrahydropyranyl, tetrahydrofuranyl, 1,3-dioxolanone, 1,3-dioxanone, 1,4-dioxanyl, piperidinonyl, tetrahydropyrimidonyl, aziridinyl, pentamethylene sulfide, pentamethylene sulfoxide, pentamethylene sulfone, tetramethylene sulfide, tetramethylene sulfoxide and tetramethylene sulfone and heteroaryl chosen from thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl, naphthyridinyl, indazolyl, triazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl and imidazo[4,5-b]pyridinyl; wherein each aryl, heterocycle or heteroaryl for $R^a$ and $R^b$ is optionally substituted by amino, C1–3 alkyl, halogen or hydroxy;

and X is O.

3. The compound according to claim 2 and wherein $Ar^1$ is chosen from (i) and (ii);

$R^5$ is:

a) $R^a$, —O—$R^a$, —S(O)$_m$—$R^a$, —N($R^a$)$_2$, N($R^a$)$_2$—(CH$_2$)$_{1-2}$—, —NH(CR$^7$R$^8$)$_n$—$R^a$, —(CR$^7$R$^8$)$_n$—$R^a$ or —O(CR$^7$R$^8$)$_n$—$R^a$;

or $R^5$ is:

b) —C(O)—$R^a$, —C(O)—O(CR$^7$R$^8$)$_n$—$R^a$, —C(O)(CR$^7$R$^8$)$_n$—$R^a$, —C(O)NHR$^a$, —C(O)NH(CR$^7$R$^8$)$_n$—, —C(O)C(O)R$^a$ or —C(O)C(O)OR$^a$;

each of the above $R^5$ is optionally substituted by C1–3 alkyl, halogen or hydroxyl, and wherein n is 1–3.

4. The compound according to claim 3 wherein Ar¹ is:

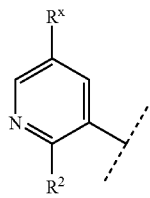

or Ar¹ is cyclobutyl, phenyl, naphthyl, tetrahydronaphthyl, indanyl or indenyl each substituted with one R¹, one R$^x$, and one R² group;

R¹ is nitrile, NO₂, NH₂, C1–3acylNH—,
J-S(O)$_m$—N(R$^c$)— where J is C1–10 alkyl, or R¹ is

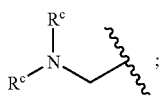

R² is independently chosen from C1–6 alkyl, C1–6 alkylS(O)$_m$—, C1–3 alkoxy and C3–6 cycloalkyl optionally substituted by C1–3 alkyl, each may optionally be partially or fully halogenated;

R³ and R⁴ are each independently chosen from hydrogen, C1–3 alkyl, fluoro and chloro;

R⁶ is chosen from hydrogen and amino;

n is 1–2;

R$^a$ and R$^b$ are each independently chosen from hydrogen, C1–6 alkyl, C3–7 cycloalkylC0–2 alkyl, aryl, C1–5 alkoxy, amino, C1–5 alkylamino, C1–5 dialkylamino, arylamino, aryl C1–5alkylamino, C1–3 acyl, C1–5 alkoxycarbonyl, C1–5 acyloxy, C1–5 acylamino, C1–5 sulphonylamino, hydroxy, halogen, —CF₃, —CH₂—CF₃ nitro, nitrile; or R$^a$ is chosen from pyrrolidinyl, pyrrolinyl, morpholinyl, thiomorpholinyl, thiomorpholinyl sulfoxide, thiomorpholinyl sulfone, piperidinyl, piperazinyl, homopiperazinyl, piperidinonyl, tetrahydropyrimidonyl, aziridinyl, isoxazolyl, oxazolyl, thiazolyl, thiadiazolyl, tetrazolyl, pyrazolyl, pyrrolyl, imidazolyl, pyridinyl, pyrimidinyl, pyrazinyl and pyridazinyl; wherein each aryl, heterocycle or heteroaryl for R$^a$ and R$^b$ is optionally substituted by amino, C1–3 alkyl, halogen or hydroxy.

5. The compound according to claim 4 and wherein Ar¹ is

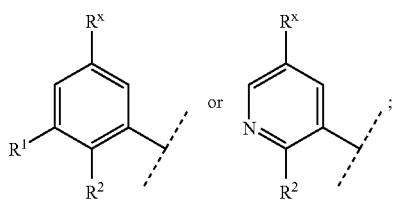

R¹ is:
J-S(O)₂—NH—, where J is C1–5 alkyl,
or R¹ is nitrile, NO₂, NH₂ or C1–3acylNH—;
wherein R$^x$=R² each are independently chosen from C1–5 alkyl, C1–5 alkylS(O)$_m$—, C1–4 alkoxy and and C3–5 cycloalkyl optionally substituted by C1–2 alkyl, each may optionally be partially or fully halogenated;

R⁸ is hydrogen, methyl, ethyl, CH₂OH and CH₂OCH₃.

6. The compound according to claim 5 and wherein
R$^a$ is chosen from hydrogen, C1–6 alkyl, C3–6 cycloalkylC0–2 alkyl, phenyl, C1–5 alkoxy, amino, C1–5 alkylamino, C1–5 dialkylamino, arylamino, aryl C1–5alkylamino, C1–3 acyl, C1–5 alkoxycarbonyl, C1–5 acyloxy, C1–5 acylamino, hydroxy, halogen, —CF₃, —CH₂—CF₃;
or R$^a$ is chosen from morpholinyl, thiomorpholinyl, thiomorpholinyl sulfoxide, thiomorpholinyl sulfone, piperazinyl, homopiperazinyl, pyrrolidinyl, piperidinyl, piperidinonyl, pyridinyl, pyrimidinyl, pyrazinyl and pyridazinyl wherein each phenyl, heterocycle or heteroaryl for R$^a$ is optionally substituted by amino, C1–3 alkyl, halogen or hydroxy.

7. The compound according to claim 6 and wherein
R$^a$ is chosen from hydrogen, C1–6 alkyl, C3–6 cycloalkyl, phenyl, C1–5 alkoxy, C1–5 alkoxycarbonyl, amino, C1–5 alkylamino, C1–5 dialkylamino, arylamino, aryl C1–5alkylamino, C1–5 acyloxy, C1–5 acylamino, hydroxy, halogen, —CF₃, —CH₂—CF₃;
or R$^a$ is chosen morpholinyl, piperidinyl piperazinyl, homopiperazinyl, pyrrolidinyl and pyridinyl wherein each phenyl, heterocycle or heteroaryl for R$^a$ is optionally substituted by amino, C1–3 alkyl, halogen or hydroxy.

8. The compound according to claim 7 and wherein

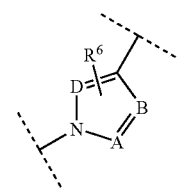

of the formula (I) is chosen from:

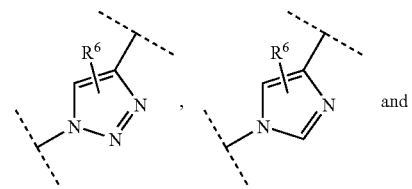

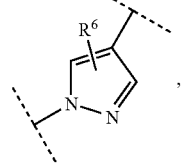

Het is;

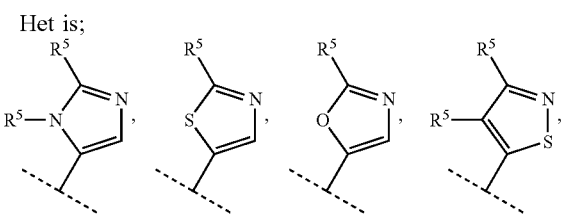

-continued

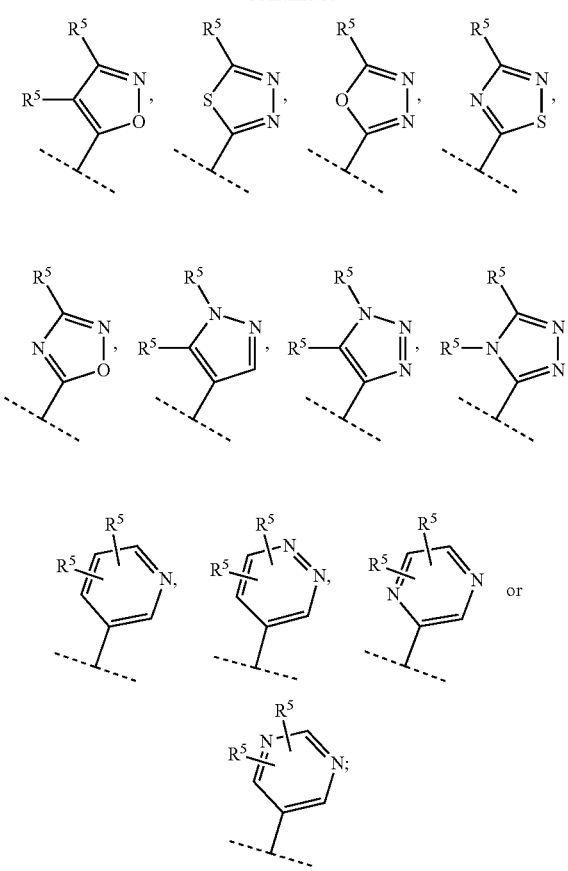

Ar¹ is

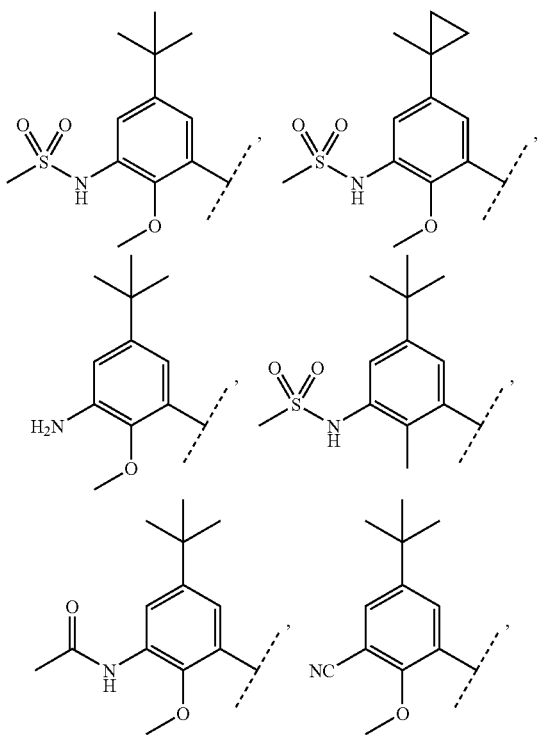

-continued

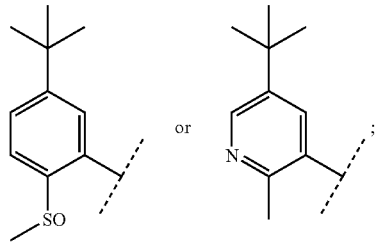

R⁵ is:

C1–5 alkyl, C3–6 cycloalkyl, N(Rᵃ)₂(CH₂)₁₋₂—, halogen, C1–3 alkoxy, hydroxy, —N(Rᵃ)₂, —CF₃, —CH₂—CF₃, aryl, —S(O)$_m$—Rᵃ, —NH(CR⁷R⁸)$_n$—Rᵃ or —(CR⁷R⁸)$_n$—N(Rᵃ)₂ each optionally substituted by C1–3 alkyl, halogen or hydroxy, or R⁵ is —C(O)Rᵃ, —C(O)C(O)Rᵃ, —C(O)NHRᵃ;

Rᵃ is chosen from hydrogen, morpholinyl, piperidinyl, piperazinyl, pyrrolidinyl, pyridinyl, C₁₋₅ mono or dialkylamino, arylamino, C3–6cylcoalkyl, C1–5 alkyl and C1–3 alkoxy wherein each phenyl or heterocycle for Rᵃ is optionally substituted by amino, C1–3 alkyl, halogen or hydroxyl.

9. The compound according to any of claims 1–8 and wherein

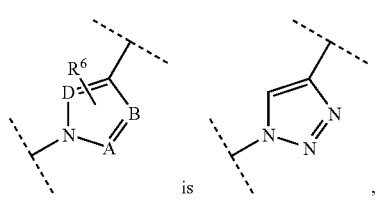

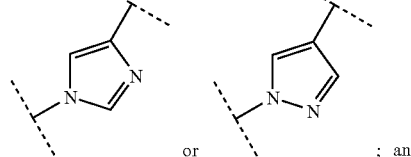

i) Het is

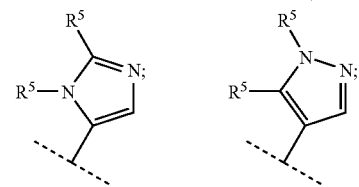

ii) Het is

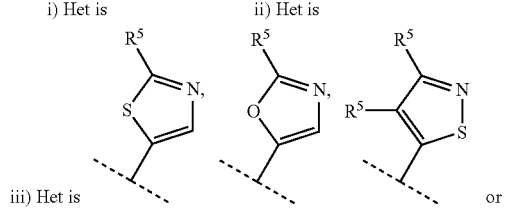

iii) Het is

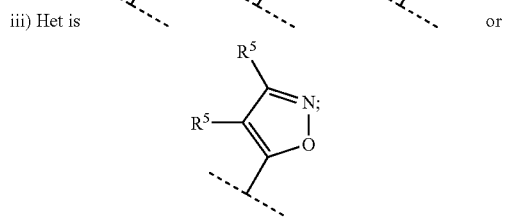

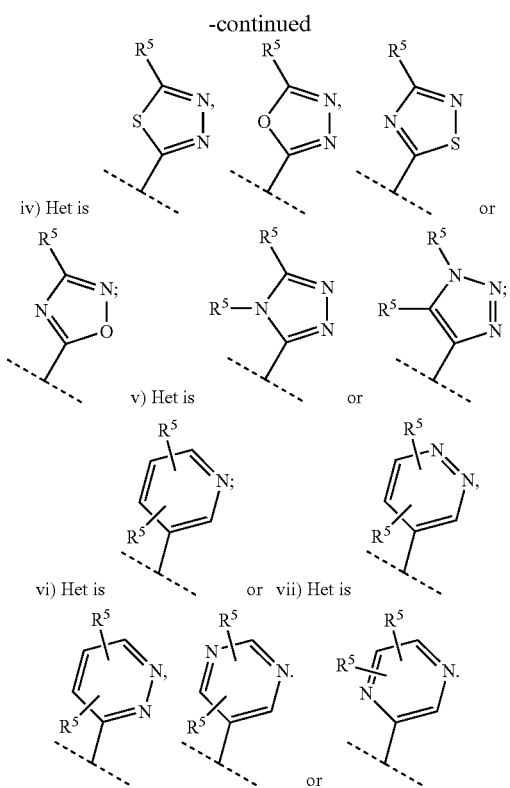

10. A compound chosen from
[2-(4-{1-[5-(5-tert-Butyl-3-methanesulfonylamino-2-methoxy-phenylcarbamoyl)-2-methyl-phenyl]-1H-1,2,3-triazol-4-yl}-2-phenyl-2H-pyrazol-3-yl)-ethyl]-carbamic acid benzyl ester 3-[4-(1-Benzyl-2-ethyl-1H-imidazol-4-yl)-1,2,3-triazol-1-yl]-N-(5-tert-butyl-3-methanesulfonylamino-2-methoxy-phenyl)-4-methyl-benzamide 3-[4-(1-Cyclopropyl-5-ethyl-1H-pyrazol-4-yl)-1,2,3-triazol-1-yl]-N-[3-methanesulfonylamino-2-methoxy-5-(1-methyl-cyclopropyl)-phenyl]-4-methyl-benzamide 3-[4-(1-Isopropyl-5-methyl-1H-pyrazol-4-yl)-1,2,3-triazol-1-yl]-N-[3-methanesulfonylamino-2-methoxy-5-(1-methyl-cyclopropyl)-phenyl]-4-methyl-benzamide 3-[4-(1-tert-Butyl-5-methyl-1H-pyrazol-4-yl)-1,2,3-triazol-1-yl]-N-[3-methanesulfonylamino-2-methoxy-5-(1-methyl-cyclopropyl)-phenyl]-4-methyl-benzamide 3-[4-(2-Acetyl-3-methyl-3H-imidazol-4-yl)-1,2,3-triazol-1-yl]-N-(5-tert-butyl-3-methanesulfonylamino-2-methoxy-phenyl)-4-methyl-benzamide 3-[4-(2-Benzenesulfonyl-3-methyl-3H-imidazol-4-yl)-1,2,3-triazol-1-yl]-N-(5-tert-butyl-3-methanesulfonylamino-2-methoxy-phenyl)-4-methyl-benzamide 3-[4-(2-Benzoyl-3-methyl-3H-imidazol-4-yl)-1,2,3-triazol-1-yl]-N-(5-tert-butyl-3-methanesulfonylamino-2-methoxy-phenyl)-4-methyl-benzamide 3-[4-(2-Benzoyl-3-methyl-3H-imidazol-4-yl)-1,2,3-triazol-1-yl]-N-[3-methanesulfonylamino-2-methoxy-5-(1-methyl-cyclopropyl)-phenyl]-4-methyl-benzamide 3-[4-(2-Benzyl-3-methyl-3H-imidazol-4-yl)-1,2,3-triazol-1-yl]-N-(5-tert-butyl-3-methanesulfonylamino-2-methoxy-phenyl)-4-methyl-benzamide 3-[4-(2-Benzyloxymethyl-3-methyl-3H-imidazol-4-yl)-[1,2,3]triazol-1-yl]-N-(5-tert-butyl-3-methanesulfonylamino-2-methoxy-phenyl)-4-methyl-benzamide 3-[4-(2-Cyclobutyl-3-methyl-3H-imidazol-4-yl)-1,2,3-triazol-1-yl]-N-[3-methanesulfonylamino-2-methoxy-5-(1-methyl-cyclopropyl)-phenyl]-4-methyl-benzamide 3-[4-(2-Cyclopropyl-3-methyl-3H-imidazol-4-yl)-1,2,3-triazol-1-yl]-N-[3-methanesulfonylamino-2-methoxy-5-(1-methyl-cyclopropyl)-phenyl]-4-methyl-benzamide 3-[4-(2-Cyclopropyl-3-methyl-3H-imidazol-4-yl)-1,2,3-triazol-1-yl]-N-[5-(2-hydroxy-1,1-dimethyl-ethyl)-3-methanesulfonylamino-2-methoxy-phenyl]-4-methyl-benzamide 3-[4-(2-Isopropyl-3-methyl-3H-imidazol-4-yl)-1,2,3-triazol-1-yl]-N-[3-methanesulfonylamino-2-methoxy-5-(1-methyl-cyclopropyl)-phenyl]-4-methyl-benzamide 3-[4-(2-tert-Butyl-3-methyl-3H-imidazol-4-yl)-1,2,3-triazol-1-yl]-N-[3-methanesulfonylamino-2-methoxy-5-(1-methyl-cyclopropyl)-phenyl]-4-methyl-benzamide 3-[4-(3-Benzyl-2-ethyl-3H-imidazol-4-yl)-1,2,3-triazol-1-yl]-N-(5-tert-butyl-3-methanesulfonylamino-2-methoxy-phenyl)-4-methyl-benzamide 3-[4-(3-tert-Butyl-2-cyclopropyl-3H-imidazol-4-yl)-1,2,3-triazol-1-yl]-N-(5-tert-butyl-3-methanesulfonylamino-2-methoxy-phenyl)-4-methyl-benzamide 3-[4-(3-tert-Butyl-2-methyl-3H-imidazol-4-yl)-1,2,3-triazol-1-yl]-N-[3-methanesulfonylamino-2-methoxy-5-(1-methyl-cyclopropyl)-phenyl]-4-methyl-benzamide 3-[4-(3-tert-Butyl-3H-imidazol-4-yl)-1,2,3-triazol-1-yl]-N-(5-tert-butyl-3-methanesulfonylamino-2-methoxy-phenyl)-4-methyl-benzamide 3-[4-(3-tert-Butyl-3H-imidazol-4-yl)-1,2,3-triazol-1-yl]-N-[3-methanesulfonylamino-2-methoxy-5-(1-methyl-cyclopropyl)-phenyl]-4-methyl-benzamide 3-[4-(5-Ethyl-1-phenyl-1H-pyrazol-4-yl)-1,2,3-triazol-1-yl]-N-[3-methanesulfonylamino-2-methoxy-5-(1-methyl-cyclopropyl)-phenyl]-4-methyl-benzamide 3-[4-(5-Ethyl-1-phenyl-1H-pyrazol-4-yl)-imidazol-1-yl]-N-(2-methoxy-5-trifluoromethyl-phenyl)-4-methyl-benzamide 3-[4-(5-Ethyl-1-phenyl-1H-pyrazol-4-yl)-imidazol-1-yl]-N-(3-methanesulfonylamino-2-methoxy-5-trifluoromethyl-phenyl)-4-methyl-benzamide 3-[4-(5-Ethyl-1-phenyl-1H-pyrazol-4-yl)-imidazol-1-yl]-N-[3-methanesulfonylamino-2-methoxy-5-(1-methyl-cyclopropyl)-phenyl]-4-methyl-benzamide 3-[4-(5-Ethyl-1-phenyl-1H-pyrazol-4-yl)-imidazol-1-yl]-N-[3-methanesulfonylamino-2-methoxy-5-(1-methyl-cyclopropyl)-phenyl]-4-methyl-benzamide 3-[4-(6-Amino-pyridin-3-yl)-1,2,3-triazol-1-yl]-N-(5-tert-butyl-3-methanesulfonylamino-2-methoxy-phenyl)-4-methyl-benzamide 3-{4-[1-(1-Benzyl-piperidin-4-yl)-5-methyl-1H-pyrazol-4-yl]-1,2,3-triazol-1-yl}-N-(5-tert-butyl-3-methanesulfonylamino-2-methoxy-phenyl)-4-methyl-benzamide 3-{4-[2-(1-Benzyloxy-cyclopropyl)-3-methyl-3H-imidazol-4-yl]-1,2,3-triazol-1-yl}-N-(5-tert-butyl-3-methanesulfonylamino-2-methoxy-phenyl)-4-methyl-benzamide 3-{4-[2-(2-Benzyloxy-1,1-dimethyl-ethyl)-3-methyl-3H-imidazol-4-yl]-1,2,3-triazol-1-yl}-N-(5-tert-butyl-3-methanesulfonylamino-2-methoxy-phenyl)-4-methyl-benzamide 3-{4-[2-(4-Benzyl-piperazin-1-yl)-1-methyl-1H-imidazol-4-yl]-1,2,3-triazol-1-yl}-N-(5-tert-butyl-3-methanesulfonylamino-2-methoxy-phenyl)-4-methyl-benzamide 3-{4-[2-(4-Benzyl-piperazin-1-yl)-3-methyl-3H-imidazol-4-yl]-1,2,3-triazol-1-yl}-N-(5-tert-butyl-3-methanesulfonylamino-2-methoxy-phenyl)-4-methyl-benzamide
3-{4-[2-(Hydroxy-phenyl-methyl)-3-methyl-3H-imidazol-4-yl]-1,2,3-triazol-1-yl}-N-[3-methanesulfonylamino-2-methoxy-5-(1-methyl-cyclopropyl)-phenyl]-4-methyl-benzamide
3-{4-[5-(2-Amino-ethyl)-1-phenyl-1H-pyrazol-4-yl]-1,2,3-triazol-1-yl}-N-(5-tert-butyl-3-methanesulfonylamino-2-methoxy-phenyl)-4-methyl-benzamide
4-(4-{1-[5-(5-tert-Butyl-3-methanesulfonylamino-2-methoxy-phenylcarbamoyl)-2-methyl-phenyl]-1H-1,2,3-triazol-4-yl}-2-cyclopropyl-2H-pyrazol-3-yl)-piperidine-1-carboxylic acid tert-butyl ester
N-(5-tert-Butyl-2-methanesulfinyl-phenyl)-3-[4-(2-cyclopropyl-3-methyl-3H-imidazol-4-yl)-1,2,3-triazol-1-yl]-4-methyl-benzamide
N-(5-tert-Butyl-2-methanesulfinyl-phenyl)-3-[4-(5-ethyl-1-phenyl-1H-pyrazol-4-yl)-imidazol-1-yl]-4-methyl-benzamide
N-(5-tert-Butyl-2-methanesulfinyl-phenyl)-3-{4-[6-(cyclopropylmethyl-amino)-pyridin-3-yl]-1,2,3-triazol-1-yl}-4-methyl-benzamide
N-(5-tert-Butyl-2-methoxy-phenyl)-3-[4-(2-cyclopropyl-3-methyl-3H-imidazol-4-yl)-1,2,3-triazol-1-yl]-4-methyl-benzamide
N-(5-tert-Butyl-2-methoxy-phenyl)-3-[4-(5-ethyl-1-phenyl-1H-pyrazol-4-yl)-imidazol-1-yl]-4-methyl-benzamide
N-(5-tert-Butyl-2-methyl-pyridin-3-yl)-3-[4-(5-ethyl-1-phenyl-1H-pyrazol-4-yl)-imidazol-1-yl]-4-methyl-benzamide
N-(5-tert-Butyl-2-methyl-pyridin-3-yl)-3-{4-[6-(cyclopropylmethyl-amino)-pyridin-3-yl]-1,2,3-triazol-1-yl}-4-methyl-benzamide
N-(5-tert-Butyl-3-{[(2-dimethylamino-ethyl)-methyl-amino]-methyl}-2-methoxy-phenyl)-4-methyl-3-(4-pyridin-3-yl-1,2,3-triazol-1-yl)-benzamide
N-(5-tert-Butyl-3-cyano-2-methoxy-phenyl)-3-[4-(2-cyclopropyl-3-methyl-3H-imidazol-4-yl)-1,2,3-triazol-1-yl]-4-methyl-benzamide
N-(5-tert-Butyl-3-cyano-2-methoxy-phenyl)-3-[4-(5-ethyl-1-phenyl-1H-pyrazol-4-yl)-imidazol-1-yl]-4-methyl-benzamide
N-(5-tert-Butyl-3-cyano-2-methoxy-phenyl)-3-{4-[6-(cyclopropylmethyl-amino)-pyridin-3-yl]-1,2,3-triazol-1-yl}-4-methyl-benzamide
N-(5-tert-Butyl-3-methanesulfonylamino-2-methoxy-phenyl)-3-(4-furan-3-yl-1,2,3-triazol-1-yl)-4-methyl-benzamide
N-(5-tert-Butyl-3-methanesulfonylamino-2-methoxy-phenyl)-3-(4-pyridin-3-yl-1,2,3-triazol-1-yl)-benzamide
N-(5-tert-Butyl-3-methanesulfonylamino-2-methoxy-phenyl)-3,4-dimethyl-5-(4-pyridin-3-yl-1,2,3-triazol-1-yl)-benzamide
N-(5-tert-Butyl-3-methanesulfonylamino-2-methoxy-phenyl)-3-[4-((S)-2,2-dimethyl-1,3-dioxolan-4-yl)-1,2,3-triazol-1-yl]-4-methyl-benzamide
N-(5-tert-Butyl-3-methanesulfonylamino-2-methoxy-phenyl)-3-[4-(1-cyclopropyl-5-methyl-1H-pyrazol-4-yl)-1,2,3-triazol-1-yl]-4-methyl-benzamide
N-(5-tert-Butyl-3-methanesulfonylamino-2-methoxy-phenyl)-3-[4-(1-cyclohexyl-5-methyl-1H-pyrazol-4-yl)-1,2,3-triazol-1-yl]-4-methyl-benzamide
N-(5-tert-Butyl-3-methanesulfonylamino-2-methoxy-phenyl)-3-[4-(1-cyclohexyl-5-ethyl-1H-pyrazol-4-yl)-1,2,3-triazol-1-yl]-4-methyl-benzamide
N-(5-tert-Butyl-3-methanesulfonylamino-2-methoxy-phenyl)-3-[4-(1-isopropyl-5-methyl-1H-pyrazol-4-yl)-1,2,3-triazol-1-yl]-4-methyl-benzamide
N-(5-tert-Butyl-3-methanesulfonylamino-2-methoxy-phenyl)-3-[4-(1-tert-butyl-5-methyl-1H-pyrazol-4-yl)-1,2,3-triazol-1-yl]-4-methyl-benzamide
N-(5-tert-Butyl-3-methanesulfonylamino-2-methoxy-phenyl)-3-[4-(1-cyclopropyl-5-isopropyl-1H-pyrazol-4-yl)-1,2,3-triazol-1-yl]-4-methyl-benzamide
N-(5-tert-Butyl-3-methanesulfonylamino-2-methoxy-phenyl)-3-[4-(1-cyclopropyl-5-ethyl-1H-pyrazol-4-yl)-1,2,3-triazol-1-yl]-4-methyl-benzamide
N-(5-tert-Butyl-3-methanesulfonylamino-2-methoxy-phenyl)-3-[4-(1-isopropyl-5-methyl-1H-pyrazol-4-yl)-imidazol-1-yl]-4-methyl-benzamide
N-(5-tert-Butyl-3-methanesulfonylamino-2-methoxy-phenyl)-3-[4-(1-cyclopropyl-5-pyridin-2-yl-1H-pyrazol-4-yl)-1,2,3-triazol-1-yl]-4-methyl-benzamide
N-(5-tert-Butyl-3-methanesulfonylamino-2-methoxy-phenyl)-3-[4-(1-cyclopropyl-5-piperidin-4-yl-1H-pyrazol-4-yl)-1,2,3-triazol-1-yl]-4-methyl-benzamide
N-(5-tert-Butyl-3-methanesulfonylamino-2-methoxy-phenyl)-3-[4-(1,5-dimethyl-1H-pyrazol-4-yl)-1,2,3-triazol-1-yl]-4-methyl-benzamide
N-(5-tert-Butyl-3-methanesulfonylamino-2-methoxy-phenyl)-3-[4-(1,2-diethyl-1H-imidazol-4-yl)-1,2,3-triazol-1-yl]-4-methyl-benzamide
N-(5-tert-Butyl-3-methanesulfonylamino-2-methoxy-phenyl)-3-[4-(1,5-diisopropyl-1H-pyrazol-4-yl)-1,2,3-triazol-1-yl]-4-methyl-benzamide
N-(5-tert-Butyl-3-methanesulfonylamino-2-methoxy-phenyl)-3-[4-(2-ethyl-3H-imidazol-4-yl)-1,2,3-triazol-1-yl]-4-methyl-benzamide
N-(5-tert-Butyl-3-methanesulfonylamino-2-methoxy-phenyl)-3-[4-(2-isopropyl-3-methyl-3H-imidazol-4-yl)-1,2,3-triazol-1-yl]-4-methyl-benzamide
N-(5-tert-Butyl-3-methanesulfonylamino-2-methoxy-phenyl)-3-[4-(2-tert-butyl-3-methyl-3H-imidazol-4-yl)-1,2,3-triazol-1-yl]-4-methyl-benzamide
N-(5-tert-Butyl-3-methanesulfonylamino-2-methoxy-phenyl)-3-[4-(2-cyclopropyl-3-methyl-3H-imidazol-4-yl)-1,2,3-triazol-1-yl]-4-methyl-benzamide
N-(5-tert-Butyl-3-methanesulfonylamino-2-methoxy-phenyl)-3-[4-(2-cyclopropyl-1-methyl-1H-imidazol-4-yl)-1,2,3-triazol-1-yl]-4-methyl-benzamide
N-(5-tert-Butyl-3-methanesulfonylamino-2-methoxy-phenyl)-3-[4-(2-cyclopropyl-3-isopropyl-3H-imidazol-4-yl)-1,2,3-triazol-1-yl]-4-methyl-benzamide
N-(5-tert-Butyl-3-methanesulfonylamino-2-methoxy-phenyl)-3-[4-(2-dimethylamino-1-methyl-1H-imidazol-4-yl)-1,2,3-triazol-1-yl]-4-methyl-benzamide
N-(5-tert-Butyl-3-methanesulfonylamino-2-methoxy-phenyl)-3-[4-(2-methanesulfonyl-3-methyl-3H-imidazol-4-yl)-1,2,3-triazol-1-yl]-4-methyl-benzamide
N-(5-tert-Butyl-3-methanesulfonylamino-2-methoxy-phenyl)-3-[4-(2-methanesulfinyl-3-methyl-3H-imidazol-4-yl)-1,2,3-triazol-1-yl]-4-methyl-benzamide
N-(5-tert-Butyl-3-methanesulfonylamino-2-methoxy-phenyl)-3-[4-(2-tert-butylsulfanyl-3-methyl-3H-imidazol-4-yl)-1,2,3-triazol-1-yl]-4-methyl-benzamide
N-(5-tert-Butyl-3-methanesulfonylamino-2-methoxy-phenyl)-3-[4-(2-hydroxymethyl-3-methyl-3H-imidazol-4-yl)-1,2,3-triazol-1-yl]-4-methyl-benzamide N-(5-tert-Butyl-3-methanesulfonylamino-2-methoxy-phenyl)-3-[4-(2-formyl-3-methyl-3H-imidazol-4-yl)-1,2,3-triazol-1-yl]-4-methyl-benzamide
N-(5-tert-Butyl-3-methanesulfonylamino-2-methoxy-phenyl)-3-[4-(2-cyclobutyl-3-methyl-3H-imidazol-4-yl)-1,2,3-triazol-1-yl]-4-methyl-benzamide
N-(5-tert-Butyl-3-methanesulfonylamino-2-methoxy-phenyl)-3-[4-(2-dimethylamino-3-methyl-3H-imidazol-4-yl)-[1,2,3]triazol-1-yl]-4-methyl-benzamide
N-(5-tert-Butyl-3-methanesulfonylamino-2-methoxy-phenyl)-3-[4-(2,3-diethyl-3H-imidazol-4-yl)-1,2,3-triazol-1-yl]-4-methyl-benzamide
N-(5-tert-Butyl-3-methanesulfonylamino-2-methoxy-phenyl)-3-[4-(2,3-dihydro-imidazo[2,1-b]thiazol-5-yl)-1,2,3-triazol-1-yl]-4-methyl-benzamide
N-(5-tert-Butyl-3-methanesulfonylamino-2-methoxy-phenyl)-3-[4-(3-cyclopropyl-2-methyl-3H-imidazol-4-yl)-1,2,3-triazol-1-yl]-4-methyl-benzamide
N-(5-tert-Butyl-3-methanesulfonylamino-2-methoxy-phenyl)-3-[4-(3-isopropyl-2-methyl-3H-imidazol-4-yl)-1,2,3-triazol-1-yl]-4-methyl-benzamide
N-(5-tert-Butyl-3-methanesulfonylamino-2-methoxy-phenyl)-3-[4-(3-cyclopropyl-2-isopropyl-3H-imidazol-4-yl)-1,2,3-triazol-1-yl]-4-methyl-benzamide
N-(5-tert-Butyl-3-methanesulfonylamino-2-methoxy-phenyl)-3-[4-(3-tert-butyl-2-methyl-3H-imidazol-4-yl)-1,2,3-triazol-1-yl]-4-methyl-benzamide
N-(5-tert-Butyl-3-methanesulfonylamino-2-methoxy-phenyl)-3-[4-(3-ethyl-2-phenyl-3H-imidazol-4-yl)-1,2,3-triazol-1-yl]-4-methyl-benzamide
N-(5-tert-Butyl-3-methanesulfonylamino-2-methoxy-phenyl)-3-[4-(5-methoxy-pyridin-3-yl)-1,2,3-triazol-1-yl]-4-methyl-benzamide
N-(5-tert-Butyl-3-methanesulfonylamino-2-methoxy-phenyl)-3-[4-(5-ethyl-1-phenyl-1H-pyrazol-4-yl)-1,2,3-triazol-1-yl]-4-methyl-benzamide
N-(5-tert-Butyl-3-methanesulfonylamino-2-methoxy-phenyl)-3-[4-(5-ethyl-1-pyridin-2-yl-1H-pyrazol-4-yl)-1,2,3-triazol-1-yl]-4-methyl-benzamide
N-(5-tert-Butyl-3-methanesulfonylamino-2-methoxy-phenyl)-3-[4-(5-ethyl-1-isopropyl-1H-pyrazol-4-yl)-1,2,3-triazol-1-yl]-4-methyl-benzamide
N-(5-tert-Butyl-3-methanesulfonylamino-2-methoxy-phenyl)-3-[4-(5-cyclopropyl-1-isopropyl-1H-pyrazol-4-yl)-1,2,3-triazol-1-yl]-4-methyl-benzamide
N-(5-tert-Butyl-3-methanesulfonylamino-2-methoxy-phenyl)-3-[4-(5-isopropyl-1-phenyl-1H-pyrazol-4-yl)-1,2,3-triazol-1-yl]-4-methyl-benzamide
N-(5-tert-Butyl-3-methanesulfonylamino-2-methoxy-phenyl)-3-[4-(5-cyclopropyl-1-phenyl-1H-pyrazol-4-yl)-1,2,3-triazol-1-yl]-4-methyl-benzamide
N-(5-tert-Butyl-3-methanesulfonylamino-2-methoxy-phenyl)-3-[4-(5-ethyl-1-phenyl-1H-pyrazol-4-yl)-imidazol-1-yl]-4-methyl-benzamide
N-(5-tert-Butyl-3-methanesulfonylamino-2-methoxy-phenyl)-3-[4-(5,5-dimethyl-6,7-dihydro-5H-pyrrolo[1,2-a]imidazol-3-yl)-[1,2,3]triazol-1-yl]-4-methyl-benzamide
N-(5-tert-Butyl-3-methanesulfonylamino-2-methoxy-phenyl)-3-[4-(6-chloro-pyridin-3-yl)-1,2,3-triazol-1-yl]-4-methyl-benzamide
N-(5-tert-Butyl-3-methanesulfonylamino-2-methoxy-phenyl)-3-[4-(6-methoxy-pyridin-3-yl)-1,2,3-triazol-1-yl]-4-methyl-benzamide
N-(5-tert-Butyl-3-methanesulfonylamino-2-methoxy-phenyl)-3-[4-(6-dimethylamino-pyridin-3-yl)-1,2,3-triazol-1-yl]-4-methyl-benzamide
N-(5-tert-Butyl-3-methanesulfonylamino-2-methoxy-phenyl)-3-[4-(6-cyclopropylamino-pyridin-3-yl)-1,2,3-triazol-1-yl]-4-methyl-benzamide
N-(5-tert-Butyl-3-methanesulfonylamino-2-methoxy-phenyl)-3-[4-(7,7-dimethyl-6,7-dihydro-5H-pyrrolo[1,2-a]imidazol-3-yl)-1,2,3-triazol-1-yl]-4-methyl-benzamide
N-(5-tert-Butyl-3-methanesulfonylamino-2-methoxy-phenyl)-3-{4-[1-(4-methoxy-phenyl)-5-methyl-1H-pyrazol-4-yl]-1,2,3-triazol-1-yl}-4-methyl-benzamide
N-(5-tert-Butyl-3-methanesulfonylamino-2-methoxy-phenyl)-3-{4-[1-(4-fluoro-phenyl)-5-methyl-1H-pyrazol-4-yl]-1,2,3-triazol-1-yl}-4-methyl-benzamide
N-(5-tert-Butyl-3-methanesulfonylamino-2-methoxy-phenyl)-3-{4-[1-(1-tert-butyl-piperidin-4-yl)-5-methyl-1H-pyrazol-4-yl]-1,2,3-triazol-1-yl}-4-methyl-benzamide
N-(5-tert-Butyl-3-methanesulfonylamino-2-methoxy-phenyl)-3-{4-[2-cyclopropyl-3-(2,2,2-trifluoro-ethyl)-3H-imidazol-4-yl]-1,2,3-triazol-1-yl}-4-methyl-benzamide
N-(5-tert-Butyl-3-methanesulfonylamino-2-methoxy-phenyl)-3-{4-[2-(hydroxy-phenyl-methyl)-3-methyl-3H-imidazol-4-yl]-1,2,3-triazol-1-yl}-4-methyl-benzamide
N-(5-tert-Butyl-3-methanesulfonylamino-2-methoxy-phenyl)-3-{4-[2-(2,2-dimethyl-propionyl)-3-methyl-3H-imidazol-4-yl]-1,2,3-triazol-1-yl}-4-methyl-benzamide
N-(5-tert-Butyl-3-methanesulfonylamino-2-methoxy-phenyl)-3-{4-[2-(1-hydroxy-2,2-dimethyl-propyl)-3-methyl-3H-imidazol-4-yl]-1,2,3-triazol-1-yl}-4-methyl-benzamide
N-(5-tert-Butyl-3-methanesulfonylamino-2-methoxy-phenyl)-3-{4-[2-(1-hydroxy-1-methyl-ethyl)-3-methyl-3H-imidazol-4-yl]-1,2,3-triazol-1-yl}-4-methyl-benzamide
N-(5-tert-Butyl-3-methanesulfonylamino-2-methoxy-phenyl)-3-{4-[2-(2-hydroxy-1,1-dimethyl-ethyl)-3-methyl-3H-imidazol-4-yl]-1,2,3-triazol-1-yl}-4-methyl-benzamide
N-(5-tert-Butyl-3-methanesulfonylamino-2-methoxy-phenyl)-3-{4-[2-(1-hydroxy-cyclopropyl)-3-methyl-3H-imidazol-4-yl]-1,2,3-triazol-1-yl}-4-methyl-benzamide
N-(5-tert-Butyl-3-methanesulfonylamino-2-methoxy-phenyl)-3-{4-[2-(1-hydroxy-ethyl)-3-methyl-3H-imidazol-4-yl]-1,2,3-triazol-1-yl}-4-methyl-benzamide
N-(5-tert-Butyl-3-methanesulfonylamino-2-methoxy-phenyl)-3-{4-[2-(cyclopropyl-hydroxy-methyl)-3-methyl-3H-imidazol-4-yl]-1,2,3-triazol-1-yl}-4-methyl-benzamide
N-(5-tert-Butyl-3-methanesulfonylamino-2-methoxy-phenyl)-3-{4-[5-(2-dimethylamino-ethyl)-1-phenyl-1H-pyrazol-4-yl]-1,2,3-triazol-1-yl}-4-methyl-benzamide
N-(5-tert-Butyl-3-methanesulfonylamino-2-methoxy-phenyl)-3-{4-[6-(2-dimethylamino-ethyl)-pyridin-3-yl]-1,2,3-triazol-1-yl}-4-methyl-benzamide
N-(5-tert-Butyl-3-methanesulfonylamino-2-methoxy-phenyl)-3-{4-[6-(cyclopropylmethyl-amino)-pyridin-3-yl]-1,2,3-triazol-1-yl}-4-methyl-benzamide
N-(5-tert-Butyl-3-methanesulfonylamino-2-methoxy-phenyl)-3-{4-[6-(2-dimethylamino-ethylamino)-pyridin-3-yl]-1,2,3-triazol-1-yl}-4-methyl-benzamide N-(5-tert-Butyl-3-methanesulfonylamino-2-methoxy-phenyl)-3-{4-[6-(cyclopropylmethyl-amino)-5-methoxy-pyridin-3-yl]-1,2,3-triazol-1-yl}-4-methyl-benzamide N-(5-tert-Butyl-3-methanesulfonylamino-2-methoxy-phenyl)-3-fluoro-4-methyl-5-(4-pyridin-3-yl-1,2,3-triazol-1-yl)-benzamide N-(5-tert-Butyl-3-methanesulfonylamino-2-methoxy-phenyl)-4-chloro-3-(4-pyridin-3-yl-1,2,3-triazol-1-yl)-benzamide N-(5-tert-Butyl-3-methanesulfonylamino-2-methoxy-phenyl)-4-fluoro-3-(4-pyridin-3-yl-1,2,3-triazol-1-yl)-benzamide N-(5-tert-Butyl-3-methanesulfonylamino-2-methoxy-phenyl)-4-methyl-3-[4-(3-methyl-3H-imidazol-4-yl)-1,2,3-triazol-1-yl]-benzamide N-(5-tert-Butyl-3-methanesulfonylamino-2-methoxy-phenyl)-4-methyl-3-(4-pyridin-3-yl-1,2,3-triazol-1-yl)-benzamide N-(5-tert-Butyl-3-methanesulfonylamino-2-methoxy-phenyl)-4-methyl-3-[4-(6-methyl-pyridin-3-yl)-1,2,3-triazol-1-yl]-benzamide N-(5-tert-Butyl-3-methanesulfonylamino-2-methoxy-phenyl)-4-methyl-3-[4-(6-morpholin-4-ylmethyl-pyridin-3-yl)-1,2,3-triazol-1-yl]-benzamide N-(5-tert-Butyl-3-methanesulfonylamino-2-methoxy-phenyl)-4-methyl-3-[4-(2-methyl-pyridin-3-yl)-1,2,3-triazol-1-yl]-benzamide N-(5-tert-Butyl-3-methanesulfonylamino-2-methoxy-phenyl)-4-methyl-3-(4-pyridin-3-yl-imidazol-1-yl)-benzamide N-(5-tert-Butyl-3-methanesulfonylamino-2-methoxy-phenyl)-4-methyl-3-[4-(6-methylamino-pyridin-3-yl)-1,2,3-triazol-1-yl]-benzamide N-(5-tert-Butyl-3-methanesulfonylamino-2-methoxy-phenyl)-4-methyl-3-(4-thiazol-5-yl-1,2,3-triazol-1-yl)-benzamide N-(5-tert-Butyl-3-methanesulfonylamino-2-methoxy-phenyl)-4-methyl-3-(4-pyrimidin-5-yl-1,2,3-triazol-1-yl)-benzamide N-(5-tert-Butyl-3-methanesulfonylamino-2-methoxy-phenyl)-4-methyl-3-[4-(6-trifluoromethyl-pyridin-3-yl)-1,2,3-triazol-1-yl]-benzamide N-(5-tert-Butyl-3-methanesulfonylamino-2-methoxy-phenyl)-4-methyl-3-[4-(tetrahydro-furan-3-yl)-1,2,3-triazol-1-yl]-benzamide N-(5-tert-Butyl-3-methanesulfonylamino-2-methoxy-phenyl)-4-methyl-3-[4-(5-methyl-1-phenyl-1H-pyrazol-4-yl)-1,2,3-triazol-1-yl]-benzamide N-(5-tert-Butyl-3-methanesulfonylamino-2-methoxy-phenyl)-4-methyl-3-[4-(4-methyl-pyridin-3-yl)-1,2,3-triazol-1-yl]-benzamide N-(5-tert-Butyl-3-methanesulfonylamino-2-methoxy-phenyl)-4-methyl-3-[4-(3-methyl-2-phenylsulfanyl-3H-imidazol-4-yl)-1,2,3-triazol-1-yl]-benzamide N-(5-tert-Butyl-3-methanesulfonylamino-2-methoxy-phenyl)-4-methyl-3-[4-(5-methyl-1-phenyl-1H-pyrazol-4-yl)-imidazol-1-yl]-benzamide N-(5-tert-Butyl-3-methanesulfonylamino-2-methoxy-phenyl)-4-methyl-3-{4-[5-methyl-1-(1-methyl-piperidin-4-yl)-1H-pyrazol-4-yl]-1,2,3-triazol-1-yl}-benzamide N-(5-tert-Butyl-3-methanesulfonylamino-2-methoxy-phenyl)-4-methyl-3-{4-[2-methyl-3-(2,2,2-trifluoro-ethyl)-3H-imidazol-4-yl]-1,2,3-triazol-1-yl}-benzamide N-(5-tert-Butyl-3-methanesulfonylamino-2-methoxy-phenyl)-4-methyl-3-[4-(5-methyl-1-pyridin-2-yl-1H-pyrazol-4-yl)-1,2,3-triazol-1-yl]-benzamide N-(5-tert-Butyl-3-methanesulfonylamino-2-methoxy-phenyl)-4-methyl-3-[4-(2-morpholin-4-yl-thiazol-5-yl)-1,2,3-triazol-1-yl]-benzamide N-(5-tert-Butyl-3-methanesulfonylamino-2-methoxy-phenyl)-4-methyl-3-{4-[6-(2-methylamino-ethyl)-pyridin-3-yl]-1,2,3-triazol-1-yl}-benzamide N-(5-tert-Butyl-3-methanesulfonylamino-2-methoxy-phenyl)-4-methyl-3-{4-[6-(2-morpholin-4-yl-ethyl)-pyridin-3-yl]-1,2,3-triazol-1-yl}-benzamide N-(5-tert-Butyl-3-methanesulfonylamino-2-methoxy-phenyl)-4-methyl-3-[4-(3-methyl-3H-imidazol-4-yl)-pyrazol-1-yl]-benzamide N-(5-tert-Butyl-3-methanesulfonylamino-2-methoxy-phenyl)-4-methyl-3-[4-(3-methyl-2-pyridin-4-yl-3H-imidazol-4-yl)-1,2,3-triazol-1-yl]-benzamide N-(5-tert-Butyl-3-methanesulfonylamino-2-methoxy-phenyl)-4-methyl-3-[4-(5-methyl-1-piperidin-4-yl-1H-pyrazol-4-yl)-1,2,3-triazol-1-yl]-benzamide N-(5-tert-Butyl-3-methanesulfonylamino-2-methoxy-phenyl)-4-methyl-3-(4-pyridin-4-yl-[1,2,3]triazol-1-yl)-benzamide N-(5-tert-Butyl-3-methanesulfonylamino-2-methoxy-phenyl)-4-methyl-3-(4-pyridin-2-yl-[1,2,3]triazol-1-yl)-benzamide N-(5-tert-Butyl-3-methanesulfonylamino-2-methoxy-phenyl)-4-methyl-3-[4-(5,6,7,8-tetrahydro-imidazo[1,2-a]pyridin-3-yl)-1,2,3-triazol-1-yl]-benzamide N-(5-tert-Butyl-3-methanesulfonylamino-2-methoxy-phenyl)-4-methyl-3-[4-(3-methyl-2-phenyl-3H-imidazol-4-yl)-1,2,3-triazol-1-yl]-benzamide N-(5-tert-Butyl-3-methanesulfonylamino-2-methoxy-phenyl)-4-methyl-3-{4-[5-(2-morpholin-4-yl-ethyl)-1-phenyl-1H-pyrazol-4-yl]-1,2,3-triazol-1-yl}-benzamide N-(5-tert-Butyl-3-methanesulfonylamino-2-methoxy-phenyl)-4-methyl-3-[4-(1-phenyl-5-trifluoromethyl-1H-pyrazol-4-yl)-1,2,3-triazol-1-yl]-benzamide N-(5-tert-Butyl-3-methanesulfonylamino-2-methoxy-phenyl)-4-methyl-3-[4-(1-methyl-2-piperazin-1-yl-1H-imidazol-4-yl)-1,2,3-triazol-1-yl]-benzamide N-(5-tert-Butyl-3-methanesulfonylamino-2-methoxy-phenyl)-4-methyl-3-[4-(3-methyl-2-piperazin-1-yl-3H-imidazol-4-yl)-1,2,3-triazol-1-yl]-benzamide N-(5-tert-Butyl-3-methanesulfonylamino-2-methoxy-phenyl)-4-methyl-3-[4-[spiro(6,7-dihydro-5H-pyrrolo[1,2-a]imidazol-3-yl-5-cyclohexane)]-[1,2,3]triazol-1-yl]-benzamide N-(5-tert-Butyl-3-methanesulfonylamino-2-methoxy-phenyl)-4-methyl-3-{4-[3-methyl-2-(1-methyl-cyclopropyl)-3H-imidazol-4-yl]-1,2,3-triazol-1-yl}-benzamide N-(5-tert-Butyl-3-methanesulfonylamino-2-methoxy-phenyl)-4-methyl-3-[4-(3-methyl-2-morpholin-4-yl-3H-imidazol-4-yl)-1,2,3-triazol-1-yl]-benzamide N-(5-tert-Butyl-3-methanesulfonylamino-2-methoxy-phenyl)-4-methyl-3-[4-[spiro(6,7-dihydro-5H-pyrrolo[1,2-a]imidazol-3-yl-5-(2'-methyl-cyproane))]-[1,2,3]triazol-1-yl]-benzamide N-(5-tert-Butyl-3-methanesulfonylamino-2-methoxy-phenyl)-4-methyl-3-[4-(3-methyl-2-methylsulfanyl-3H-imidazol-4-yl)-1,2,3-triazol-1-yl]-benzamide N-(5-tert-Butyl-3-methanesulfonylamino-2-methoxy-phenyl)-4-methyl-3-{4-[3-methyl-2-(1-methyl-1-phenyl-ethyl)-3H-imidazol-4-yl]-1,2,3-triazol-1-yl}-benzamide N-(5-tert-Butyl-3-methanesulfonylamino-2-methoxy-phenyl)-4-methyl-3-{4-[3-methyl-2-(2-methyl-propane-2-sulfonyl)-3H-imidazol-4-yl]-1,2,3-triazol-1-yl}-benzamide N-(5-tert-Butyl-3-methanesulfonylamino-2-methyl-phenyl)-3-[4-(2-cyclopropyl-3-methyl-3H-imidazol-4-yl)-1,2,3-triazol-1-yl]-4-methyl-benzamide N-(5-tert-Butyl-3-methanesulfonylamino-2-methyl-phenyl)-3-[4-(5-ethyl-1-phenyl-1H-pyrazol-4-yl)-imidazol-1-yl]-4-methyl-benzamide N-[3-Methanesulfonylamino-2-methoxy-5-(1-methyl-cyclopropyl)-phenyl]-3-[4-(5-methoxy-pyridin-3-yl)-1,2,3-triazol-1-yl]-4-methyl-benzamide N-[3-Methanesulfonylamino-2-methoxy-5-(1-methyl-cyclopropyl)-phenyl]-4-methyl-3-[4-(5-methyl-1-phenyl-1H-pyrazol-4-yl)-1,2,3-triazol-1-yl]-benzamide N-[3-Methanesulfonylamino-2-methoxy-5-(1-methyl-cyclopropyl)-phenyl]-4-methyl-3-{4-[3-methyl-2-(1-methyl-cyclopropyl)-3H-imidazol-4-yl]-1,2,3-triazol-1-yl}-benzamide N-[3-Methanesulfonylamino-2-methoxy-5-(1-methyl-cyclopropyl)-phenyl]-4-methyl-3-{4-[3-methyl-2-(1-methyl-1-phenyl-ethyl)-3H-imidazol-4-yl]-1,2,3-triazol-1-yl}-benzamide and N-[5-(2-Hydroxy-1,1-dimethyl-ethyl)-3-methanesulfonylamino-2-methoxy-phenyl]-4-methyl-3-{4-[3-methyl-2-(1-methyl-cyclopropyl)-3H-imidazol-4-yl]-1,2,3-triazol-1-yl}-benzamide or the pharmaceutically acceptable salts thereof.

11. The compound according to claim 10 wherein the compound is chosen from

3-[4-(6-Amino-pyridin-3-yl)-1,2,3-triazol-1-yl]-N-(5-tert-butyl-3-methanesulfonylamino-2-methoxy-phenyl)-4-methyl-benzamide N-(5-tert-Butyl-2-methanesulfinyl-phenyl)-3-{4-[6-(cyclopropylmethyl-amino)-pyridin-3-yl]-1,2,3-triazol-1-yl}-4-methyl-benzamide N-(5-tert-Butyl-2-methyl-pyridin-3-yl)-3-{4-[6-(cyclopropylmethyl-amino)-pyridin-3-yl]-1,2,3-triazol-1-yl}-4-methyl-benzamide N-(5-tert-Butyl-3-{[(2-dimethylamino-ethyl)-methyl-amino]-methyl}-2-methoxy-phenyl)-4-methyl-3-(4-pyridin-3-yl-1,2,3-triazol-1-yl)-benzamide N-(5-tert-Butyl-3-cyano-2-methoxy-phenyl)-3-{4-[6-(cyclopropylmethyl-amino)-pyridin-3-yl]-1,2,3-triazol-1-yl}-4-methyl-benzamide N-(5-tert-Butyl-3-methanesulfonylamino-2-methoxy-phenyl)-3-(4-pyridin-3-yl-1,2,3-triazol-1-yl)-benzamide N-(5-tert-Butyl-3-methanesulfonylamino-2-methoxy-phenyl)-3,4-dimethyl-5-(4-pyridin-3-yl-1,2,3-triazol-1-yl)-benzamide N-(5-tert-Butyl-3-methanesulfonylamino-2-methoxy-phenyl)-3-[4-(5-methoxy-pyridin-3-yl)-1,2,3-triazol-1-yl]-4-methyl-benzamide N-(5-tert-Butyl-3-methanesulfonylamino-2-methoxy-phenyl)-3-[4-(6-chloro-pyridin-3-yl)-1,2,3-triazol-1-yl]-4-methyl-benzamide N-(5-tert-Butyl-3-methanesulfonylamino-2-methoxy-phenyl)-3-[4-(6-methoxy-pyridin-3-yl)-1,2,3-triazol-1-yl]-4-methyl-benzamide N-(5-tert-Butyl-3-methanesulfonylamino-2-methoxy-phenyl)-3-[4-(6-dimethylamino-pyridin-3-yl)-1,2,3-triazol-1-yl]-4-methyl-benzamide N-(5-tert-Butyl-3-methanesulfonylamino-2-methoxy-phenyl)-3-[4-(6-cyclopropylamino-pyridin-3-yl)-1,2,3-triazol-1-yl]-4-methyl-benzamide N-(5-tert-Butyl-3-methanesulfonylamino-2-methoxy-phenyl)-3-{4-[6-(cyclopropylmethyl-amino)-pyridin-3-yl]-1,2,3-triazol-1-yl}-4-methyl-benzamide N-(5-tert-Butyl-3-methanesulfonylamino-2-methoxy-phenyl)-3-{4-[6-(2-dimethylamino-ethylamino)-pyridin-3-yl]-1,2,3-triazol-1-yl}-4-methyl-benzamide N-(5-tert-Butyl-3-methanesulfonylamino-2-methoxy-phenyl)-3-{4-[6-(cyclopropylmethyl-amino)-5-methoxy-pyridin-3-yl]-1,2,3-triazol-1-yl}-4-methyl-benzamide N-(5-tert-Butyl-3-methanesulfonylamino-2-methoxy-phenyl)-3-{4-[6-(2-dimethylamino-ethyl)-pyridin-3-yl]-1,2,3-triazol-1-yl}-4-methyl-benzamide N-(5-tert-Butyl-3-methanesulfonylamino-2-methoxy-phenyl)-3-fluoro-4-methyl-5-(4-pyridin-3-yl-1,2,3-triazol-1-yl)-benzamide N-(5-tert-Butyl-3-methanesulfonylamino-2-methoxy-phenyl)-4-chloro-3-(4-pyridin-3-yl-1,2,3-triazol-1-yl)-benzamide N-(5-tert-Butyl-3-methanesulfonylamino-2-methoxy-phenyl)-4-fluoro-3-(4-pyridin-3-yl-1,2,3-triazol-1-yl)-benzamide N-(5-tert-Butyl-3-methanesulfonylamino-2-methoxy-phenyl)-4-methyl-3-(4-pyridin-3-yl-1,2,3-triazol-1-yl)-benzamide N-(5-tert-Butyl-3-methanesulfonylamino-2-methoxy-phenyl)-4-methyl-3-[4-(6-methyl-pyridin-3-yl)-1,2,3-triazol-1-yl]-benzamide N-(5-tert-Butyl-3-methanesulfonylamino-2-methoxy-phenyl)-4-methyl-3-[4-(6-morpholin-4-ylmethyl-pyridin-3-yl)-1,2,3-triazol-1-yl]-benzamide N-(5-tert-Butyl-3-methanesulfonylamino-2-methoxy-phenyl)-4-methyl-3-[4-(2-methyl-pyridin-3-yl)-1,2,3-triazol-1-yl]-benzamide N-(5-tert-Butyl-3-methanesulfonylamino-2-methoxy-phenyl)-4-methyl-3-[4-(6-methylamino-pyridin-3-yl)-1,2,3-triazol-1-yl]-benzamide N-(5-tert-Butyl-3-methanesulfonylamino-2-methoxy-phenyl)-4-methyl-3-(4-pyrimidin-5-yl-1,2,3-triazol-1-yl)-benzamide N-(5-tert-Butyl-3-methanesulfonylamino-2-methoxy-phenyl)-4-methyl-3-[4-(6-trifluoromethyl-pyridin-3-yl)-1,2,3-triazol-1-yl]-benzamide N-(5-tert-Butyl-3-methanesulfonylamino-2-methoxy-phenyl)-4-methyl-3-[4-(4-methyl-pyridin-3-yl)-1,2,3-triazol-1-yl]-benzamide N-(5-tert-Butyl-3-methanesulfonylamino-2-methoxy-phenyl)-4-methyl-3-{4-[6-(2-methylamino-ethyl)-pyridin-3-yl]-1,2,3-triazol-1-yl}-benzamide N-(5-tert-Butyl-3-methanesulfonylamino-2-methoxy-phenyl)-4-methyl-3-{4-[6-(2-morpholin-4-yl-ethyl)-pyridin-3-yl]-1,2,3-triazol-1-yl}-benzamide and N-[3-Methanesulfonylamino-2-methoxy-5-(1-methyl-cyclopropyl)-phenyl]-3-[4-(5-methoxy-pyridin-3-yl)-1,2,3-triazol-1-yl]-4-methyl-benzamide.

12. The compound according to claim 10 wherein the compound is chosen from:

3-[4-(2-Benzoyl-3-methyl-3H-imidazol-4-yl)-1,2,3-triazol-1-yl]-N-(5-tert-butyl-3-methanesulfonylamino-2-methoxy-phenyl)-4-methyl-benzamide 3-[4-(2-Benzoyl-3-methyl-3H-imidazol-4-yl)-1,2,3-triazol-1-yl]-N-[3-methanesulfonylamino-2-methoxy-5-(1-methyl-cyclopropyl)-phenyl]-4-methyl-benzamide 3-[4-(2-Cyclopropyl-3-methyl-3H-imidazol-4-yl)-1,2,3-triazol-1-yl]-N-[3-methanesulfonylamino-2-methoxy-5-(1-methyl-cyclopropyl)-phenyl]-4-methyl-benzamide 3-[4-(2-Cyclopropyl-3-methyl-3H-imidazol-4-yl)-1,2,3-triazol-1-yl]-N-[5-(2-hydroxy-1,1-dimethyl-ethyl)-3-methanesulfonylamino-2-methoxy-phenyl]-4-methyl-benzamide 3-[4-(2-Isopropyl-3-methyl-3H-imidazol-4-yl)-1,2,3-triazol-1-yl]-N-[3-methanesulfonylamino-2-methoxy-5-(1-methyl-cyclopropyl)-phenyl]-4-methyl-benzamide 3-[4-(2-tert-Butyl-3-methyl-3H-imidazol-4-yl)-1,2,3-triazol-1-yl]-N-[3-methanesulfonylamino-2-methoxy-5-(1-methyl-cyclopropyl)-phenyl]-4-methyl-benzamide 3-[4-(3-Benzyl-2-ethyl-3H-imidazol-4-yl)-1,2,3-triazol-1-yl]-N-(5-tert-butyl-3-methanesulfonylamino-2-methoxy-phenyl)-4-methyl-benzamide 3-[4-(3-Ethyl-2-phenyl-3H-imidazol-4-yl)-1,2,3-triazol-1-yl]-N-[3-methanesulfonylamino-2-methoxy-5-(1-methyl-cyclopropyl)-phenyl]-4-methyl-benzamide 3-[4-(3-tert-Butyl-2-cyclopropyl-3H-imidazol-4-yl)-1,2,3-triazol-1-yl]-N-(5-tert-butyl-3-methanesulfonylamino-2-methoxy-phenyl)-4-methyl-benzamide 3-[4-(3-tert-Butyl-2-methyl-3H-imidazol-4-yl)-1,2,3-triazol-1-yl]-N-[3-methanesulfonylamino-2-methoxy-5-(1-methyl-cyclopropyl)-phenyl]-4-methyl-benzamide 3-[4-(3-tert-Butyl-3H-imidazol-4-yl)-1,2,3-triazol-1-yl]-N-(5-tert-butyl-3-methanesulfonylamino-2-methoxy-phenyl)-4-methyl-benzamide 3-[4-(3-tert-Butyl-3H-imidazol-4-yl)-1,2,3-triazol-1-yl]-N-[3-methanesulfonylamino-2-methoxy-5-(1-methyl-cyclopropyl)-phenyl]-4-methyl-benzamide 3-{4-[2-(2-Benzyloxy-1,1-dimethyl-ethyl)-3-methyl-3H-imidazol-4-yl]-1,2,3-triazol-1-yl}-N-(5-tert-butyl-3-methanesulfonylamino-2-methoxy-phenyl)-4-methyl-benzamide 3-{4-[2-(4-Benzyl-piperazin-1-yl)-3-methyl-3H-imidazol-4-yl]-1,2,3-triazol-1-yl}-N-(5-tert-butyl-3-methanesulfonylamino-2-methoxy-phenyl)-4-methyl-benzamide 3-{4-[2-(Hydroxy-phenyl-methyl)-3-methyl-3H-imidazol-4-yl]-1,2,3-triazol-1-yl}-N-[3-methanesulfonylamino-2-methoxy-5-(1-methyl-cyclopropyl)-phenyl]-4-methyl-benzamide N-(5-tert-Butyl-3-methanesulfonylamino-2-methoxy-phenyl)-3-[4-(1,5-diisopropyl-1H-pyrazol-4-yl)-1,2,3-triazol-1-yl]-4-methyl-benzamide N-(5-tert-Butyl-3-methanesulfonylamino-2-methoxy-phenyl)-3-[4-(2-isopropyl-3-methyl-3H-imidazol-4-yl)-1,2,3-triazol-1-yl]-4-methyl-benzamide N-(5-tert-Butyl-3-methanesulfonylamino-2-methoxy-phenyl)-3-[4-(2-tert-butyl-3-methyl-3H-imidazol-4-yl)-1,2,3-triazol-1-yl]-4-methyl-benzamide N-(5-tert-Butyl-3-methanesulfonylamino-2-methoxy-phenyl)-3-[4-(2-cyclopropyl-3-methyl-3H-imidazol-4-yl)-1,2,3-triazol-1-yl]-4-methyl-benzamide N-(5-tert-Butyl-3-methanesulfonylamino-2-methoxy-phenyl)-3-[4-(2-cyclopropyl-3-isopropyl-3H-imidazol-4-yl)-1,2,3-triazol-1-yl]-4-methyl-benzamide N-(5-tert-Butyl-3-methanesulfonylamino-2-methoxy-phenyl)-3-[4-(2-methanesulfonyl-3-methyl-3H-imidazol-4-yl)-1,2,3-triazol-1-yl]-4-methyl-benzamide N-(5-tert-Butyl-3-methanesulfonylamino-2-methoxy-phenyl)-3-[4-(2-methanesulfinyl-3-methyl-3H-imidazol-4-yl)-1,2,3-triazol-1-yl]-4-methyl-benzamide N-(5-tert-Butyl-3-methanesulfonylamino-2-methoxy-phenyl)-3-[4-(2,3-diethyl-3H-imidazol-4-yl)-1,2,3-triazol-1-yl]-4-methyl-benzamide N-(5-tert-Butyl-3-methanesulfonylamino-2-methoxy-phenyl)-3-[4-(3-cyclopropyl-2-methyl-3H-imidazol-4-yl)-1,2,3-triazol-1-yl]-4-methyl-benzamide N-(5-tert-Butyl-3-methanesulfonylamino-2-methoxy-phenyl)-3-[4-(3-isopropyl-2-methyl-3H-imidazol-4-yl)-1,2,3-triazol-1-yl]-4-methyl-benzamide N-(5-tert-Butyl-3-methanesulfonylamino-2-methoxy-phenyl)-3-[4-(3-cyclopropyl-2-isopropyl-3H-imidazol-4-yl)-1,2,3-triazol-1-yl]-4-methyl-benzamide N-(5-tert-Butyl-3-methanesulfonylamino-2-methoxy-phenyl)-3-[4-(3-tert-butyl-2-methyl-3H-imidazol-4-yl)-1,2,3-triazol-1-yl]-4-methyl-benzamide N-(5-tert-Butyl-3-methanesulfonylamino-2-methoxy-phenyl)-3-[4-(3-ethyl-2-phenyl-3H-imidazol-4-yl)-1,2,3-triazol-1-yl]-4-methyl-benzamide N-(5-tert-Butyl-3-methanesulfonylamino-2-methoxy-phenyl)-3-[4-(7,7-dimethyl-6,7-dihydro-5H-pyrrolo[1,2-a]imidazol-3-yl)-1,2,3-triazol-1-yl]-4-methyl-benzamide N-(5-tert-Butyl-3-methanesulfonylamino-2-methoxy-phenyl)-3-{4-[2-cyclopropyl-3-(2,2,2-trifluoro-ethyl)-3H-imidazol-4-yl]-1,2,3-triazol-1-yl}-4-methyl-benzamide N-(5-tert-Butyl-3-methanesulfonylamino-2-methoxy-phenyl)-3-{4-[2-(hydroxy-phenyl-methyl)-3-methyl-3H-imidazol-4-yl]-1,2,3-triazol-1-yl}-4-methyl-benzamide N-(5-tert-Butyl-3-methanesulfonylamino-2-methoxy-phenyl)-3-{4-[2-(2,2-dimethyl-propionyl)-3-methyl-3H-imidazol-4-yl]-1,2,3-triazol-1-yl}-4-methyl-benzamide N-(5-tert-Butyl-3-methanesulfonylamino-2-methoxy-phenyl)-3-{4-[2-(1-hydroxy-2,2-dimethyl-propyl)-3-methyl-3H-imidazol-4-yl]-1,2,3-triazol-1-yl}-4-methyl-benzamide N-(5-tert-Butyl-3-methanesulfonylamino-2-methoxy-phenyl)-3-{4-[2-(1-hydroxy-1-methyl-ethyl)-3-methyl-3H-imidazol-4-yl]-1,2,3-triazol-1-yl}-4-methyl-benzamide N-(5-tert-Butyl-3-methanesulfonylamino-2-methoxy-phenyl)-3-{4-[2-(2-hydroxy-1,1-dimethyl-ethyl)-3-methyl-3H-imidazol-4-yl]-1,2,3-triazol-1-yl}-4-methyl-benzamide N-(5-tert-Butyl-3-methanesulfonylamino-2-methoxy-phenyl)-4-methyl-3-[4-(3-methyl-3H-imidazol-4-yl)-1,2,3-triazol-1-yl]-benzamide N-(5-tert-Butyl-3-methanesulfonylamino-2-methoxy-phenyl)-4-methyl-3-[4-(3-methyl-2-phenylsulfanyl-3H-imidazol-4-yl)-1,2,3-triazol-1-yl]-benzamide N-(5-tert-Butyl-3-methanesulfonylamino-2-methoxy-phenyl)-4-methyl-3-{4-[2-methyl-3-(2,2,2-trifluoro-ethyl)-3H-imidazol-4-yl]-1,2,3-triazol-1-yl}-benzamide N-(5-tert-Butyl-3-methanesulfonylamino-2-methoxy-phenyl)-4-methyl-3-[4-(3-methyl-2-pyridin-4-yl-3H-imidazol-4-yl)-1,2,3-triazol-1-yl]-benzamide N-(5-tert-Butyl-3-methanesulfonylamino-2-methoxy-phenyl)-4-methyl-3-[4-(5,6,7,8-tetrahydro-imidazo[1,2-a]pyridin-3-yl)-1,2,3-triazol-1-yl]-benzamide N-(5-tert-Butyl-3-methanesulfonylamino-2-methoxy-phenyl)-4-methyl-3-[4-(3-methyl-2-phenyl-3H-imidazol-4-yl)-1,2,3-triazol-1-yl]-benzamide N-(5-tert-Butyl-3-methanesulfonylamino-2-methoxy-phenyl)-4-methyl-3-[4-(3-methyl-2-piperazin-1-yl-3H-imidazol-4-yl)-1,2,3-triazol-1-yl]-benzamide N-(5-tert-Butyl-3-methanesulfonylamino-2-methoxy-phenyl)-4-methyl-3-[4-[spiro(6,7-dihydro-5H-pyrrolo[1,2-a]imidazol-3-yl-5-cyclohexane)]-[1,2,3]triazol-1-yl]-benzamide N-(5-tert-Butyl-3-methanesulfonylamino-2-methoxy-phenyl)-4-methyl-3-{4-[3-methyl-2-(1-methyl-cyclopropyl)-3H-imidazol-4-yl]-1,2,3-triazol-1-yl}-benzamide N-(5-tert-Butyl-3-methanesulfonylamino-2-methoxy-phenyl)-4-methyl-3-[4-(3-methyl-2-morpholin-4-yl-3H-imidazol-4-yl)-1,2,3-triazol-1-yl]-benzamide N-(5-tert-Butyl-3-methanesulfonylamino-2-methoxy-phenyl)-4-methyl-3-[4-[spiro(6,7-dihydro-5H-pyrrolo[1,2-a]imidazol-3-yl-5-(2'-methyl-cyploroane))]-[1,2,3]triazol-1-yl]-benzamide N-(5-tert-Butyl-3-methanesulfonylamino-2-methoxy-phenyl)-4-methyl-3-[4-(3-methyl-2-methylsulfanyl-3H-imidazol-4-yl)-1,2,3-triazol-1-yl]-benzamide N-(5-tert-Butyl-3-methanesulfonylamino-2-methoxy-phenyl)-4-methyl-3-{4-[3-methyl-2-(1-methyl-1-phenyl-ethyl)-3H-imidazol-4-yl]-1,2,3-triazol-1-yl}-benzamide N-[3-Methanesulfonylamino-2-methoxy-5-(1-methyl-cyclopropyl)-phenyl]-4-methyl-3-{4-[3-methyl-2-(1-methyl-cyclopropyl)-3H-imidazol-4-yl]-1,2,3-triazol-1-yl}-benzamide N-(5-tert-Butyl-3-methanesulfonylamino-2-methoxy-phenyl)-3-[4-(2-tert-butylsulfanyl-3-methyl-3H-imidazol-4-yl)-1,2,3-triazol-1-yl]-4-methyl-benzamide N-(5-tert-Butyl-3-methanesulfonylamino-2-methoxy-phenyl)-4-methyl-3-{4-[3-methyl-2-(2-methyl-propane-2-sulfonyl)-3H-imidazol-4-yl]-1,2,3-triazol-1-yl}-benzamide 3-{4-[2-(1-Benzyloxy-cyclopropyl)-3-methyl-3H-imidazol-4-yl]-1,2,3-triazol-1-yl}-N-(5-tert-butyl-3-methanesulfonylamino-2-methoxy-phenyl)-4-methyl-benzamide N-(5-tert-Butyl-3-methanesulfonylamino-2-methoxy-phenyl)-3-{4-[2-(1-hydroxy-cyclopropyl)-3-methyl-3H-imidazol-4-yl]-1,2,3-triazol-1-yl}-4-methyl-benzamide 3-[4-(2-Benzyl-3-methyl-3H-imidazol-4-yl)-1,2,3-triazol-1-yl]-N-(5-tert-butyl-3-methanesulfonylamino-2-methoxy-phenyl)-4-methyl-benzamide N-[3-Methanesulfonylamino-2-methoxy-5-(1-methyl-cyclopropyl)-phenyl]-4-methyl-3-{4-[3-methyl-2-(1-methyl-1-phenyl-ethyl)-3H-imidazol-4-yl]-1,2,3-triazol-1-yl}-benzamide N-(5-tert-Butyl-3-methanesulfonylamino-2-methoxy-phenyl)-3-[4-(2-hydroxymethyl-3-methyl-3H-imidazol-4-yl)-1,2,3-triazol-1-yl]-4-methyl-benzamide N-(5-tert-Butyl-3-methanesulfonylamino-2-methoxy-phenyl)-3-{4-[2-(1-hydroxy-ethyl)-3-methyl-3H-imidazol-4-yl]-1,2,3-triazol-1-yl}-4-methyl-benzamide N-(5-tert-Butyl-2-methoxy-phenyl)-3-[4-(2-cyclopropyl-3-methyl-3H-imidazol-4-yl)-1,2,3-triazol-1-yl]-4-methyl-benzamide N-(5-tert-Butyl-3-methanesulfonylamino-2-methoxy-phenyl)-3-[4-(5,5-dimethyl-6,7-dihydro-5H-pyrrolo[1,2-a]imidazol-3-yl)-[1,2,3]triazol-1-yl]-4-methyl-benzamide N-(5-tert-Butyl-3-cyano-2-methoxy-phenyl)-3-[4-(2-cyclopropyl-3-methyl-3H-imidazol-4-yl)-1,2,3-triazol-1-yl]-4-methyl-benzamide N-(5-tert-Butyl-2-methanesulfinyl-phenyl)-3-[4-(2-cyclopropyl-3-methyl-3H-imidazol-4-yl)-1,2,3-triazol-1-yl]-4-methyl-benzamide N-(5-tert-Butyl-3-methanesulfonylamino-2-methyl-phenyl)-3-[4-(2-cyclopropyl-3-methyl-3H-imidazol-4-yl)-1,2,3-triazol-1-yl]-4-methyl-benzamide N-[5-(2-Hydroxy-1,1-dimethyl-ethyl)-3-methanesulfonylamino-2-methoxy-phenyl]-4-methyl-3-{4-[3-methyl-2-(1-methyl-cyclopropyl)-3H-imidazol-4-yl]-1,2,3-triazol-1-yl}-benzamide N-(5-tert-Butyl-3-methanesulfonylamino-2-methoxy-phenyl)-3-{4-[2-(cyclopropyl-hydroxy-methyl)-3-methyl-3H-imidazol-4-yl]-1,2,3-triazol-1-yl}-4-methyl-benzamide 3-[4-(2-Acetyl-3-methyl-3H-imidazol-4-yl)-1,2,3-triazol-1-yl]-N-(5-tert-butyl-3-methanesulfonylamino-2-methoxy-phenyl)-4-methyl-benzamide N-(5-tert-Butyl-3-methanesulfonylamino-2-methoxy-phenyl)-3-[4-(2-formyl-3-methyl-3H-imidazol-4-yl)-1,2,3-triazol-1-yl]-4-methyl-benzamide and N-(5-tert-Butyl-3-methanesulfonylamino-2-methoxy-phenyl)-3-[4-(2,3-dihydro-imidazo[2,1-b]thiazol-5-yl)-1,2,3-triazol-1-yl]-4-methyl-benzamide.

13. The compound according to claim 10 wherein the compound is chosen from:

[2-(4-{1-[5-(5-tert-Butyl-3-methanesulfonylamino-2-methoxy-phenylcarbamoyl)-2-methyl-phenyl]-1H-1,2,3-triazol-4-yl}-2-phenyl-2H-pyrazol-3-yl)-ethyl]-carbamic acid benzyl ester 3-[4-(1-Cyclopropyl-5-ethyl-1H-pyrazol-4-yl)-1,2,3-triazol-1-yl]-N-[3-methanesulfonylamino-2-methoxy-5-(1-methyl-cyclopropyl)-phenyl]-4-methyl-benzamide 3-[4-(1-Isopropyl-5-methyl-1H-pyrazol-4-yl)-1,2,3-triazol-1-yl]-N-[3-methanesulfonylamino-2-methoxy-5-(1-methyl-cyclopropyl)-phenyl]-4-methyl-benzamide 3-[4-(1-tert-Butyl-5-methyl-1H-pyrazol-4-yl)-1,2,3-triazol-1-yl]-N-[3-methanesulfonylamino-2-methoxy-5-(1-methyl-cyclopropyl)-phenyl]-4-methyl-benzamide 3-[4-(5-Ethyl-1-phenyl-1H-pyrazol-4-yl)-1,2,3-triazol-1-yl]-N-[3-methanesulfonylamino-2-methoxy-5-(1-methyl-cyclopropyl)-phenyl]-4-methyl-benzamide 3-{4-[1-(1-Benzyl-piperidin-4-yl)-5-methyl-1H-pyrazol-4-yl]-1,2,3-triazol-1-yl}-N-(5-tert-butyl-3-methanesulfonylamino-2-methoxy-phenyl)-4-methyl-benzamide 3-{4-[5-(2-Amino-ethyl)-1-phenyl-1H-pyrazol-4-yl]-1,2,3-triazol-1-yl}-N-(5-tert-butyl-3-methanesulfonylamino-2-methoxy-phenyl)-4-methyl-benzamide 4-(4-{1-[5-(5-tert-Butyl-3-methanesulfonylamino-2-methoxy-phenylcarbamoyl)-2-methyl-phenyl]-1H-1,2,3-triazol-4-yl}-2-cyclopropyl-2H-pyrazol-3-yl)-piperidine-1-carboxylic acid tert-butyl ester N-(5-tert-Butyl-3-methanesulfonylamino-2-methoxy-phenyl)-3-[4-(1-cyclohexyl-5-methyl-1H-pyrazol-4-yl)-1,2,3-triazol-1-yl]-4-methyl-benzamide N-(5-tert-Butyl-3-methanesulfonylamino-2-methoxy-phenyl)-3-[4-(1-cyclohexyl-5-ethyl-1H-pyrazol-4-yl)-1,2,3-triazol-1-yl]-4-methyl-benzamide N-(5-tert-Butyl-3-methanesulfonylamino-2-methoxy-phenyl)-3-[4-(1-isopropyl-5-methyl-1H-pyrazol-4-yl)-1,2,3-triazol-1-yl]-4-methyl-benzamide N-(5-tert-Butyl-3-methanesulfonylamino-2-methoxy-phenyl)-3-[4-(1-cyclopropyl-5-methyl-1H-pyrazol-4-yl)-1,2,3-triazol-1-yl]-4-methyl-benzamide N-(5-tert-Butyl-3-methanesulfonylamino-2-methoxy-phenyl)-3-[4-(1-tert-butyl-5-methyl-1H-pyrazol-4-yl)-1,2,3-triazol-1-yl]-4-methyl-benzamide N-(5-tert-Butyl-3-methanesulfonylamino-2-methoxy-phenyl)-3-[4-(1-cyclopropyl-5-isopropyl-1H-pyrazol-4-yl)-1,2,3-triazol-1-yl]-4-methyl-benzamide N-(5-tert-Butyl-3-methanesulfonylamino-2-methoxy-phenyl)-3-[4-(1-cyclopropyl-5-ethyl-1H-pyrazol-4-yl)-1,2,3-triazol-1-yl]-4-methyl-benzamide N-(5-tert-Butyl-3-methanesulfonylamino-2-methoxy-phenyl)-3-[4-(1-cyclopropyl-5-pyridin-2-yl-1H-pyrazol-4-yl)-1,2,3-triazol-1-yl]-4-methyl-benzamide N-(5-tert-Butyl-3-methanesulfonylamino-2-methoxy-phenyl)-3-[4-(1-cyclopropyl-5-piperidin-4-yl-1H-pyrazol-4-yl)-1,2,3-triazol-1-yl]-4-methyl-benzamide N-(5-tert-Butyl-3-methanesulfonylamino-2-methoxy-phenyl)-3-[4-(1,5-dimethyl-1H-pyrazol-4-yl)-1,2,3-triazol-1-yl]-4-methyl-benzamide N-(5-tert-Butyl-3-methanesulfonylamino-2-methoxy-phenyl)-3-[4-(5-ethyl-1-phenyl-1H-pyrazol-4-yl)-1,2,3-triazol-1-yl]-4-methyl-benzamide N-(5-tert-Butyl-3-methanesulfonylamino-2-methoxy-phenyl)-3-[4-(5-ethyl-1-pyridin-2-yl-1H-pyrazol-4-yl)-1,2,3-triazol-1-yl]-4-methyl-benzamide N-(5-tert-Butyl-3-methanesulfonylamino-2-methoxy-phenyl)-3-[4-(5-ethyl-1-isopropyl-1H-pyrazol-4-yl)-1,2,3-triazol-1-yl]-4-methyl-benzamide N-(5-tert-Butyl-3-methanesulfonylamino-2-methoxy-phenyl)-3-[4-(5-cyclopropyl-1-isopropyl-1H-pyrazol-4-yl)-1,2,3-triazol-1-yl]-4-methyl-benzamide N-(5-tert-Butyl-3-methanesulfonylamino-2-methoxy-phenyl)-3-[4-(5-isopropyl-1-phenyl-1H-pyrazol-4-yl)-1,2,3-triazol-1-yl]-4-methyl-benzamide N-(5-tert-Butyl-3-methanesulfonylamino-2-methoxy-phenyl)-3-[4-(5-cyclopropyl-1-phenyl-1H-pyrazol-4-yl)-1,2,3-triazol-1-yl]-4-methyl-benzamide N-(5-tert-Butyl-3-methanesulfonylamino-2-methoxy-phenyl)-3-{4-[1-(4-fluoro-phenyl)-5-methyl-1H-pyrazol-4-yl]-1,2,3-triazol-1-yl}-4-methyl-benzamide N-(5-tert-Butyl-3-methanesulfonylamino-2-methoxy-phenyl)-3-{4-[1-(4-methoxy-phenyl)-5-methyl-1H-pyrazol-4-yl]-1,2,3-triazol-1-yl}-4-methyl-benzamide N-(5-tert-Butyl-3-methanesulfonylamino-2-methoxy-phenyl)-3-{4-[1-(1-tert-butyl-piperidin-4-yl)-5-methyl-1H-pyrazol-4-yl]-1,2,3-triazol-1-yl}-4-methyl-benzamide N-(5-tert-Butyl-3-methanesulfonylamino-2-methoxy-phenyl)-3-{4-[5-(2-dimethylamino-ethyl)-1-phenyl-1H-pyrazol-4-yl]-1,2,3-triazol-1-yl}-4-methyl-benzamide N-(5-tert-Butyl-3-methanesulfonylamino-2-methoxy-phenyl)-4-methyl-3-[4-(5-methyl-1-phenyl-1H-pyrazol-4-yl)-1,2,3-triazol-1-yl]-benzamide N-(5-tert-Butyl-3-methanesulfonylamino-2-methoxy-phenyl)-4-methyl-3-{4-[5-methyl-1-(1-methyl-piperidin-4-yl)-1H-pyrazol-4-yl]-1,2,3-triazol-1-yl}-benzamide N-(5-tert-Butyl-3-methanesulfonylamino-2-methoxy-phenyl)-4-methyl-3-[4-(5-methyl-1-pyridin-2-yl-1H-pyrazol-4-yl)-1,2,3-triazol-1-yl]-benzamide N-(5-tert-Butyl-3-methanesulfonylamino-2-methoxy-phenyl)-3-[4-(3-methyl-3H-imidazol-4-yl)-pyrazol-1-yl]-benzamide N-(5-tert-Butyl-3-methanesulfonylamino-2-methoxy-phenyl)-4-methyl-3-[4-(5-methyl-1-piperidin-4-yl-1H-pyrazol-4-yl)-1,2,3-triazol-1-yl]-benzamide N-(5-tert-Butyl-3-methanesulfonylamino-2-methoxy-phenyl)-4-methyl-3-{4-[5-(2-morpholin-4-yl-ethyl)-1-phenyl-1H-pyrazol-4-yl]-1,2,3-triazol-1-yl}-benzamide N-(5-tert-Butyl-3-methanesulfonylamino-2-methoxy-phenyl)-4-methyl-3-[4-(1-phenyl-5-trifluoromethyl-1H-pyrazol-4-yl)-1,2,3-triazol-1-yl]-benzamide and N-[3-Methanesulfonylamino-2-methoxy-5-(1-methyl-cyclopropyl)-phenyl]-4-methyl-3-[4-(5-methyl-1-phenyl-1H-pyrazol-4-yl)-1,2,3-triazol-1-yl]-benzamide.

14. The compound according to claim 10 wherein the compound is chosen from:

N-(5-tert-Butyl-3-methanesulfonylamino-2-methoxy-phenyl)-4-methyl-3-(4-thiazol-5-yl-1,2,3-triazol-1-yl)-benzamide and N-(5-tert-Butyl-3-methanesulfonylamino-2-methoxy-phenyl)-4-methyl-3-[4-(2-morpholin-4-yl-thiazol-5-yl)-1,2,3-triazol-1-yl]-benzamide.

15. The compound according to claim 10 wherein the compound is chosen from:

3-[4-(2-Benzyl-3-methyl-3H-imidazol-4-yl)-1,2,3-triazol-1-yl]-N-(5-tert-butyl-3-methanesulfonylamino-2-methoxy-phenyl)-4-methyl-benzamide 3-[4-(2-tert-Butyl-3-methyl-3H-imidazol-4-yl)-1,2,3-triazol-1-yl]-N-[3-methanesulfonylamino-2-methoxy-5-(1-methyl-cyclopropyl)-phenyl]-4-methyl-benzamide 3-[4-(3-Ethyl-2-phenyl-3H-imidazol-4-yl)-1,2,3-triazol-1-yl]-N-[3-methanesulfonylamino-2-methoxy-5-(1-methyl-cyclopropyl)-phenyl]-4-methyl-benzamide 3-[4-(3-tert-Butyl-3H-imidazol-4-yl)- 1,2,3-triazol-1-yl]-N-(5-tert-butyl-3-methanesulfonylamino-2-methoxy-phenyl)-4-methyl-benzamide 3-[4-(3-tert-Butyl-3H-imidazol-4-yl)-1,2,3-triazol-1-yl]-N-[3-methanesulfonylamino-2-methoxy-5-(1-methyl-cyclopropyl)-phenyl]-4-methyl-benzamide 3-{4-[2-(Hydroxy-phenyl-methyl)-3-methyl-3H-imidazol-4-yl]-1,2,3-triazol-1-yl}-N-[3-methanesulfonylamino-2-methoxy-5-(1-methyl-cyclopropyl)-phenyl]-4-methyl-benzamide N-(5-tert-Butyl-3-methanesulfonylamino-2-methoxy-phenyl)-3-[4-(1,5-diisopropyl-1H-pyrazol-4-yl)-1,2,3-triazol-1-yl]-4-methyl-benzamide N-(5-tert-Butyl-3-methanesulfonylamino-2-methoxy-phenyl)-3-[4-(2-isopropyl-3-methyl-3H-imidazol-4-yl)-1,2,3-triazol-1-yl]-4-methyl-benzamide N-(5-tert-Butyl-3-methanesulfonylamino-2-methoxy-phenyl)-3-[4-(2-tert-butyl-3-methyl-3H-imidazol-4-yl)-1,2,3-triazol-1-yl]-4-methyl-benzamide N-(5-tert-Butyl-3-methanesulfonylamino-2-methoxy-phenyl)-3-[4-(2-cyclopropyl-3-methyl-3H-imidazol-4-yl)-1,2,3-triazol-1-yl]-4-methyl-benzamide N-(5-tert-Butyl-3-methanesulfonylamino-2-methoxy-phenyl)-3-[4-(2-cyclopropyl-3-isopropyl-3H-imidazol-4-yl)-1,2,3-triazol-1-yl]-4-methyl-benzamide N-(5-tert-Butyl-3-methanesulfonylamino-2-methoxy-phenyl)-3-[4-(2-methanesulfonyl-3-methyl-3H-imidazol-4-yl)-1,2,3-triazol-1-yl]-4-methyl-benzamide N-(5-tert-Butyl-3-methanesulfonylamino-2-methoxy-phenyl)-3-[4-(2-methanesulfinyl-3-methyl-3H-imidazol-4-yl)-1,2,3-triazol-1-yl]-4-methyl-benzamide N-(5-tert-Butyl-3-methanesulfonylamino-2-methoxy-phenyl)-3-[4-(2-tert-butylsulfanyl-3-methyl-3H-imidazol-4-yl)-1,2,3-triazol-1-yl]-4-methyl-benzamide N-(5-tert-Butyl-3-methanesulfonylamino-2-methoxy-phenyl)-3-[4-(2-hydroxymethyl-3-methyl-3H-imidazol-4-yl)-1,2,3-triazol-1-yl]-4-methyl-benzamide N-(5-tert-Butyl-3-methanesulfonylamino-2-methoxy-phenyl)-3-[4-(2,3-diethyl-3H-imidazol-4-yl)-1,2,3-triazol-1-yl]-4-methyl-benzamide N-(5-tert-Butyl-3-methanesulfonylamino-2-methoxy-phenyl)-3-[4-(3-isopropyl-2-methyl-3H-imidazol-4-yl)-1,2,3-triazol-1-yl]-4-methyl-benzamide N-(5-tert-Butyl-3-methanesulfonylamino-2-methoxy-phenyl)-3-[4-(3-ethyl-2-phenyl-3H-imidazol-4-yl)-1,2,3-triazol-1-yl]-4-methyl-benzamide N-(5-tert-Butyl-3-methanesulfonylamino-2-methoxy-phenyl)-3-[4-(7,7-dimethyl-6,7-dihydro-5H-pyrrolo[1,2-a]imidazol-3-yl)-1,2,3-triazol-1-yl]-4-methyl-benzamide N-(5-tert-Butyl-3-methanesulfonylamino-2-methoxy-phenyl)-3-{4-[2-(hydroxy-phenyl-methyl)-3-methyl-3H-imidazol-4-yl]-1,2,3-triazol-1-yl}-4-methyl-benzamide N-(5-tert-Butyl-3-methanesulfonylamino-2-methoxy-phenyl)-3-{4-[2-(1-hydroxy-2,2-dimethyl-propyl)-3-methyl-3H-imidazol-4-yl]-1,2,3-triazol-1-yl}-4-methyl-benzamide N-(5-tert-Butyl-3-methanesulfonylamino-2-methoxy-phenyl)-3-{4-[2-(1-hydroxy-1-methyl-ethyl)-3-methyl-3H-imidazol-4-yl]-1,2,3-triazol-1-yl}-4-methyl-benzamide N-(5-tert-Butyl-3-methanesulfonylamino-2-methoxy-phenyl)-3-{4-[2-(2-hydroxy-1,1-dimethyl-ethyl)-3-methyl-3H-imidazol-4-yl]-1,2,3-triazol-1-yl}-4-methyl-benzamide N-(5-tert-Butyl-3-methanesulfonylamino-2-methoxy-phenyl)-3-{4-[2-(1-hydroxy-cyclopropyl)-3-methyl-3H-imidazol-4-yl]-1,2,3-triazol-1-yl}-4-methyl-benzamide N-(5-tert-Butyl-3-methanesulfonylamino-2-methoxy-phenyl)-3-{4-[2-(1-hydroxy-ethyl)-3-methyl-3H-imidazol-4-yl]-1,2,3-triazol-1-yl}-4-methyl-benzamide N-(5-tert-Butyl-3-methanesulfonylamino-2-methoxy-phenyl)-3-{4-[2-(cyclopropyl-hydroxy-methyl)-3-methyl-3H-imidazol-4-yl]-1,2,3-triazol-1-yl}-4-methyl-benzamide N-(5-tert-Butyl-3-methanesulfonylamino-2-methoxy-phenyl)-4-methyl-3-[4-(3-methyl-2-phenylsulfanyl-3H-imidazol-4-yl)-1,2,3-triazol-1-yl]-benzamide N-(5-tert-Butyl-3-methanesulfonylamino-2-methoxy-phenyl)-4-methyl-3-{4-[2-methyl-3-(2,2,2-trifluoro-ethyl)-3H-imidazol-4-yl]-1,2,3-triazol-1-yl}-benzamide N-(5-tert-Butyl-3-methanesulfonylamino-2-methoxy-phenyl)-4-methyl-3-[4-(3-methyl-2-pyridin-4-yl-3H-imidazol-4-yl)-1,2,3-triazol-1-yl]-benzamide N-(5-tert-Butyl-3-methanesulfonylamino-2-methoxy-phenyl)-4-methyl-3-[4-(1-methyl-2-pyridin-4-yl-1H-imidazol-4-yl)-1,2,3-triazol-1-yl]-benzamide N-(5-tert-Butyl-3-methanesulfonylamino-2-methoxy-phenyl)-4-methyl-3-[4-(5,6,7,8-tetrahydro-imidazo[1,2-a]pyridin-3-yl)-1,2,3-triazol-1-yl]-benzamide N-(5-tert-Butyl-3-methanesulfonylamino-2-methoxy-phenyl)-4-methyl-3-[4-(3-methyl-2-phenyl-3H-imidazol-4-yl)-1,2,3-triazol-1-yl]-benzamide N-(5-tert-Butyl-3-methanesulfonylamino-2-methoxy-phenyl)-4-methyl-3-[4-[spiro(6,7-dihydro-5H-pyrrolo[1,2-a]imidazol-3-yl-5-(2'-methyl-cyclopraone))]-[1,2,3]triazol-1-yl]-benzamide N-(5-tert-Butyl-3-methanesulfonylamino-2-methoxy-phenyl)-4-methyl-3-{4-[3-methyl-2-(1-methyl-cyclopropyl)-3H-imidazol-4-yl]-1,2,3-triazol-1-yl}-benzamide N-(5-tert-Butyl-3-methanesulfonylamino-2-methoxy-phenyl)-4-methyl-3-[4-(3-methyl-2-morpholin-4-yl-3H-imidazol-4-yl)-1,2,3-triazol-1-yl]-benzamide N-(5-tert-Butyl-3-methanesulfonylamino-2-methoxy-phenyl)-4-methyl-3-[4-[spiro(6,7-dihydro-5H-pyrrolo[1,2-a]imidazol-3-yl-5-cyclohexane)]-[1,2,3]triazol-1-yl]-benzamide N-(5-tert-Butyl-3-methanesulfonylamino-2-methoxy-phenyl)-4-methyl-3-[4-(3-methyl-2-methylsulfanyl-3H-imidazol-4-yl)-1,2,3-triazol-1-yl]-benzamide N-(5-tert-Butyl-3-methanesulfonylamino-2-methoxy-phenyl)-4-methyl-3-{4-[3-methyl-2-(2-methyl-propane-2-sulfonyl)-3H-imidazol-4-yl]-1,2,3-triazol-1-yl}-benzamide and N-[3-Methanesulfonylamino-2-methoxy-5-(1-methyl-cyclopropyl)-phenyl]-4-methyl-3-{4-[3-methyl-2-(1-methyl-cyclopropyl)-3H-imidazol-4-yl]-1,2,3-triazol-1-yl}-benzamide.

16. The compound according to claim 10 wherein the compound is chosen from

3-[4-(1-Cyclopropyl-5-ethyl-1H-pyrazol-4-yl)-1,2,3-triazol-1-yl]-N-[3-methanesulfonylamino-2-methoxy-5-(1-methyl-cyclopropyl)-phenyl]-4-methyl-benzamide 3-[4-(5-Ethyl-1-phenyl-1H-pyrazol-4-yl)-1,2,3-triazol-1-yl]-N-[3-methanesulfonylamino-2-methoxy-5-(1-methyl-cyclopropyl)-phenyl]-4-methyl-benzamide N-(5-tert-Butyl-3-methanesulfonylamino-2-methoxy-phenyl)-3-[4-(1-cyclohexyl-5-methyl-1H-pyrazol-4-yl)-1,2,3-triazol-1-yl]-4-methyl-benzamide N-(5-tert-Butyl-3-methanesulfonylamino-2-methoxy-phenyl)-3-[4-(1-cyclohexyl-5-ethyl-1H-pyrazol-4-yl)-1,2,3-triazol-1-yl]-4-methyl-benzamide N-(5-tert-Butyl-3-methanesulfonylamino-2-methoxy-phenyl)-3-[4-(1-isopropyl-5-methyl-1H-pyrazol-4-yl)-1,2,3-triazol-1-yl]-4-methyl-benzamide N-(5-tert-Butyl-3-methanesulfonylamino-2-methoxy-phenyl)-3-[4-(1-cyclopropyl-5-methyl-1H-pyrazol-4-yl)-1,2,3-triazol-1-yl]-4-methyl-benzamide N-(5-tert-Butyl-3-methanesulfonylamino-2-methoxy-phenyl)-3-[4-(1-tert-butyl-5-methyl-1H-pyrazol-4-yl)-1,2,3-triazol-1-yl]-4-methyl-benzamide N-(5-tert-Butyl-3-methanesulfonylamino-2-methoxy-phenyl)-3-[4-(1-cyclopropyl-5-isopropyl-1H-pyrazol-4-yl)-1,2,3-triazol-1-yl]-4-methyl-benzamide N-(5-tert-Butyl-3-methanesulfonylamino-2-methoxy-phenyl)-3-[4-(1-cyclopropyl-5-ethyl-1H-pyrazol-4-yl)-1,2,3-triazol-1-yl]-4-methyl-benzamide N-(5-tert-Butyl-3-methanesulfonylamino-2-methoxy-phenyl)-3-[4-(1,5-dimethyl-1H-pyrazol-4-yl)-1,2,3-triazol-1-yl]-4-methyl-benzamide N-(5-tert-Butyl-3-methanesulfonylamino-2-methoxy-phenyl)-3-[4-(5-ethyl-1-phenyl-1H-pyrazol-4-yl)-1,2,3-triazol-1-yl]-4-methyl-benzamide N-(5-tert-Butyl-3-methanesulfonylamino-2-methoxy-phenyl)-3-[4-(5-ethyl-1-pyridin-2-yl-1H-pyrazol-4-yl)-1,2,3-triazol-1-yl]-4-methyl-benzamide N-(5-tert-Butyl-3-methanesulfonylamino-2-methoxy-phenyl)-3-[4-(5-ethyl-1-isopropyl-1H-pyrazol-4-yl)-1,2,3-triazol-1-yl]-4-methyl-benzamide N-(5-tert-Butyl-3-methanesulfonylamino-2-methoxy-phenyl)-3-[4-(5-isopropyl-1-phenyl-1H-pyrazol-4-yl)-1,2,3-triazol-1-yl]-4-methyl-benzamide N-(5-tert-Butyl-3-methanesulfonylamino-2-methoxy-phenyl)-3-{4-[1-(4-fluoro-phenyl)-5-methyl-1H-pyrazol-4-yl]-1,2,3-triazol-1-yl}-4-methyl-benzamide N-(5-tert-Butyl-3-methanesulfonylamino-2-methoxy-phenyl)-3-{4-[5-(2-dimethylamino-ethyl)-1-phenyl-1H-pyrazol-4-yl]-1,2,3-triazol-1-yl}-4-methyl-benzamide N-(5-tert-Butyl-3-methanesulfonylamino-2-methoxy-phenyl)-4-methyl-3-[4-(5-methyl-1-phenyl-1H-pyrazol-4-yl)-1,2,3-triazol-1-yl]-benzamide N-(5-tert-Butyl-3-methanesulfonylamino-2-methoxy-phenyl)-4-methyl-3-{4-[5-methyl-1-(1-methyl-piperidin-4-yl)-1H-pyrazol-4-yl]-1,2,3-triazol-1-yl}-benzamide N-(5-tert-Butyl-3-methanesulfonylamino-2-methoxy-phenyl)-4-methyl-3-[4-(5-methyl-1-pyridin-2-yl-1H-pyrazol-4-yl)-1,2,3-triazol-1-yl]-benzamide N-(5-tert-Butyl-3-methanesulfonylamino-2-methoxy-phenyl)-4-methyl-3-{4-[5-(2-morpholin-4-yl-ethyl)-1-phenyl-1H-pyrazol-4-yl]-1,2,3-triazol-1-yl}-benzamide and N-[3-Methanesulfonylamino-2-methoxy-5-(1-methyl-cyclopropyl)-phenyl]-4-methyl-3-[4-(5-methyl-1-phenyl-1H-pyrazol-4-yl)-1,2,3-triazol-1-yl]-benzamide.

17. The compound according to claim 10 wherein the compound is chosen from:

3-[4-(2-Benzenesulfonyl-3-methyl-3H-imidazol-4-yl)-1,2,3-triazol-1-yl]-N-(5-tert-butyl-3-methanesulfonylamino-2-methoxy-phenyl)-4-methyl-benzamide 3-[4-(5-Ethyl-1-phenyl-1H-pyrazol-4-yl)-imidazol-1-yl]-N-(2-methoxy-5-trifluoromethyl-phenyl)-4-methyl-benzamide 3-[4-(5-Ethyl-1-phenyl-1H-pyrazol-4-yl)-imidazol-1-yl]-N-(3-methanesulfonylamino-2-methoxy-5-trifluoromethyl-phenyl)-4-methyl-benzamide 3-[4-(5-Ethyl-1-phenyl-1H-pyrazol-4-yl)-imidazol-1-yl]-N-[3-methanesulfonylamino-2-methoxy-5-(1-methyl-cyclopropyl)-phenyl]-4-methyl-benzamide N-(5-tert-Butyl-2-methanesulfinyl-phenyl)-3-[4-(5-ethyl-1-phenyl-1H-pyrazol-4-yl)-imidazol-1-yl]-4-methyl-benzamide N-(5-tert-Butyl-2-methoxy-phenyl)-3-[4-(5-ethyl-1-phenyl-1H-pyrazol-4-yl)-imidazol-1-yl]-4-methyl-benzamide N-(5-tert-Butyl-2-methyl-pyridin-3-yl)-3-[4-(5-ethyl-1-phenyl-1H-pyrazol-4-yl)-imidazol-1-yl]-4-methyl-benzamide N-(5-tert-Butyl-3-cyano-2-methoxy-phenyl)-3-[4-(5-ethyl-1-phenyl-1H-pyrazol-4-yl)-imidazol-1-yl]-4-methyl-benzamide N-(5-tert-Butyl-3-methanesulfonylamino-2-methoxy-phenyl)-3-[4-(1-isopropyl-5-methyl-1H-pyrazol-4-yl)-imidazol-1-yl]-4-methyl-benzamide N-(5-tert-Butyl-3-methanesulfonylamino-2-methoxy-phenyl)-3-[4-(5-ethyl-1-phenyl-1H-pyrazol-4-yl)-imidazol-1-yl]-4-methyl-benzamide N-(5-tert-Butyl-3-methanesulfonylamino-2-methoxy-phenyl)-4-methyl-3-(4-pyridin-3-yl-imidazol-1-yl)-benzamide N-(5-tert-Butyl-3-methanesulfonylamino-2-methoxy-phenyl)-4-methyl-3-[4-(5-methyl-1-phenyl-1H-pyrazol-4-yl)-imidazol-1-yl]-benzamide and N-(5-tert-Butyl-3-methanesulfonylamino-2-methyl-phenyl)-3-[4-(5-ethyl-1-phenyl-1H-pyrazol-4-yl)-imidazol-1-yl]-4-methyl-benzamide.

18. A pharmaceutical composition containing a pharmaceutically effective amount of a compound according to claim 1 and one or more pharmaceutically acceptable carriers and/or adjuvants.

* * * * *

UNITED STATES PATENT AND TRADEMARK OFFICE
CERTIFICATE OF CORRECTION

| | | |
|---|---|---|
| PATENT NO. | : 7,214,802 B2 | Page 1 of 7 |
| APPLICATION NO. | : 11/074354 | |
| DATED | : May 8, 2007 | |
| INVENTOR(S) | : Derek Cogan et al. | |

It is certified that error appears in the above-identified patent and that said Letters Patent is hereby corrected as shown below:

On attached sheets 2-7, replace formula as shown below.

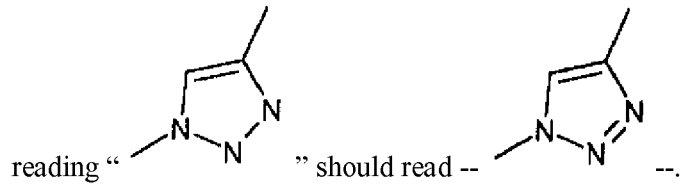

UNITED STATES PATENT AND TRADEMARK OFFICE
CERTIFICATE OF CORRECTION

PATENT NO. : 7,214,802 B2
APPLICATION NO. : 11/074354
DATED : May 8, 2007
INVENTOR(S) : Derek Cogan et al.

It is certified that error appears in the above-identified patent and that said Letters Patent is hereby corrected as shown below:

| Column | Line/Table/Example | Compound Structure |
|---|---|---|
| 17 | Table 1 | 1 |
| 19 | Table 1 | 3, 4 |
| 21 | Table 1 | 1, 3, 4, 5 |
| 23 | Table 1 | 1, 2 4 |
| 25 | Table 1 | 1, 5 |
| 27 | Table 1 | 1 |
| 31 | Table 1 | 1, 2, 3, 4 |
| 33 | Table 1 | 1, 2, 3, 4 |
| 35 | Table 1 | 3 |
| 37 | Table 1 | 4 |
| 41 | Table 1 | 1 |
| 43 | Table 1 | 1, 2, 3, 5 |
| 45 | Table 1 | 1 |
| 49 | Table 1 | 2, 3, 4, 5 |
| 51 | Table 1 | 1, 2, 3, 5 |
| 53 | Table 1 | 5 |
| 57 | Table 1 | 3 |
| 59 | Table 1 | 1 |
| 61 | Table 1 | 2 |
| 63 | Table 1 | 1, 2, 3, 4 |
| 65 | Table 1 | 1, 2, 3, 4 |
| 67 | Table 1 | 1, 2, 3 |
| 83 | Table 1 | 1, 2, 3, 4 |
| 85 | Table 1 | 1, 2, 3, 4 |
| 87 | Table 1 | 1, 2, 3, 4, 5 |
| 89 | Table 1 | 1, 4 |
| 91 | Table 1 | 1, 2, 3 |

UNITED STATES PATENT AND TRADEMARK OFFICE
CERTIFICATE OF CORRECTION

PATENT NO. : 7,214,802 B2
APPLICATION NO. : 11/074354
DATED : May 8, 2007
INVENTOR(S) : Derek Cogan et al.

It is certified that error appears in the above-identified patent and that said Letters Patent is hereby corrected as shown below:

| | | |
|---|---|---|
| 102 | Line 45 | |
| 103 | Line 10 | |
| 103 | Line 20 | |
| 105 | Line 10 | |
| 105 | Line 62 | |
| 106 | Line 10 | |
| 106 | Line 37 | |
| 106 | Line 57 | |
| 107 | Line 15 | |
| 107 | Line 43 | |
| 107 | Line 62 | |
| 108 | Line 23 | |
| 109 | Line 15 | |
| 109 | Line 34 | |
| 109 | Line 60 | |
| 110 | Line 17 | |
| 111 | Line 10 | |

| | | |
|---|---|---|
| 111 | Line 25 | |
| 111 | Line 46 | |
| 112 | Line 15 | |
| 112 | Line 34 | |
| 112 | Line 60 | |
| 113 | Line 12 | |
| 113 | Line 56 | |
| 114 | Line 10 | |
| 114 | Line 59 | |
| 115 | Line 17 | |
| 115 | Line 46 | |
| 115 | Line 56 | |
| 117 | Line 43 | |
| 118 | Line 35 | |
| 118 | Line 60 | |
| 119 | Line 19 | |

UNITED STATES PATENT AND TRADEMARK OFFICE
CERTIFICATE OF CORRECTION

PATENT NO.       : 7,214,802 B2
APPLICATION NO.  : 11/074354
DATED            : May 8, 2007
INVENTOR(S)      : Derek Cogan et al.

It is certified that error appears in the above-identified patent and that said Letters Patent is hereby corrected as shown below:

| 120 | Line 15 | |
|-----|---------|--|
| 120 | Line 56 | |
| 121 | Line 36 | |
| 122 | Line 14 | |
| 122 | Line 56 | |
| 123 | Line 54 | |
| 125 | Line 10 | |
| 125 | Line 60 | |
| 127 | Line 26 | |
| 127 | Line 56 | |
| 128 | Line 56 | |
| 129 | Line 32 | |
| 130 | Line 27 | |
| 132 | Line 10 | |
| 133 | Line 35 | |
| 133 | Line 62 | |
| 134 | Line 24 | |
| 135 | Line 55 | |
| 136 | Line 14 | |
| 136 | Line 25 | |

| 138 | Line 54 | |
|-----|---------|--|
| 139 | Line 28 | |
| 139 | Line 56 | |
| 140 | Line 14 | |
| 140 | Line 39 | |
| 140 | Line 64 | |
| 141 | Line 55 | |
| 142 | Line 45 | |
| 143 | Line 26 | |
| 144 | Line 7  | |
| 145 | Line 26 | |
| 146 | Line 61 | |
| 146 | Line 10 | |
| 147 | Line 23 | |
| 147 | Line 60 | |
| 148 | Line 14 | |
| 149 | Line 15 | |
| 149 | Line 55 | |

UNITED STATES PATENT AND TRADEMARK OFFICE
CERTIFICATE OF CORRECTION

PATENT NO. : 7,214,802 B2
APPLICATION NO. : 11/074354
DATED : May 8, 2007
INVENTOR(S) : Derek Cogan et al.

It is certified that error appears in the above-identified patent and that said Letters Patent is hereby corrected as shown below:

| | | | | | |
|---|---|---|---|---|---|
| 151 | Line 13 | | 165 | Line 38 | |
| 151 | Line 25 | | 166 | Line 15 | |
| 152 | Line 29 | | 166 | Line 57 | |
| 152 | Line 40 | | 167 | Line 35 | |
| 153 | Line 14 | | 167 | Line 62 | |
| 153 | Line 57 | | 168 | Line 35 | |
| 154 | Line 31 | | 169 | Line 15 | |
| 155 | Line 10 | | 169 | Line 55 | |
| 155 | Line 55 | | 170 | Line 37 | |
| 156 | Line 35 | | 171 | Line 13 | |
| 157 | Line 10 | | 171 | Line 43 | |
| 157 | Line 55 | | 172 | Line 29 | |
| 158 | Line 35 | | 173 | Line 57 | |
| 159 | Line 13 | | 174 | Line 40 | |
| 159 | Line 39 | | 175 | Line 58 | |
| 160 | Line 15 | | 176 | Line 37 | |
| 160 | Line 60 | | 176 | Line 62 | |
| 161 | Line 40 | | 177 | Line 55 | |
| 162 | Line 27 | | 178 | Line 16 | |
| 163 | Line 10 | | 178 | Line 60 | |
| 163 | Line 38 | | 179 | Line 56 | |
| 164 | Line 15 | | | | |
| 164 | Line 57 | | | | |

UNITED STATES PATENT AND TRADEMARK OFFICE
CERTIFICATE OF CORRECTION

PATENT NO. : 7,214,802 B2
APPLICATION NO. : 11/074354
DATED : May 8, 2007
INVENTOR(S) : Derek Cogan et al.

It is certified that error appears in the above-identified patent and that said Letters Patent is hereby corrected as shown below:

| | | |
|---|---|---|
| 180 | Line 28 | |
| 180 | Line 63 | |
| 181 | Line 53 | |
| 183 | Line 38 | |
| 184 | Line 56 | |
| 186 | Line 10 | |
| 186 | Line 63 | |
| 188 | Line 40 | |
| 189 | Line 55 | |
| 190 | Line 35 | |
| 191 | Line 14 | |
| 191 | Line 60 | |
| 192 | Line 35 | |
| 192 | Line 61 | |
| 193 | Line 24 | |
| 193 | Line 55 | |
| 194 | Line 15 | |

| | | |
|---|---|---|
| 194 | Line 40 | |
| 194 | Line 62 | |
| 195 | Line 19 | |
| 195 | Line 42 | |
| 195 | Line 64 | |
| 196 | Line 55 | |
| 197 | Line 14 | |
| 197 | Line 40 | |
| 197 | Line 63 | |
| 198 | Line 20 | |
| 198 | Line 29 | |
| 198 | Line 54 | |
| 198 | Line 64 | |
| 199 | Line 23 | |
| 199 | Line 33 | |
| 199 | Line 63 | |

UNITED STATES PATENT AND TRADEMARK OFFICE
CERTIFICATE OF CORRECTION

PATENT NO. : 7,214,802 B2
APPLICATION NO. : 11/074354
DATED : May 8, 2007
INVENTOR(S) : Derek Cogan et al.

It is certified that error appears in the above-identified patent and that said Letters Patent is hereby corrected as shown below:

| | | | | | | |
|---|---|---|---|---|---|---|
| 200 | Line 10 | | | 210 | Line 52 | |
| 200 | Line 40 | | | 211 | Line 15 | |
| 200 | Line 58 | | | 211 | Line 24 | |
| 202 | Line 40 | | | 211 | Line 52 | |
| 203 | Line 16 | | | 211 | Line 62 | |
| 204 | Example 135 | 1, 2 | | 212 | Line 20 | |
| | | | | 212 | Line 30 | |
| 206 | Example 136 | 1, 2 | | 212 | Line 64 | |
| | | | | 213 | Line 14 | |
| 206 | Example 137 | 1 | | 214 | Example 146 | 1, 2 |
| 207 | Example 137 | 1 | | 216 | Example 147 | 1, 2 |
| 207 | Example 138 – Lines 36, 54 | | | 218 | Example 148 | 1, 2 |
| | | | | 228 | Line 55 | |
| 208 | Line 36 | | | 228 | Line 65 | |
| 208 | Line 50 | | | 229 | Line 12 | |
| 209 | Line 15 | | | 229 | Line 57 | |
| 209 | Line 30 | | | 230 | Line 18 | |
| 209 | Line 62 | | | | | |
| 210 | Line 35 | | | | | |

Signed and Sealed this

Ninth Day of June, 2009

JOHN DOLL
*Acting Director of the United States Patent and Trademark Office*